US009440994B2

(12) United States Patent
Chen et al.

(10) Patent No.: US 9,440,994 B2
(45) Date of Patent: *Sep. 13, 2016

(54) BORON CONTAINING SMALL MOLECULES AS ANTIPROTOZOAL AGENTS

(75) Inventors: Daitao Chen, Raleigh, NC (US); Matthew Orr, Raleigh, NC (US); Jessica Sligar, Cary, NC (US); Robert Jacobs, Wake Forest, NC (US); Jacob J. Plattner, Orinda, CA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 418 days.

This patent is subject to a terminal disclaimer.

(21) Appl. No.: 12/852,351

(22) Filed: Aug. 6, 2010

(65) Prior Publication Data

US 2011/0190235 A1 Aug. 4, 2011

Related U.S. Application Data

(60) Provisional application No. 61/234,213, filed on Aug. 14, 2009, provisional application No. 61/315,774, filed on Mar. 19, 2010.

(51) Int. Cl.
C07F 5/02 (2006.01)

(52) U.S. Cl.
CPC .................................. C07F 5/025 (2013.01)

(58) Field of Classification Search
CPC .............................. A61K 31/69; C07F 5/02
See application file for complete search history.

(56) References Cited

U.S. PATENT DOCUMENTS

| | | |
|---|---|---|
| 2,260,336 A | 10/1941 | Prescott et al. |
| 3,686,398 A | 8/1972 | Kohn et al. |
| 3,873,279 A | 3/1975 | Singer |
| 4,602,011 A | 7/1986 | West et al. |
| 4,716,035 A | 12/1987 | Sampathkumar |
| 4,766,113 A | 8/1988 | West et al. |
| 4,894,220 A | 1/1990 | Nabi et al. |
| 4,919,934 A | 4/1990 | Deckner et al. |
| 5,274,792 A | 12/1993 | Sato |
| 5,348,947 A | 9/1994 | Patel et al. |
| 5,348,948 A | 9/1994 | Patel et al. |
| 5,591,731 A | 1/1997 | Kennedy et al. |
| 5,668,258 A | 9/1997 | Stolowitz |
| 5,688,928 A | 11/1997 | Stolowitz |
| 5,831,045 A | 11/1998 | Stolowitz et al. |
| 5,880,188 A | 3/1999 | Austin et al. |
| 5,962,498 A | 10/1999 | Driedger et al. |
| 6,083,903 A | 7/2000 | Adams et al. |
| 6,221,640 B1 | 4/2001 | Tao et al. |
| 6,306,628 B1 | 10/2001 | Rothschild et al. |
| 6,369,098 B1 | 4/2002 | Pershadsingh et al. |
| 6,521,619 B2 | 2/2003 | Link et al. |

(Continued)

FOREIGN PATENT DOCUMENTS

| | | |
|---|---|---|
| EP | 0969531 | 1/2000 |
| EP | 1155698 A1 | 11/2001 |

(Continued)

OTHER PUBLICATIONS

Patani et al. "Bioisosterism: A Rational Approach in Drug Design". Chem. Rev. 1996. 96:3147-3176.*
Austin, et al., "Oxaboroles and Salts and their Use of Biocides for Plastics", CAS, vol. 124, pp. 234-024, (1996).
Bailey, et al., "Boron-Containing Antibacterial Agents: Effects on Growth and Morphology of Bacteria Under Various Culture Conditions," Antimicrobial Agents and Chemotherapy, 17(04):549-553, (Apr. 1980).
Baker, et al., "Discovery of New Boron-Containing Antifungal Agent, 5-Fluoro-1,3-dihydro-1-hydroxy-2, 1-benzoxaborole (AN2690) for Potential Treatment of Onychomoycosis", Journal of Medicinal Chemistry, vol. 49, No. 15; pp. 4447-4450, (Jul. 27, 2006).
Baker, et al., "Progress on New Therapeutics for Fungal Nail Infections", Annual Reports in Medicinal Chemistry, vol. 40: pp. 323-335, (2005).
Bessis, N., "Gene Therapy for Rheumatoid Arthritis," J. Gene Med, vol. 4; pp. 581-591 (2002).

(Continued)

*Primary Examiner* — Leslie A. Royds Draper
(74) *Attorney, Agent, or Firm* — Morgan, Lewis & Bockius LLP

(57) ABSTRACT

This invention provides, among other things, novel compounds useful for treating protozoal infections, pharmaceutical compositions containing such compounds, as well as combinations of these compounds with at least one additional therapeutically effective agent. The exemplary compounds have the following formula:

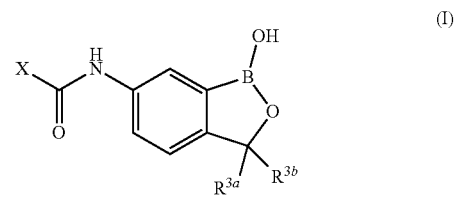

(I)

wherein X is selected from the group consisting of substituted phenyl, substituted or unsubstituted heteroaryl and unsubstituted cycloalkyl; $R^{3a}$ is selected from the group consisting of H, unsubstituted $C_1$ or $C_2$ or $C_3$ or $C_4$ or $C_5$ or $C_6$ alkyl and unsubstituted $C_3$ or $C_4$ or $C_5$ or $C_6$ cycloalkyl; $R^{3b}$ is selected from the group consisting of H, unsubstituted $C_1$ or $C_2$ or $C_3$ or $C_4$ or $C_5$ or $C_6$ alkyl and unsubstituted $C_3$ or $C_4$ or $C_5$ or $C_6$ cycloalkyl;
with the proviso that $R^{3a}$ and $R^{3b}$, along with the atom to which they are attached, are optionally joined to form a 3 or 4 or 5 or 6 membered ring, with the proviso that $R^{3a}$ and $R^{3b}$ cannot both be H, or a salt thereof.

41 Claims, 5 Drawing Sheets

(56) References Cited

U.S. PATENT DOCUMENTS

| | | | |
|---|---|---|---|
| 6,800,645 B1 | 10/2004 | Cox et al. |
| 6,855,848 B2 | 2/2005 | Scherer et al. |
| 7,169,603 B2 | 1/2007 | Hedley et al. |
| 7,205,425 B2 | 4/2007 | Shibasaki et al. |
| 7,217,701 B2 | 5/2007 | Mikoshiba et al. |
| 7,390,806 B2 | 6/2008 | Lee et al. |
| 7,446,236 B2 | 11/2008 | Naud et al. |
| 7,465,836 B2 | 12/2008 | Lee et al. |
| 7,582,621 B2 | 9/2009 | Baker et al. |
| 7,652,000 B2 | 1/2010 | Perry et al. |
| 7,767,657 B2 | 8/2010 | Baker et al. |
| 7,816,344 B2 | 10/2010 | Baker et al. |
| 7,888,356 B2 | 2/2011 | Lee et al. |
| 8,039,450 B2 | 10/2011 | Akama et al. |
| 8,039,451 B2 | 10/2011 | Baker et al. |
| 8,106,031 B2 | 1/2012 | Lee et al. |
| 8,168,614 B2 | 5/2012 | Baker et al. |
| 8,343,944 B2 | 1/2013 | Xia et al. |
| 8,440,642 B2 | 5/2013 | Baker et al. |
| 8,461,134 B2 | 6/2013 | Hernandez et al. |
| 8,461,135 B2 | 6/2013 | Akama et al. |
| 8,461,336 B2 | 6/2013 | Zhou et al. |
| 8,470,803 B2 | 6/2013 | Akama et al. |
| 8,501,712 B2 | 8/2013 | Baker et al. |
| 2002/0028831 A1 | 3/2002 | Manley |
| 2002/0161230 A1 | 10/2002 | Meudt et al. |
| 2003/0032673 A1 | 2/2003 | Nagy |
| 2004/0077601 A1 | 4/2004 | Adams et al. |
| 2004/0224923 A1 | 11/2004 | Lee et al. |
| 2005/0054644 A1 | 3/2005 | Lee et al. |
| 2005/0125852 A1 | 6/2005 | Caenepeel et al. |
| 2006/0009386 A1 | 1/2006 | Stossel et al. |
| 2006/0222671 A1 | 10/2006 | Weidner |
| 2006/0234981 A1 | 10/2006 | Baker et al. |
| 2007/0155699 A1 | 7/2007 | Baker et al. |
| 2007/0286822 A1 | 12/2007 | Sanders et al. |
| 2007/0293457 A1 | 12/2007 | Baker et al. |
| 2009/0227541 A1 | 9/2009 | Baker et al. |
| 2010/0048570 A1 | 2/2010 | Kim et al. |
| 2010/0256092 A1 | 10/2010 | Xia et al. |
| 2011/0124597 A1 | 5/2011 | Hernandez et al. |
| 2011/0207701 A1 | 8/2011 | Zhou et al. |
| 2011/0207702 A1 | 8/2011 | Jacobs et al. |
| 2012/0035132 A1 | 2/2012 | Jarnagin et al. |
| 2012/0115813 A1 | 5/2012 | Hernandez et al. |
| 2012/0295875 A1 | 11/2012 | Zhou et al. |
| 2013/0035501 A1 | 2/2013 | Conde et al. |
| 2013/0231304 A1 | 9/2013 | Jacobs et al. |

FOREIGN PATENT DOCUMENTS

| | | |
|---|---|---|
| EP | 1 444 981 A1 | 8/2004 |
| WO | WO 9533754 | 5/1995 |
| WO | WO 9622023 A1 | 7/1996 |
| WO | WO 9812206 A1 | 3/1998 |
| WO | WO 0044387 A1 | 8/2000 |
| WO | WO 0075142 A2 | 12/2000 |
| WO | WO 0114578 A1 | 3/2001 |
| WO | WO 0149303 A1 | 7/2001 |
| WO | WO 01187846 A2 | 11/2001 |
| WO | WO 200244184 | 6/2002 |
| WO | WO 03033002 A1 | 4/2003 |
| WO | WO 030059916 A2 | 7/2003 |
| WO | WO 2004056322 A2 | 7/2004 |
| WO | WO 2005013892 A3 | 2/2005 |
| WO | WO 2005123094 A2 | 12/2005 |
| WO | WO 2006007384 | 1/2006 |
| WO | WO 2006062731 A1 | 6/2006 |
| WO | WO 2006079843 A1 | 8/2006 |
| WO | WO 2006089067 A2 | 8/2006 |
| WO | WO 2006096131 A1 | 9/2006 |
| WO | WO 2007022437 A2 | 2/2007 |
| WO | WO 2007078340 A2 | 7/2007 |
| WO | WO 2007095638 A2 | 8/2007 |
| WO | WO 2007146965 A2 | 12/2007 |
| WO | WO 2008157726 A1 | 12/2008 |
| WO | WO 2009111676 A2 | 9/2009 |
| WO | WO 200914309 A2 | 11/2009 |
| WO | WO 2010027975 A1 | 3/2010 |
| WO | WO 2010028005 A1 | 3/2010 |
| WO | WO 2010045503 A | 4/2010 |
| WO | WO 2010045505 A1 | 4/2010 |
| WO | WO 2010088394 A1 | 8/2010 |
| WO | WO 2011/019612 A1 | 2/2011 |
| WO | WO 2011/019618 A1 | 2/2011 |
| WO | WO 2011017125 A1 | 2/2011 |
| WO | WO 2011022337 A1 | 2/2011 |
| WO | WO 2011037731 A | 3/2011 |
| WO | WO 2011049971 A1 | 4/2011 |
| WO | WO 2011/060196 A1 | 5/2011 |
| WO | WO 2011/063293 A1 | 5/2011 |
| WO | WO 2011/116348 A1 | 9/2011 |

OTHER PUBLICATIONS

Brown, et al., "Chiral Synthesis Via Organoboranes. 35. Simple Procedures for the Efficient Recycling of the Terpenyl Chiral Auxiliaries and Convenient Isolation of the Homoallylic Alcohols in Asymmetric Allyl- and Crotylboration of Aldehydes," J. Org. Chem., vol. 57, No. 24; pp. 6608-6614, (1992).

Cairns, et al., "Derivatives of 1,4-Xylene-2,5-diboronic acid and 1,4-xylene-2-boronic acid", J. Org. Chem. vol. 29; pp. 2810-2812, (1964).

Chander, et al. "Prevalence of Fungal Corneal Ulcers in Northern India", Infections, vol. 22, No. 3; pp. 207-209, (1994).

Chemical Abstracts Registry No. 845302-09-2, Entered STN Mar. 11, 2005.

Cui, et al., "Organoboron Compounds with an 8-Hydroxyquinolato Chelate and Its Derivatives: Substituent Effects on Structures and Luminescence," Inorganic Chemistry, vol. 44, No. 03; pp. 601-609, (Feb. 7, 2005).

Dale, et al., "Substituted Styrenes VIII Syntheses and some Reactions of the Vinylbenzeneboronic Acids" J. Org. Chem. vol. 27; pp. 2598-2603, (1962).

Denis, "Pharmacology 1104 Lecture: Drug Classifications & Characteristics of Antimicrobials" (2003).

Farfan, et al., "Through-Bond Modulation on N-B Ring Formation Shown by NMR and X-Ray Diffraction Studies of Borate Derivatives of Pyridyl Alcohols," J. Chem. Soc. Perkin Trans., vol. 2; pp. 527-532 (1992).

Ferrer, Targeting Aminocytl-tRNA Synthetases for the Treatment of Fungal Infections, Drug News Perspective, vol. 19, No. 6; pp. 347-348, (Jul./Aug. 2006).

Fungicide: Definition from Answer.com, (1998).

Grassberger, et al., "Degradation of 1,2-dihydro-1-hydroxy-2-(organosulfonyl)2,3,1-benzodiasaborines and -thieno[3,2-d][1,,3]diazaborines in Alkaline Aqueous Solutions", Liebigs Annalen Der Chemie, vol. 4; pp. 683-688, (1985).

Guo-Zheng, et al., "Single Site Transarylation of 2,2'-Dimetalized-1,1'-Binaphthyl to Aminocloroborates and Synthesis of 2-Binaphthyl Boron Compounds," Youji Huaxue/Organic Chemistry, Science Press, vol. 16, No. 02; pp. 139-144, (1996) (English Abstract).

Haynes, et al., "Arylboronic Acids VIII. Reactions of boronphthalide" J. Org. Chem. vol. 29, No. 11; pp. 3229-3233, (1964).

Hauck, et al., "Preparation and Anticonvulsant Activity of Some Arydialkkylsuccinimides" Research Lab of Parke Davis Co. (1967).

He, et al., "Small-Molecule Inhibition of TNF-alpha", Science, vol. 310, No. 5750; pp. 1022-1025, (Nov. 11, 2005).

Lampe, et al., "Synthesis and Protien Kinase Inhibitory Activity of Balanol Analogues with Modified Benzophenone Subunits", J. Med. Chem., vol. 45; pp. 2624-2643, (2002).

Lennarz, et al., "Arylboronic Acids. IV. Reactions of Boronophthalide" J. Am. Chem. Soc. vol. 82; pp. 2172-2175, (1960).

Li, et al., "An Improved Protocol for Preparation of 3-Pyridyl- and Some Arylboronic Acids", J. Org. Chem., vol. 67; pp. 5394-5397, (2002).

(56) References Cited

OTHER PUBLICATIONS

Koster, et al., "Cyclisierugen von Bor-Stickstoff-Verbindugen in der Hietz" Liebigs Ann. Chem., vol. 720; pp. 23-31, (1968).

Koster, et al., "Boron Compounds, XXXIX. Alkenoxy(diorgany)boranes Substituted at the Alkeonxy Group from 2-methylacrolein and triorganylboranes," Justus Liebigs Annalen Der Chemie, No. 06; pp. 1116-1134, (1976).

McMillin, et al., "Systemic Aspects of Psoriasis: An Intergrative Model Based on Intestinal Etiology", Int. Med. vol. 2, Issue 2/3, (1999).

Moeder, et al., "Kinetic Analysis of the Asymmetric Amplification exhibited by B-chlorodiisopinocampheylborane," Journal of Physical Organic Chemistry, vol. 17, No. 4; pp. 317-324, (Apr. 2004).

Morissette, et al., "High-throughput Crystallization: Polymorphs, Salts, Co-Crystals and Solvates of Pharmaceutical Solids", Advanced Drug Delivery Reviews, vol. 56; pp. 273-300, (2004).

Mudran, "Drug Delivery to the Nail Following Topical Application", International Journal of Pharmaceutics, vol. 236: pp. 1-26, (2002).

Patani, et al., "Bioterrorism: A Rational Approach to Drug Design", Chem. Rev., vol. 96; pp. 3147-3176 (1996).

Qin, et al., "Luminescent Organoboron Quinolate Polymers," Journal of the American Chemical Society, vol. 126, No. 22; pp. 7015-7018, (Jun. 9, 2004).

Rock, et al., "An Antifungal Agents Inhibits Aminoacyl-tRNA Synthetase by Trapping tRNA in the Editing Site", Science, vol. 316, No. 5832; pp. 1759-1761, (Jun. 22, 2007).

Snyder, et al. "Common Bacteria Whose Susceptibility to Antimicrobials in no longer Predictable" J. Med. Liban, vol. 48 No. 4; pp. 208-214, (2000).

Sugar, et al., "Comparison of Three Methods of Antifungal Susceptibility Testing with the Proposed NCCLS Stardard Broth Macrodilution Assay: Lack of Effect of Phenol Red" Diagn. Microbiol. Infect. Dis. vol. 21; pp. 129-133, (1995).

Tabuchi, et al., "Anticoccidial Activity of some Azacyclo Organoborinates," Heterocycles, vol. 60, No. 01; pp. 177-182, (2003).

Toporcer, et al., "Preparation and Properties of some Tetracoordinate Boron Compounds. The Pseudo-metal Ion Concept," Inorganic Chemistry, vol. 4, No. 11; pp. 649-1655, (Nov. 1965).

Trujillo, et al., "X-Ray Crystallographic Study of Boroxazolidones, Obtained from L-ornithine, L-methionine, Kainic acid and 2,6-pyridinedicarboxylic acid", Journal of Organometallic Chemistry, vol. 571; pp. 21-29, (1998).

Tschampel, et al., "Arylboronic Acids. VII. Some Reactions to o-Formybenzeneboronic Acids", J. Org. Chem. vol. 29, No. 8; pp. 2168-2172, (1964).

Turner, et al., Current Pharmaceutical Design, vol. 2; pp. 209-224 (1996).

Vippagunta, "Crystalline Solids", Advanced Drug Delivery Reviews, vol. 48; pp. 3-26, (2001).

Wang, et al., "Expression, Purification and Characterization of Human cAMP-SpecificPhosphodiesterase (PDE4) Subtypes A, B, C, and D", Biochemical and Biophysical Research Communications, vol. 234; pp. 320-324, (1997).

Ye, et al., "Convenient and Versatile Syntheis of formyl-substituted Benzoxaboroles", Tetrahedron, vol. 65; pp. 8738-8744, (2009).

Zhdankin, et al., "Synthesis and Structure of Benzoboroxoles: Novel Organboron Heterocycles," Tetrahedron Letters, vol. 40; pp. 6705-6708, (1999).

Zhou, et al., "Hemodextrin: a Self-assembled Cyclodextrin-Porphyrin Construct That Binds Dioxygen," Biophysical Chemistry, 105:639-648 (2003).

Zhou, et al., "Structure-activity Studies on a Library of Potent Calix[4]arene-based PDGF Antagonists that Inhibit PDGF-stimulated PDGFR Tyrosine Phosphorylation," Org. Biomol. Chem., 4:2376-2386 (2006).

Zhou, et al., "Pattern Recognition of Proteins Based on an Array of Functionalized Porphyrins," J. Am. Chem. Soc., 128:2421-2425 (2006).

Zixing, et al., "Synthesis of Aromatic Nitrogen-containing Heterocyclic Derivatives of Asymmetric Diarylborinic Acids," Wuhan Daxue Xuebo-Wuhan University Journal, vol. 3; pp. 67-71, (1990), (English Abstract).

Adamczyk-Wozniac, et al., "Benzoxaboroles-Old Compounds with new applications", Journal of Organometalic Chemistry 694;3533-3541 (2009).

Akama, et al., "Discovery and structure-activity study of novel benzoxaborole anti-inflammatory agent (AN2728) for the potential topical treatment of psoriasis and atopic dernatitis", Bioorganic & Medicinal Chemistry Letters, (2009) 19: 2129-2132.

Alley, et al., "Recent Progress on Topical Therapy of Onychomycosis", Expert Opinion Investigate Drugs(Feb. 2007) 16(2): 157-67.

Baker, et al., "Identification of a Novel Boron-Containing Antibacterial Agent (AN0128) with Anti-inflammatory activity, for the Potential Treatment of Cutaneous Diseases", Bioorganic & Medicinal Chemistry Letters (2006) 16: 5963-5937.

Cummings, et al., "Arylboronic Acids. A Medium-Size Ring Containing Boronic Ester Groups", Arylboronic Acids, vol. 34, No. 6; pp. 1669-1674 (Jun. 1969).

Cusack, S., et al., "The 2 A Crystal Structure of leucyl-tRNA Synthetase and its Complex with a Leucyl-Adenylate Analogue." EMBO Journal, vol. 19; pp. 2351-2361, (2000).

Dian, "International Nomenclature of Organics", China Petrochemical Press, 1st Edition; 50-51 (Jan. 21, 2004).

Falck, et al., "Bromo-Boronolactonization of Olefins", J. Org. Chem., vol. 66; pp. 7148-7150 (2001).

Goodman, et al., "Goodman & Gilman's Manual of Pharmacology and Therapeutics" Chapter 40;681-694 (2008).

Hui, et al., "In Vitro Penetration of a Novel Oxaborole Antifungal (AN2690) into the Human Nail Plate", Journal of Pharmaceutical Sciences (2007) 96(10): 2622-2631.

Lee, K., et al., "Molecular Study of the Editing Active Site of Escherichia coli Leucyl-tRNA Synthetase: Two Amino Acid Binding Site in the Editing Domain", vol. 54; pp. 693-704, (2004).

Luan, et al., "Inhibition of Experimental Periodontitis by a topical boron-base antimicrobial" J Dent. Res, 87(2):148-152 (2008).

Koster, et al., "Ein Am Bor Alkyliertes Carboran-2,3" Tetrahedron Letters, No. 25; pp. 1667-1670 (1964).

Murugesan, et al., "Biphenylsulfonamide Endothelin Antagonists: Structure-Activity Relationships of a Series of Mono- and Disubstituted Analogues and Pharmacology of the Orally Active Endothelin Antagonist 2'-Amino-N-(3,4-dimethyl-5-isoxazoly1)-4'-(2-methylpropyl)[1,1'-biphenyl]-2-sulfonamide",J. Med. Chem vol. 41; pp. 5198-5218 (1998).

Perola, E., et al., "Successful Virtual Screening of a Chemical Database for Farnesltransferase Inhibitor Leads." vol. 43; pp. 401-4008, (2000).

Silverman, "The Organic Chemistry of Drug Design and Drug Action", 2nd Edition, Northwestern University, Department of Chemistry, Evanston, Illinois, Section 2: 29-32 (2004).

Sporzynski, et al., "1,3-Dihydro-1-hydroxy-3-morpholin-4-yl-2,1-benzoxaborole: product of the reaction of o-formylphenylboronic acid with morpholine", Appl. Organometal. Chem., vol. 19; pp. 1202-1203, (2005).

Tatsumi, et al., "Therapeutic Efficacy of Topically applied KP-103 against Experimental Tinea Uguium in Guinea Pigs in Comparison with Amorolfine and Terbinafine", Antimicrobial Agents and Chemotherapy, vol. 46, No. 12; pp. 3797-3801 (2002).

"Structure-Activity Studies led to the Discovery of AN2898 in Development for Topical Treatment of Psoriasis and Atopic Dermatitis", Scientific Presentation at the American Academy of Dermatology Annual Meeting, San Francisco, CA Mar. 6-10- 2009.

"AN2898 Inhibits Cytokines Relevant to Topical Treatment of Psoriasis and Atopic Dermatitis", Scientific Presentation at the American Academy of Dermatology Annual Meeting, San Francisco, CA Mar. 6-10, 2009.

"AN2718 has Broad Spectrum Antifungal Activity Necessary for the Topical Treatment of Skin and Nail Fungal Infections", Scien-

(56) References Cited

OTHER PUBLICATIONS tific Presentation at the American Academy of Dermatology Annual Meeting, San Francisco, CA Mar. 6-10, 2009.
"AN2718 Demonstrates Significant Efficacy in Three Phase lb Psoriasis Microplaque Trials" Scientific Presentation at the American Academy of Dermatology Annual Meeting, San Francisco, CA Mar. 6-10, 2009.
"AN2728 Demonstrates Significant Safety and Efficacy in Phase IIa Double Blind Trial in Plaque Type Psoriasis", Scientific Presentation at the American Academy of Dermatology Annual Meeting, San Francisco, CA Mar. 6-10, 2009.
"AN2728 Preclinical Studies Demonstrate an Acceptable Safety Profile for the Topical Treatment of Psoriasis and Atopic Dermatitis", Scientific Presentation at the American Academy of Dermatology Annual Meeting, San Francisco, CA May 6-10, 2009.
"A New Class of Benzoxaborole-based Potent Antitrypanosomal Agents: Probing Effect of Different Linkage Groups in *Trypanosoma brucei* Growth Inhibition", Scientific Presentation at the American Society of Tropical Medicine and Hygiene Conference, New Orleans, LA Dec. 7-11, 2008.
"Antifungal Activity and Mechanism of Action of a Benzoxaborole, AN2718, which is in Development for the Treatment of Tinea Pedis", Scientific Presentation at the 48th Interscience Conference on Antimicrobial Agents and Chemotherapy, Washington, D.C. Oct. 25-28, 2008.
"AN2728 Ointment, a Novel Oxaborole with Anti-Inflammatory Activity, Demonstrates Safety and Significant Efficacy in a Phase lb Psoriasis Plaque Test", Scientific Presentation at Montagna Symposium on Biology of Skin, Gleneden Beach, OR, Oct. 2-6, 2008.
"Preclinical Toxicology of AN2728, a Novel Oxaborole in Development for the Topical Treatment of Psoriasis", Scientific Presentation at the International Investigative Dermatology Conference, Kyoto, Japan, May 14-18, 2008.
"AN2898, a Novel Oxaborole Compound with Anti-Inflammatory Activity: Mechanism of Action and in vitro Cytokine Inhibition", Scientific Presentation at the International Investigative Dermatology Conference, Kyoto, Japan, May 14-18, 2008.
"Structure-Activity Studies of AN2728 and AN2898, Novel Oxaborole Compounds with Anti-Inflammatory Activity", Scientific Presentation at the International Investigative Dermatology Conference, Kyoto, Japan, May 14-18, 2008.
"In Vitro Activity and Mechanism of Action of AN2728, a Novel Oxaborole in Development for Treatment of Psoriasis", Scientific Presentation at the International Investigative Dermatology Conference, Kyoto, Japan, May 14-18, 2008.
"AN2898, a Novel Oxaborole Compound with Anti-Inflammatory Activity: Results of In Vivo Efficacy and Preclinical Safety Studies", Scientific Presentation at the International Investigative Dermatology Conference, Kyoto, Japan, May 14-18, 2008.
"Preclinical Toxicology of AN2728, a Novel Borinic Acid Ester with Anti-Inflammatory Activity", American Academy of Dermatology, 65th Annual Meeting, Washington, DC, Feb. 2-6, 2007.
"AN2728, a Novel Oxaborole with Broad-Spectrum In Vitro Anti-Inflammatory Activity", American Academy of Dermatology, 65th Annual Meeting, Washington, DC, Feb. 2-6, 2007.
"In Vitro Nail Penetration of AN2690, Effect of Vehicle and Co-Efficient of Efficacy", American Academy of Dermatology, 65th Annual Meeting, Washington, DC, Feb. 2-6, 2007.
"Interim Results of a Multi-Center Study to Evaluate the Safety and Efficacy of Topically Applied AN2690 5.0% and 7.5% Solutions for the Treatment of Onychomycosis of the Great Toenail", American Academy of Dermatology, 65th Annual Meeting, Washington, DC, Feb. 2-6, 2007.
"In vivo Nail Residence Time of AN2690, a Novel Broad-Spectrum Antifungal Agent in Development for the Topical Treatment of Onychomycosis", American Academy of Dermatology, 65th Annual Meeting, Washington, DC, Feb. 2-6, 2007.
"An Open-Label, Multi-dose Study of Absorption and Systemic Pharmacokinetics of AN2690 Applied as a 7.5% Solution to All Toenails of Adult Patients with Moderate to Severe Onychomycosis", American Academy of Dermatology, 65th Annual Meeting, Washington, DC, Feb. 2-6, 2007.
"Medicinal Chemistry Development of AN2728, A Novel Oxaborole in Development for the Topical Treatment of Psoriasis", American Academy of Dermatology, 65th Annual Meeting, Washington, DC, Feb. 2-6, 2007.
"Skin Penetration and Anti-Inflammatory Activity of AN2728, a Novel Oxaborole", American Academy of Dermatology, 65th Annual Meeting, Washington, DC, Feb. 2-6, 2007.
"Nail Penetration and Nail Concentration of AN2690, a Novel Broad-Spectrum Antifungal Agent in Development for the Topical Treatment of Onychomycosis", Scientific Presentation at the American Associate of Pharmaceutical Scientist, Annual Meeting, San Antonio, TX, Oct. 29-Nov. 2, 2006.
Baker SJ, et al., "Therapeutic potential of boron-containing compounds," *Future Med. Chem.* (2009) 1(7), 1275-1288.
Ding, et al. "Discovery of Novel Benzoxaborole-Based Potent Antitrypanosomal Agents," ACS *Med. Chem. Lett.* 2010, 1, 165-169
Nare et al., "Discovery of Novel Orally Bioavailable Oxaborole 6-Carboxamides That Demonstrate Cure in a Murine Model of Late-Stage Central Nervous System African Trypanosomiasis," Antimicrobial Agents and Chemotherapy, 2010, 4379-4388 vol. 54, No. 10.
Seiradake E. et al., "Crystal Structures of the Human and Fungal Cytosolic Leucyl-tRNA Synthetase Editing Domains: A Structural Basis for the Rational Design of Antifungal Benzoxaboroles," *Journal of Molecular Biology* 390 (2009) 196-207.
Zhang, et al., "Synthesis and structure-activity relationships of novel benzoxaboroles as a new class of antimalarial agents," Bioarg Med Chem Lett 2010, 21, pp. 644-651.
Zhang, et al., "Synthesis and biological evalutations of P4-benzoxaborole-substituted macrocyclic inhibitors of HCV NS3 protease," Bioorg Med Chem Lett 2010, 20, pp. 7317-7322
Zhang, et al. "Synthesis of new acyisulfamoyl benzoxaboroles as potent inhibitors of HCV NS3 protease," *Bioorg Med Chem Lett 2010*, 20, pp. 7493-7497.
Zhang YK et al., "Design and Synthesis of Boron-Containing PDE4 Inhibitors Using Soft-Drug Strategy for Potential Dermatologic Anti-Inflammatory Application," *Bioorganic & Medicinal Chemistry Letters 20* (2010) 2270-2274.
"A Series of Potent Orally-Availabie Benzaxaborole PDE4 inhibitors which Gain Potency by use of Novel Contacts Within the PDE4 Active Site," Gordon Conference on Cyclic Nucleotide Phosphocliesterases, Jun. 13-18, 2010, Waterviile Valley, NH.
"AN2728 Demonstrates Significant Efficacy in Three Phase lb Psoriasis Microplaque Trials" Scientific Presentation at the American Academy of Dermatology Annual Meeting, San Francisco, CA Mar. 6-10, 2009.
"AN6415: A Novel, Highly Potent, PDE4 Inhibitor with Oral Activity and Broad Spectrum Cytokine Suppression," 8th Annual Cytokines and Inflammation Conference. Jan. 28-29, 2010, La Jolla, CA.
"Boron and non-boron HCV NS3/4 protease inhibitors : new motifs with high potency against PI-resistant mutants," HCV Drug Discovery 5th CHI Conference, Apr. 28-29, 2010, San Diego, CA.
"Discovery of Novel Boron Containing Compounds as Dual Inhibitors of TNF-a and IL-23 Release," World Congress of Inflammation, Jul. 6-10, 2009, Tokyo, Japan.
"Discovery and Mechanism of Action of AN3365: A Novel Boron-containing Antibacterial Agent in Clinical Development for Gram-negative Infections," 2010 Interscience Conference on Antimicrobial Agents and Chemotherapy, Sep. 12-15, 2010, Boston, MA.
"Lead Optimization Investigation of Oxaboroles for the Treatment of Human African Trypanosomiasis," American Chemical Society, Aug. 16-20, 2009, Washington, DC.
"Novel Boron-Containing Small Molecules Demonstrate Potent Activity Against Malaria Parasites with Excellent Drug-like Properties," The American Society of Tropical Medicine and Hygiene, Nov. 20, 2009, Washington, DC.

(56) References Cited

OTHER PUBLICATIONS

"Novel Boron-Containing Small Molecules as Potential Therapeutics Against Human Lymphatic Filariasis," The American Society of Tropical Medicine and Hygiene, Nov. 20, 2009, Washington, DC.

"Novel Boron-Containing Small, Molecules Demonstrate Potent Activity Against *Trypanosoma cruzi*," The XIIth International Congress of Parasitology, Aug. 15-20, 2010, Melbourne, Australia.

"Novel Cyclic Boronates as HCV NS3/4A Protease Inhibitors," 7th Annual Congress of International Drug Discovery Science and Technology, Oct. 22-25, 2009, Shanghai, China.

"Novel Oxaborole 6-Carboxamides Demonstrate Potential for Treatment of CNS-Stage Human African Trypanosomiasis," Key Stone Symposium, Mar. 22-26, 2009, Breckenridge, CO.

"Structure-Activity Studies Led to the Discovery of AN2898 in Development for Topical Treatment of Psoriasis and Atopic Dermatitis," Society for Investigative Dermatology Annual Meeting, May 6-9, 2009, Montreal, Canada.

"Structure-Guided Discovery of (S)-3-(aminomethyl)benzo[c][1,2]oxaborol-1 (3H)-ol hydrochloride (ABX): A First in Class Gram-negative Antibacterial," Anti-Infectives Summit, Jan. 25-27, 2010, Philadelphia, PA.

\* cited by examiner

FIGURE 1A

| Compound # | T.b. brucei IC50 (µg/mL) | T.b. bruci IC50 (nM) | L. donovani axenic amastigotes IC50 (µg/mL) | L. donovani axenic amastigotes IC50 (nM) | Cytotox L.929 IC50 (µg/mL) | Selectivity Index (Tb/L929) | Selectivity Index (Ld/L929) | Solubility (uM) |
|---|---|---|---|---|---|---|---|---|
| 1 | 0.091 | 258 | 0.185 | 524 | 1.21 | 13 | 7 | 50 |
| 2 | 0.078 | 233 | 0.278 | 830 | 0.53 | 7 | 2 | 3 |
| 3 | 0.05 | 175 | 0.098 | 344 | >10 | >200 | >10 | 100 |
| 4 | 0.024 | 80 | 0.138 | 458 | 1.24 | 52 | 9 | >200 |
| 5 | 0.054 | 182 | 0.107 | 360 | >10 | >185 | >93 | 100 |
| 6 | 0.046 | 155 | | | >10 | >217 | | |
| 7 | 0.041 | 146 | | | 5.61 | 137 | | 100 |
| 8 | 0.07 | 246 | | | 5.86 | 84 | | 50 |
| 9 | 0.048 | 159 | | | >10 | >208 | | 25 |
| 10 | 0.037 | 130 | | | >10 | >207 | | |
| 11 | 0.036 | 119 | | | 6.06 | 168 | | |
| 12 | 0.081 | 267 | | | >10 | >123 | | 100 |
| 13 | 0.043 | 135 | | | 2.00 | 47 | | >200 |
| 14 | 0.043 | 124 | | | 1.67 | 39 | | 100 |
| 15 | 0.068 | 173 | | | 2.45 | 36 | | 100 |
| 16 | 0.107 | 294 | | | 3.06 | 29 | | |
| 17 | 0.655 | 1683 | | | >10 | >15 | | 25 |
| 18 | 4.22 | 11866 | | | 9.29 | 2 | | |
| 19 | 3.18 | 7810 | | | >10 | >3 | | 100 |
| 20 | >5 | >14472 | | | >10 | 2 | | |
| 21 | >5 | >19297 | | | >10 | 2 | | |
| 22 | 0.866 | 2296 | | | >10 | >12 | | 25 |
| 23 | 2.41 | 6009 | | | >10 | >4 | | |
| 24 | >5 | >15283 | | | >10 | 2 | | |
| 25 | >5 | >14551 | | | >10 | 2 | | |
| 26 | >5 | | | | >10 | | | 200 |
| 27 | 2.24 | | | | >10 | | | |
| 28 | 3.17 | | | | >10 | | | |
| 29 | 3.62 | | | | >10 | | | |
| 30 | 0.427 | | | | >10 | | | |
| 31 | 0.397 | | | | | | | |
| 32 | 0.349 | | | | | | | |

FIGURE 1B

| Compound # | T.b. brucei IC50 (ug/mL) | T. b. brucei IC50 (nM) | L. donovani axenic amastigotes IC50 (ug/mL) | L. donovani axenic amastigotes IC50 (nM) | Cytotox L929 IC50 (ug/mL) | Selectivity Index (Tb/L929) | Selectivity Index (Ld/L929) | Solubility (uM) |
|---|---|---|---|---|---|---|---|---|
| 33 | 0.229 | | | | >10 | | | 6 |
| 34 | 0.108 | 304 | | | >10 | >94 | | 50 |
| 35 | 2.74 | | | | >10 | | | |
| 36 | 4.05 | | | | >10 | | | |
| 37 | 1.42 | | | | >10 | | | |
| 38 | 0.168 | 532 | | | >10 | >60 | | 13 |
| 39 | 0.227 | 631 | | | >10 | >44 | | 50 |
| 40 | 0.699 | | | | >10 | | | |
| 41 | >5 | | | | >10 | | | |
| 42 | 2.12 | | | | >10 | | | |
| 43 | 2.2 | | | | >10 | | | |
| 44 | >5 | >16710 | | | >10 | 2 | | 100 |
| 45 | 3.64 | | | | >10 | | | |
| 46 | 3.01 | | | | >10 | | | |
| 47 | 2.35 | | | | >10 | | | |
| 48 | 1.11 | 3667 | | | >10 | >9 | | |
| 49 | >5 | | | | >10 | | | |
| 50 | 1.4 | | | | >10 | | | |
| 51 | 1.15 | | | | >10 | | | |
| 52 | 2.27 | | | | >10 | | | |
| 53 | 0.407 | | | | >10 | | | |
| 54 | 0.571 | | | | >10 | | | |
| 55 | 0.122 | | | | >10 | | | |
| 56 | >5 | | | | >10 | | | |
| 57 | >5 | | | | >10 | | | |
| 58 | 1.11 | | | | >10 | | | |
| 59 | 1.61 | | | | >10 | | | |
| 60 | 0.205 | | | | >10 | | | |
| 61 | 1.6 | | | | >10 | | | |
| 62 | 0.365 | | | | >10 | | | |
| 63 | 2.88 | 8389 | | | >10 | >4 | | |
| 64 | 0.724 | | | | >10 | | | |

FIGURE 1C

| Compound # | T. b. brucei IC50 (ug/mL) | T. b. brucei IC50 (nM) | L. donovani axenic amastigotes IC50 (ug/mL) | L. donovani axenic amastigotes IC50 (nM) | Cytotox L.929 IC50 (ug/mL) | Selectivity Index (Tb/L929) | Selectivity Index (Ld/L929) | Solubility (uM) |
|---|---|---|---|---|---|---|---|---|
| 65 | 0.279 | | | | >10 | | | 50 |
| 66 | 0.292 | | | | >10 | | | |
| 67 | >5 | | | | >10 | | | |
| 68 | 2.23 | | | | >10 | | | |
| 69 | 0.282 | 846 | | | >10 | >35 | | 100 |
| 70 | 0.377 | | | | >10 | | | |
| 71 | 0.697 | | | | >10 | | | |
| 72 | 0.407 | | | | >10 | | | |
| 73 | 2.44 | | | | >10 | | | |
| 74 | 0.564 | 1492 | | | >10 | >18 | | |
| 75 | 0.405 | | | | >10 | | | |
| 76 | 0.185 | | | | >10 | | | 25 |
| 77 | 0.05 | | | | >10 | | | |
| 78 | 1.1 | | | | >10 | | | |
| 79 | 1.1 | | | | >10 | | | |
| 80 | >5 | | | | >10 | | | |
| 81 | 0.103 | | | | >10 | | | |
| 82 | 0.204 | 558 | | | >10 | >49 | | 25 |
| 83 | 0.543 | | | | >10 | | | |
| 84 | 0.533 | | | | >10 | | | |
| 85 | 1.14 | | | | >10 | | | |
| 86 | 0.425 | | | | >10 | | | |
| 87 | 3.88 | | | | >10 | | | |
| 88 | 0.313 | | | | >10 | | | |
| 89 | 0.152 | | | | >10 | | | |
| 90 | 0.514 | | | | >10 | | | |
| 91 | 0.793 | | | | >10 | | | |
| 92 | 0.158 | | | | 2.68 | | | |
| 93 | 0.197 | | | | >10 | | | |
| 94 | 0.4 | | | | >10 | | | |
| 95 | 0.663 | | | | >10 | | | |
| 96 | 2.72 | | | | >10 | | | |

FIGURE 1D

| Compound # | T.b. brucei IC50 (ug/mL) | T. b. brucei IC50 (nM) | L. donovani axenic amastigotes IC50 (ug/mL) | L. donovani axenic amastigotes IC50 (nM) | Cytotox L-929 IC50 (ug/mL) | Selectivity index (Tb/L929) | Selectivity index (Ld/L929) | Solubility (uM) |
|---|---|---|---|---|---|---|---|---|
| 97 | 0.05 | | | | >10 | | | |
| 98 | 0.091 | | | | >10 | | | |
| 99 | 0.19 | | | | 8.80 | | | |
| 100 | 0.077 | | | | 9.55 | | | |
| 101 | 0.35 | | | | 8.43 | | | 25 |
| 102 | 0.125 | | | | >10 | | | |
| 103 | 0.184 | | | | >10 | | | |
| 104 | 1.12 | | | | >10 | | | |
| 105 | 0.788 | | | | >10 | | | |
| 106 | >5 | | | | >10 | | | |
| 107 | 0.566 | | | | >10 | | | 4.3 |
| 108 | 0.378 | | | | >10 | | | |
| 109 | 0.379 | | | | >10 | | | |
| 110 | >5 | | | | >10 | | | |
| 111 | 1.23 | | | | >10 | | | |
| 112 | 0.278 | | | | >10 | | | 50 |
| 113 | >5 | | | | >10 | | | |
| 114 | 0.814 | | | | >10 | | | 100 |
| 115 | >5 | | | | >10 | | | |
| 116 | >5 | | | | >10 | | | |
| 117 | 1.65 | | | | >10 | | | |
| 118 | 0.814 | | | | >10 | | | |
| 119 | >5 | | | | >10 | | | |
| 120 | >5 | | | | >10 | | | |
| 121 | 3.2 | | | | >10 | | | |
| 122 | >5 | | | | >10 | | | |
| 123 | >5 | | | | >10 | | | |
| 124 | 2.7 | | | | >10 | | | |
| 125 | >5 | | | | >10 | | | |
| 126 | >5 | | | | >10 | | | |
| 127 | 2.85 | | | | >10 | | | |
| 128 | >5 | | | | >10 | | | |

FIGURE 1E

| Compound # | T. b. brucei IC50 (ug/mL) | T. b. brucei IC50 (nM) | L. donovani axenic amastigotes IC50 (ug/mL) | L. donovani axenic amastigotes IC50 (nM) | Cytotox L-929 IC50 (ug/mL) | Selectivity Index (Tb/L929) | Selectivity Index (Ld/L929) | Solubility (uM) |
|---|---|---|---|---|---|---|---|---|
| 129 | >5 | | | | >10 | | | |
| 130 | >5 | | | | >10 | | | |
| 131 | >5 | | | | >10 | | | |
| 132 | 3.81 | | | | >10 | | | |
| 133 | 0.101 | | | | >10 | 100 | | |
| 134 | 0.338 | 892 | | | >10 | >30 | | 100 |
| 135 | 0.172 | 498 | | | >10 | >58 | | 25 |
| 136 | >5 | >12718 | | | >10 | 2 | | 25 |
| 137 | 3.62 | 10597 | | | >10 | >3 | | |

BORON CONTAINING SMALL MOLECULES AS ANTIPROTOZOAL AGENTS

CROSS-REFERENCE TO RELATED APPLICATIONS

This application claims the benefit of U.S. Provisional Pat. App. No. 61/234,213, filed Aug. 14, 2009, and U.S. Provisional Pat. App. No. 61/315,774, filed Mar. 19, 2010, each of which is incorporated by reference in its entirety for all purposes.

BACKGROUND OF THE INVENTION

The global rise of protozoa resistant to antimicrobials in general, poses a major threat. Deployment of massive quantities of antimicrobial agents into the ecosphere during the past 60 years has introduced a powerful selective pressure for the emergence and spread of antimicrobial-resistant pathogens. Thus, there is a need to discover new broad spectrum antimicrobials, such as antiprotozoals, useful in combating microorganisms, especially those with multi-drug-resistance.

Boron-containing molecules, such as oxaboroles, useful as antimicrobials have been described previously, such as in U.S. Pat. Pubs. US20060234981 and US20070155699. Generally speaking, an oxaborole has the following structure and substituent numbering system:

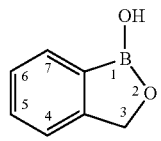

It has now been discovered that certain classes of oxaboroles which are surprisingly effective antiprotozoals. This, and other uses of these oxaboroles are described herein.

SUMMARY OF THE INVENTION

This invention provides, among other things, novel compounds useful for treating protozoa infections, pharmaceutical compositions containing such compounds, as well as combinations of these compounds with at least one additional therapeutic cally effective agent.

BRIEF DESCRIPTION OF THE DRAWINGS

Biological data for exemplary compounds of the invention is provided in FIGS. 1A-1E.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato)diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, in general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino)pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl)amide; KHMDS is potassium bis(trimethylsilyl)amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; $MgSO_4$ is magnesium sulfate; mins or min is minutes; Mp or MP is melting point; $NaCNBH_3$ is sodium cyanoborohydride; NaOH is sodium hydroxide; $Na_2SO_4$ is sodium sulfate; NBS is N-bromosuccinimide; $NH_4Cl$ is ammonium chloride; NIS is N-iodosuccinimide; $N_2$ is nitrogen; NMM is N-methylmorpholine; n-BuLi is n-butyllithium; overnight is O/N; $PdCl_2(pddf)$ is 1,1'-Bis(diphenylphosphino) ferrocene]dichloropalladium(II); Pd/C is the catalyst known as palladium on carbon; $Pd_2(dba)_3$ is an organometallic catalyst known as tris(dibenzylideneacetone) dipalladium(0); Ra Ni or Raney Ni is Raney nickel; Ph is phenyl; PMB is p-methoxybenzyl; PrOH is 1-propanol; iPrOH is 2-propanol; $POCl_3$ is phosphorus chloride oxide; PTSA is para-toluene sulfonic acid; Pyr. or Pyr or Py as used herein means Pyridine; RT or rt or r.t. is room temperature; sat. is saturated; Si-amine or Si—$NH_2$ is amino-functionalized silica, available from SiliCycle; Si-pyr is pyridyl-functionalized silica, available from SiliCycle; TEA or $Et_3N$ is triethylamine; TFA is trifluoroacetic acid; $Tf_2O$ is trifluoromethanesulfonic anhydride; THF is tetrahydrofuran; TFAA is trifluoroacetic anhydride; THP is tetrahydropyranyl; TMSI is trimethylsilyl iodide; $H_2O$ is water; $diNO_2PhSO_2Cl$ is dinitrophenyl sulfonyl chloride; $3-F-4-NO_2-PhSO_2Cl$ is 3-fluoro-4-nitrophenylsulfonyl chloride; $2-MeO-4-NO_2-PhSO_2Cl$ is 2-methoxy-4-nitrophenylsulfonyl chloride; and $(EtO)_2POCH_2COOEt$ is a triethylester of phosphonoacetic acid known as triethyl phosphonoacetate.

"Compound of the invention," as used herein refers to the compounds discussed herein, salts (e.g. pharmaceutically acceptable salts), prodrugs, solvates and hydrates of these compounds.

"Combination of the invention," as used herein refers to the compounds and antiprotozoals discussed herein as well as acids, bases, salt forms (such as pharmaceutically acceptable salts), prodrugs, solvates and hydrates of these compounds and antiprotozoals.

"Boron containing compounds", as used herein, refers to the compounds of the invention that contain boron as part of their chemical formula.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "poly" as used herein means at least 2. For example, a polyvalent metal ion is a metal ion having a valency of at least 2.

"Moiety" refers to a radical of a molecule that is attached to the remainder of the molecule.

The symbol $\sim\!\sim\!\sim$, whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkenylene" by itself or as part of another substituent means a divalent radical derived from an alkene.

The term "cycloalkylene" by itself or as part of another substituent means a divalent radical derived from a cycloalkane.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 or 2 or 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")=NR"", —NR""—C(NR'R")=NR'", —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to (2 m'+1), where m' is the total number of carbon atoms in such radical. R', R", R'", R"" and R""" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'", R"" and R""" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")=NR"", —NR""—C(NR'R")=NR'", —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", R"" and R""" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R"" and R""" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$—NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted C$_1$ or C$_2$ or C$_3$ or C$_4$ or C$_5$ or C$_6$ alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 or 6 or 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "Topically effective," "pharmaceutically effective," or "therapeutically effective" amount refers to the amount of drug needed to effect the desired therapeutic result.

"Topically effective" refers to a material that, when applied to the skin, nail, hair, claw or hoof produces a desired pharmacological result either locally at the place of application or systemically as a result of transdermal passage of an active ingredient in the material.

The term "pharmaceutically acceptable salt" is meant to include a salt of a compound of the invention which is prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, 1-arginine, d-lysine, 1-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and/isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). The compounds may also be labeled with stable isotopes such as deuterium. All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in Remington: The Science and Practice of Pharmacy, 21st Ed., Lippincott, Williams & Wilkins (2005) which is incorporated herein by reference.

"Pharmaceutically acceptable topical carrier" and equivalent terms refer to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The terms "enhancement," "penetration enhancement" or "permeation enhancement" relate to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal skin, nail, hair, claw or hoof using a diffusion cell apparatus. A diffusion cell is described by Merritt et al. Diffusion Apparatus for Skin Penetration, *J of Controlled Release*, 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "excipients" is conventionally known to mean carriers, diluents and/or vehicles used in formulating drug compositions effective for the desired use.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to a broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "oral dosage form" means any pharmaceutical composition administered to a subject via the oral cavity. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. An oral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package. In a preferred embodiment, the oral dosage form is one, two or three units. In a particularly preferred embodiment, the oral dosage form is one unit.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

The term, "prodrug", as defined herein, is a derivative of a parent drug molecule that exerts its pharmacological effect only after chemical and/or enzymatic conversion to its active form in vivo. Prodrugs include those designed to circumvent problems associated with delivery of the parent drug. This may be due to poor physicochemical properties, such as poor chemical stability or low aqueous solubility, and may also be due to poor pharmacokinetic properties, such as poor bioavailability or poor half-life. Thus, certain advantages of prodrugs may include improved chemical stability, absorption, and/or PK properties of the parent carboxylic acids. Prodrugs may also be used to make drugs more "patient friendly," by minimizing the frequency (e.g., once daily) or route of dosing (e.g., oral), or to improve the taste or odor if given orally, or to minimize pain if given parenterally.

In some embodiments, the prodrugs are chemically more stable than the active drug, thereby improving formulation and delivery of the parent drug, compared to the drug alone.

Prodrugs for carboxylic acid analogs of the invention may include a variety of esters. In an exemplary embodiment, the pharmaceutical compositions of the invention include a carboxylic acid ester. In an exemplary embodiment, the prodrug is suitable for treatment/prevention of those diseases and conditions that require the drug molecule to cross the blood brain barrier. In an exemplary embodiment, the prodrug enters the brain, where it is converted into the active form of the drug molecule. In one embodiment, a prodrug is used to enable an active drug molecule to reach the inside of the eye after topical application of the prodrug to the eye. Additionally, a prodrug can be converted to its parent compound by chemical or biochemical methods in an ex vivo environment. For example, a prodrug can be slowly converted to its parent compound when placed in a transdermal patch reservoir with a suitable enzyme or chemical reagent.

"Antibiotic", as used herein, is a compound which can kill or inhibit the growth of bacteria. The term antibiotic is broad enough to encompass acids, bases, salt forms (such as pharmaceutically acceptable salts), prodrugs, solvates and hydrates of the antibiotic compound.

"Antiprotozoal" or "antiprotozoa", as used herein, is a compound which can kill or inhibit the growth of protozoa. The term antiprotozoal or antiprotozoa is broad enough to encompass acids, bases, salt forms (such as pharmaceutically acceptable salts), prodrugs, solvates and hydrates of the antiprotozoal or antiprotozoa compound.

The term "microbial infection" or "infection by a microorganism" refers to any infection of a host by an infectious agent including, but not limited to, viruses, bacteria, mycobacteria, fungus and parasites (see, e.g., Harrison's Principles of Internal Medicine, pp. 93-98 (Wilson et al., eds., 12th ed. 1991); Williams et al., *J. of Medicinal Chem.* 42:1481-1485 (1999), herein each incorporated by reference in their entirety).

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of an enzyme, such as a beta-lactamase or a leucyl t-RNA synthetase.

Boron is able to form additional covalent or dative bonds with oxygen, sulfur or nitrogen under some circumstances in this invention.

Embodiments of the invention also encompass compounds that are poly- or multi-valent species, including, for example, species such as dimers, trimers, tetramers and higher homologs of the compounds of use in the invention or reactive analogues thereof.

"Salt counterion", as used herein, refers to positively charged ions that associate with a compound of the invention when the boron is fully negatively or partially negatively charged. Examples of salt counterions include $H^+$, $H_3O^+$, ammonium, potassium, calcium, magnesium, organic amino (such as choline or diethylamine or amino acids such as d-arginine, 1-arginine, d-lysine, 1-lysine), and sodium.

The compounds comprising a boron bonded to a carbon and three heteroatoms (such as three oxygens described in this section) can optionally contain a fully negatively charged boron or partially negatively charged boron. Due to the negative charge, a positively charged counterion may associate with this compound, thus forming a salt. Examples of positively charged counterions include $H^+$, $H_3O^+$, ammonium, potassium, calcium, magnesium, organic amino (such as choline or diethylamine or amino acids such as d-arginine, 1-arginine, d-lysine, 1-lysine), and sodium. These salts of the compounds are implicitly contained in descriptions of these compounds.

II. Introduction

The invention provides novel boron compounds. The novel compounds, as well as pharmaceutical compositions containing such compounds or combinations of these compounds with at least one additional therapeutically effective agent, can be used for, among other things, treating protozoal infections.

III. The Compounds

III. a) Cyclic Boronic Esters

In one aspect, the invention provides a compound of the invention. In an exemplary embodiment, the invention is a compound described herein. In an exemplary embodiment, the invention is a compound according to a formula described herein.

In another aspect, the invention provides a compound having a structure according to the following formula:

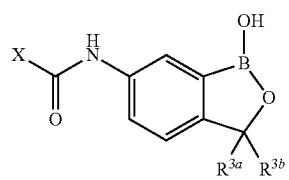

wherein X is selected from the group consisting of substituted phenyl, substituted or unsubstituted heteroaryl and unsubstituted cycloalkyl; $R^{3a}$ is selected from the group consisting of H, unsubstituted $C_1$ or $C_2$ or $C_3$ or $C_4$ or $C_5$ or $C_6$ alkyl, and $C_3$ or $C_4$ or $C_5$ or $C_6$ unsubstituted cycloalkyl; $R^{3b}$ is selected from the group consisting of H, unsubstituted $C_1$ or $C_2$ or $C_3$ or $C_4$ or $C_5$ or $C_6$ alkyl and $C_3$ or $C_4$ or $C_5$ or $C_6$ unsubstituted cycloalkyl; with the proviso that $R^{3a}$ and $R^{3b}$, along with the atom to which they are attached, are optionally joined to form a 3 or 4 or 5 or 6 membered ring with the proviso that $R^{3a}$ and $R^{3b}$ cannot both be H, or a salt thereof.

In an exemplary embodiment, the compound having a structure according to the following formula:

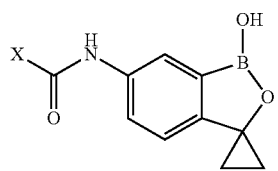

wherein X is as described herein, or a salt thereof. In an exemplary embodiment, the compound having a structure according to the following formula:

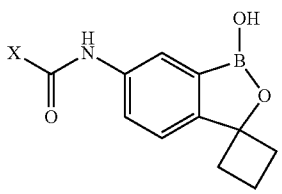

wherein X is as described herein, or a salt thereof. In an exemplary embodiment, the compound having a structure according to the following formula:

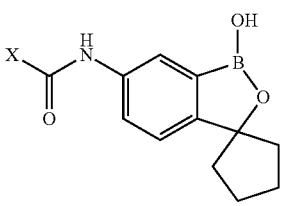

wherein X is as described herein, or a salt thereof.

In an exemplary embodiment, $R^{3a}$ is methyl. In an exemplary embodiment, $R^{3a}$ is ethyl. In an exemplary embodiment, $R^{3a}$ is unsubstituted $C_3$ alkyl. In an exemplary embodiment, $R^{3a}$ is unsubstituted $C_4$ alkyl. In an exemplary embodiment, $R^{3a}$ is unsubstituted $C_5$ alkyl. In an exemplary embodiment, $R^{3a}$ is unsubstituted $C_6$ alkyl.

In an exemplary embodiment, $R^{3b}$ is methyl. In an exemplary embodiment, $R^{3b}$ is ethyl. In an exemplary embodiment, $R^{3b}$ is unsubstituted $C_3$ alkyl. In an exemplary embodiment, $R^{3b}$ is unsubstituted $C_4$ alkyl. In an exemplary embodiment, $R^{3b}$ is unsubstituted $C_5$ alkyl. In an exemplary embodiment, $R^{3b}$ is unsubstituted $C_6$ alkyl.

In an exemplary embodiment, $R^{3a}$ is methyl and $R^{3b}$ is H. In an exemplary embodiment, $R^{3a}$ is ethyl and $R^{3b}$ is H. In an exemplary embodiment, $R^{3a}$ is unsubstituted $C_3$ alkyl and $R^{3b}$ is H. In an exemplary embodiment, $R^{3a}$ is unsubstituted $C_4$ alkyl and $R^{3b}$ is H. In an exemplary embodiment, $R^{3a}$ is unsubstituted $C_5$ alkyl and $R^{3b}$ is H. In an exemplary embodiment, $R^{3a}$ is unsubstituted $C_6$ alkyl and $R^{3b}$ is H.

In an exemplary embodiment, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, $R^{3a}$ is methyl and $R^{3b}$ is methyl. In an exemplary embodiment, $R^{3a}$ is methyl and $R^{3b}$ is ethyl. In an exemplary embodiment, $R^{3a}$ is methyl and $R^{3b}$ is unsubstituted $C_3$ alkyl. In an exemplary embodiment, $R^{3a}$ is methyl and $R^{3b}$ is unsubstituted $C_4$ alkyl. In an exemplary embodiment, $R^{3a}$ is methyl and $R^{3b}$ is unsubstituted $C_5$ alkyl. In an exemplary embodiment, $R^{3a}$ is methyl and $R^{3b}$ is unsubstituted $C_6$ alkyl.

In an exemplary embodiment, the compound of the invention has a structure according to the following formula:

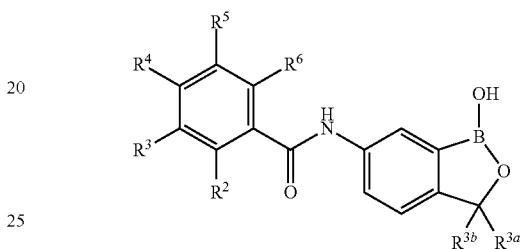

wherein $R^{3a}$ and $R^{3b}$ are as described herein, with the proviso that $R^{3a}$ and $R^{3b}$ cannot both be H, and $R^2$, $R^3$, $R^4$, $R^5$ and $R^6$ are according to the entries in the following table, or a salt thereof.

| $R^2$ | $R^3$ | $R^4$ | $R^5$ | $R^6$ |
|---|---|---|---|---|
| H | H | H | H | H |
| F | H | H | H | H |
| H | F | H | H | H |
| H | H | F | H | H |
| H | H | H | F | H |
| H | H | H | H | F |
| Cl | H | H | H | H |
| H | Cl | H | H | H |
| H | H | Cl | H | H |
| H | H | H | Cl | H |
| H | H | H | H | Cl |
| Br | H | H | H | H |
| H | Br | H | H | H |
| H | H | Br | H | H |
| H | H | H | Br | H |
| H | H | H | H | Br |
| I | H | H | H | H |
| H | I | H | H | H |
| H | H | I | H | H |
| H | H | H | I | H |
| H | H | H | H | I |
| CN | H | H | H | H |
| H | CN | H | H | H |
| H | H | CN | H | H |
| H | H | H | CN | H |
| H | H | H | H | CN |
| $NO_2$ | H | H | H | H |
| H | $NO_2$ | H | H | H |
| H | H | $NO_2$ | H | H |
| H | H | H | $NO_2$ | H |
| H | H | H | H | $NO_2$ |
| $C_6H_5$ | H | H | H | H |
| H | $C_6H_5$ | H | H | H |
| H | H | $C_6H_5$ | H | H |
| H | H | H | $C_6H_5$ | H |
| H | H | H | H | $C_6H_5$ |

In an exemplary embodiment, for any of the entries in the above table, $R^{3a}$ and $R^{3b}$, together with the atom to which they are attached, are joined to form cyclopropyl or cyclobutyl or cyclopentyl. In an exemplary embodiment, for any of the entries in the above table, $R^{3a}$ is unsubstituted alkyl and $R^{3b}$ is unsubstituted alkyl. In an exemplary embodiment, for any of the entries in the above table, $R^{3a}$ is methyl and $R^{3b}$ is methyl.

In an exemplary embodiment, the compound of the invention has a structure according to the following formula:

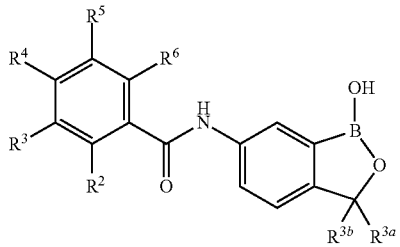

wherein $R^{3a}$ and $R^{3b}$ are as described herein, with the proviso that $R^{3a}$ and $R^{3b}$ cannot both be H, and $R^2$, $R^3$, $R^4$, $R^5$ and $R^6$ are according to the entries in the following table, or a salt thereof

| $R^2$ | $R^3$ | $R^4$ | $R^5$ | $R^6$ |
|---|---|---|---|---|
| $Y^1$ | H | H | H | H |
| H | $Y^1$ | H | H | H |
| H | H | $Y^1$ | H | H |
| H | H | H | $Y^1$ | H |
| H | H | H | H | $Y^1$ | wherein $Y^1$ is $C_1$ or $C_2$ or $C_3$ or $C_4$ or $C_5$ or $C_6$ unsubstituted alkyl. In an exemplary embodiment, $Y^1$ is methyl. In an exemplary embodiment, $Y^1$ is ethyl. In an exemplary embodiment, $Y^1$ is unsubstituted $C_3$ alkyl. In an exemplary embodiment, $Y^1$ is isopropyl. In an exemplary embodiment, $Y^1$ is unsubstituted $C_4$ alkyl. In an exemplary embodiment, $Y^1$ is n-butyl. In an exemplary embodiment, $Y^1$ is t-butyl. In an exemplary embodiment, $Y^1$ is unsubstituted $C_5$ alkyl. In an exemplary embodiment, $Y^1$ is unsubstituted $C_6$ alkyl. In an exemplary embodiment, for any of the entries in the above table, $R^{3a}$ and $R^{3b}$, together with the atom to which they are attached, are joined to form cyclopropyl or cyclobutyl or cyclopentyl. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure according to the following formula:

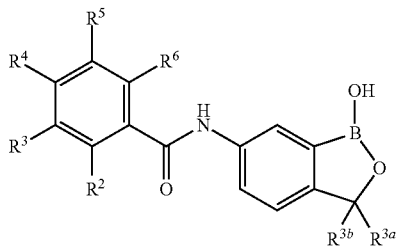

wherein $R^{3a}$ and $R^{3b}$ are as described herein, with the proviso that $R^{3a}$ and $R^{3b}$ cannot both be H, and $R^2$, $R^3$, $R^4$, $R^5$ and $R^6$ are according to the entries in the following table, or a salt thereof

| $R^2$ | $R^3$ | $R^4$ | $R^5$ | $R^6$ |
|---|---|---|---|---|
| $Y^2$ | H | H | H | H |
| H | $Y^2$ | H | H | H |
| H | H | $Y^2$ | H | H |
| H | H | H | $Y^2$ | H |
| H | H | H | H | $Y^2$ | wherein $Y^2$ is unsubstituted alkoxy. In an exemplary embodiment, $Y^2$ is unsubstituted $C_1$ alkoxy. In an exemplary embodiment, $Y^2$ is unsubstituted $C_2$ alkoxy. In an exemplary embodiment, $Y^2$ is unsubstituted $C_3$ alkoxy. In an exemplary embodiment, $Y^2$ is n-propoxy. In an exemplary embodiment, $Y^2$ is isopropoxy. In an exemplary embodiment, $Y^2$ is unsubstituted $C_4$ alkoxy. In an exemplary embodiment, $Y^2$ is unsubstituted $C_5$ alkoxy. In an exemplary embodiment, $Y^2$ is unsubstituted $C_6$ alkoxy. In an exemplary embodiment, for any of the entries in the above table, $R^{3a}$ and $R^{3b}$, together with the atom to which they are attached, are joined to form cyclopropyl or cyclobutyl or cyclopentyl. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure according to the following formula:

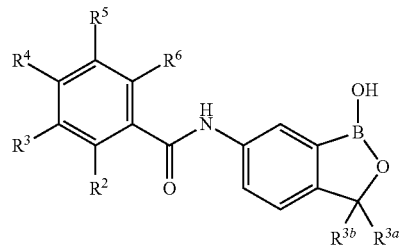

wherein $R^{3a}$ and $R^{3b}$ are as described herein, with the proviso that $R^{3a}$ and $R^{3b}$ cannot both be H, and $R^2$, $R^3$, $R^4$, $R^5$ and $R^6$ are according to the entries in the following table, or a salt thereof

| $R^2$ | $R^3$ | $R^4$ | $R^5$ | $R^6$ |
|---|---|---|---|---|
| $Y^3$ | H | H | H | H |
| H | $Y^3$ | H | H | H |
| H | H | $Y^3$ | H | H |
| H | H | H | $Y^3$ | H |
| H | H | H | H | $Y^3$ | wherein $Y^3$ is halosubstituted alkyl. In an exemplary embodiment, $Y^3$ is halosubstituted $C_1$ alkyl. In an exemplary embodiment, $Y^3$ is halosubstituted $C_2$ alkyl. In an exemplary embodiment, $Y^3$ is halosubstituted $C_3$ alkyl. In an exemplary embodiment, $Y^3$ is halosubstituted $C_4$ alkyl. In an exemplary embodiment, $Y^3$ is halosubstituted $C_5$ alkyl. In an exemplary embodiment, $Y^3$ is halosubstituted $C_6$ alkyl. In an exemplary embodiment, $Y^3$ is fluoro-substituted $C_1$ or $C_2$ or $C_3$ or $C_4$ or $C_5$ or $C_6$ alkyl. In an exemplary embodiment, $Y^3$ is alkyl substituted with one or two or three halogens. In an exemplary embodiment, $Y^3$ is trifluoro-substituted $C_1$ or $C_2$ or $C_3$ or $C_4$ or $C_5$ or $C_6$ alkyl. In an exemplary embodiment, $Y^3$ is trifluoromethyl. In an exemplary embodiment, for any of the entries in the above table, $R^{3a}$ and $R^{3b}$, together with the atom to which they are attached, are joined to form cyclopropyl or cyclobutyl or cyclopentyl. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure according to the following formula:

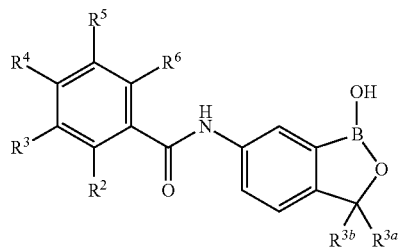

wherein $R^{3a}$ and $R^{3b}$ are as described herein, with the proviso that $R^{3a}$ and $R^{3b}$ cannot both be H, and $R^2$, $R^3$, $R^4$, $R^5$ and $R^6$ are according to the entries in the following table, or a salt thereof

| $R^2$ | $R^3$ | $R^4$ | $R^5$ | $R^6$ |
| --- | --- | --- | --- | --- |
| $Y^4$ | H | H | H | H |
| H | $Y^4$ | H | H | H |
| H | H | $Y^4$ | H | H |
| H | H | H | $Y^4$ | H |
| H | H | H | H | $Y^4$ | wherein $Y^4$ is halosubstituted alkoxy. In an exemplary embodiment, $Y^4$ is halosubstituted $C_1$ alkoxy. In an exemplary embodiment, $Y^4$ is halosubstituted $C_2$ alkoxy. In an exemplary embodiment, $Y^4$ is halosubstituted $C_3$ alkoxy. In an exemplary embodiment, $Y^4$ is halosubstituted $C_4$ alkoxy. In an exemplary embodiment, $Y^4$ is halosubstituted $C_5$ alkoxy. In an exemplary embodiment, $Y^4$ is halosubstituted $C_6$ alkoxy. In an exemplary embodiment, $Y^4$ is fluoro-substituted $C_1$ or $C_2$ or $C_3$ or $C_4$ or $C_5$ or $C_6$ alkoxy. In an exemplary embodiment, $Y^4$ is alkoxy substituted with one or two or three halogens. In an exemplary embodiment, $Y^4$ is trifluoro-substituted $C_1$ or $C_2$ or $C_3$ or $C_4$ or $C_5$ or $C_6$ alkoxy. In an exemplary embodiment, $Y^4$ is trifluoromethoxy. In an exemplary embodiment, for any of the entries in the above table, $R^{3a}$ and $R^{3b}$, together with the atom to which they are attached, are joined to form cyclopropyl or cyclobutyl or cyclopentyl. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure according to the following formula:

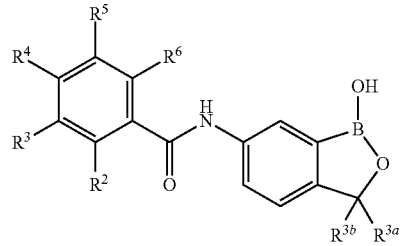

wherein $R^{3a}$ and $R^{3b}$ are as described herein, with the proviso that $R^{3a}$ and $R^{3b}$ cannot both be H, and $R^2$, $R^3$, $R^4$, $R^5$ and $R^6$ are according to the entries in the following table, or a salt thereof

| $R^2$ | $R^3$ | $R^4$ | $R^5$ | $R^6$ |
| --- | --- | --- | --- | --- |
| $Y^5$ | H | H | H | H |
| H | $Y^5$ | H | H | H |
| H | H | $Y^5$ | H | H |
| H | H | H | $Y^5$ | H |
| H | H | H | H | $Y^5$ | wherein $Y^5$ is halosubstituted alkylthio. In an exemplary embodiment, $Y^5$ is halosubstituted $C_1$ alkylthio. In an exemplary embodiment, $Y^5$ is halosubstituted $C_2$ alkylthio. In an exemplary embodiment, $Y^5$ is halosubstituted $C_3$ alkylthio. In an exemplary embodiment, $Y^5$ is halosubstituted $C_4$ alkylthio. In an exemplary embodiment, $Y^5$ is halosubstituted $C_5$ alkylthio. In an exemplary embodiment, $Y^5$ is halosubstituted $C_6$ alkylthio. In an exemplary embodiment, $Y^5$ is fluoro-substituted $C_1$ or $C_2$ or $C_3$ or $C_4$ or $C_5$ or $C_6$ alkylthio. In an exemplary embodiment, $Y^5$ is alkylthio substituted with one or two or three halogens. In an exemplary embodiment, $Y^5$ is trifluoro-substituted $C_1$ or $C_2$ or $C_3$ or $C_4$ or $C_5$ or $C_6$ alkylthio. In an exemplary embodiment, $Y^5$ is trifluoromethylthio. In an exemplary embodiment, for any of the entries in the above table, $R^{3a}$ and $R^{3b}$, together with the atom to which they are attached, are joined to form cyclopropyl or cyclobutyl or cyclopentyl. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure according to the following formula:

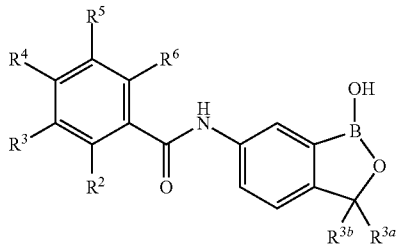

wherein $R^{3a}$ and $R^{3b}$ are as described herein, with the proviso that $R^{3a}$ and $R^{3b}$ cannot both be H, and $R^2$, $R^3$, $R^4$, $R^5$ and $R^6$ are according to the entries in the following table, or a salt thereof

| $R^2$ | $R^3$ | $R^4$ | $R^5$ | $R^6$ |
|---|---|---|---|---|
| $NR^8R^9$ | H | H | H | H |
| H | $NR^8R^9$ | H | H | H |
| H | H | $NR^8R^9$ | H | H |
| H | H | H | $NR^8R^9$ | H |
| H | H | H | H | $NR^8R^9$ | wherein $R^8$ is H or $C_1$ or $C_2$ or $C_3$ or $C_4$ or $C_5$ or $C_6$ unsubstituted alkyl and $R^9$ is H or $C_1$ or $C_2$ or $C_3$ or $C_4$ or $C_5$ or $C_6$ unsubstituted alkyl or $C(O)R^{10}$, wherein $R^{10}$ is $C_1$ or $C_2$ or $C_3$ or $C_4$ or $C_5$ or $C_6$ unsubstituted alkyl. In an exemplary embodiment, $R^8$ is $C_1$ or $C_2$ or $C_3$ or $C_4$ or $C_5$ or $C_6$ unsubstituted alkyl and $R^9$ is $C_1$ or $C_2$ or $C_3$ or $C_4$ or $C_5$ or $C_6$ unsubstituted alkyl. In an exemplary embodiment, $R^8$ is methyl and $R^9$ is $C_1$ or $C_2$ or $C_3$ or $C_4$ or $C_5$ or $C_6$ unsubstituted alkyl. In an exemplary embodiment, $R^8$ is methyl and $R^9$ is methyl. In an exemplary embodiment, $R^8$ is H. In an exemplary embodiment, $R^9$ is H. In an exemplary embodiment, $R^8$ is H and $R^9$ is H. In an exemplary embodiment, $R^8$ is H and $R^9$ is —$C(O)R^{10}$. In an exemplary embodiment, $R^8$ is H and $R^9$ is —$C(O)CH_3$. In an exemplary embodiment, for any of the entries in the above table, $R^{3a}$ and $R^{3b}$, together with the atom to which they are attached, are joined to form cyclopropyl or cyclobutyl or cyclopentyl. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure according to the following formula:

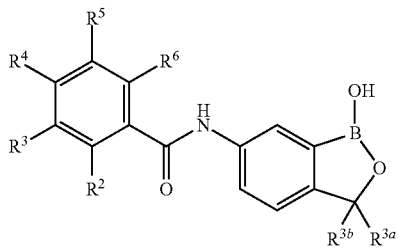

wherein $R^{3a}$ and $R^{3b}$ are as described herein, with the proviso that $R^{3a}$ and $R^{3b}$ cannot both be H, and $R^2$, $R^3$, $R^4$, $R^5$ and $R^6$ are according to the entries in the following table, or a salt thereof

| $R^2$ | $R^3$ | $R^4$ | $R^5$ | $R^6$ |
|---|---|---|---|---|
| $COOR^8$ | H | H | H | H |
| H | $COOR^8$ | H | H | H |
| H | H | $COOR^8$ | H | H |
| H | H | H | $COOR^8$ | H |
| H | H | H | H | $COOR^8$ | wherein $R^8$ is H or $C_1$ or $C_2$ or $C_3$ or $C_4$ or $C_5$ or $C_6$ unsubstituted alkyl. In an exemplary embodiment, $R^8$ is methyl. In an exemplary embodiment, $R^8$ is methyl and $R^9$ is methyl. In an exemplary embodiment, $R^8$ is H. In an exemplary embodiment, for any of the entries in the above table, $R^{3a}$ and $R^{3b}$, together with the atom to which they are attached, are joined to form cyclopropyl or cyclobutyl or cyclopentyl. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure according to the following formula:

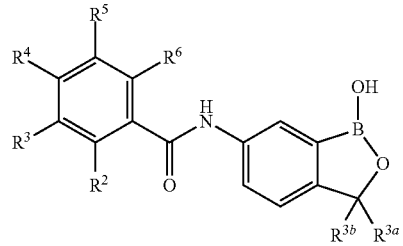

wherein $R^{3a}$ and $R^{3b}$ are as described herein, with the proviso that $R^{3a}$ and $R^{3b}$ cannot both be H, and $R^2$, $R^3$, $R^4$, $R^5$ and $R^6$ are according to the entries in the following table, or a salt thereof

| $R^2$ | $R^3$ | $R^4$ | $R^5$ | $R^6$ |
|---|---|---|---|---|
| —$SO_2R^7$ | H | H | H | H |
| H | —$SO_2R^7$ | H | H | H |
| H | H | —$SO_2R^7$ | H | H |
| H | H | H | —$SO_2R^7$ | H |
| H | H | H | H | —$SO_2R^7$ | wherein $R^7$ is $C_1$ or $C_2$ or $C_3$ or $C_4$ or $C_5$ or $C_6$ unsubstituted alkyl. In an exemplary embodiment, $R^7$ is methyl. In an exemplary embodiment, $R^7$ is ethyl. In an exemplary embodiment, $R^7$ is unsubstituted $C_3$ alkyl. In an exemplary embodiment, $R^7$ is unsubstituted $C_4$ alkyl. In an exemplary embodiment, $R^7$ is unsubstituted $C_5$ alkyl. In an exemplary embodiment, $R^7$ is unsubstituted $C_6$ alkyl. In an exemplary embodiment, for any of the entries in the above table, $R^{3a}$ and $R^{3b}$, together with the atom to which they are attached, are joined to form cyclopropyl or cyclobutyl or cyclopentyl. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure according to the following formula:

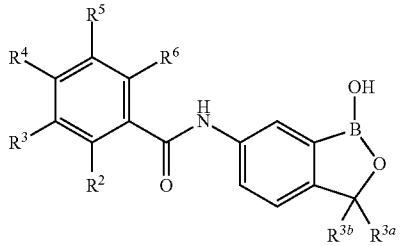

wherein $R^{3a}$ and $R^{3b}$ are as described herein, with the proviso that $R^{3a}$ and $R^{3b}$ cannot both be H, and $R^2$, $R^3$, $R^4$, $R^5$ and $R^6$ are according to the entries in the following table, or a salt thereof

| $R^2$ | $R^3$ | $R^4$ | $R^5$ | $R^6$ |
|---|---|---|---|---|
| —$SO_2N(R^7)(R^8)$ | H | H | H | H |
| H | —$SO_2N(R^7)(R^8)$ | H | H | H |
| H | H | —$SO_2N(R^7)(R^8)$ | H | H |
| H | H | H | —$SO_2N(R^8)(R^8)$ | H |
| H | H | H | H | —$SO_2N(R^7)(R^8)$ | wherein $R^7$ is H or $C_1$ or $C_2$ or $C_3$ or $C_4$ or $C_5$ or $C_6$ unsubstituted alkyl and $R^8$ is H or $C_1$ or $C_2$ or $C_3$ or $C_4$ or $C_5$ or $C_6$ unsubstituted alkyl. In an exemplary embodiment, $R^7$ is $C_1$ or $C_2$ or $C_3$ or $C_4$ or $C_5$ or $C_6$ unsubstituted alkyl and $R^8$ is $C_1$ or $C_2$ or $C_3$ or $C_4$ or $C_5$ or $C_6$ unsubstituted alkyl. In an exemplary embodiment, $R^7$ is methyl and $R^8$ is $C_1$ or $C_2$ or $C_3$ or $C_4$ or $C_5$ or $C_6$ unsubstituted alkyl. In an exemplary embodiment, $R^7$ is methyl and $R^8$ is methyl. In an exemplary embodiment, $R^7$ is H. In an exemplary embodiment, $R^8$ is H. In an exemplary embodiment, $R^7$ is H and $R^8$ is H. In an exemplary embodiment, for any of the entries in the above table, $R^{3a}$ and $R^{3b}$, together with the atom to which they are attached, are joined to form cyclopropyl or cyclobutyl or cyclopentyl. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure according to the following formula:

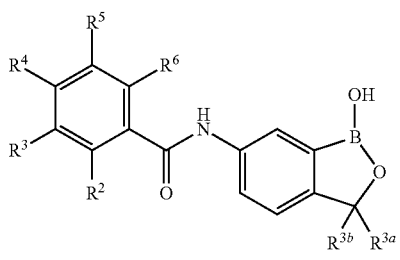

wherein $R^{3a}$ and $R^{3b}$ are as described herein, with the proviso that $R^{3a}$ and $R^{3b}$ cannot both be H, and $R^2$, $R^3$, $R^4$, $R^5$ and $R^6$ are according to the entries in the following table, or a salt thereof.

| $R^2$ | $R^3$ | $R^4$ | $R^5$ | $R^6$ |
|---|---|---|---|---|
| —$Y^6$ | H | H | H | H |
| H | —$Y^6$ | H | H | H |
| H | H | —$Y^6$ | H | H |
| H | H | H | —$Y^6$ | H |
| H | H | H | H | —$Y^6$ | wherein $Y^6$ is unsubstituted heteroaryl or unsubstituted aryl or unsubstituted cycloalkyl. In an exemplary embodiment, $Y^6$ is unsubstituted 2-thiazolyl or unsubstituted 3-thiazolyl. In an exemplary embodiment, $Y^6$ is unsubstituted morpholinyl. In an exemplary embodiment, $Y^6$ is unsubstituted phenyl. In an exemplary embodiment, for any of the entries in the above table, $R^{3a}$ and $R^{3b}$, together with the atom to which they are attached, are joined to form cyclopropyl or cyclobutyl or cyclopentyl. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound has a structure according to the following formula:

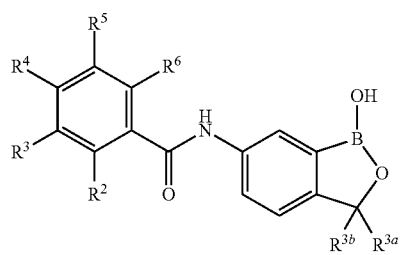

(II)

wherein $R^{3a}$ is as described herein, $R^{3b}$ is as described herein, $R^2$, $R^3$, $R^4$, $R^5$ and $R^6$ are according to the entries in the following table, or a salt thereof.

| $R^2$ | $R^3$ | $R^4$ | $R^5$ | $R^6$ |
|---|---|---|---|---|
| $CF_3$ | F | H | H | H |
| $CF_3$ | H | F | H | H |
| $CF_3$ | H | H | F | H |
| $CF_3$ | H | H | H | F |
| F | $CF_3$ | H | H | H |

-continued

| R² | R³ | R⁴ | R⁵ | R⁶ |
|---|---|---|---|---|
| H | CF₃ | F | H | H |
| H | CF₃ | H | F | H |
| H | CF₃ | H | H | F |
| F | H | CF₃ | H | H |
| H | F | CF₃ | H | H |
| H | H | CF₃ | F | H |
| H | H | CF₃ | H | F |
| F | H | H | CF₃ | H |
| H | F | H | CF₃ | H |
| H | H | F | CF₃ | H |
| H | H | H | CF₃ | F |
| F | H | H | H | CF₃ |
| H | F | H | H | CF₃ |
| H | H | F | H | CF₃ |
| H | H | H | F | CF₃ |
| CF₃ | Cl | H | H | H |
| CF₃ | H | Cl | H | H |
| CF₃ | H | H | Cl | H |
| CF₃ | H | H | H | Cl |
| Cl | CF₃ | H | H | H |
| H | CF₃ | Cl | H | H |
| H | CF₃ | H | Cl | H |
| H | CF₃ | H | H | Cl |
| Cl | H | CF₃ | H | H |
| H | Cl | CF₃ | H | H |
| H | H | CF₃ | Cl | H |
| H | H | CF₃ | H | Cl |
| Cl | H | H | CF₃ | H |
| H | Cl | H | CF₃ | H |
| H | H | Cl | CF₃ | H |
| H | H | H | CF₃ | Cl |
| Cl | H | H | H | CF₃ |
| H | Cl | H | H | CF₃ |
| H | H | Cl | H | CF₃ |
| H | H | H | Cl | CF₃ |
| CH₃ | F | H | H | H |
| CH₃ | H | F | H | H |
| CH₃ | H | H | F | H |
| CH₃ | H | H | H | F |
| F | CH₃ | H | H | H |
| H | CH₃ | F | H | H |
| H | CH₃ | H | F | H |
| H | CH₃ | H | H | F |
| F | H | CH₃ | H | H |
| H | F | CH₃ | H | H |
| H | H | CH₃ | F | H |
| H | H | CH₃ | H | F |
| F | H | H | CH₃ | H |
| H | F | H | CH₃ | H |
| H | H | F | CH₃ | H |
| H | H | H | CH₃ | F |
| F | H | H | H | CH₃ |
| H | F | H | H | CH₃ |
| H | H | F | H | CH₃ |
| H | H | H | F | CH₃ |
| CH₃ | Cl | H | H | H |
| CH₃ | H | Cl | H | H |
| CH₃ | H | H | Cl | H |
| CH₃ | H | H | H | Cl |
| Cl | CH₃ | H | H | H |
| H | CH₃ | Cl | H | H |
| H | CH₃ | H | Cl | H |
| H | CH₃ | H | H | Cl |
| Cl | H | CH₃ | H | H |
| H | Cl | CH₃ | H | H |
| H | H | CH₃ | Cl | H |
| H | H | CH₃ | H | Cl |
| Cl | H | H | CH₃ | H |
| H | Cl | H | CH₃ | H |
| H | H | Cl | CH₃ | H |
| H | H | H | CH₃ | Cl |
| Cl | H | H | H | CH₃ |
| H | Cl | H | H | CH₃ |
| H | H | Cl | H | CH₃ |
| H | H | H | Cl | CH₃ |
| CH₃ | Br | H | H | H |
| CH₃ | H | Br | H | H |

-continued

| R² | R³ | R⁴ | R⁵ | R⁶ |
|---|---|---|---|---|
| CH₃ | H | H | Br | H |
| CH₃ | H | H | H | Br |
| Br | CH₃ | H | H | H |
| H | CH₃ | Br | H | H |
| H | CH₃ | H | Br | H |
| H | CH₃ | H | H | Br |
| Br | H | CH₃ | H | H |
| H | Br | CH₃ | H | H |
| H | H | CH₃ | Br | H |
| H | H | CH₃ | H | Br |
| Br | H | H | CH₃ | H |
| H | Br | H | CH₃ | H |
| H | H | Br | CH₃ | H |
| H | H | H | CH₃ | Br |
| Br | H | H | H | CH₃ |
| H | Br | H | H | CH₃ |
| H | H | Br | H | CH₃ |
| H | H | H | Br | CH₃ |
| CF₃ | CF₃ | H | H | H |
| CF₃ | H | CF₃ | H | H |
| CF₃ | H | H | CF₃ | H |
| CF₃ | H | H | H | CF₃ |
| H | CF₃ | CF₃ | H | H |
| H | CF₃ | H | CF₃ | H |
| H | CF₃ | H | H | CF₃ |
| H | H | CF₃ | CF₃ | H |
| H | H | CF₃ | H | CF₃ |
| H | H | H | CF₃ | CF₃ |
| F | F | H | H | H |
| F | H | F | H | H |
| F | H | H | F | H |
| F | H | H | H | F |
| H | F | F | H | H |
| H | F | H | F | H |
| H | F | H | H | F |
| H | H | F | F | H |
| H | H | F | H | F |
| H | H | H | F | F |
| Cl | Cl | H | H | H |
| Cl | H | Cl | H | H |
| Cl | H | H | Cl | H |
| Cl | H | H | H | Cl |
| H | Cl | Cl | H | H |
| H | Cl | H | Cl | H |
| H | Cl | H | H | Cl |
| H | H | Cl | Cl | H |
| H | H | Cl | H | Cl |
| H | H | H | Cl | Cl |
| F | Cl | H | H | H |
| Cl | F | H | H | H |
| F | H | Cl | H | H |
| Cl | H | F | H | H |
| F | H | H | Cl | H |
| Cl | H | H | F | H |
| F | H | H | H | Cl |
| Cl | H | H | H | F |
| H | F | Cl | H | H |
| H | Cl | F | H | H |
| H | F | H | Cl | H |
| H | Cl | H | F | H |
| H | F | H | H | Cl |
| H | Cl | H | H | F |
| H | H | F | Cl | H |
| H | H | Cl | F | H |
| H | H | F | H | Cl |
| H | H | Cl | H | F |
| H | H | H | F | Cl |
| H | H | H | Cl | F |
| Br | F | H | H | H |
| Br | H | F | H | H |
| Br | H | H | F | H |
| Br | H | H | H | F |
| H | Br | F | H | H |
| H | Br | H | F | H |
| H | Br | H | H | F |
| H | H | Br | F | H |
| H | H | Br | H | F |

| $R^2$ | $R^3$ | $R^4$ | $R^5$ | $R^6$ |
|---|---|---|---|---|
| H | H | H | Br | F |
| F | Br | H | H | H |
| F | H | Br | H | H |
| F | H | H | Br | H |
| F | H | H | H | Br |
| H | F | Br | H | H |
| H | F | H | Br | H |
| H | F | H | H | Br |
| H | H | F | Br | H |
| H | H | F | H | Br |
| H | H | H | F | Br |
| Br | Cl | H | H | H |
| Br | H | Cl | H | H |
| Br | H | H | Cl | H |
| Br | H | H | H | Cl |
| H | Br | Cl | H | H |
| H | Br | H | Cl | H |
| H | Br | H | H | Cl |
| H | H | Br | Cl | H |
| H | H | Br | H | Cl |
| H | H | H | Br | Cl |
| Cl | Br | H | H | H |
| Cl | H | Br | H | H |
| Cl | H | H | Br | H |
| Cl | H | H | H | Br |
| H | Cl | Br | H | H |
| H | Cl | H | Br | H |
| H | Cl | H | H | Br |
| H | H | Cl | Br | H |
| H | H | Cl | H | Br |
| H | H | H | Cl | Br |
| I | Cl | H | H | H |
| I | H | Cl | H | H |
| I | H | H | Cl | H |
| I | H | H | H | Cl |
| H | I | Cl | H | H |
| H | I | H | Cl | H |
| H | I | H | H | Cl |
| H | H | I | Cl | H |
| H | H | I | H | Cl |
| H | H | H | I | Cl |
| Cl | I | H | H | H |
| Cl | H | I | H | H |
| Cl | H | H | I | H |
| Cl | H | H | H | I |
| H | Cl | I | H | H |
| H | Cl | H | I | H |
| H | Cl | H | H | I |
| H | H | Cl | I | H |
| H | H | Cl | H | I |
| H | H | H | Cl | I |
| $NO_2$ | $Y^7$ | H | H | H |
| $NO_2$ | H | $Y^7$ | H | H |
| $NO_2$ | H | H | $Y^7$ | H |
| $NO_2$ | H | H | H | $Y^7$ |
| H | $NO_2$ | $Y^7$ | H | H |
| H | $NO_2$ | H | $Y^7$ | H |
| H | $NO_2$ | H | H | $Y^7$ |
| H | H | $NO_2$ | $Y^7$ | H |
| H | H | $NO_2$ | H | $Y^7$ |
| H | H | H | $NO_2$ | $Y^7$ |
| $Y^7$ | $NO_2$ | H | H | H |
| $Y^7$ | H | $NO_2$ | H | H |
| $Y^7$ | H | H | $NO_2$ | H |
| $Y^7$ | H | H | H | $NO_2$ |
| H | $Y^7$ | $NO_2$ | H | H |
| H | $Y^7$ | H | $NO_2$ | H |
| H | $Y^7$ | H | H | $NO_2$ |
| H | H | $Y^7$ | $NO_2$ | H |
| H | H | $Y^7$ | H | $NO_2$ |
| H | H | H | $Y^7$ | $NO_2$ |
| $NO_2$ | Cl | H | H | H |
| $NO_2$ | H | Cl | H | H |
| $NO_2$ | H | H | Cl | H |
| $NO_2$ | H | H | H | Cl |
| H | $NO_2$ | Cl | H | H |
| H | $NO_2$ | H | Cl | H |
| H | $NO_2$ | H | H | Cl |
| H | H | $NO_2$ | Cl | H |
| H | H | $NO_2$ | H | Cl |
| H | H | H | $NO_2$ | Cl |
| Cl | $NO_2$ | H | H | H |
| Cl | H | $NO_2$ | H | H |
| Cl | H | H | $NO_2$ | H |
| Cl | H | H | H | $NO_2$ |
| H | Cl | $NO_2$ | H | H |
| H | Cl | H | $NO_2$ | H |
| H | Cl | H | H | $NO_2$ |
| H | H | Cl | $NO_2$ | H |
| H | H | Cl | H | $NO_2$ |
| H | H | H | Cl | $NO_2$ |
| —$CH_3$ | —$CH_3$ | H | H | H |
| —$CH_3$ | H | —$CH_3$ | H | H |
| —$CH_3$ | H | H | —$CH_3$ | H |
| —$CH_3$ | H | H | H | —$CH_3$ |
| H | —$CH_3$ | —$CH_3$ | H | H |
| H | —$CH_3$ | H | —$CH_3$ | H |
| H | —$CH_3$ | H | H | —$CH_3$ |
| H | H | —$CH_3$ | —$CH_3$ | H |
| H | H | —$CH_3$ | H | —$CH_3$ |
| H | H | H | —$CH_3$ | —$CH_3$ |
| —$Y^3$ | —$CH_3$ | H | H | H |
| —$Y^3$ | H | —$CH_3$ | H | H |
| —$Y^3$ | H | H | —$CH_3$ | H |
| —$Y^3$ | H | H | H | —$CH_3$ |
| H | —$Y^3$ | —$CH_3$ | H | H |
| H | —$Y^3$ | H | —$CH_3$ | H |
| H | —$Y^3$ | H | H | —$CH_3$ |
| H | H | —$Y^3$ | —$CH_3$ | H |
| H | H | —$Y^3$ | H | —$CH_3$ |
| H | H | H | —$Y^3$ | —$CH_3$ |
| —$CH_3$ | —$Y^3$ | H | H | H |
| —$CH_3$ | H | —$Y^3$ | H | H |
| —$CH_3$ | H | H | —$Y^3$ | H |
| —$CH_3$ | H | H | H | —$Y^3$ |
| H | —$CH_3$ | —$Y^3$ | H | H |
| H | —$CH_3$ | H | —$Y^3$ | H |
| H | —$CH_3$ | H | H | —$Y^3$ |
| H | H | —$CH_3$ | —$Y^3$ | H |
| H | H | —$CH_3$ | H | —$Y^3$ |
| H | H | H | —$CH_3$ | —$Y^3$ |
| —$Y^2$ | —$OCH_3$ | H | H | H |
| —$Y^2$ | H | —$OCH_3$ | H | H |
| —$Y^2$ | H | H | —$OCH_3$ | H |
| —$Y^2$ | H | H | H | —$OCH_3$ |
| H | —$Y^2$ | —$OCH_3$ | H | H |
| H | —$Y^2$ | H | —$OCH_3$ | H |
| H | —$Y^2$ | H | H | —$OCH_3$ |
| H | H | —$Y^2$ | —$OCH_3$ | H |
| H | H | —$Y^2$ | H | —$OCH_3$ |
| H | H | H | —$Y^2$ | —$OCH_3$ |
| —$OCH_3$ | —$Y^2$ | H | H | H |
| —$OCH_3$ | H | —$Y^2$ | H | H |
| —$OCH_3$ | H | H | —$Y^2$ | H |
| —$OCH_3$ | H | H | H | —$Y^2$ |
| H | —$OCH_3$ | —$Y^2$ | H | H |
| H | —$OCH_3$ | H | —$Y^2$ | H |
| H | —$OCH_3$ | H | H | —$Y^2$ |
| H | H | —$OCH_3$ | —$Y^2$ | H |
| H | H | —$OCH_3$ | H | —$Y^2$ |
| H | H | H | —$OCH_3$ | —$Y^2$ |
| —$OCH_3$ | —$OCH_3$ | H | H | H |
| —$OCH_3$ | H | —$OCH_3$ | H | H |
| —$OCH_3$ | H | H | —$OCH_3$ | H |
| —$OCH_3$ | H | H | H | —$OCH_3$ |
| H | —$OCH_3$ | —$OCH_3$ | H | H |
| H | —$OCH_3$ | H | —$OCH_3$ | H |
| H | —$OCH_3$ | H | H | —$OCH_3$ |
| H | H | —$OCH_3$ | —$OCH_3$ | H |
| H | H | —$OCH_3$ | H | —$OCH_3$ |
| H | H | H | —$OCH_3$ | —$OCH_3$ |
| —$CH_3$ | —$OCH_3$ | H | H | H |
| —$CH_3$ | H | —$OCH_3$ | H | H |
| —$CH_3$ | H | H | —$OCH_3$ | H |

-continued

| R² | R³ | R⁴ | R⁵ | R⁶ |
|---|---|---|---|---|
| —CH₃ | H | H | H | —OCH₃ |
| H | —CH₃ | —OCH₃ | H | H |
| H | —CH₃ | H | —OCH₃ | H |
| H | —CH₃ | H | H | —OCH₃ |
| H | H | —CH₃ | —OCH₃ | H |
| H | H | —CH₃ | H | —OCH₃ |
| H | H | H | —CH₃ | —OCH₃ |
| —OCH₃ | —CH₃ | H | H | H |
| —OCH₃ | H | —CH₃ | H | H |
| —OCH₃ | H | H | —CH₃ | H |
| —OCH₃ | H | H | H | —CH₃ |
| H | —OCH₃ | —CH₃ | H | H |
| H | —OCH₃ | H | —CH₃ | H |
| H | —OCH₃ | H | H | —CH₃ |
| H | H | —OCH₃ | —CH₃ | H |
| H | H | —OCH₃ | H | —CH₃ |
| H | H | H | —OCH₃ | —CH₃ |
| —Y² | —Y² | H | H | H |
| —Y² | H | —Y² | H | H |
| —Y² | H | H | —Y² | H |
| —Y² | H | H | H | —Y² |
| H | —Y² | —Y² | H | H |
| H | —Y² | H | —Y² | H |
| H | —Y² | H | H | —Y² |
| H | H | —Y² | H | —Y² |
| —Y³ | —Y³ | H | H | H |
| —Y³ | H | —Y³ | H | H |
| —Y³ | H | H | —Y³ | H |
| —Y³ | H | H | H | —Y³ |
| H | —Y³ | —Y³ | H | H |
| H | —Y³ | H | —Y³ | H |
| H | —Y³ | H | H | —Y³ |
| H | H | —Y³ | H | —Y³ |
| —Y² | —Y³ | H | H | H |
| —Y² | H | —Y³ | H | H |
| —Y² | H | H | —Y³ | H |
| —Y² | H | H | H | —Y³ |
| H | —Y² | —Y³ | H | H |
| H | —Y² | H | —Y³ | H |
| H | —Y² | H | H | —Y³ |
| H | H | —Y² | H | —Y³ |
| —Y³ | —Y² | H | H | H |
| —Y³ | H | —Y² | H | H |
| —Y³ | H | H | —Y² | H |
| —Y³ | H | H | H | —Y² |
| H | —Y³ | —Y² | H | H |
| H | —Y³ | H | —Y² | H |
| H | —Y³ | H | H | —Y² |
| H | H | —Y³ | H | —Y² |
| —Y¹ | —Y⁷ | H | H | H |
| —Y¹ | H | —Y⁷ | H | H |
| —Y¹ | H | H | —Y⁷ | H |
| —Y¹ | H | H | H | —Y⁷ |
| H | —Y¹ | —Y⁷ | H | H |
| H | —Y¹ | H | —Y⁷ | H |
| H | —Y¹ | H | H | —Y⁷ |
| H | H | —Y¹ | H | —Y⁷ |
| —Y⁷ | —Y¹ | H | H | H |
| —Y⁷ | H | —Y¹ | H | H |
| —Y⁷ | H | H | —Y¹ | H |
| —Y⁷ | H | H | H | —Y¹ |
| H | —Y⁷ | —Y¹ | H | H |
| H | —Y⁷ | H | —Y¹ | H |
| H | —Y⁷ | H | H | —Y¹ |
| H | H | —Y⁷ | H | —Y¹ |

In an exemplary embodiment, for any of the entries in the above table, $R^{3a}$ and $R^{3b}$, together with the atom to which they are attached, are joined to form cyclopropyl or cyclobutyl or cyclopentyl. In an exemplary embodiment, for any of the entries in the above table, $Y^7$ is F or Cl or Br or I. In an exemplary embodiment, for any of the entries in the above table, $Y^7$ is F. In an exemplary embodiment, for any of the entries in the above table, $Y^7$ is Cl. In an exemplary embodiment, for any of the entries in the above table, $Y^1$ is $C_1$ or $C_2$ or $C_3$ or $C_4$ or $C_5$ or $C_6$ unsubstituted alkyl. In an exemplary embodiment, for any of the entries in the above table, $Y^1$ is $C_2$ or $C_3$ or $C_4$ or $C_5$ or $C_6$ alkenyl. In an exemplary embodiment, $Y^7$ is a halogen and $Y^1$ is $C_2$ or $C_3$ or $C_4$ or $C_5$ alkenyl. In an exemplary embodiment, $Y^7$ is Cl and $Y^1$ is $C_2$ or $C_3$ or $C_4$ or $C_5$ alkenyl. In an exemplary embodiment, $Y^7$ is a halogen and $Y^1$ is $C_2$ or $C_3$ or $C_4$ or $C_5$ alkenyl. In an exemplary embodiment, $Y^7$ is Cl and $Y^1$ is $C_1$ or $C_2$ or $C_3$ or $C_4$ or $C_5$ or $C_6$ unsubstituted alkyl. In an exemplary embodiment, $Y^7$ is Cl and $Y^1$ is $C_3$ or $C_4$ unsubstituted alkyl. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound has a structure according to the following formula:

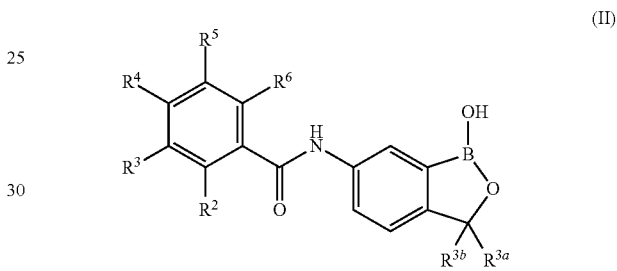

(II)

wherein $R^{3a}$ is as described herein, $R^{3b}$ is as described herein, $R^2$, $R^3$, $R^4$, $R^5$ and $R^6$ are according to the entries in the following table, or a salt thereof.

| R² | R³ | R⁴ | R⁵ | R⁶ |
|---|---|---|---|---|
| Y⁷ | Y⁷ | Y⁷ | H | H |
| Y⁷ | Y⁷ | H | Y⁷ | H |
| Y⁷ | Y⁷ | H | H | Y⁷ |
| Y⁷ | H | Y⁷ | Y⁷ | H |
| Y⁷ | H | Y⁷ | H | Y⁷ |
| Y⁷ | H | H | Y⁷ | Y⁷ | wherein each $Y^7$ are the same or different and are each selected from halogen, $R^{3a}$ is as described herein and $R^{3b}$ is as described herein, or a salt thereof. In an exemplary embodiment, for any of the entries in the above table, each $Y^7$ is as described herein, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, each $Y^7$ is as described herein, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, each $Y^7$ is as described herein, $R^{3a}$ is methyl and $R^{3b}$ is methyl. In an exemplary embodiment, for any of the entries in the above table, each $Y^7$ is chlorine, $R^{3a}$ is methyl and $R^{3b}$ is methyl. In an exemplary embodiment, for any of the entries in the above table, one $Y^7$ is fluorine, one $Y^7$ is fluorine, and one $Y^7$ is chlorine, $R^{3a}$ is methyl and $R^{3b}$ is methyl.

In an exemplary embodiment, the compound has a structure according to the following formula:

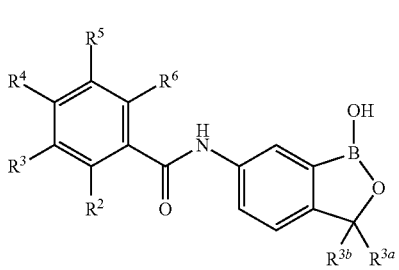

(II)

wherein $R^{3a}$ is as described herein, $R^{3b}$ is as described herein, $R^2$, $R^3$, $R^4$, $R^5$ and $R^6$ are according to the entries in the following table, or a salt thereof.

| $R^2$ | $R^3$ | $R^4$ | $R^5$ | $R^6$ |
|---|---|---|---|---|
| $Y^1$ | $Y^7$ | $Y^7$ | H | H |
| $Y^7$ | $Y^1$ | $Y^7$ | H | H |
| $Y^7$ | $Y^7$ | $Y^1$ | H | H |
| $Y^1$ | $Y^7$ | H | $Y^7$ | H |
| $Y^7$ | $Y^1$ | H | $Y^7$ | H |
| $Y^7$ | $Y^7$ | H | $Y^1$ | H |
| $Y^1$ | $Y^7$ | H | H | $Y^7$ |
| $Y^7$ | $Y^1$ | H | H | $Y^7$ |
| $Y^7$ | $Y^7$ | H | H | $Y^1$ |
| $Y^1$ | H | $Y^7$ | $Y^7$ | H |
| $Y^7$ | H | $Y^1$ | $Y^7$ | H |
| $Y^7$ | H | $Y^7$ | $Y^1$ | H |
| $Y^1$ | H | $Y^7$ | H | $Y^7$ |
| $Y^7$ | H | $Y^1$ | H | $Y^7$ |
| $Y^7$ | H | $Y^7$ | H | $Y^1$ |
| $Y^1$ | H | H | $Y^7$ | $Y^7$ |
| $Y^7$ | H | H | $Y^1$ | $Y^7$ |
| $Y^7$ | H | H | $Y^7$ | $Y^1$ | wherein $Y^1$ is unsubstituted alkyl, each $Y^7$ are the same or different and are each selected from halogen, $R^{3a}$ is as described herein and $R^{3b}$ is as described herein, or a salt thereof. In an exemplary embodiment, for any of the entries in the above table, $Y^1$ is unsubstituted $C_1$ or $C_2$ or $C_3$ or $C_4$ or $C_5$ or $C_6$ alkyl, each $Y^7$ are the same or different and are each selected from halogen, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $Y^1$ is unsubstituted $C_1$ or $C_2$ or $C_3$ alkyl, each $Y^7$ are the same or different and are each selected from halogen, $R^{3a}$ is methyl and $R^{3b}$ is methyl. In an exemplary embodiment, for any of the entries in the above table, $Y^1$ is unsubstituted $C_1$ or $C_2$ or $C_3$ alkyl, one $Y^7$ is F, one $Y^7$ is Cl, $R^{3a}$ is methyl and $R^{3b}$ is methyl. In an exemplary embodiment, for any of the entries in the above table, $Y^1$ is methyl, one $Y^7$ is F, one $Y^7$ is Cl, $R^{3a}$ is methyl and $R^{3b}$ is methyl.

In an exemplary embodiment, the compound of the invention has a structure which is:

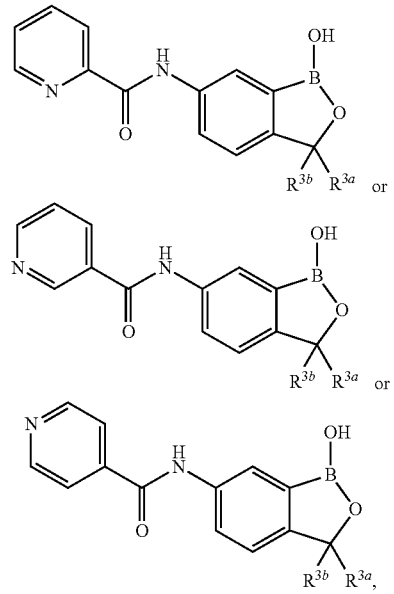

$R^{3a}$ is as described herein and $R^{3b}$ is as described herein, or a salt thereof. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound has a structure according to the following formula:

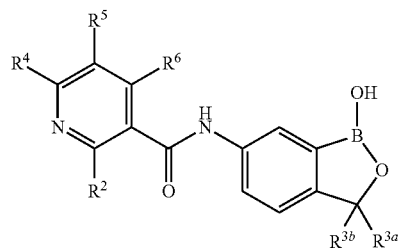

(II)

wherein $R^{3a}$ is as described herein, $R^{3b}$ is as described herein, $R^2$, $R^4$, $R^5$ and $R^6$ are according to the entries in the following table, or a salt thereof

| $R^2$ | $R^4$ | $R^5$ | $R^6$ |
|---|---|---|---|
| $Y^1$ | $Y^7$ | H | H |
| $Y^7$ | $Y^7$ | H | H |
| $Y^7$ | $Y^1$ | H | H |
| $Y^1$ | H | $Y^7$ | H |
| $Y^7$ | H | $Y^1$ | H |
| $Y^7$ | H | $Y^7$ | H |
| $Y^1$ | H | $Y^7$ | H |
| $Y^7$ | H | $Y^7$ | H |

-continued

| $R^2$ | $R^4$ | $R^5$ | $R^6$ |
|---|---|---|---|
| $Y^1$ | H | H | $Y^7$ |
| $Y^7$ | H | H | $Y^1$ |
| $Y^7$ | H | H | $Y^7$ |
| H | $Y^7$ | $Y^1$ | H |
| H | $Y^1$ | $Y^7$ | H |
| H | $Y^7$ | $Y^7$ | H |
| H | H | $Y^1$ | $Y^7$ |
| H | H | $Y^7$ | $Y^1$ |
| H | H | $Y^7$ | $Y^7$ |
| H | $Y^1$ | H | $Y^7$ |
| H | $Y^7$ | H | $Y^1$ |
| H | $Y^7$ | H | $Y^7$ | wherein $Y^1$ is unsubstituted alkyl, each $Y^7$ are the same or different and are each selected from halogen, $R^{3a}$ is as described herein and $R^{3b}$ is as described herein, or a salt thereof. In an exemplary embodiment, for any of the entries in the above table, $Y^1$ is unsubstituted $C_1$ or $C_2$ or $C_3$ or $C_4$ or $C_5$ or $C_6$ alkyl, $Y^7$ are the same or different and are each selected from halogen, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $Y^1$ is unsubstituted $C_1$ or $C_2$ or $C_3$ alkyl, $Y^7$ are the same or different and are each selected from halogen, $R^{3a}$ is methyl and $R^{3b}$ is methyl. In an exemplary embodiment, for any of the entries in the above table, $Y^1$ is unsubstituted $C_1$ or $C_2$ or $C_3$ alkyl, $Y^7$ is Cl, $R^{3a}$ is methyl and $R^{3b}$ is methyl. In an exemplary embodiment, for any of the entries in the above table, $Y^1$ is methyl, one $Y^7$ is Cl, $R^{3a}$ is methyl and $R^{3b}$ is methyl.

In an exemplary embodiment, the compound of the invention has a structure according to the following formula:

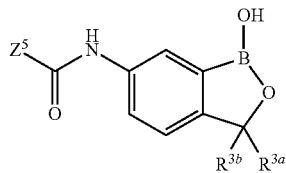

wherein $Z^5$ is selected from the group consisting of unsubstituted pyrimidinyl, unsubstituted pyrazinyl and unsubstituted pyridazinyl, $R^{3a}$ is as described herein and $R^{3b}$ is as described herein. In an exemplary embodiment, the compound of the invention has a structure which is selected from the group consisting of

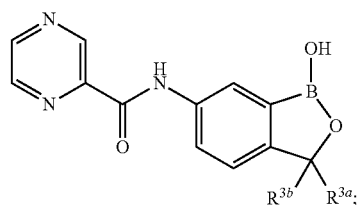

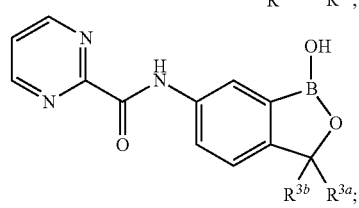

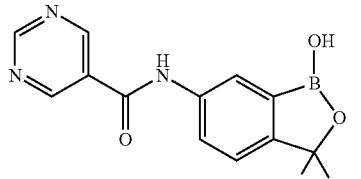

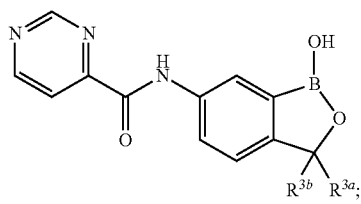

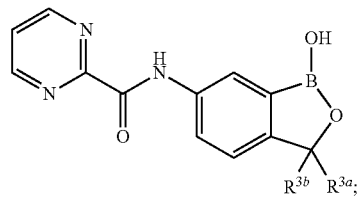

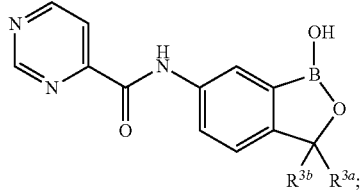

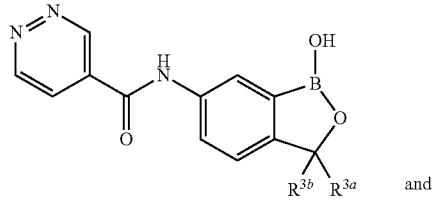 and

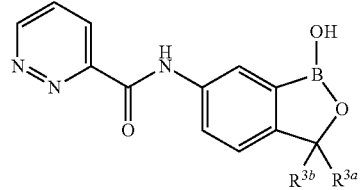

wherein $R^{3a}$ is as described herein and $R^{3b}$ is as described herein, or a salt thereof. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure according to the following formula:

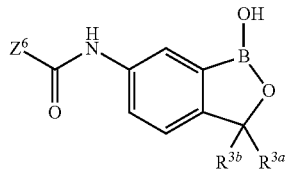

wherein $Z^6$ is halosubstituted pyridazinyl, $R^{3a}$ is as described herein and $R^{3b}$ is as described herein, or a salt thereof. In an exemplary embodiment, $Z^6$ is pyridazinyl, substituted with one halogen. In an exemplary embodiment, $Z^6$ is pyridazinyl, substituted with two halogens. In an exemplary embodiment, $Z^6$ is pyridazinyl, substituted with two chlorines. In an exemplary embodiment, the compound of the invention has a structure which is

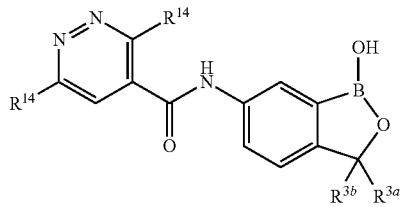

wherein each $R^{14}$ is chlorine or fluorine, $R^{3a}$ is as described herein and $R^{3b}$ is as described herein, or a salt thereof. In an exemplary embodiment, each $R^{14}$ is chlorine.

In an exemplary embodiment, the compound of the invention has a structure according to the following formula:

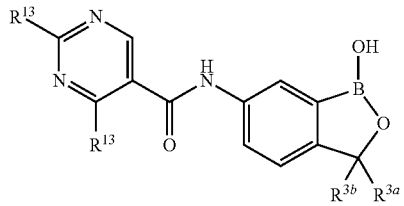

wherein each $R^{13}$ are the same or different and are each selected from the group consisting of H, —SH and —OH, $R^{3a}$ is as described herein and $R^{3b}$ is as described herein. In an exemplary embodiment, each $R^{13}$ are the same or different and are each selected from —SH or —OH.

In an exemplary embodiment, the compound of the invention has a structure according to the following formula:

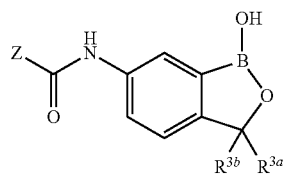

wherein Z is thiophenyl, $R^{3a}$ is as described herein and $R^{3b}$ is as described herein. In an exemplary embodiment, the compound of the invention has a structure which is:

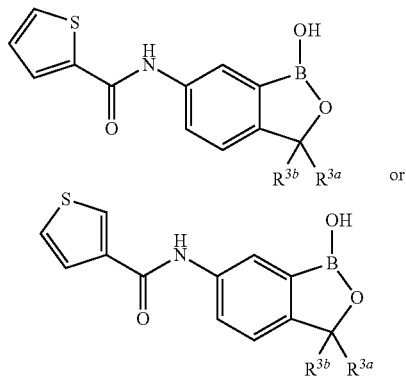

wherein $R^{3a}$ is as described herein and $R^{3b}$ is as described herein, or a salt thereof. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure according to the following formula:

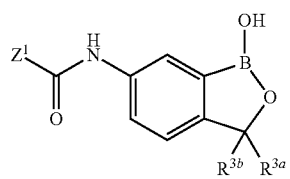

wherein $Z^1$ is unsubstituted alkylthiophenyl, $R^{3a}$ is as described herein and $R^{3b}$ is as described herein, or a salt thereof. In an exemplary embodiment, the compound of the invention has a structure which is

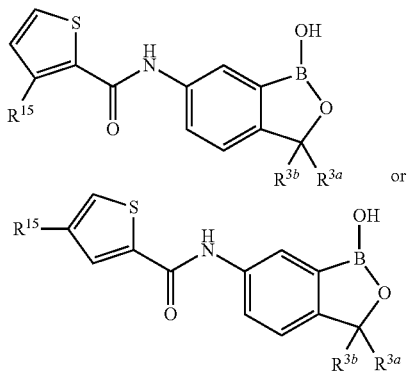

wherein $R^{15}$ is unsubstituted alkyl, $R^{3a}$ is as described herein and $R^{3b}$ is as described herein. In an exemplary embodiment, $R^{15}$ is unsubstituted $C_1$ alkyl. In an exemplary embodiment, $R^{15}$ is unsubstituted $C_2$ alkyl. In an exemplary embodiment, $R^{15}$ is unsubstituted $C_3$ alkyl. In an exemplary embodiment, $R^{15}$ is unsubstituted $C_4$ alkyl. In an exemplary embodiment, $R^{15}$ is unsubstituted $C_5$ alkyl. In an exemplary embodiment, $R^{15}$ is unsubstituted $C_6$ alkyl.

In an exemplary embodiment, the compound of the invention has a structure according to the following formula:

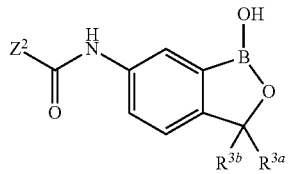

wherein $Z^2$ is unsubstituted benzothiophenyl, or a salt thereof.

In an exemplary embodiment, the compound of the invention has a structure according to the following formula:

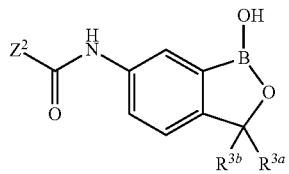

wherein $Z^2$ is halosubstituted benzothiophenyl, $R^{3a}$ is as described herein and $R^{3b}$ is as described herein. In an exemplary embodiment, $Z^2$ is benzothiophenyl substituted with chloro. In an exemplary embodiment, $Z^2$ is benzothiophenyl substituted with fluoro. In an exemplary embodiment, $Z^2$ is benzothiophenyl substituted with one halogen. In an exemplary embodiment, $Z^2$ is benzothiophenyl substituted with two halogens. In an exemplary embodiment, $Z^2$ is benzothiophenyl substituted with two fluorines. In an exemplary embodiment, $Z^2$ is benzothiophenyl substituted with two chlorines. In an exemplary embodiment, $Z^2$ is benzothiophenyl substituted with a fluorine and a chlorine. In an exemplary embodiment, the compound of the invention is:

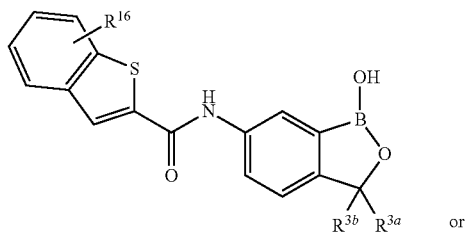

or

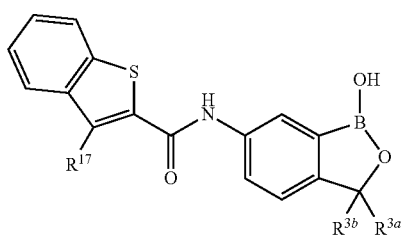

wherein $R^{16}$ is halogen, $R^{17}$ is halogen, $R^{3a}$ is as described herein and $R^{3b}$ is as described herein. In an exemplary embodiment, the compound of the invention is:

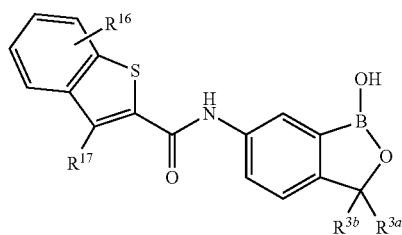

wherein each $R^{16}$ and $R^{17}$ are each the same or different and are each selected from halogen, $R^{3a}$ is as described herein and $R^{3b}$ is as described herein.

In an exemplary embodiment, the compound of the invention has a structure according to the following formula:

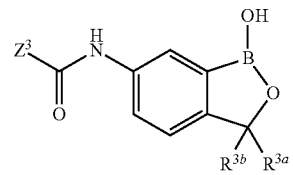

wherein $Z^3$ is unsubstituted oxazolyl, $R^{3a}$ is as described herein and $R^{3b}$ is as described herein, or a salt thereof. In an exemplary embodiment, the compound of the invention has a structure which is

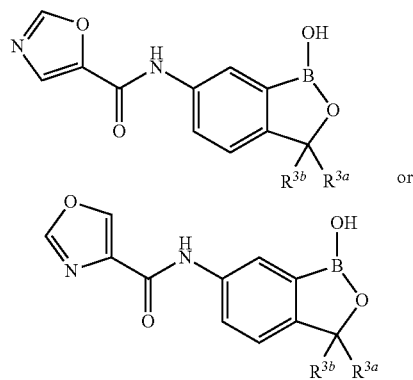

wherein $R^{3a}$ is as described herein and $R^{3b}$ is as described herein.

In an exemplary embodiment, the compound of the invention has a structure according to the following formula:

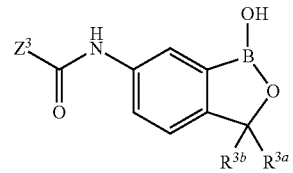

wherein $Z^3$ is unsubstituted alkyl oxazolyl, $R^{3a}$ is as described herein and $R^{3b}$ is as described herein, or a salt thereof. In an exemplary embodiment, the compound of the invention has a structure which is

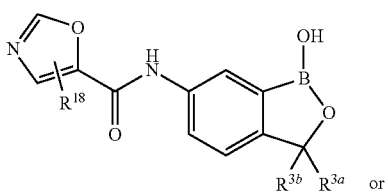

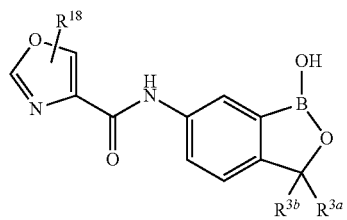

wherein $R^{18}$ is unsubstituted alkyl, $R^{3a}$ is as described herein and $R^{3b}$ is as described herein. In an exemplary embodiment, the compound of the invention has a structure according to the following formula:

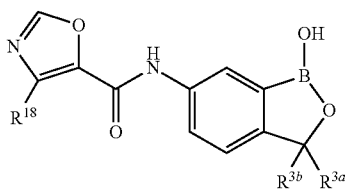

wherein $R^{18}$ is unsubstituted alkyl, $R^{3a}$ is as described herein and $R^{3b}$ is as described herein. In an exemplary embodiment, $R^{18}$ is $C_1$ or $C_2$ or $C_3$ or $C_4$ or $C_5$ or $C_6$ alkyl.

In an exemplary embodiment, the compound of the invention has a structure according to the following formula:

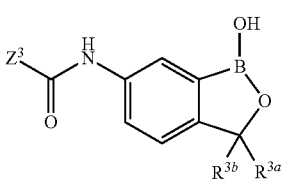

wherein $Z^3$ is unsubstituted isoxazolyl, $R^{3a}$ is as described herein and $R^{3b}$ is as described herein, or a salt thereof. In an exemplary embodiment, the compound of the invention has a structure which is

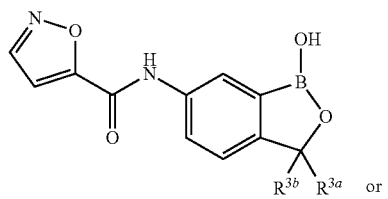

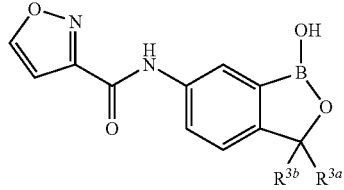

wherein $R^{3a}$ is as described herein and $R^{3b}$ is as described herein.

In an exemplary embodiment, the compound of the invention has a structure according to the following formula:

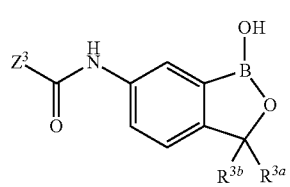

wherein $Z^3$ is unsubstituted alkyl isoxazolyl, $R^{3a}$ is as described herein and $R^{3b}$ is as described herein, or a salt thereof. In an exemplary embodiment, the compound of the invention has a structure which is

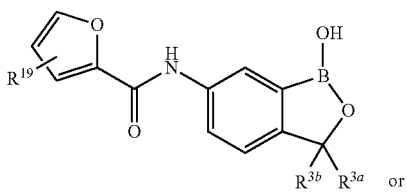

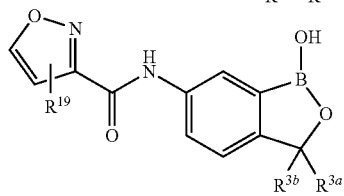

wherein $R^{19}$ is unsubstituted $C_1$ or $C_2$ or $C_3$ or $C_4$ or $C_5$ or $C_6$ alkyl, $R^{3a}$ is as described herein and $R^{3b}$ is as described herein. In an exemplary embodiment, the compound of the invention has a structure according to the following formula:

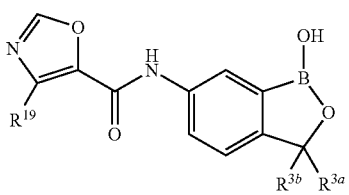

wherein $R^{19}$ is unsubstituted alkyl, $R^{3a}$ is as described herein and $R^{3b}$ is as described herein. In an exemplary embodiment, $R^{19}$ is unsubstituted $C_1$ alkyl. In an exemplary embodiment, $R^{19}$ is unsubstituted $C_2$ alkyl. In an exemplary embodiment, $R^{19}$ is unsubstituted $C_3$ alkyl. In an exemplary embodiment, $R^{19}$ is unsubstituted $C_4$ alkyl. In an exemplary embodiment, $R^{19}$ is unsubstituted $C_5$ alkyl. In an exemplary embodiment, $R^{19}$ is unsubstituted $C_6$ alkyl.

In an exemplary embodiment, the compound of the invention has a structure according to the following formula:

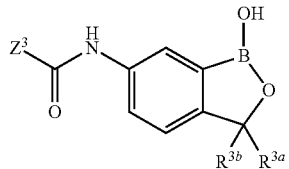

wherein $Z^3$ is unsubstituted thiazolyl, $R^{3a}$ is as described herein and $R^{3b}$ is as described herein, or a salt thereof. In an exemplary embodiment, the compound of the invention has a structure which is

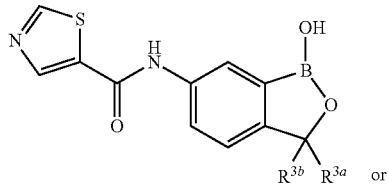

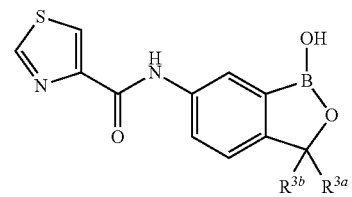

wherein $R^{3a}$ is as described herein and $R^{3b}$ is as described herein.

In an exemplary embodiment, the compound of the invention has a structure according to the following formula:

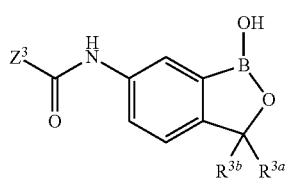

wherein $Z^3$ is unsubstituted alkyl thiazolyl, $R^{3a}$ is as described herein and $R^{3b}$ is as described herein, or a salt thereof. In an exemplary embodiment, the compound of the invention has a structure which is

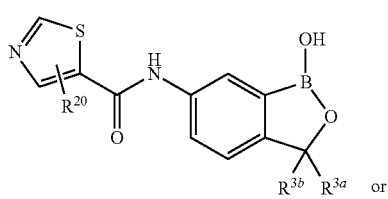

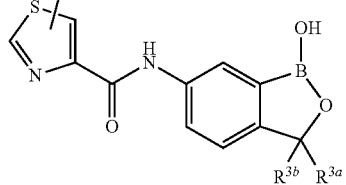

wherein $R^{20}$ is unsubstituted alkyl, $R^{3a}$ is as described herein and $R^{3b}$ is as described herein. In an exemplary embodiment, the compound of the invention has a structure which is

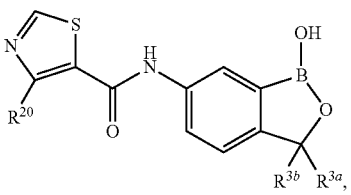

wherein $R^{20}$ is unsubstituted alkyl, $R^{3a}$ is as described herein and $R^{3b}$ is as described herein. In an exemplary embodiment, $R^{20}$ is $C_1$ or $C_2$ or $C_3$ or $C_4$ or $C_5$ or $C_6$ alkyl.

In an exemplary embodiment, the compound of the invention has a structure according to the following formula:

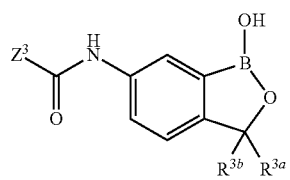

wherein $Z^3$ is unsubstituted pyrazolyl, $R^{3a}$ is as described herein and $R^{3b}$ is as described herein, or a salt thereof. In an exemplary embodiment, the compound of the invention has a structure which is

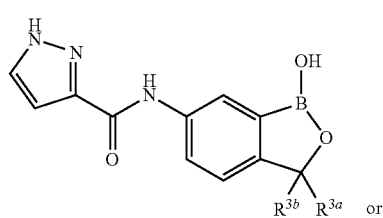

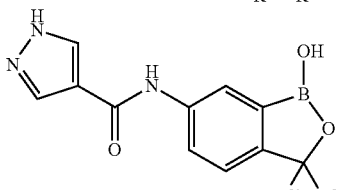

wherein $R^{3a}$ is as described herein and $R^{3b}$ is as described herein. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure according to the following formula:

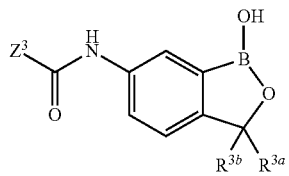

wherein $Z^3$ is selected from the group consisting of unsubstituted alkyl pyrrolyl, unsubstituted phenyl pyrrolyl and unsubstituted phenyl (unsubstituted alkyl)pyrrolyl, $R^{3a}$ is as described herein and $R^{3b}$ is as described herein, or a salt thereof. In an exemplary embodiment, the compound of the invention has a structure which is

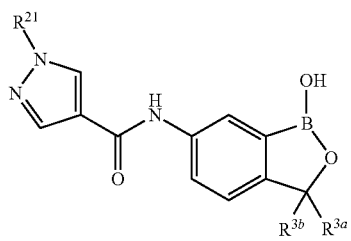

wherein each $R^{21}$ are the same or different and are each selected from unsubstituted $C_1$ or $C_2$ or $C_3$ or $C_4$ or $C_5$ or $C_6$ alkyl or phenyl, $R^{3a}$ is as described herein and $R^{3b}$ is as described herein. In an exemplary embodiment, the compound of the invention has a structure which is

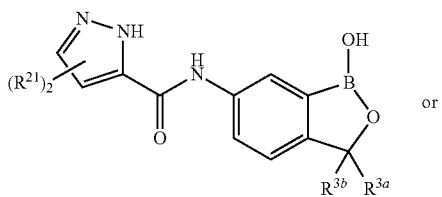

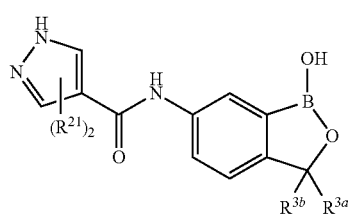

wherein each $R^{21}$ are the same or different and are each selected from unsubstituted $C_1$ or $C_2$ or $C_3$ or $C_4$ or $C_5$ or $C_6$ alkyl or phenyl, $R^{3a}$ is as described herein and $R^{3b}$ is as described herein. In an exemplary embodiment, the compound of the invention has a structure which is

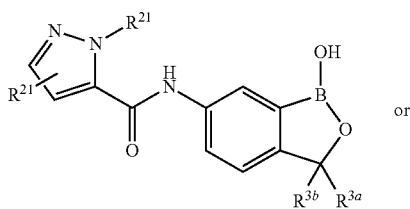

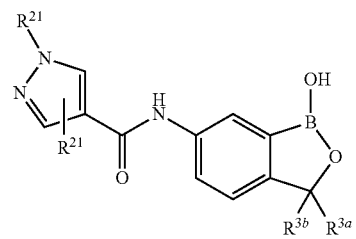

wherein $R^{3a}$ is as described herein and $R^{3b}$ is as described herein. In an exemplary embodiment, each $R^{21}$ is unsubstituted $C_1$ alkyl. In an exemplary embodiment, $R^{21}$ is unsubstituted $C_2$ alkyl. In an exemplary embodiment, $R^{21}$ is unsubstituted $C_3$ alkyl. In an exemplary embodiment, $R^{21}$ is unsubstituted $C_4$ alkyl. In an exemplary embodiment, $R^{21}$ is unsubstituted $C_5$ alkyl. In an exemplary embodiment, $R^{21}$ is unsubstituted $C_6$ alkyl. In an exemplary embodiment, $R^{21}$ is unsubstituted phenyl. In an exemplary embodiment, the compound of the invention has a structure according to the following formula:

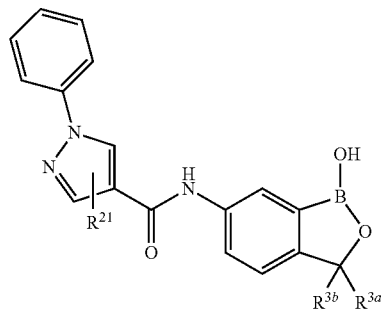

wherein $R^{21}$ is as described herein, $R^{3a}$ is as described herein and $R^{3b}$ is as described herein.

In an exemplary embodiment, the compound of the invention has a structure according to the following formula:

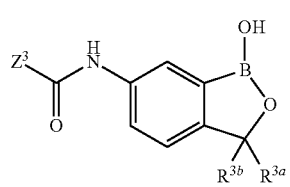

wherein $Z^3$ is unsubstituted furanyl, $R^{3a}$ is as described herein and $R^{3b}$ is as described herein, or a salt thereof. In an exemplary embodiment, the compound is:

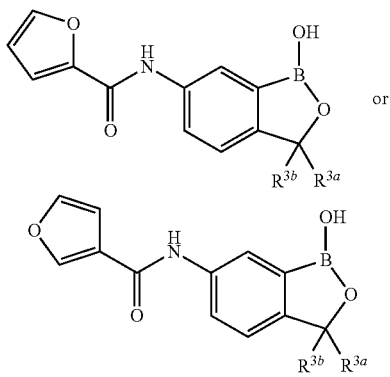

wherein $R^{3a}$ is as described herein and $R^{3b}$ is as described herein. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure according to the following formula:

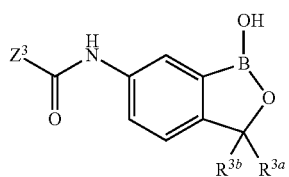

wherein $Z^3$ is unsubstituted alkylfuranyl, $R^{3a}$ is as described herein and $R^{3b}$ is as described herein. In an exemplary embodiment, the compound of the invention is:

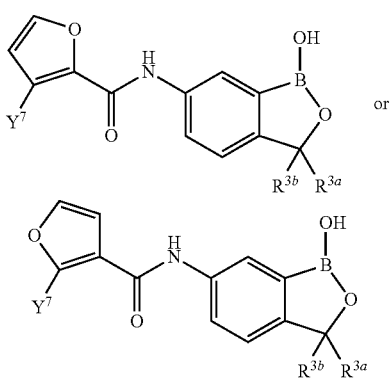

wherein $Y^7$ is unsubstituted alkyl, $R^{3a}$ is as described herein and $R^{3b}$ is as described herein. In an exemplary embodiment, $Y^7$ is unsubstituted $C_1$ alkyl. In an exemplary embodiment, $Y^7$ is unsubstituted $C_2$ alkyl. In an exemplary embodiment, $Y^7$ is unsubstituted $C_3$ alkyl. In an exemplary embodiment, $Y^7$ is unsubstituted $C_4$ alkyl. In an exemplary embodiment, $Y^7$ is unsubstituted $C_5$ alkyl. In an exemplary embodiment, $Y^7$ is unsubstituted $C_6$ alkyl. In an exemplary embodiment, for any of the entries in the above table, $Y^7$ is as described herein, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $Y^7$ is as described herein, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $Y^7$ is as described herein, $R^{3a}$ is methyl and $R^{3b}$ is methyl.

In an exemplary embodiment, the compound of the invention has a structure according to the following formula:

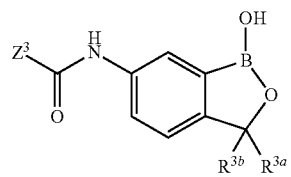

wherein $Z^3$ is unsubstituted pyrrole, $R^{3a}$ is as described herein and $R^{3b}$ is as described herein. In an exemplary embodiment, the compound is:

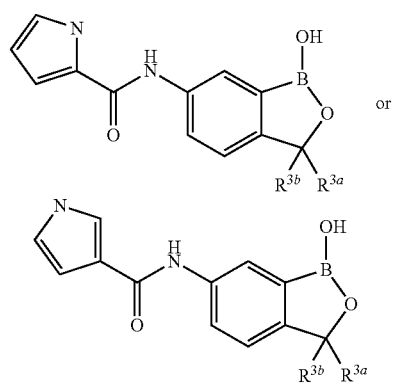

wherein $R^{3a}$ is as described herein and $R^{3b}$ is as described herein, or a salt thereof.

In an exemplary embodiment, the compound of the invention has a structure according to the following formula:

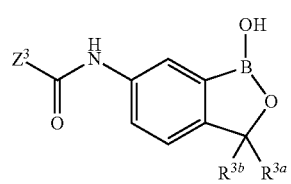

wherein $Z^3$ is unsubstituted alkyl pyrrole, $R^{3a}$ is as described herein and $R^{3b}$ is as described herein. In an exemplary embodiment, the compound is:

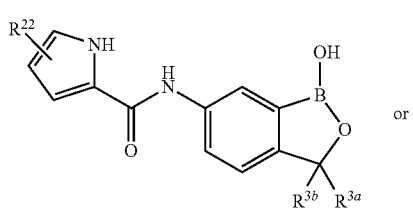

-continued

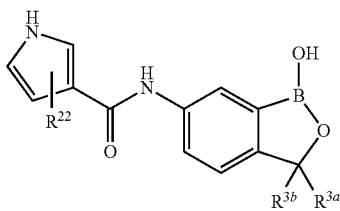

wherein $R^{22}$ is unsubstituted alkyl, $R^{3a}$ is as described herein and $R^{3b}$ is as described herein, or a salt thereof.

In an exemplary embodiment, the compound is:

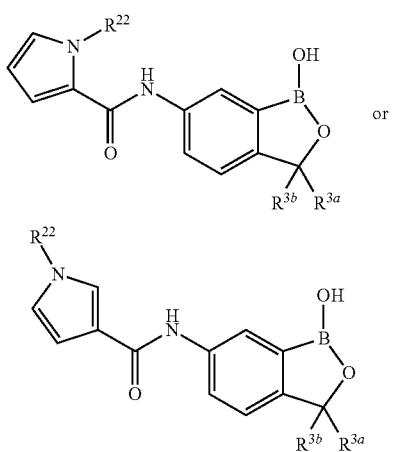

wherein $R^{22}$ is unsubstituted alkyl, $R^{3a}$ is as described herein and $R^{3b}$ is as described herein, or a salt thereof. In an exemplary embodiment, $R^{22}$ is unsubstituted $C_1$ alkyl. In an exemplary embodiment, $R^{22}$ is unsubstituted $C_2$ alkyl. In an exemplary embodiment, $R^{22}$ is unsubstituted $C_3$ alkyl. In an exemplary embodiment, $R^{22}$ is unsubstituted $C_4$ alkyl. In an exemplary embodiment, $R^{22}$ is unsubstituted $C_5$ alkyl. In an exemplary embodiment, $R^{22}$ is unsubstituted $C_6$ alkyl.

In an exemplary embodiment, the compound of the invention has a structure selected from the group consisting of

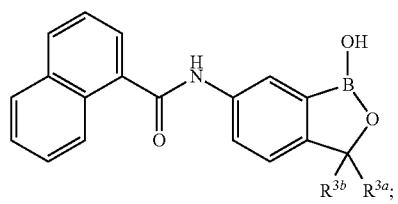

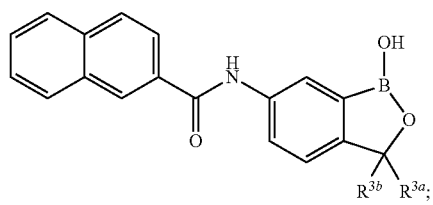

-continued

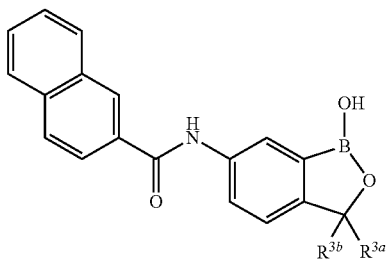

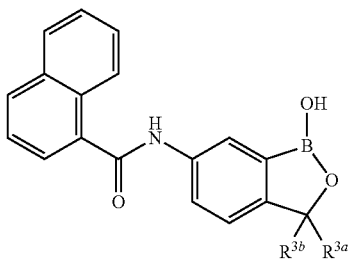

wherein $R^{3a}$ is as described herein and $R^{3b}$ is as described herein, or a salt thereof. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure selected from the group consisting of

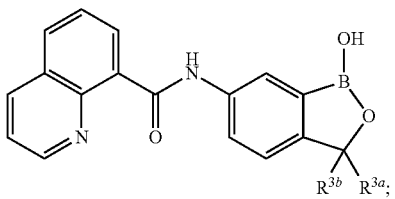

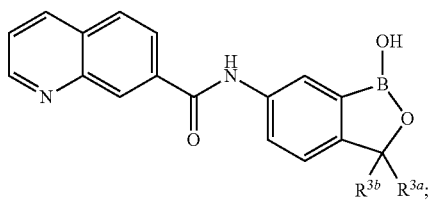

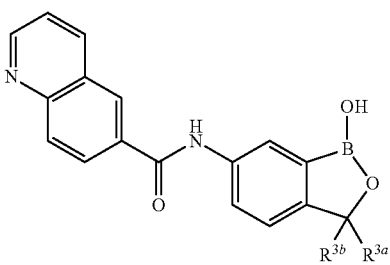

-continued

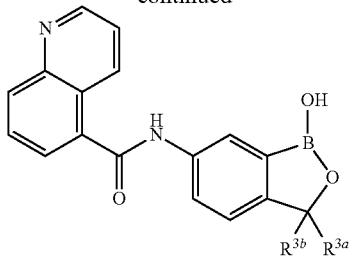

wherein $R^{3a}$ is as described herein and $R^{3b}$ is as described herein, or a salt thereof. In an exemplary embodiment, for any of the entries in the above table, $R^{3a}$ and $R^{3b}$, together with the atom to which they are attached, are joined to form cyclopropyl or cyclobutyl or cyclopentyl. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure selected from the group consisting of

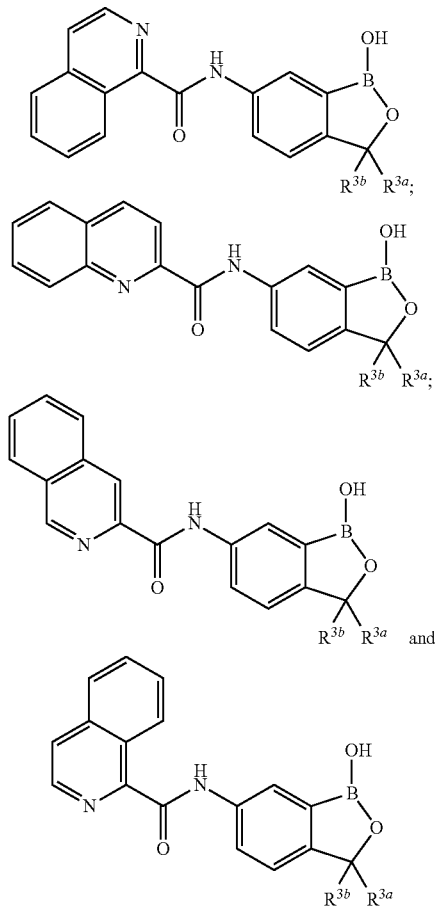

wherein $R^{3a}$ is as described herein and $R^{3b}$ is as described herein, or a salt thereof. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure selected from the group consisting of

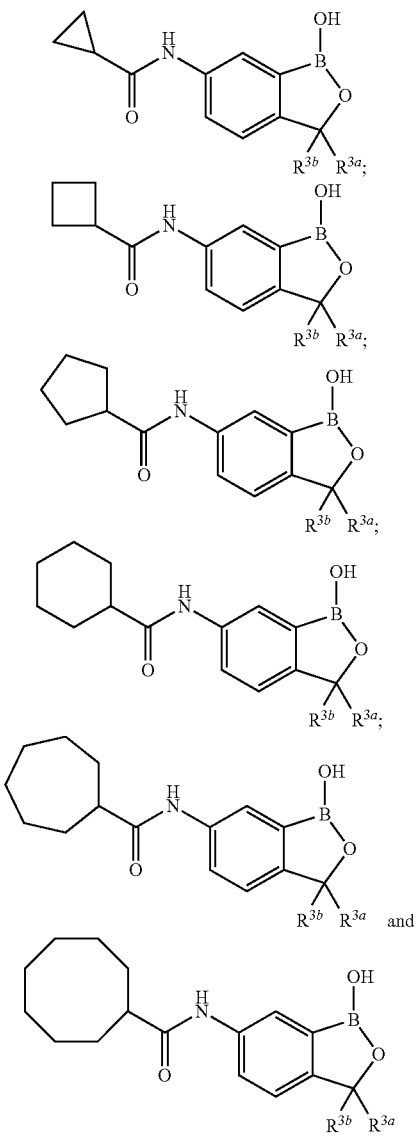

wherein $R^{3a}$ is as described herein and $R^{3b}$ is as described herein, or a salt thereof. In an exemplary embodiment, for any of the entries in the above table, $R^{3a}$ is $C_1$ or $C_2$ or $C_3$ or $C_4$ or $C_5$ or $C_6$ unsubstituted alkyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is $C_1$ or $C_2$ or $C_3$ or $C_4$ or $C_5$ or $C_6$ unsubstituted alkyl. In an exemplary embodiment, for any of the entries in the above table, $R^{3a}$ is methyl and $R^{3b}$ is methyl.

In an exemplary embodiment, the compound of the invention has a structure according to the following formula:

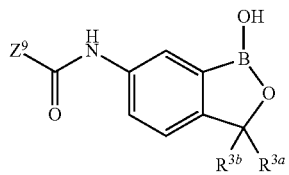

wherein $Z^9$ is unsubstituted alkyl, $R^{3a}$ is as described herein and $R^{3b}$ is as described herein. In an exemplary embodiment, $Z^9$ is unsubstituted $C_1$ or $C_2$ or $C_3$ or $C_4$ or $C_5$ or $C_6$ alkyl. In an exemplary embodiment, $Z^9$ is methyl. In an exemplary embodiment, $Z^9$ is unsubstituted $C_4$ alkyl. In an exemplary embodiment, $Z^9$ is n-butyl or sec-butyl or isobutyl or tert-butyl. In an exemplary embodiment, $Z^9$ is tert-butyl. In an exemplary embodiment, $Z^9$ is unsubstituted $C_5$ alkyl. In an exemplary embodiment, $Z^9$ is (1,1-dimethyl)propyl.

In an exemplary embodiment, the compound of the invention has a structure according to the following formula:

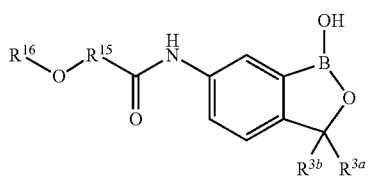

wherein $R^{15}$ is unsubstituted alkyl, $R^{16}$ is H or phenyl substituted alkyl, $R^{3a}$ is as described herein and $R^{3b}$ is as described herein. In an exemplary embodiment, $R^{15}$ is unsubstituted $C_1$ or $C_2$ or $C_3$ or $C_4$ or $C_5$ or $C_6$ alkyl. In an exemplary embodiment, $R^{15}$ is unsubstituted $C_3$ alkyl. In an exemplary embodiment, $R^{16}$ is benzyl. In an exemplary embodiment, $R^{16}$ is H.

In an exemplary embodiment, the compound of the invention has a structure according to the following formula:

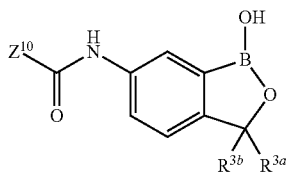

wherein $Z^{10}$ is hydroxy-substituted alkyl, $R^{3a}$ is as described herein and $R^{3b}$ is as described herein. In an exemplary embodiment, $Z^{10}$ is hydroxylsubstituted $C_1$ or $C_2$ or $C_3$ or $C_4$ or $C_5$ or $C_6$ alkyl.

In an exemplary embodiment, a compound of the invention essentially does not inhibit a cytochrome P450 enzyme. In an exemplary embodiment, a compound of the invention does not inhibit a cytochrome P450 enzyme. In an exemplary embodiment, the cytochrome P450 enzyme is selected from CP1A2, 2C9, 2D6 and 3A4. In an exemplary embodiment, the cytochrome P450 enzyme is CYP2C19.

In an exemplary embodiment, a compound of the invention is essentially not a substrate for the P-gp transporter. In an exemplary embodiment, a compound of the invention is not a substrate for the P-gp transporter.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

In an exemplary embodiment, alkyl is linear alkyl. In another exemplary embodiment, alkyl is branched alkyl.

In an exemplary embodiment, heteroalkyl is linear heteroalkyl. In another exemplary embodiment, heteroalkyl is branched heteroalkyl.

III. b) Compositions Involving Stereoisomers

As used herein, the term "chiral", "enantiomerically enriched" or "diastereomerically enriched" refers to a composition having an enantiomeric excess (ee) or a diastereomeric excess (de) of greater than about 50%, preferably greater than about 70% and more preferably greater than about 90%. In general, higher than about 90% enantiomeric or diastereomeric excess is particularly preferred, e.g., those compositions with greater than about 95%, greater than about 97% and greater than about 99% ee or de.

When a first compound and a second compound are present in a composition, and the first compound is a non-superimposable mirror image of the second compound, and the first compound is present in the composition in a greater amount than the second compound, then the first compound is referred to herein as being present in "enantiomeric excess".

The term "enantiomeric excess" of a compound z, as used herein, is defined as:

$$ee_z = \left(\frac{\text{conc. of } z - \text{conc. of } y}{\text{conc. of } z + \text{conc. of } y}\right) \times 100$$

wherein z is a first compound in a composition, y is a second compound in the composition, and the first compound is a non-superimposable mirror image of the second compound.

The term "enantiomeric excess" is related to the older term "optical purity" in that both are measures of the same phenomenon. The value of ee will be a number from 0 to 100, zero being racemic and 100 being enantiomerically pure. A composition which in the past might have been called 98% optically pure is now more precisely characterized by 96% ee. A 90% ee reflects the presence of 95% of one enantiomer and 5% of the other(s) in the material in question.

When a first compound and at least one additional compound are present in a composition, and the first compound and each of the additional compounds are stereoisomers, but not mirror images, of one another, and the first compound is present in the composition in a greater amount than each of the additional compounds, then the first compound is referred to herein as being present in "diastereomeric excess".

When dealing with mixtures of diastereomers, the term "diastereomeric excess" or "de" is defined analogously to enantiomeric excess. Thus:

$$de_w = \left( \frac{\text{conc. of major diastereomer} - \text{conc. of min or diastereomer(s)}}{\text{conc. of major diastereomer} + \text{conc. of min or diastereomer(s)}} \right) \times 100$$

wherein the major diastereomer is a first compound in a composition, and the minor diastereomer(s) is at least one additional compound in the composition, and the major diastereomer and minor diastereomer(s) are stereoisomers, but not mirror images, of one another.

The value of de will likewise be a number from 0 to 100, zero being an equal mixture of a first diastereomer and the remaining diastereomer(s), and 100 being 100% of a single diastereomer and zero % of the other(s)—i.e. diastereomerically pure. Thus, 90% de reflects the presence of 95% of one diastereomer and 5% of the other diastereomer(s) in the material in question.

Hence, in one embodiment, the invention provides a composition including a first compound of the invention, wherein the first compound of the invention has at least one stereocenter, and at least one stereoisomer of the first compound of the invention. In another embodiment, the invention provides a composition including a first compound of the invention, wherein the first compound of the invention has at least one stereocenter, and a second compound of the invention, wherein the first compound of the invention is a stereoisomer of the second compound of the invention. In another embodiment, the invention provides a composition including a first compound of the invention, wherein the first compound of the invention has at least one stereocenter, and only one stereoisomer of the first compound of the invention.

In another embodiment, the invention provides a composition including a first compound of the invention, wherein the first compound of the invention has only one stereocenter, and an enantiomer of the first compound of the invention. In another embodiment, the invention provides a composition including a first compound of the invention, wherein the first compound of the invention has two stereocenters, and an enantiomer of the first compound of the invention. In another embodiment, the invention provides a composition including a first compound of the invention, wherein the first compound of the invention has two stereocenters, and at least one diasteromer of the first compound of the invention. In another embodiment, the invention provides a composition including a first compound of the invention, wherein the first compound of the invention has two stereocenters, and only one diasteromer of the first compound of the invention.

In situations where the first compound of the invention and its enantiomer are present in a composition, the first compound of the invention can be present in an enantiomeric excess of at least about 80%, or at least about 90%, or at least about 92% or at least about 95%. In another embodiment, where the first compound of the invention and its enantiomer are present in a composition, the first compound of the invention can be present in an enantiomeric excess of at least about 96%, at least about 97%, at least about 98%, at least about 99% or at least about 99.5%. In another embodiment, the first compound of the invention has at least one stereocenter and is enantiomerically pure (enantiomeric excess is about 100%).

In situations where the first compound of the invention and at least one diastereomer of the first compound of the invention are present in a composition, the first compound of the invention can be present in a diastereomeric excess of at least about 80%, or at least about 90%, or at least about 92% or at least about 95%. In situations where the first compound of the invention and at least one diastereomer of the first compound of the invention are present in a composition, the first compound of the invention can be present in a diastereomeric excess of at least about 96%, at least about 97%, at least about 98%, at least about 99% or at least about 99.5%. In another embodiment, the first compound of the invention has at least two stereocenters and is diastereomerically pure (diastereomeric excess is about 100%).

Enantiomeric or diastereomeric excess can be determined relative to exactly one other stereoisomer, or can be determined relative to the sum of at least two other stereoisomers. In an exemplary embodiment, enantiomeric or diastereomeric excess is determined relative to all other detectable stereoisomers, which are present in the mixture. Stereoisomers are detectable if a concentration of such stereoisomer in the analyzed mixture can be determined using common analytical methods, such as chiral HPLC.

As used herein, and unless otherwise indicated, a composition that is "substantially free" of a compound means that the composition contains less than about 20% by weight, or less than about 15% by weight, or less than about 10% by weight, or less than about 5% by weight, or less than about 3% by weight, or less than about 2% by weight, or less than about 1% by weight of the compound.

As used herein, the term "substantially free of the (or its) enantiomer" means that a composition contains a significantly greater proportion of a first compound of the invention than a second compound of the invention, wherein the first compound is a non-superimposable mirror image of the second compound. In one embodiment of the invention, the term "substantially free of the enantiomer" means that the composition is made up of at least about 90% by weight of a first compound of the invention, and about 10% by weight or less of a second compound of the invention, wherein the first compound is a non-superimposable mirror image of the second compound. In one embodiment of the invention, the term "substantially free of the (R) enantiomer" means that the composition is made up of at least about 90% by weight of a first compound of the invention which has only one stereocenter and the stereocenter is in an (S) configuration, and about 10% by weight or less of a second compound of the invention, wherein the second compound is the enantiomer of the first compound. In one embodiment of the invention, the term "substantially free of the enantiomer" means that the composition is made up of at least about 95% by weight of a first compound of the invention, and about 5% by weight or less of a second compound of the invention, wherein the first compound is a non-superimposable mirror image of the second compound. In one embodiment of the invention, the term "substantially free of the (R) enantiomer" means that the composition is made up of at least about 95% by weight of a first compound of the invention which has only one stereocenter and the stereocenter is in an (S) configuration, and about 5% by weight or less of a second compound of the invention, wherein the second compound is the enantiomer of the first compound. In one embodiment of the invention, the term "substantially free of the enantiomer" means that the composition is made up of at least about 98% by weight of a first compound of the invention, and about 2% by weight or less of a second compound of the invention, wherein the first compound is a non-superimposable mirror image of the second compound. In one embodiment of the invention, the term "substantially free of the (R) enantiomer" means that the composition is made up of at least about 98% by weight of a first compound of the invention which has only one stereocenter and the stereocenter is in an (S) configuration, and about 2% by weight or less of a second compound of the invention, wherein the second compound is the enantiomer of the first compound. In one embodiment of the invention, the term "substantially free of the enantiomer" means that the composition is made up of at least about 99% by weight of a first compound of the invention, and about 1% by weight or less of a second compound of the invention, wherein the first compound is a non-superimposable mirror image of the second compound. In one embodiment of the invention, the term "substantially free of the (R) enantiomer" means that the composition is made up of at least about 99% by weight of a first compound of the invention which has only one stereocenter and the stereocenter is in an (S) configuration, and about 1% by weight or less of a second compound of the invention, wherein the second compound is the enantiomer of the first compound.

In an exemplary embodiment, the invention provides a composition comprising a) first compound described herein; and b) the enantiomer of the first compound, wherein the first compound described herein is present in an enantiomeric excess of at least 80%. In an exemplary embodiment, the enantiomeric excess is at least 92%.

III. b) Combinations Comprising Additional Therapeutic Agents

The compounds of the invention may also be used in combination with additional therapeutic agents. The invention thus provides, in a further aspect, a combination comprising a compound described herein or a pharmaceutically acceptable salt thereof together with at least one additional therapeutic agent. In an exemplary embodiment, the additional therapeutic agent is a compound of the invention. In an exemplary embodiment, the additional therapeutic agent includes a boron atom. In an exemplary embodiment, the additional therapeutic agent does not contain a boron atom.

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. In an exemplary embodiment, the additional therapeutic agent is berenil. In an exemplary embodiment, the additional therapeutic agent is diminazene. In an exemplary embodiment, the additional therapeutic agent is an antiprotozoa. In an exemplary embodiment, the additional therapeutic agent is selected from the group consisting of benznidazole, buparvaquone, carbarsone, clioquinol, disulfuram, eflornithine, emetine, etofamide, furazolidone, meglumine antimoniate, melarsoprol, metronidazole, miltefosine, nifurtimox, nimorazole, nitazoxanide, ornidazole, paromomycin sulfate, pentamidine, pyrimethamine, secnidazole and tinidazole. In an exemplary embodiment, the additional therapeutic agent is pentamidine. In an exemplary embodiment, the additional therapeutic agent is suramin. In an exemplary embodiment, the additional therapeutic agent is eflornithine. In an exemplary embodiment, the additional therapeutic agent is melarsoprol. In an exemplary embodiment, the additional therapeutic agent is nifurtimox. In an exemplary embodiment, the additional therapeutic agent contains a 5-nitrofuran moiety. In an exemplary embodiment, the additional therapeutic agent contains a 5-nitroimidazolyl moiety. In an exemplary embodiment, the additional therapeutic agent is fexinidazole. In an exemplary embodiment, the additional therapeutic agent is an antiparasitic. In an exemplary embodiment, the additional therapeutic agent is selected from the group consisting of amitraz, avermectin, carbadox, diethylcarbamazine, dimetridazole, diminazene, ivermectin, macrofilaricide, malathion, mitaban, organophosphate, oxamniquine, permethrin, praziquantel, pyrantel pamoate, selamectin, sodium stibogluconate and thiabendazole. In an exemplary embodiment, the additional therapeutic agent is selected from the group consisting of antimony, meglumine antimoniate, sodium stibogluconate, amphotericin, miltefosine and paromomycin.

The compounds of the invention, or pharmaceutical formulations thereof may also be used in combination with other therapeutic agents, for example immune therapies [e.g. interferon, such as interferon alfa-2a (ROFERON®-A; Hoffmann-La Roche), interferon alpha-2b (INTRON®-A; Schering-Plough), interferon alfacon-1 (INFERGEN®; Intermune), peginterferon alpha-2b (PEGINTRON™; Schering-Plough) or peginterferon alpha-2a (PEGASYS®; Hoffmann-La Roche)], therapeutic vaccines, antifibrotic agents, anti-inflammatory agents [such as corticosteroids or NSAIDs], bronchodilators [such as beta-2 adrenergic agonists and xanthines (e.g. theophylline)], mucolytic agents, anti-muscarinics, anti-leukotrienes, inhibitors of cell adhesion [e.g. ICAM antagonists], anti-oxidants [e.g. N-acetylcysteine], cytokine agonists, cytokine antagonists, lung surfactants and/or antimicrobial. The compositions according to the invention may also be used in combination with gene replacement therapy.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the patient ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient.

It is to be understood that the invention covers all combinations of aspects and/or embodiments, as well as suitable, convenient and preferred groups described herein.

III. c) Preparation of Boron-Containing Compounds

Compounds of use in the invention can be prepared using commercially available starting materials, known intermediates, or by using the synthetic methods described herein, or published in references described and incorporated by reference herein, such as PCT Pub. No. WO2008157726 and U.S. Pat. Pubs. US20060234981, US20070155699 and US20070293457.

In one embodiment, the compound of the invention can be synthesized according to the following scheme:

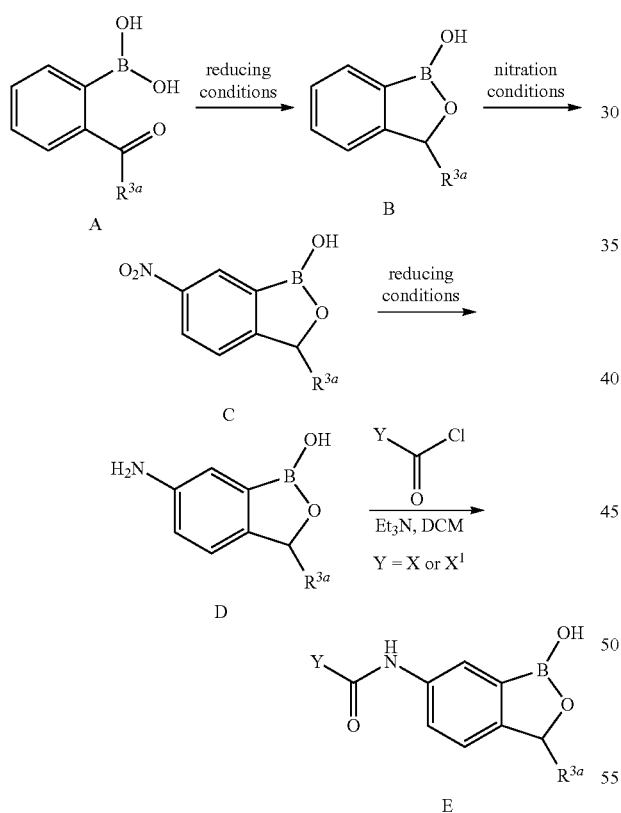

wherein A is commercially available from, for example, Sigma-Aldrich. A can be converted to B through subjecting it to reducing conditions, such as those involving sodium borohydride. B can be converted to C through subjecting it to nitration conditions, such as those involving fuming nitric acid. C can be converted to D through subjecting it to reducing conditions, such as those involving catalytic hydrogenation. D can be converted to E through subjecting it to acid chloride addition conditions.

In one embodiment, the compound of the invention can be synthesized according to the following scheme:

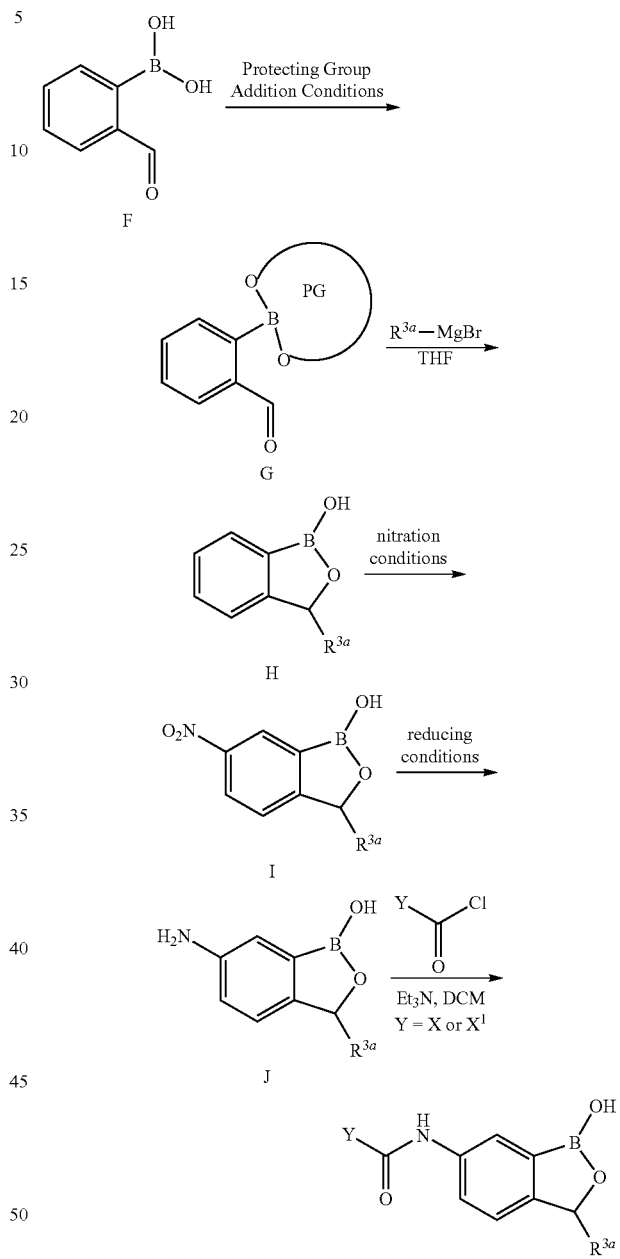

wherein F is commercially available from, for example, Sigma-Aldrich. F can be converted to G through subjecting it to protecting group addition conditions, such as those involving N-butyldiethanolamine. G can be converted to H through subjecting it to Grignard addition conditions. H can be converted to I through subjecting it to nitration conditions, such as those involving fuming nitric acid. I can be converted to J through subjecting it to reducing conditions, such as those involving catalytic hydrogenation. J can be converted to K through subjecting it to acid chloride addition conditions.

In one embodiment, the compound of the invention can be synthesized according to the following scheme:

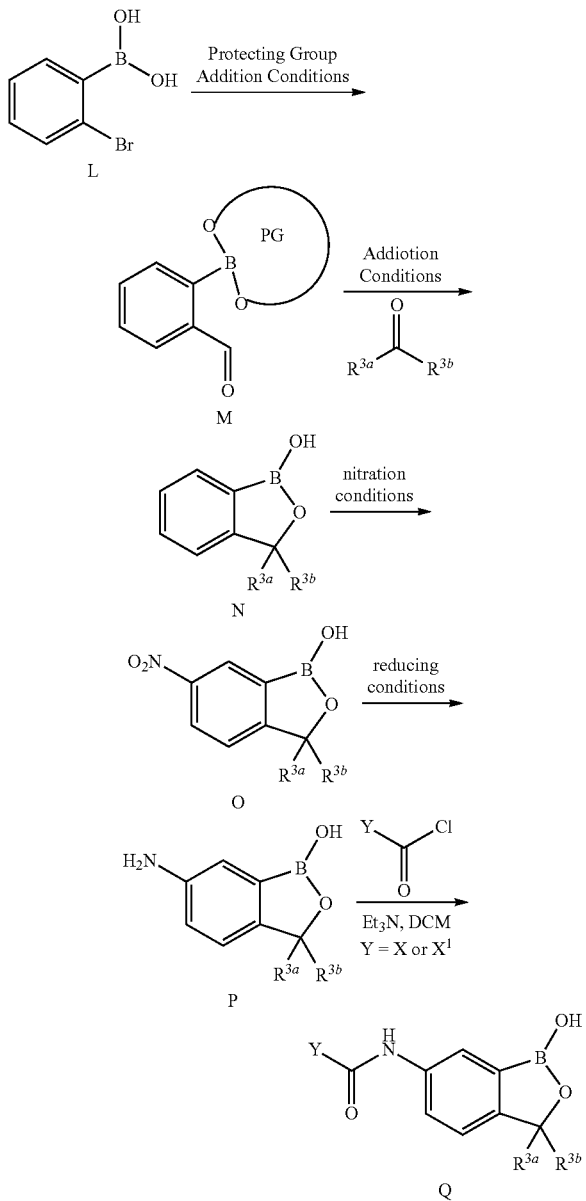

wherein L is commercially available from, for example, Sigma-Aldrich. L can be converted to M through subjecting it to protecting group addition conditions, such as those involving N-butyldiethanolamine. M can be converted to N through subjecting it to addition conditions, such as those involving an organolithium agent such as n-butyl lithium. N can be converted to O through subjecting it to nitration conditions, such as those involving fuming nitric acid. O can be converted to P through subjecting it to reducing conditions, such as those involving catalytic hydrogenation. P can be converted to Q through subjecting it to acid chloride addition conditions.

Compounds described herein can be converted into hydrates and solvates by methods similar to those described herein.

IV. Methods of Inhibiting Microorganism Growth or Killing Microorganisms

The compounds of the invention exhibit potency against microorganisms, such as protozoa, and therefore have the potential to kill and/or inhibit the growth of microorganisms.

In a further aspect, the invention provides a method of killing and/or inhibiting the growth of a microorganism, said method comprising: contacting said microorganism with an effective amount of a compound of the invention, thereby killing and/or inhibiting the growth of the microorganism. In an exemplary embodiment, the microorganism is a protozoa. In an exemplary embodiment, the microorganism is a kinetoplastid. In another exemplary embodiment, the protozoa is a *Trypanosoma*. In an exemplary embodiment, the *Trypanosoma* is selected from the group consisting of *T. avium, T. boissoni, T. brucei, T. carassii, T. cruzi, T. congolense, T. equinum, T. equiperdum, T evansi, T. hosei, T. levisi, T. melophagium, T. parroti, T. percae, T. rangeli, T. rotatorium, T. rugosae, T. sergenti, T. simiae, T. sinipercae, T. suis, T. theileri, T. triglae* and *T. vivax*. In another exemplary embodiment, the protozoa is a *Trypanosoma brucei*. In another exemplary embodiment, the protozoa is *Trypanosoma brucei brucei*. In another exemplary embodiment, the protozoa is *Trypanosoma brucei rhodesiense*. In another exemplary embodiment, the protozoa is *Trypanosoma brucei gambiense*. In another exemplary embodiment, the protozoa is *Trypanosoma cruzi*. In another exemplary embodiment, the protozoa is a member of the genus *Leishmania*. In another exemplary embodiment, the protozoa is a member of *Leishmania Viannia*. In an exemplary embodiment, the protozoa is selected from the group consisting of *L. donovani, L. infantum, L. chagasi; L. mexicana, L. amazonensis, L. venezuelensis, L. tropica, L. major, L. aethiopica, L. (V.) braziliensis, L. (V.) guyanensis, L. (V.) panamensis*, and *L. (V.) peruviana*. In an exemplary embodiment, the protozoa is *L. donovani*. In an exemplary embodiment, the protozoa is L. infantum. In an exemplary embodiment, the compound is 4-fluoro-N-(1-hydroxy-3,3-dimethyl-1,3-dihydro-benzo[c][1,2]oxaborol-6-yl-2-trifluoromethyl benzamide, or a salt, prodrug, hydrate or solvate thereof, or a combination thereof. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. Such conditions are known to one skilled in the art and specific conditions are set forth in the Examples appended hereto.

In another aspect, the microorganism is inside, or on the surface of an animal. In an exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human.

In an exemplary embodiment, the microorganism is killed or its growth is inhibited through oral administration of the compound of the invention. In an exemplary embodiment, the microorganism is killed or its growth is inhibited through intravenous administration of the compound of the invention. In an exemplary embodiment, the microorganism is killed or its growth is inhibited through topical administration of the compound of the invention. In an exemplary embodiment, the microorganism is killed or its growth is inhibited through intraperitoneal administration of the compound of the invention. In an exemplary embodiment, the compound is administered in a topically effective amount. In an exemplary embodiment, the compound is administered in a cosmetically effective amount. In an exemplary embodiment, the pharmaceutical formulation is administered in an orally effective amount.

V. Methods of Treating and/or Preventing Disease

The compounds of the invention exhibit potency against microorganisms, such as protozoa, and therefore have the potential to achieve therapeutic efficacy in the animals described herein.

In another aspect, the invention provides a method of treating and/or preventing a disease. The method includes administering to the animal a therapeutically effective amount of the compound of the invention, sufficient to treat and/or prevent the disease. In an exemplary embodiment, the compound of the invention can be used in human or veterinary medical therapy, particularly in the treatment or prophylaxis of protozoa-associated disease. In an exemplary embodiment, the compound of the invention can be used in human or veterinary medical therapy, particularly in the treatment or prophylaxis of kinetoplastid-associated disease. In an exemplary embodiment, the disease is associated with a *Trypanosoma*. In an exemplary embodiment, the *Trypanosoma* is selected from the group consisting of *T. avium, T. boissoni, T. brucei, T. carassii, T. cruzi, T. congolense, T. equinum, T. equiperdum, T. evansi, T. hosei, T. levisi, T. melophagium, T. parroti, T. percae, T. rangeli, T. rotatorium, T. rugosae, T. sergenti, T. simiae, T. sinipercae, T. suis, T. theileri, T. triglae* and *T. vivax*. In an exemplary embodiment, the disease is associated with a *Trypanosoma brucei*. In an exemplary embodiment, the disease is associated with a member selected from the group consisting of *Trypanosoma brucei brucei, Trypanosoma brucei rhodesiense* and *Trypanosoma brucei gambiense*. In an exemplary embodiment, the disease is associated with *Trypanosoma brucei rhodesiense*. In an exemplary embodiment, the disease is associated with *Trypanosoma brucei gambiense*. In an exemplary embodiment, the disease is associated with *Trypanosoma cruzi*. In an exemplary embodiment, the disease is a trypanosomiasis. In an exemplary embodiment, the disease is a human trypanosomiasis. In an exemplary embodiment, the disease is an animal trypanosomiasis. In an exemplary embodiment, the disease is selected from the group consisting of nagana, surra, mal de caderas, murrina de caderas, dourine, cachexial fevers, Gambian horse sickness, baleri, kaodzera, tahaga, galziekte or galzietzke and peste-boba. In an exemplary embodiment, the disease is selected from the group consisting of Chagas disease (or Human American trypanosomiasis), nagana, surra, Covering sickness (or dourine) and sleeping sickness (or African sleeping sickness or Human African trypanosomiasis). In an exemplary embodiment, the disease is Chagas disease. In an exemplary embodiment, the disease is sleeping sickness (or African sleeping sickness). In an exemplary embodiment, the disease is acute phase sleeping sickness. In an exemplary embodiment, the disease is chronic phase sleeping sickness.

In an exemplary embodiment, the disease is an acute phase of a trypanosomiasis. In an exemplary embodiment, the disease is a chronic phase of a trypanosomiasis. In an exemplary embodiment, the disease is the non-CNS form of a trypanosomiasis. In an exemplary embodiment, the disease is the CNS form of a trypanosomiasis. In an exemplary embodiment, the disease is the non-CNS form of sleeping sickness. In an exemplary embodiment, the disease is the CNS form of sleeping sickness. In an exemplary embodiment, the disease is early stage Human African trypanosomiasis. In an exemplary embodiment, the disease is late stage Human African trypanosomiasis. In another exemplary embodiment, the disease is associated with a member of the genus *Leishmania*. In another exemplary embodiment, the disease is associated with a member of *Leishmania Viannia*. In an exemplary embodiment, the disease is associated with a member selected from the group consisting of *L. donovani, L. infantum, L. chagasi; L. mexicana, L. amazonensis, L. venezuelensis, L. tropica, L. major, L. aethiopica, L. (V.) braziliensis, L. (V.) guyanensis, L. (V.) panamensis*, and *L. (V.) peruviana*. In an exemplary embodiment, the disease is associated with *L. donovani*. In an exemplary embodiment, the disease is associated with *L. infantum*. In an exemplary embodiment, the disease is leishmaniasis. In an exemplary embodiment, the disease is visceral leishmaniasis. In an exemplary embodiment, the disease is cutaneous leishmaniasis. In an exemplary embodiment, the disease is diffuse cutaneous leishmaniasis and/or mucocutaneous leishmaniasis. In an exemplary embodiment, the compound is 4-fluoro-N-(1-hydroxy-3,3-dimethyl-1,3-dihydro-benzo[c][1,2]oxaborol-6-yl)-2-trifluoromethyl benzamide, or a salt, prodrug, hydrate or solvate thereof, or a combination thereof. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. Such conditions are known to one skilled in the art and specific conditions are set forth in the Examples appended hereto.

In another exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is a mouse. In another exemplary embodiment, the animal is selected from the group consisting of a human, cattle, goat, pig, sheep, horse, cow, bull, dog, guinea pig, gerbil, rabbit, cat, chicken and turkey. In another exemplary embodiment, the animal is a human.

In an exemplary embodiment, the disease is treated through oral administration of the compound of the invention. In an exemplary embodiment, the disease is treated through intravenous administration of the compound of the invention. In an exemplary embodiment, the disease is treated through topical administration of the compound of the invention. In an exemplary embodiment, the disease is treated through intraperitoneal administration of the compound of the invention. In an exemplary embodiment, the compound is administered in a topically effective amount. In an exemplary embodiment, the compound is administered in a cosmetically effective amount. In an exemplary embodiment, the pharmaceutical formulation is administered in an orally effective amount.

In an exemplary embodiment, the disease is associated with an infection by a microorganism described herein. In an exemplary embodiment, the disease is associated with an infection by a protozoa described herein.

VI. Pharmaceutical Formulations

In another aspect, the invention is a pharmaceutical formulation which includes: (a) a pharmaceutically acceptable excipient; and (b) a compound of the invention. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof, or a combination thereof. In another aspect, the pharmaceutical formulation includes: (a) a pharmaceutically acceptable excipient; and (b) a compound described herein, or a salt, hydrate or solvate thereof, or a combination thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a salt of a compound described herein. In an exemplary embodiment, the salt is a pharmaceutically acceptable salt. In another aspect, the pharmaceutical formulation includes: (a) a pharmaceutically acceptable excipient; and (b) a prodrug of a compound described herein. In another aspect, the pharmaceutical formulation includes: (a) a pharmaceutically acceptable excipient; and (b) a compound described herein. In an exemplary embodiment, the pharmaceutical formulation includes: (a) a pharmaceutically acceptable excipient; and (b) 4-fluoro-N-(1-hydroxy-3,3-dimethyl-1,3-dihydro-benzo[c][1,2]oxaborol-6-yl-2-trifluoromethyl benzamide. In an exemplary embodiment, the pharmaceutical formulation includes: (a) a pharmaceutically acceptable excipient; and (b) a pharmaceutically acceptable salt of 4-fluoro-N-(1-hydroxy-3,3-dimethyl-1,3-dihydro-benzo[c][1,2]oxaborol-6-yl-2-trifluoromethyl benzamide. In an exemplary embodiment, the pharmaceutical formulation is a unit dosage form. In an exemplary embodiment, the pharmaceutical formulation is a single unit dosage form.

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulation of the invention may be administered orally, topically, intraperitoneally, parenterally, by inhalation or spray or rectally in unit dosage forms containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In an exemplary embodiment, the pharmaceutical formulation is administered orally. In an exemplary embodiment, the pharmaceutical formulation is administered intravenously. In an exemplary embodiment, the pharmaceutical formulation is administered in a topically effective dose. In an exemplary embodiment, the pharmaceutical formulation is administered in a cosmetically effective dose. In an exemplary embodiment, the pharmaceutical formulation is administered in an orally effective dose.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a unit dosage form will vary depending upon the condition being treated and the particular mode of administration. Unit dosage forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

In an exemplary embodiment, the unit dosage form contains from about 1 mg to about 800 mg of a compound of the invention. In an exemplary embodiment, the unit dosage form contains from about 1 mg to about 500 mg of an active ingredient. In an exemplary embodiment, the unit dosage form contains from about 100 mg to about 800 mg of a compound of the invention. In an exemplary embodiment, the unit dosage form contains from about 200 mg to about 500 mg of a compound of the invention. In an exemplary embodiment, the unit dosage form contains from about 500 mg to about 800 mg of a compound of the invention. In an exemplary embodiment, the unit dosage form contains from about 1 mg to about 100 mg of a compound of the invention. In an exemplary embodiment, the unit dosage form contains from about 10 mg to about 100 mg of a compound of the invention. In an exemplary embodiment, the unit dosage form contains from about 50 mg to about 100 mg of a compound of the invention. In an exemplary embodiment, the unit dosage form contains from about 25 mg to about 75 mg of a compound of the invention. In an exemplary embodiment, the unit dosage form contains from about 40 mg to about 60 mg of a compound of the invention. In an exemplary embodiment, the unit dosage form contains from about 75 mg to about 200 mg of a compound of the invention. In an exemplary embodiment, the unit dosage form contains from about 1 mg to about 5 mg of a compound of the invention. In an exemplary embodiment, the unit dosage form contains from about 10 mg to about 25 mg of a compound of the invention. In an exemplary embodiment, the unit dosage form contains from about 50 mg to about 350 mg of a compound of the invention. In an exemplary embodiment, the unit dosage form contains from about 200 mg to about 400 mg of a compound of the invention.

In an exemplary embodiment, the daily dosage contains from about 1 mg to about 800 mg of a compound of the invention. In an exemplary embodiment, the daily dosage contains from about 1 mg to about 500 mg of an active ingredient. In an exemplary embodiment, the daily dosage contains from about 100 mg to about 800 mg of a compound of the invention. In an exemplary embodiment, the daily dosage contains from about 200 mg to about 500 mg of a compound of the invention. In an exemplary embodiment, the daily dosage contains from about 500 mg to about 800 mg of a compound of the invention. In an exemplary embodiment, the daily dosage contains from about 1 mg to about 100 mg of a compound of the invention. In an exemplary embodiment, the daily dosage contains from about 10 mg to about 100 mg of a compound of the invention. In an exemplary embodiment, the daily dosage contains from about 50 mg to about 100 mg of a compound of the invention. In an exemplary embodiment, the daily dosage contains from about 75 mg to about 200 mg of a compound of the invention. In an exemplary embodiment, the daily dosage contains from about 1 mg to about 5 mg of a compound of the invention. In an exemplary embodiment, the daily dosage contains from about 10 mg to about 25 mg of a compound of the invention. In an exemplary embodiment, the daily dosage contains from about 50 mg to about 350 mg of a compound of the invention. In an exemplary embodiment, the daily dosage contains from about 200 mg to about 400 mg of a compound of the invention.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocycles may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the patient and will ultimately be at the discretion of the attendant physician or clinician.

VI. a) Testing

Preferred compounds for use in the pharmaceutical formulations described herein will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers.

Serum protein binding may be predicted from albumin binding assays. Such assays are described in a review by Oravcova et al. (1996, J. Chromat. B677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the unit dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

VI. b) Administration

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of protozoa cell growth. Such information can be used to more accurately determine useful doses in humans.

In general, the compounds prepared by the methods, and from the intermediates, described herein will be administered in a therapeutically or cosmetically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain protozoa cell growth inhibitory effects. Usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages range from 50-91 mg/m$^2$/day.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

Exemplary embodiments are summarized herein below.

In an exemplary embodiment, the invention provides a compound having a structure according to the following formula:

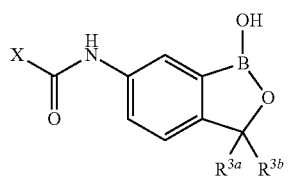

wherein X is selected from the group consisting of substituted phenyl, substituted or unsubstituted heteroaryl and unsubstituted cycloalkyl; $R^{3a}$ is selected from the group consisting of H, unsubstituted $C_1$ or $C_2$ or $C_3$ or $C_4$ or $C_5$ or $C_6$ alkyl and unsubstituted $C_3$ or $C_4$ or $C_5$ or $C_6$ cycloalkyl; $R^{3b}$ is selected from the group consisting of H, unsubstituted $C_1$ or $C_2$ or $C_3$ or $C_4$ or $C_5$ or $C_6$ alkyl and unsubstituted $C_3$ or $C_4$ or $C_5$ or $C_6$ cycloalkyl; with the proviso that $R^{3a}$ and $R^{3b}$, along with the atom to which they are attached, are optionally joined to form a 3 to 6 membered ring with the proviso that $R^{3a}$ and $R^{3b}$ cannot both be H, or a salt thereof. In an exemplary embodiment, the salt is a pharmaceutically acceptable salt.

In an exemplary embodiment, according to the above paragraph, the compound has a structure according to the following formula:

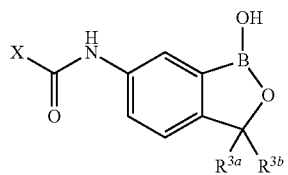

wherein X is phenyl or heteroaryl, in which one substituent on said phenyl or said heteroaryl is selected from the group consisting of halogen, cyano, nitro, unsubstituted $C_1$ or $C_2$ or $C_3$ or $C_4$ or $C_5$ or $C_6$ alkyl, unsubstituted $C_1$ or $C_2$ or $C_3$ or $C_4$ or $C_5$ or $C_6$ alkoxy, halosubstituted $C_1$ or $C_2$ or $C_3$ or $C_4$ or $C_5$ or $C_6$ alkyl, halosubstituted $C_1$ or $C_2$ or $C_3$ or $C_4$ or $C_5$ or $C_6$ alkoxy, unsubstituted $C_1$ or $C_2$ or $C_3$ or $C_4$ or $C_5$ or $C_6$ alkylthio, unsubstituted phenyl, $NR^8R^9$, —$SO_2(R^7)$ and —$SO_2N(R^7)(R^8)$, wherein $R^7$ is H or unsubstituted $C_1$ or $C_2$ or $C_3$ or $C_4$ or $C_5$ or $C_6$ alkyl; $R^8$ is H or unsubstituted $C_1$ or $C_2$ or $C_3$ or $C_4$ or $C_5$ or $C_6$ alkyl; and $R^9$ is selected from the group consisting of H, unsubstituted $C_1$ or $C_2$ or $C_3$ or $C_4$ or $C_5$ or $C_6$ alkyl and —$C(O)R^{10}$ wherein $R^{10}$ is unsubstituted $C_1$ or $C_2$ or $C_3$ or $C_4$ or $C_5$ or $C_6$ alkyl.

In an exemplary embodiment, according to any of the above paragraphs, the compound has a structure according to the following formula:

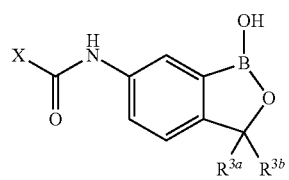

wherein X is phenyl or heteroaryl, in which one substituent on said phenyl or said heteroaryl is selected from the group consisting of F, Cl, CN, $NO_2$, —$CH_3$, —$CH_2CH_3$, $CH(CH_3)_2$, $C(CH_3)_3$, $CF_3$, —$OCH_3$, —$OCH_2CH_3$, —$OCF_3$, —$N(CH_3)_2$, —$NH(C(O)CH_3)$, —$SCH_3$, —$S(O)_2CH_3$ and —$S(O)_2N(CH_3)_2$.

In an exemplary embodiment, according to any of the above paragraphs, the compound has a structure according to the following formula:

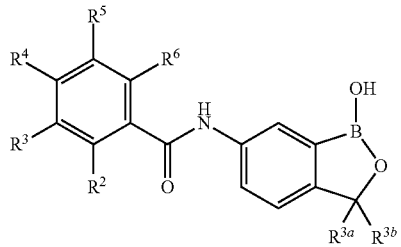

wherein $R^2$, $R^3$, $R^4$, $R^5$ and $R^6$ are the same or different and are each selected from the group consisting of H, halogen, cyano, nitro, unsubstituted $C_1$ or $C_2$ or $C_3$ or $C_4$ or $C_5$ or $C_6$ alkyl, unsubstituted $C_1$ or $C_2$ or $C_3$ or $C_4$ or $C_5$ or $C_6$ alkoxy, halosubstituted $C_1$ or $C_2$ or $C_3$ or $C_4$ or $C_5$ or $C_6$ alkyl, halosubstituted $C_1$ or $C_2$ or $C_3$ or $C_4$ or $C_5$ or $C_6$ alkoxy, unsubstituted $C_1$ or $C_2$ or $C_3$ or $C_4$ or $C_5$ or $C_6$ alkylthio, unsubstituted phenyl, $NR^8R^9$, —$SO_2(R^7)$, —$SO_2N(R^7)(R^8)$ wherein $R^7$ is H or unsubstituted $C_1$ or $C_2$ or $C_3$ or $C_4$ or $C_5$ or $C_6$ alkyl; $R^8$ is H or unsubstituted $C_1$ or $C_2$ or $C_3$ or $C_4$ or $C_5$ or $C_6$ alkyl; and $R^9$ is selected from the group consisting of H, unsubstituted $C_1$ or $C_2$ or $C_3$ or $C_4$ or $C_5$ or $C_6$ alkyl and —$C(O)R^{10}$ wherein $R^{10}$ is unsubstituted $C_1$ or $C_2$ or $C_3$ or $C_4$ or $C_5$ or $C_6$ alkyl with the proviso that $R^2$, $R^3$, $R^4$, $R^5$ and $R^6$ cannot all be H.

In an exemplary embodiment, according to any of the above paragraphs, the compound has a structure according to the following formula:

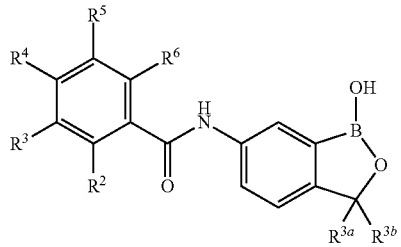

wherein $R^2$, $R^3$, $R^4$, $R^5$ and $R^6$ are the same or different and are each selected from the group consisting of H, F, Cl, CN, $NO_2$, —$CH_3$, —$CH_2CH_3$, $CH(CH_3)_2$, $C(CH_3)_3$, $CF_3$, —$OCH_3$, —$OCH_2CH_3$, —$OCF_3$, —$N(CH_3)_2$, —$NH(C(O)CH_3)$, —$SCH_3$, —$S(O)_2CH_3$, —$S(O)_2N(CH_3)_2$ with the proviso that $R^2$, $R^3$, $R^4$, $R^5$ and $R^6$ cannot all be H.

In an exemplary embodiment, according to any of the above paragraphs, the compound has a structure according to the following formula:

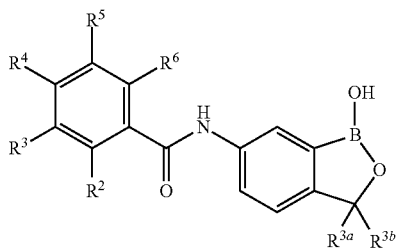

wherein one member selected from the group consisting of $R^2$, $R^3$, $R^4$, $R^5$ and $R^6$ is selected from the group consisting of halogen, cyano, nitro, unsubstituted $C_1$ or $C_2$ or $C_3$ or $C_4$ or $C_5$ or $C_6$ alkyl, unsubstituted $C_1$ or $C_2$ or $C_3$ or $C_4$ or $C_5$ or $C_6$ alkoxy, halosubstituted $C_1$ or $C_2$ or $C_3$ or $C_4$ or $C_5$ or $C_6$ alkyl, halosubstituted $C_1$ or $C_2$ or $C_3$ or $C_4$ or $C_5$ or $C_6$ alkoxy, unsubstituted $C_1$ or $C_2$ or $C_3$ or $C_4$ or $C_5$ or $C_6$ alkylthio, unsubstituted phenyl, $NR^8R^9$, —$SO_2(R^7)$, —$SO_2N(R^7)(R^8)$ wherein $R^7$ is H or unsubstituted $C_1$ or $C_2$ or $C_3$ or $C_4$ or $C_5$ or $C_6$ alkyl; $R^8$ is H or unsubstituted $C_1$ or $C_2$ or $C_3$ or $C_4$ or $C_5$ or $C_6$ alkyl; and $R^9$ is a member selected from H, unsubstituted $C_1$ or $C_2$ or $C_3$ or $C_4$ or $C_5$ or $C_6$ alkyl and —$C(O)R^{10}$ wherein $R^{10}$ is unsubstituted $C_1$ or $C_2$ or $C_3$ or $C_4$ or $C_5$ or $C_6$ alkyl, and the remaining members of $R^2$, $R^3$, $R^4$, $R^5$ and $R^6$ are H.

In an exemplary embodiment, according to any of the above paragraphs, the compound has a structure according to the following formula:

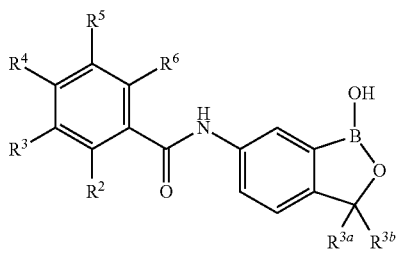

wherein one member selected from the group consisting of $R^2$, $R^3$, $R^4$, $R^5$ and $R^6$ is selected from the group consisting of F, Cl, CN, $NO_2$, —$CH_3$, —$CH_2CH_3$, $CH(CH_3)_2$, $C(CH_3)_3$, $CF_3$, —$OCH_3$, —$OCH_2CH_3$, —$OCF_3$, —$N(CH_3)_2$, —$NH(C(O)CH_3)$, —$SCH_3$, —$S(O)_2CH_3$, —$S(O)_2N(CH_3)_2$, and the remaining members of $R^2$, $R^3$, $R^4$, $R^5$ and $R^6$ are H.

In an exemplary embodiment, according to any of the above paragraphs, the compound has a structure wherein one member selected from the group consisting of $R^2$, $R^3$, $R^4$, $R^5$ and $R^6$ is selected from the group consisting of halogen, unsubstituted $C_1$ or $C_2$ or $C_3$ or $C_4$ or $C_5$ or $C_6$ alkyl and halosubstituted $C_1$ or $C_2$ or $C_3$ or $C_4$ or $C_5$ or $C_6$ alkyl, and the remaining members of $R^2$, $R^3$, $R^4$, $R^5$ and $R^6$ are H.

In an exemplary embodiment, according to any of the above paragraphs, the compound has a structure wherein one member selected from the group consisting of $R^2$, $R^3$, $R^4$, $R^5$ and $R^6$ is selected from the group consisting of F, Cl, Br, I, $CH_3$, $CF_3$ and $OCH_3$; and the remaining members of $R^2$, $R^3$, $R^4$, $R^5$ and $R^6$ are H.

In an exemplary embodiment, according to any of the above paragraphs, the compound has a structure wherein one member selected from the group consisting of $R^2$, $R^3$, $R^4$, $R^5$ and $R^6$ is selected from the group consisting of F, Cl, $CH_3$ and $CF_3$; and the remaining members of $R^2$, $R^3$, $R^4$, $R^5$ and $R^6$ are H.

In an exemplary embodiment, according to any of the above paragraphs, the compound has a structure wherein two members which are selected from the group consisting of $R^2$, $R^3$, $R^4$, $R^5$ and $R^6$ are the same or different and are each selected from halogen; and the remaining members of $R^2$, $R^3$, $R^4$, $R^5$ and $R^6$ are H.

In an exemplary embodiment, according to any of the above paragraphs, the compound has a structure wherein one member selected from the group consisting of $R^2$, $R^3$, $R^4$, $R^5$ and $R^6$ is halogen; one member selected from the group consisting of $R^2$, $R^3$, $R^4$, $R^5$ and $R^6$ is selected from the group consisting of halogen, unsubstituted $C_1$ or $C_2$ or $C_3$ or $C_4$ or $C_5$ or $C_6$ alkyl and halosubstituted $C_1$ or $C_2$ or $C_3$ or $C_4$ or $C_5$ or $C_6$ alkyl; and the remaining members of $R^2$, $R^3$, $R^4$, $R^5$ and $R^6$ are H.

In an exemplary embodiment, according to any of the above paragraphs, the compound has a structure wherein one member selected from the group consisting of $R^2$, $R^3$, $R^4$, $R^5$ and $R^6$ is halogen; one member selected from the group consisting of $R^2$, $R^3$, $R^4$, $R^5$ and $R^6$ is selected from the group consisting of F, Cl, Br, I, $CH_3$, $CF_3$ and $OCH_3$; and the remaining members of $R^2$, $R^3$, $R^4$, $R^5$ and $R^6$ are H.

In an exemplary embodiment, according to any of the above paragraphs, the compound has a structure wherein one member selected from the group consisting of $R^2$, $R^3$, $R^4$, $R^5$ and $R^6$ is F; one member selected from the group consisting of $R^2$, $R^3$, $R^4$, $R^5$ and $R^6$ is selected from the group consisting of halogen, unsubstituted $C_1$ or $C_2$ or $C_3$ or $C_4$ or $C_5$ or $C_6$ alkyl and halosubstituted $C_1$ or $C_2$ or $C_3$ or $C_4$ or $C_5$ or $C_6$ alkyl; and the remaining members of $R^2$, $R^3$, $R^4$, $R^5$ and $R^6$ are H.

In an exemplary embodiment, according to any of the above paragraphs, the compound has a structure wherein one member selected from the group consisting of $R^2$, $R^3$, $R^4$, $R^5$ and $R^6$ is F; and one member selected from the group consisting of $R^2$, $R^3$, $R^4$, $R^5$ and $R^6$ is Cl, $CH_3$ and $CF_3$; and the remaining members of $R^2$, $R^3$, $R^4$, $R^5$ and $R^6$ are H.

In an exemplary embodiment, according to any of the above paragraphs, the compound has a structure according to the following formula:

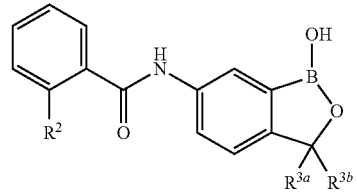

wherein $R^2$ is selected from the group consisting of halogen, cyano, nitro, unsubstituted $C_1$ or $C_2$ or $C_3$ or $C_4$ or $C_5$ or $C_6$ alkyl, unsubstituted $C_1$ or $C_2$ or $C_3$ or $C_4$ or $C_5$ or $C_6$ alkoxy, halosubstituted $C_1$ or $C_2$ or $C_3$ or $C_4$ or $C_5$ or $C_6$ alkyl, halosubstituted $C_1$ or $C_2$ or $C_3$ or $C_4$ or $C_5$ or $C_6$ alkoxy, unsubstituted $C_1$ or $C_2$ or $C_3$ or $C_4$ or $C_5$ or $C_6$ alkylthio, unsubstituted phenyl, $NR^8R^9$, —$SO_2(R^7)$ and —$SO_2N(R^7)(R^8)$ wherein $R^7$ is a H or unsubstituted $C_1$ or $C_2$ or $C_3$ or $C_4$ or $C_5$ or $C_6$ alkyl; $R^8$ is H or unsubstituted $C_1$ or $C_2$ or $C_3$ or $C_4$ or $C_5$ or $C_6$ alkyl; and $R^9$ is selected from the group consisting of H, unsubstituted $C_1$ or $C_2$ or $C_3$ or $C_4$ or $C_5$ or $C_6$ alkyl and —C(O)$R^{10}$ wherein $R^{10}$ is unsubstituted $C_1$ or $C_2$ or $C_3$ or $C_4$ or $C_5$ or $C_6$ alkyl.

In an exemplary embodiment, according to any of the above paragraphs, the compound has a structure according to the following formula:

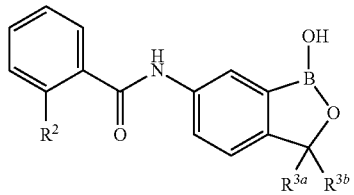

wherein $R^2$ is selected from the group consisting of halogen, unsubstituted $C_1$ or $C_2$ or $C_3$ or $C_4$ or $C_5$ or $C_6$ alkyl and halosubstituted $C_1$ or $C_2$ or $C_3$ or $C_4$ or $C_5$ or $C_6$ alkyl.

In an exemplary embodiment, according to any of the above paragraphs, the compound has a structure wherein $R^2$ is selected from the group consisting of F, Cl, $CH_3$ and $CF_3$.

In an exemplary embodiment, according to any of the above paragraphs, the compound has a structure according to the following formula:

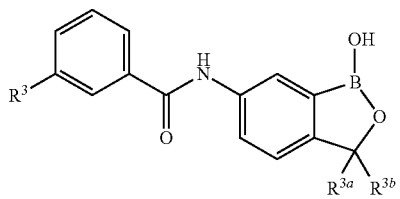

wherein $R^3$ is selected from the group consisting of halogen, cyano, nitro, unsubstituted $C_1$ or $C_2$ or $C_3$ or $C_4$ or $C_5$ or $C_6$ alkyl, unsubstituted $C_1$ or $C_2$ or $C_3$ or $C_4$ or $C_5$ or $C_6$ alkoxy, halosubstituted $C_1$ or $C_2$ or $C_3$ or $C_4$ or $C_5$ or $C_6$ alkyl, halosubstituted $C_1$ or $C_2$ or $C_3$ or $C_4$ or $C_5$ or $C_6$ alkoxy, unsubstituted $C_1$ or $C_2$ or $C_3$ or $C_4$ or $C_5$ or $C_6$ alkylthio, unsubstituted phenyl, $NR^8R^9$, —$SO_2(R^7)$ and —$SO_2N(R^7)(R^8)$ wherein $R^7$ is H or unsubstituted $C_1$ or $C_2$ or $C_3$ or $C_4$ or $C_5$ or $C_6$ alkyl; $R^8$ is H or unsubstituted $C_1$ or $C_2$ or $C_3$ or $C_4$ or $C_5$ or $C_6$ alkyl; and $R^9$ is selected from the group consisting of H, unsubstituted $C_1$ or $C_2$ or $C_3$ or $C_4$ or $C_5$ or $C_6$ alkyl and —C(O)$R^{10}$ wherein $R^{10}$ is unsubstituted $C_1$ or $C_2$ or $C_3$ or $C_4$ or $C_5$ or $C_6$ alkyl.

In an exemplary embodiment, according to any of the above paragraphs, the compound has a structure according to the following formula:

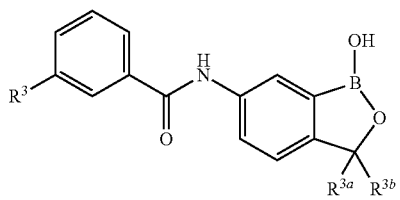

wherein $R^3$ is selected from the group consisting of halogen, unsubstituted $C_1$ or $C_2$ or $C_3$ or $C_4$ or $C_5$ or $C_6$ alkyl and halosubstituted $C_1$ or $C_2$ or $C_3$ or $C_4$ or $C_5$ or $C_6$ alkyl.

In an exemplary embodiment, according to any of the above paragraphs, the compound has a structure wherein $R^3$ is selected from the group consisting of F, Cl, $CH_3$ and $CF_3$.

In an exemplary embodiment, according to any of the above paragraphs, the compound has a structure according to the following formula:

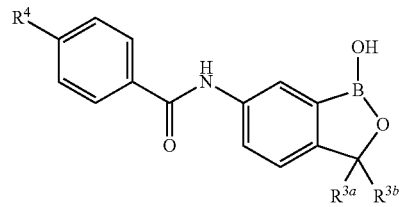

wherein $R^4$ is selected from the group consisting of halogen, cyano, nitro, unsubstituted $C_1$ or $C_2$ or $C_3$ or $C_4$ or $C_5$ or $C_6$ alkyl, unsubstituted $C_1$ or $C_2$ or $C_3$ or $C_4$ or $C_5$ or $C_6$ alkoxy, halosubstituted $C_1$ or $C_2$ or $C_3$ or $C_4$ or $C_5$ or $C_6$ alkyl, halosubstituted $C_1$ or $C_2$ or $C_3$ or $C_4$ or $C_5$ or $C_6$ alkoxy, unsubstituted $C_1$ or $C_2$ or $C_3$ or $C_4$ or $C_5$ or $C_6$ alkylthio, unsubstituted phenyl, $NR^8R^9$, —$SO_2(R^7)$ and —$SO_2N(R^7)(R^8)$ wherein $R^7$ is H or unsubstituted $C_1$ or $C_2$ or $C_3$ or $C_4$ or $C_5$ or $C_6$ alkyl; $R^8$ is H or unsubstituted $C_1$ or $C_2$ or $C_3$ or $C_4$ or $C_5$ or $C_6$ alkyl; and $R^9$ is selected from the group consisting of H, unsubstituted $C_1$ or $C_2$ or $C_3$ or $C_4$ or $C_5$ or $C_6$ alkyl and —C(O)$R^{10}$ wherein $R^{10}$ is unsubstituted $C_1$ or $C_2$ or $C_3$ or $C_4$ or $C_5$ or $C_6$ alkyl.

In an exemplary embodiment, according to any of the above paragraphs, the compound has a structure according to the following formula:

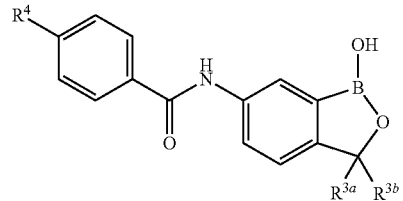

wherein $R^4$ is selected from the group consisting of halogen, unsubstituted $C_1$ or $C_2$ or $C_3$ or $C_4$ or $C_5$ or $C_6$ alkyl and halosubstituted $C_1$ or $C_2$ or $C_3$ or $C_4$ or $C_5$ or $C_6$ alkyl.

In an exemplary embodiment, according to any of the above paragraphs, the compound has a structure wherein $R^4$ is selected from the group consisting of F, Cl, $CH_3$ and $CF_3$.

In an exemplary embodiment, according to any of the above paragraphs, the compound has a structure according to the following formula:

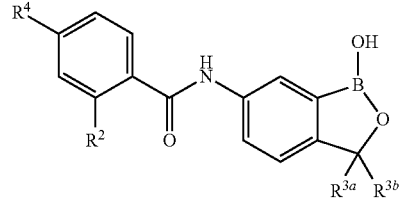

wherein $R^4$ is halogen; and $R^2$ is selected from the group consisting of halogen, cyano, nitro, unsubstituted $C_1$ or $C_2$ or $C_3$ or $C_4$ or $C_5$ or $C_6$ alkyl, unsubstituted $C_1$ or $C_2$ or $C_3$ or $C_4$ or $C_5$ or $C_6$ alkoxy, halosubstituted $C_1$ or $C_2$ or $C_3$ or $C_4$ or $C_5$ or $C_6$ alkyl, halosubstituted $C_1$ or $C_2$ or $C_3$ or $C_4$ or $C_5$ or $C_6$ alkoxy, unsubstituted $C_1$ or $C_2$ or $C_3$ or $C_4$ or $C_5$ or $C_6$ alkylthio, unsubstituted phenyl, $NR^8R^9$, —$SO_2(R^7)$ and —$SO_2N(R^7)(R^8)$ wherein $R^7$ is H or unsubstituted $C_1$ or $C_2$ or $C_3$ or $C_4$ or $C_5$ or $C_6$ alkyl; $R^8$ is H or unsubstituted $C_1$ or $C_2$ or $C_3$ or $C_4$ or $C_5$ or $C_6$ alkyl; and $R^9$ is selected from the group consisting of H, unsubstituted $C_1$ or $C_2$ or $C_3$ or $C_4$ or $C_5$ or $C_6$ alkyl and —$C(O)R^{10}$ wherein $R^{10}$ is unsubstituted $C_1$ or $C_2$ or $C_3$ or $C_4$ or $C_5$ or $C_6$ alkyl.

In an exemplary embodiment, according to any of the above paragraphs, the compound has a structure according to the following formula:

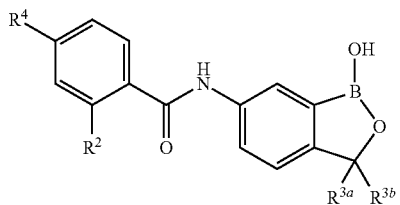

wherein $R^4$ is halogen; and $R^2$ is selected from the group consisting of F, Cl, CN, $NO_2$, —$CH_3$, —$CH_2CH_3$, $CH(CH_3)_2$, $C(CH_3)_3$, $CF_3$, —$OCH_3$, —$OCH_2CH_3$, —$OCF_3$, —$N(CH_3)_2$, —$NH(C(O)CH_3)$, —$SCH_3$, —$S(O)_2CH_3$ and —$S(O)_2N(CH_3)_2$.

In an exemplary embodiment, according to any of the above paragraphs, the compound has a structure according to the following formula:

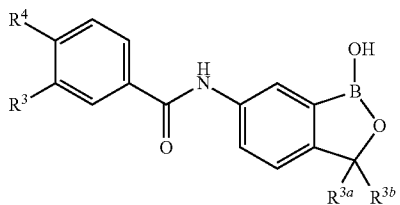

wherein $R^4$ is halogen; and $R^3$ is selected from the group consisting of H, halogen, cyano, nitro, unsubstituted $C_1$ or $C_2$ or $C_3$ or $C_4$ or $C_5$ or $C_6$ alkyl, unsubstituted $C_1$ or $C_2$ or $C_3$ or $C_4$ or $C_5$ or $C_6$ alkoxy, halosubstituted $C_1$ or $C_2$ or $C_3$ or $C_4$ or $C_5$ or $C_6$ alkyl, halosubstituted $C_1$ or $C_2$ or $C_3$ or $C_4$ or $C_5$ or $C_6$ alkoxy, unsubstituted $C_1$ or $C_2$ or $C_3$ or $C_4$ or $C_5$ or $C_6$ alkylthio, unsubstituted phenyl, $NR^8R^9$, —$SO_2(R^7)$ and —$SO_2N(R^7)(R^8)$ wherein $R^7$ is H or unsubstituted $C_1$ or $C_2$ or $C_3$ or $C_4$ or $C_5$ or $C_6$ alkyl; $R^8$ is H or unsubstituted $C_1$ or $C_2$ or $C_3$ or $C_4$ or $C_5$ or $C_6$ alkyl; and $R^9$ is selected from the group consisting of H, unsubstituted $C_1$ or $C_2$ or $C_3$ or $C_4$ or $C_5$ or $C_6$ alkyl and —$C(O)R^{10}$ wherein $R^{10}$ is unsubstituted $C_1$ or $C_2$ or $C_3$ or $C_4$ or $C_5$ or $C_6$ alkyl.

In an exemplary embodiment, according to any of the above paragraphs, the compound has a structure according to the following formula:

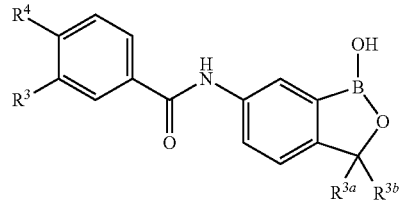

wherein $R^4$ is halogen; and $R^3$ is selected from the group consisting of F, Cl, CN, $NO_2$, —$CH_3$, —$CH_2CH_3$, $CH(CH_3)_2$, $C(CH_3)_3$, $CF_3$, —$OCH_3$, —$OCH_2CH_3$, —$OCF_3$, —$N(CH_3)_2$, —$NH(C(O)CH_3)$, —$SCH_3$, —$S(O)_2CH_3$ and —$S(O)_2N(CH_3)_2$.

In an exemplary embodiment, according to any of the above paragraphs, the compound has a structure according to the following formula:

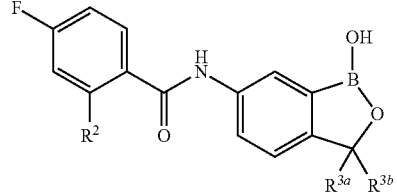

wherein $R^2$ is selected from the group consisting of H, halogen, cyano, nitro, unsubstituted $C_1$ or $C_2$ or $C_3$ or $C_4$ or $C_5$ or $C_6$ alkyl, unsubstituted $C_1$ or $C_2$ or $C_3$ or $C_4$ or $C_5$ or $C_6$ alkoxy, halosubstituted $C_1$ or $C_2$ or $C_3$ or $C_4$ or $C_5$ or $C_6$ alkyl, halosubstituted $C_1$ or $C_2$ or $C_3$ or $C_4$ or $C_5$ or $C_6$ alkoxy, unsubstituted $C_1$ or $C_2$ or $C_3$ or $C_4$ or $C_5$ or $C_6$ alkylthio, unsubstituted phenyl, $NR^8R^9$, —$SO_2(R^7)$ and —$SO_2N(R^7)(R^8)$ wherein $R^7$ is H or unsubstituted $C_1$ or $C_2$ or $C_3$ or $C_4$ or $C_5$ or $C_6$ alkyl; $R^8$ is H or unsubstituted $C_1$ or $C_2$ or $C_3$ or $C_4$ or $C_5$ or $C_6$ alkyl; and $R^9$ is selected from the group consisting of H, unsubstituted $C_1$ or $C_2$ or $C_3$ or $C_4$ or $C_5$ or $C_6$ alkyl and —$C(O)R^{10}$ wherein $R^{10}$ is unsubstituted $C_1$ or $C_2$ or $C_3$ or $C_4$ or $C_5$ or $C_6$ alkyl.

In an exemplary embodiment, according to any of the above paragraphs, the compound has a structure according to the following formula:

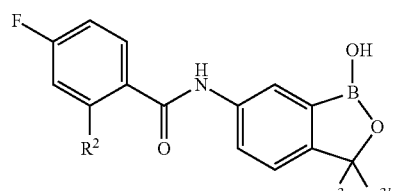

wherein $R^2$ is selected from the group consisting of F, Cl, CN, $NO_2$, —$CH_3$, —$CH_2CH_3$, $CH(CH_3)_2$, $C(CH_3)_3$, $CF_3$, —$OCH_3$, —$OCH_2CH_3$, —$OCF_3$, —$N(CH_3)_2$, —$NH(C(O)CH_3)$, —$SCH_3$, —$S(O)_2CH_3$ and —$S(O)_2N(CH_3)_2$.

In an exemplary embodiment, according to any of the above paragraphs, the compound has a structure according to the following formula:

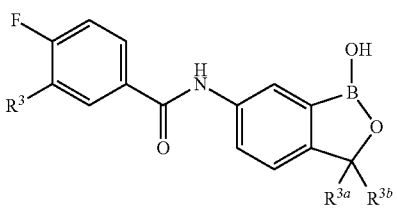

wherein R³ is selected from the group consisting of H, halogen, cyano, nitro, unsubstituted C₁ or C₂ or C₃ or C₄ or C₅ or C₆ alkyl, unsubstituted C₁ or C₂ or C₃ or C₄ or C₅ or C₆ alkoxy, halosubstituted C₁ or C₂ or C₃ or C₄ or C₅ or C₆ alkyl, halosubstituted C₁ or C₂ or C₃ or C₄ or C₅ or C₆ alkoxy, unsubstituted C₁ or C₂ or C₃ or C₄ or C₅ or C₆ alkylthio, unsubstituted phenyl, NR⁸R⁹, —SO₂(R⁷) and —SO₂N(R⁷)(R⁸) wherein R⁷ is H or unsubstituted C₁ or C₂ or C₃ or C₄ or C₅ or C₆ alkyl; R⁸ is H or unsubstituted C₁ or C₂ or C₃ or C₄ or C₅ or C₆ alkyl; and R⁹ is selected from the group consisting of H, unsubstituted C₁ or C₂ or C₃ or C₄ or C₅ or C₆ alkyl and —C(O)R¹⁰ wherein R¹⁰ is unsubstituted C₁ or C₂ or C₃ or C₄ or C₅ or C₆ alkyl.

In an exemplary embodiment, according to any of the above paragraphs, the compound has a structure according to the following formula:

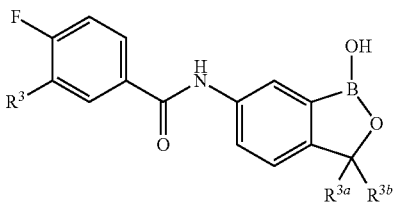

wherein R³ is selected from the group consisting of F, Cl, CN, NO₂, —CH₃, —CH₂CH₃, CH(CH₃)₂, C(CH₃)₃, CF₃, —OCH₃, —OCH₂CH₃, —OCF₃, —N(CH₃)₂, —NH(C(O)CH₃), —SCH₃, —S(O)₂CH₃ and —S(O)₂N(CH₃)₂.

In an exemplary embodiment, according to any of the above paragraphs, the compound has a structure according to the following formula:

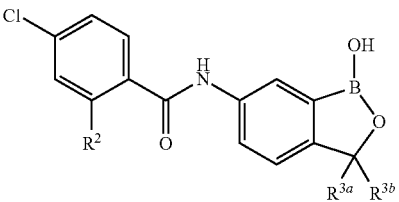

wherein R² is selected from the group consisting of H, halogen, cyano, nitro, unsubstituted C₁ or C₂ or C₃ or C₄ or C₅ or C₆ alkyl, unsubstituted C₁ or C₂ or C₃ or C₄ or C₅ or C₆ alkoxy, halosubstituted C₁ or C₂ or C₃ or C₄ or C₅ or C₆ alkyl, halosubstituted C₁ or C₂ or C₃ or C₄ or C₅ or C₆ alkoxy, unsubstituted C₁ or C₂ or C₃ or C₄ or C₅ or C₆ alkylthio, unsubstituted phenyl, NR⁸R⁹, —SO₂(R⁷) and —SO₂N(R⁷)(R⁸) wherein R⁷ is H or unsubstituted C₁ or C₂ or C₃ or C₄ or C₅ or C₆ alkyl; R⁸ is H or unsubstituted C₁ or C₂ or C₃ or C₄ or C₅ or C₆ alkyl; and R⁹ is a member selected from H, unsubstituted C₁ or C₂ or C₃ or C₄ or C₅ or C₆ alkyl and —C(O)R¹⁰ wherein R¹⁰ is unsubstituted C₁ or C₂ or C₃ or C₄ or C₅ or C₆ alkyl.

In an exemplary embodiment, according to any of the above paragraphs, the compound has a structure according to the following formula:

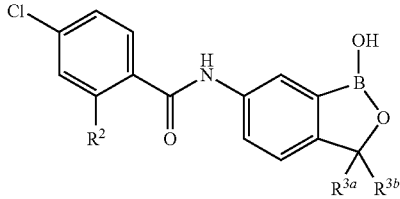

wherein R² is selected from the group consisting of F, Cl, CN, NO₂, —CH₃, —CH₂CH₃, CH(CH₃)₂, C(CH₃)₃, CF₃, —OCH₃, —OCH₂CH₃, —OCF₃, —N(CH₃)₂, —NH(C(O)CH₃), —SCH₃, —S(O)₂CH₃ and —S(O)₂N(CH₃)₂.

In an exemplary embodiment, according to any of the above paragraphs, the compound has a structure according to the following formula:

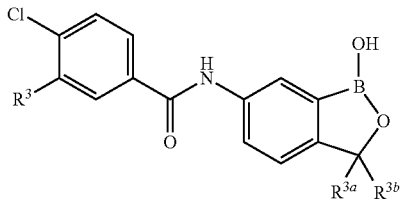

wherein R³ is selected from the group consisting of H, halogen, cyano, nitro, unsubstituted C₁ or C₂ or C₃ or C₄ or C₅ or C₆ alkyl, unsubstituted C₁ or C₂ or C₃ or C₄ or C₅ or C₆ alkoxy, halosubstituted C₁ or C₂ or C₃ or C₄ or C₅ or C₆ alkyl, halosubstituted C₁ or C₂ or C₃ or C₄ or C₅ or C₆ alkoxy, unsubstituted C₁ or C₂ or C₃ or C₄ or C₅ or C₆ alkylthio, unsubstituted phenyl, NR⁸R⁹, —SO₂(R⁷) and —SO₂N(R⁷)(R⁸) wherein R⁷ is H or unsubstituted C₁ or C₂ or C₃ or C₄ or C₅ or C₆ alkyl; R⁸ is H or unsubstituted C₁ or C₂ or C₃ or C₄ or C₅ or C₆ alkyl; and R⁹ is selected from the group consisting of H, unsubstituted C₁ or C₂ or C₃ or C₄ or C₅ or C₆ alkyl and —C(O)R¹⁰ wherein R¹⁰ is unsubstituted C₁ or C₂ or C₃ or C₄ or C₅ or C₆ alkyl.

In an exemplary embodiment, according to any of the above paragraphs, the compound has a structure according to the following formula:

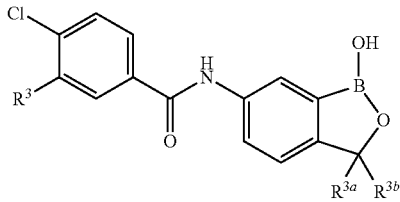

wherein R³ is selected from the group consisting of F, Cl, CN, NO₂, —CH₃, —CH₂CH₃, CH(CH₃)₂, C(CH₃)₃, CF₃, —OCH₃, —OCH₂CH₃, —OCF₃, —N(CH₃)₂, —NH(C(O)CH₃), —SCH₃, —S(O)₂CH₃ and —S(O)₂N(CH₃)₂.

In an exemplary embodiment, according to any of the above paragraphs, the compound has a structure according to the following formula:

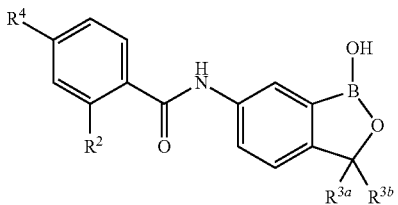

wherein $R^4$ is halogen; and $R^2$ is selected from the group consisting of Cl, $CH_3$ and $CF_3$.

In an exemplary embodiment, according to any of the above paragraphs, the compound has a structure according to the following formula:

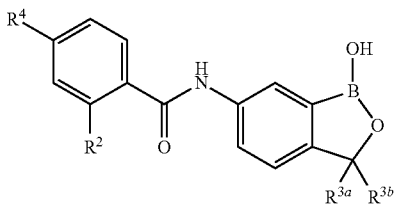

wherein $R^4$ is halogen; and $R^2$ is selected from the group consisting of halogen, unsubstituted $C_1$ or $C_2$ or $C_3$ or $C_4$ or $C_5$ or $C_6$ alkyl and halosubstituted $C_1$ or $C_2$ or $C_3$ or $C_4$ or $C_5$ or $C_6$ alkyl.

In an exemplary embodiment, according to any of the above paragraphs, the compound has a structure according to the following formula:

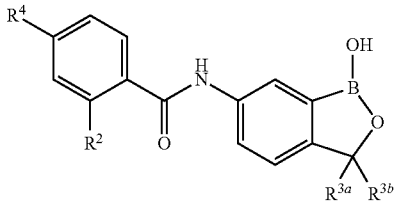

wherein $R^4$ is halogen and $R^2$ is halogen.

In an exemplary embodiment, according to any of the above paragraphs, the compound has a structure according to the following formula:

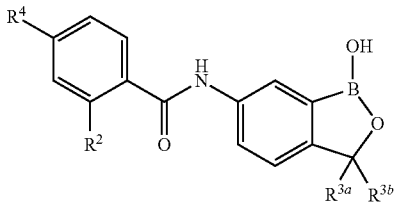

wherein $R^4$ is F; and $R^2$ is selected from the group consisting of Cl, $CH_3$ and $CF_3$.

In an exemplary embodiment, according to any of the above paragraphs, the compound has a structure according to the following formula:

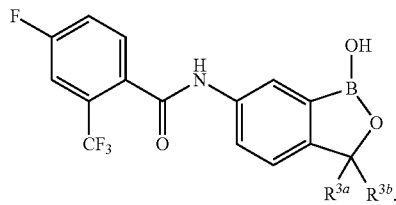

In an exemplary embodiment, according to any of the above paragraphs, the compound has a structure according to the following formula:

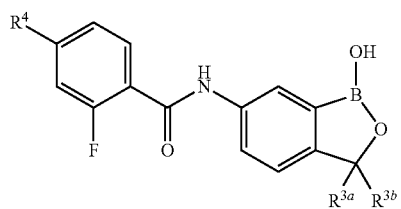

wherein $R^4$ is halogen.

In an exemplary embodiment, according to any of the above paragraphs, the compound has a structure according to the following formula:

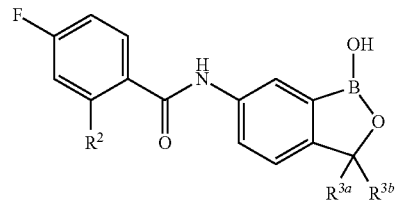

wherein $R^2$ is halogen.

In an exemplary embodiment, according to any of the above paragraphs, the compound has a structure according to the following formula:

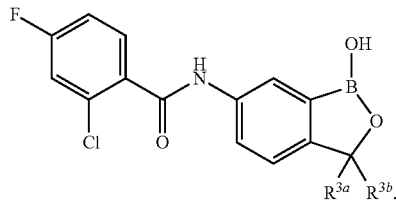

In an exemplary embodiment, according to any of the above paragraphs, the compound has a structure wherein said halosubstituted $C_1$ or $C_2$ or $C_3$ or $C_4$ or $C_5$ or $C_6$ alkyl is trifluorosubstituted $C_1$ or $C_2$ or $C_3$ or $C_4$ or $C_5$ or $C_6$ alkyl.

In an exemplary embodiment, according to any of the above paragraphs, the compound has a structure wherein said halosubstituted $C_1$ or $C_2$ or $C_3$ or $C_4$ or $C_5$ or $C_6$ alkoxy is trifluorosubstituted $C_1$ or $C_2$ or $C_3$ or $C_4$ or $C_5$ or $C_6$ alkoxy.

In an exemplary embodiment, the invention provides a compound having a structure according to the following formula:

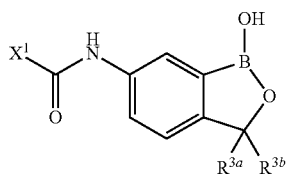

wherein $X^1$ is substituted and unsubstituted $C_1$ or $C_2$ or $C_3$ or $C_4$ or $C_5$ or $C_6$ or $C_7$ or $C_8$ or $C_9$ or $C_{10}$ alkyl; $R^{3a}$ is selected from the group consisting of H, unsubstituted $C_1$ or $C_2$ or $C_3$ or $C_4$ or $C_5$ or $C_6$ alkyl and unsubstituted $C_3$ or $C_4$ or $C_5$ or $C_6$ cycloalkyl; $R^{3b}$ is selected from the group consisting of H, unsubstituted $C_1$ or $C_2$ or $C_3$ or $C_4$ or $C_5$ or $C_6$ alkyl and unsubstituted $C_3$ or $C_4$ or $C_5$ or $C_6$ cycloalkyl; with the proviso that $R^{3a}$ and $R^{3b}$, along with the atom to which they are attached, are optionally joined to form a 3 or 4 or 5 or 6 membered ring with the proviso that $R^{3a}$ and $R^{3b}$ cannot both be H, or a salt thereof.

In an exemplary embodiment, according to the above paragraph, the compound is a structure according to the following formula:

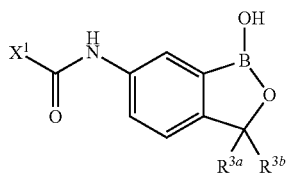

wherein $X^1$ is $C_1$ or $C_2$ or $C_3$ or $C_4$ or $C_5$ or $C_6$ or $C_7$ or $C_8$ or $C_9$ or $C_{10}$ alkyl, optionally substituted with a member selected from the group consisting of substituted or unsubstituted phenyl, hydroxy and phenylalkyloxy.

In an exemplary embodiment, according to any of the above paragraphs, the compound has a structure according to the following formula:

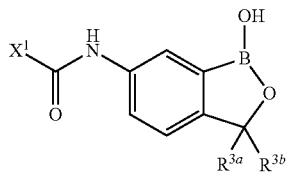

wherein $X^1$ is $C_1$ or $C_2$ or $C_3$ or $C_4$ or $C_5$ or $C_6$ or $C_7$ or $C_8$ or $C_9$ or $C_{10}$ alkyl, substituted with substituted or unsubstituted phenyl on the carbon adjacent to the carbonyl carbon.

In an exemplary embodiment, according to any of the above paragraphs, the compound has a structure according to the following formula:

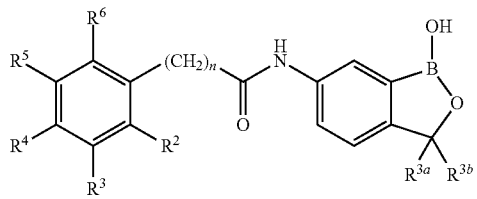

wherein n is an integer from 1 or 2 or 3 or 4 or 5 or 6; and at least one member selected from the group consisting of $R^2$, $R^3$, $R^4$, $R^5$ and $R^6$ is selected from the group consisting of halogen, cyano, nitro, unsubstituted $C_1$ or $C_2$ or $C_3$ or $C_4$ or $C_5$ or $C_6$ alkyl, unsubstituted $C_1$ or $C_2$ or $C_3$ or $C_4$ or $C_5$ or $C_6$ alkoxy, halosubstituted $C_1$ or $C_2$ or $C_3$ or $C_4$ or $C_5$ or $C_6$ alkyl, halosubstituted $C_1$ or $C_2$ or $C_3$ or $C_4$ or $C_5$ or $C_6$ alkoxy, unsubstituted $C_1$ or $C_2$ or $C_3$ or $C_4$ or $C_5$ or $C_6$ alkylthio, unsubstituted phenyl, $NR^8R^9$, $—SO_2(R^7)$ and $—SO_2N(R^7)(R^8)$, wherein $R^7$ is H or unsubstituted $C_1$ or $C_2$ or $C_3$ or $C_4$ or $C_5$ or $C_6$ alkyl; and $R^8$ is H or unsubstituted $C_1$ or $C_2$ or $C_3$ or $C_4$ or $C_5$ or $C_6$ alkyl; $R^9$ is selected from the group consisting of H, unsubstituted $C_1$ or $C_2$ or $C_3$ or $C_4$ or $C_5$ or $C_6$ alkyl and $—C(O)R^{10}$ wherein $R^{10}$ is unsubstituted $C_1$ or $C_2$ or $C_3$ or $C_4$ or $C_5$ or $C_6$ alkyl and the remaining members of $R^2$, $R^3$, $R^4$, $R^5$ and $R^6$ are H.

In an exemplary embodiment, according to any of the above paragraphs, the compound has a structure according to the following formula:

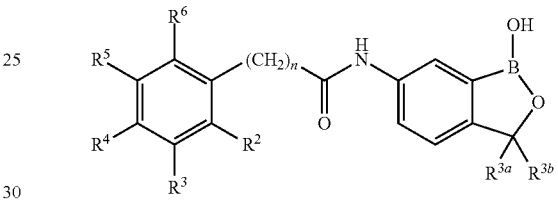

wherein n is an integer from 1 to 6; and one member selected from the group consisting of $R^2$, $R^3$, $R^4$, $R^5$ and $R^6$ is F, Cl, CN, $NO_2$, $—CH_3$, $—CH_2CH_3$, $CH(CH_3)_2$, $C(CH_3)_3$, $CF_3$, $—OCH_3$, $—OCH_2CH_3$, $—OCF_3$, $—N(CH_3)_2$, $—NH(C(O)CH_3)$, $—SCH_3$, $—S(O)_2CH_3$ and $—S(O)_2N(CH_3)_2$, and the remaining members of $R^2$, $R^3$, $R^4$, $R^5$ and $R^6$ are H.

In an exemplary embodiment, according to any of the above paragraphs, the compound has a structure according to the following formula:

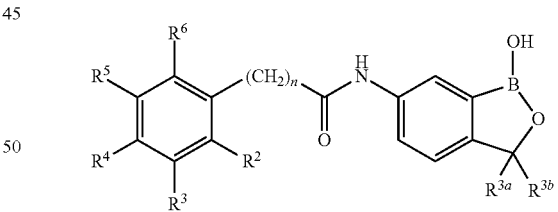

wherein one member selected from the group consisting of $R^2$, $R^3$, $R^4$, $R^5$ and $R^6$ is halogen; one member selected from the group consisting of $R^2$, $R^3$, $R^4$, $R^5$ and $R^6$ is selected from the group consisting of halogen, unsubstituted $C_1$ or $C_2$ or $C_3$ or $C_4$ or $C_5$ or $C_6$ alkyl and halosubstituted $C_1$ or $C_2$ or $C_3$ or $C_4$ or $C_5$ or $C_6$ alkyl; and the remaining members of $R^2$, $R^3$, $R^4$, $R^5$ and $R^6$ are H.

In an exemplary embodiment, according to any of the above paragraphs, the compound has a structure according to the following formula:

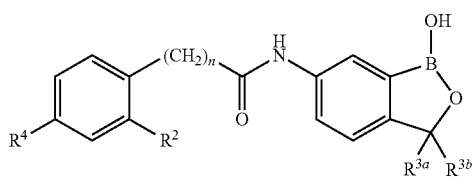

wherein $R^4$ is halogen; and $R^2$ is selected from the group consisting of halogen, unsubstituted $C_1$ or $C_2$ or $C_3$ or $C_4$ or $C_5$ or $C_6$ alkyl and halosubstituted $C_1$ or $C_2$ or $C_3$ or $C_4$ or $C_5$ or $C_6$ alkyl.

In an exemplary embodiment, according to any of the above paragraphs, the compound has a structure wherein n is 1 or n is 2.

In an exemplary embodiment, according to any of the above paragraphs, the compound has a structure wherein $R^{3a}$ is H.

In an exemplary embodiment, according to any of the above paragraphs, the compound has a structure wherein $R^{3b}$ is selected from the group consisting of $CH_3$, $CH_2CH_3$, $CH_2C(CH_3)_2$, cyclopentyl and cyclohexyl.

In an exemplary embodiment, according to any of the above paragraphs, the compound has a structure wherein $R^{3a}$ is H and $R^{3b}$ is selected from the group consisting of $CH_3$, $CH_2CH_3$, $CH_2C(CH_3)_2$, cyclopentyl and cyclohexyl.

In an exemplary embodiment, according to any of the above paragraphs, the compound has a structure wherein $R^{3a}$ and $R^{3b}$ are each the same or different and are each selected from unsubstituted $C_1$ or $C_2$ or $C_3$ or $C_4$ or $C_5$ or $C_6$ alkyl.

In an exemplary embodiment, according to any of the above paragraphs, the compound has a structure wherein $R^{3a}$ is $CH_3$ and $R^{3b}$ is unsubstituted $C_1$ or $C_2$ or $C_3$ or $C_4$ or $C_5$ or $C_6$ alkyl.

In an exemplary embodiment, according to any of the above paragraphs, the compound has a structure wherein $R^{3a}$ is $CH_3$ and $R^{3b}$ is selected from the group consisting of $CH_3$, $CH_2CH_3$, $CH_2C(CH_3)_2$, cyclopentyl and cyclohexyl.

In an exemplary embodiment, according to any of the above paragraphs, the compound has a structure wherein $R^{3a}$ is $CH_3$ and $R^{3b}$ is $CH_3$.

In an exemplary embodiment, according to any of the above paragraphs, the compound has a structure wherein $R^{3a}$ and $R^{3b}$ are combined to form cyclobutyl or cyclopentyl.

In an exemplary embodiment, according to any of the above paragraphs, the compound has a structure according to the following formula:

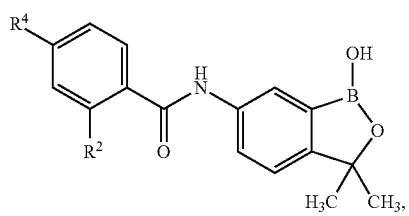

or a salt thereof.

In an exemplary embodiment, according to any of the above paragraphs, the compound is

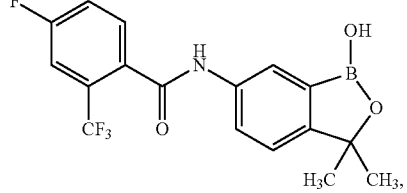

or a salt thereof.
In an exemplary embodiment, the salt is a pharmaceutically acceptable salt. In an exemplary embodiment, the pharmaceutically acceptable salt is a potassium salt of the compound.

In an exemplary embodiment, according to any of the above paragraphs, the compound is

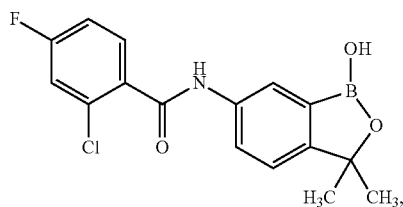 [SMILES: CC1(C)OB(O)c2cc(NC(=O)c3ccc(F)cc3Cl)ccc21]

or a salt thereof.
In an exemplary embodiment, the salt is a pharmaceutically acceptable salt. In an exemplary embodiment, the pharmaceutically acceptable salt is a potassium salt of the compound.

In an exemplary embodiment, according to any of the above paragraphs, the compound has a structure which is

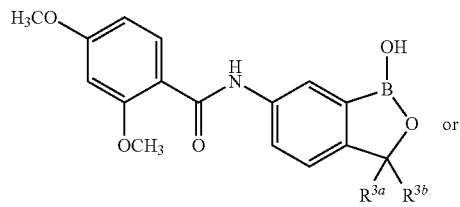

or

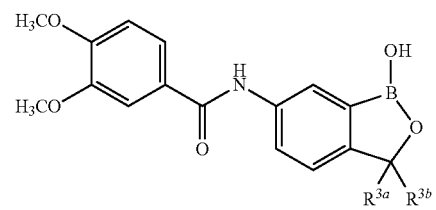

or a salt thereof. In an exemplary embodiment, the salt is a pharmaceutically acceptable salt. In an exemplary embodiment, the pharmaceutically acceptable salt is a potassium salt of the compound.

In an exemplary embodiment, according to any of the above paragraphs, the compound has a structure which is

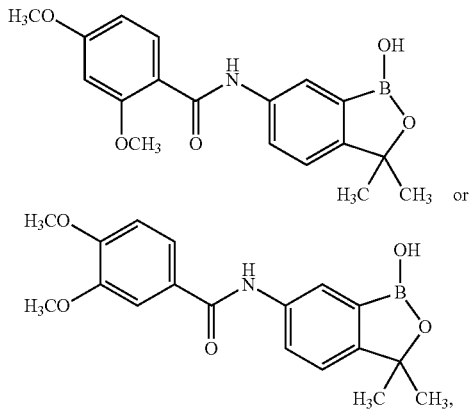

or a salt thereof. In an exemplary embodiment, the salt is a pharmaceutically acceptable salt. In an exemplary embodiment, the pharmaceutically acceptable salt is a potassium salt of the compound.

In an exemplary embodiment, the invention provides a combination comprising the compound according to any of the above paragraphs, together with at least one other therapeutically active agent.

In an exemplary embodiment, the invention provides a pharmaceutical formulation comprising: a) the compound according to any of the above paragraphs, or a salt thereof; and b) a pharmaceutically acceptable excipient.

In an exemplary embodiment, according to any of the above paragraphs, the pharmaceutical formulation is a unit dosage form.

In an exemplary embodiment, according to any of the above paragraphs, the salt of the compound according to any of the above paragraphs is a pharmaceutically acceptable salt.

In an exemplary embodiment, the invention provides a method of killing and/or preventing the growth of a protozoa, comprising: contacting the protozoa with an effective amount of the compound of the invention, thereby killing and/or preventing the growth of the protozoa.

In an exemplary embodiment, according to any of the above paragraphs, the compound has a structure described herein.

In an exemplary embodiment, according to any of the above paragraphs, the protozoa is a member of the trypanosome genus.

In an exemplary embodiment, according to any of the above paragraphs, the protozoa is a member of the *leishmania* genus.

In an exemplary embodiment, according to any of the above paragraphs, the protozoa is *Trypanosoma brucei*.

In an exemplary embodiment, according to any of the above paragraphs, the *Trypanosoma brucei* is selected from the group consisting of *Trypanosoma brucei brucei, Trypanosoma brucei gambiense* and *Trypanosoma brucei rhodesiense*.

In an exemplary embodiment, according to any of the above paragraphs, the protozoa is selected from the group consisting of *Leishmania donovani, Leishmania infantum, Leishmania chagasi, Leishmania mexicana, Leishmania amazonensis, Leishmania venezuelensis, Leishmania tropica, Leishmania major* and *Leishmania aethiopica*.

In an exemplary embodiment, according to any of the above paragraphs, the protozoa is *Leishmania donovani*.

In an exemplary embodiment, the invention provides a method of treating and/or preventing a disease in an animal, comprising: administering to the animal a therapeutically effective amount of the compound of the invention, thereby treating and/or preventing the disease.

In an exemplary embodiment, according to any of the above paragraphs, the compound has a structure described herein.

In an exemplary embodiment, according to any of the above paragraphs, the disease is African sleeping sickness.

In an exemplary embodiment, according to any of the above paragraphs, the disease is leishmaniasis.

In an exemplary embodiment, according to any of the above paragraphs, the leishmaniasis is selected from the group consisting of visceral leishmaniasis, cutaneous leishmaniasis, diffuse cutaneous leishmaniasis and mucocutaneous leishmaniasis.

In an exemplary embodiment, according to any of the above paragraphs, the leishmaniasis is visceral leishmaniasis.

In an exemplary embodiment, according to any of the above paragraphs, the leishmaniasis is cutaneous leishmaniasis.

In an exemplary embodiment, according to any of the above paragraphs, the animal is a human.

In an exemplary embodiment, according to any of the above paragraphs, the invention is a use of a compound of the invention or a combination of the invention in the manufacture of a medicament for the treatment and/or prophylaxis of protozoal infection.

The invention is further illustrated by the Examples that follow. The Examples are not intended to define or limit the scope of the invention.

EXAMPLES

The following Examples illustrate the synthesis of representative compounds used in the invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the invention are possible in view of the teachings herein and, therefore, are within the scope of the invention.

All temperatures are given in degrees Centigrade. Room temperature means 20 to 25° C. Reagents were purchased from commercial sources or prepared following standard literature procedures. Unless otherwise noted, reactions were carried out under a positive pressure of nitrogen. Reaction vessels were sealed with either rubber septa or Teflon screw caps. Nitrogen was introduced through Tygon tubing, fitted with a large bore syringe needle. Concentration under vacuum refers to the removal of solvent on a Büchi Rotary Evaporator.

Analytical HPLC was performed using a Supelco discovery $C_{18}$ 15 cm×4.6 mm/5 μm column coupled with an Agilent 1050 series VWD UV detector at 210 nm. Conditions: Solvent A: $H_2O$/1% acetonitrile/0.1% $HCO_2H$; Solvent B: methanol.

Proton magnetic resonance ($^1H$ NMR) spectra were recorded on a Varian INOVA NMR spectrometer [400 MHz ($^1H$) or 500 MHz ($^1H$)]. All spectra were determined in the solvents indicated. Although chemical shifts are reported in ppm downfield of tetramethylsilane, they are referenced to the residual proton peak of the respective solvent peak for $^1$H NMR. Interproton coupling constants are reported in Hertz (Hz).

LCMS spectra were obtained using a ThermoFinnigan AQA MS ESI instrument utilizing a Phenomenex Aqua 5 micron $C_{18}$ 125 Å 50×4.60 mm column. The spray setting for the MS probe was at 350 µL/min with a cone voltage at 25 mV and a probe temperature at 450° C. The spectra were recorded using ELS and UV (254 nm) detection. Alternatively, LCMS spectra were obtained using an Agilent 1200SL HPLC equipped with a 6130 mass spectrometer operating with electrospray ionization.

Silica gel chromatography was carried out on either a Teledyne ISCO CombiFlash Companion or Companion Rf Flash Chromatography System with a variable flow rate from 5-100 mL/min. The columns used were Teledyne ISCO RediSep Disposable Flash Columns (4, 12, 40, 80, or 120 g prepacked silica gel), which were run with a maximum capacity of 1 g crude sample per 10 g silica gel. Samples were preloaded on Celite in Analogix Sample Loading Cartridges with fits (1/in, 1/out). The eluent was 0-100% EtOAc in heptane or 0-10% MeOH in $CH_2Cl_2$ as a linear gradient over the length of the run (14-20 minutes). Peaks were detected by variable wavelength UV absorption (200-360 nm). The resulting fractions were analyzed, combined as appropriate, and evaporated under reduced pressure to provide purified material.

Example 1

1 4-Fluoro-N-(1-hydroxy-3-methyl-1,3-dihydro-benzo[c][1,2]oxaborol-6-yl-2-trifluoromethyl benzamide

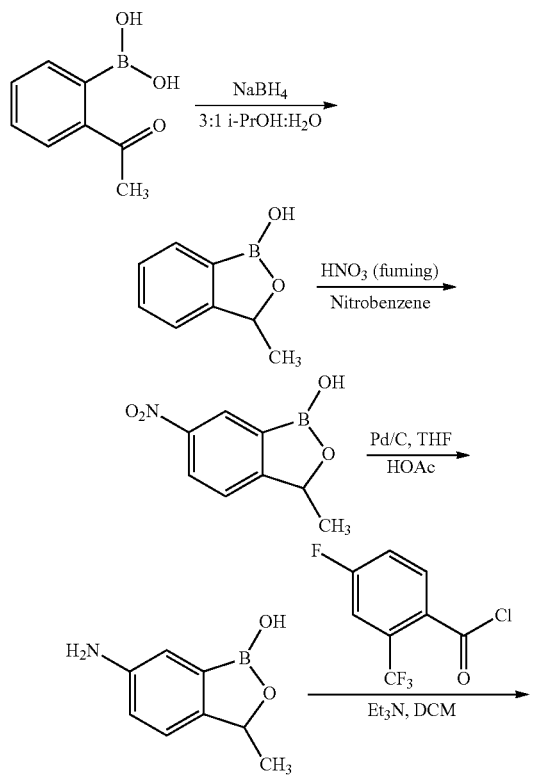

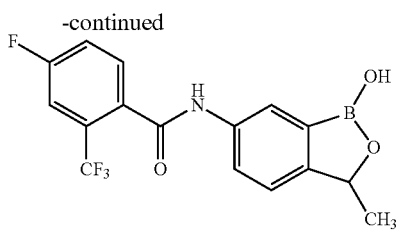

To a solution of 2-acetylphenylboronic acid (1.00 g, 6.1 mmol) in 40 ml 3:1 i-PrOH:$H_2O$, sodium borohydride (941.0 mg, 24.3 mmol 4.0 eq.) was added in portions. The reaction solution was allowed to stir for 2.5 hrs at room temperature then the reaction was quenched by dropwise addition of 6M HCl until gas evolution ceased and the reaction mixture reach pH=1-2. Once the pH was established, the aqueous solution was allowed to stir for an additional 0.5 hr. The aqueous solution was then extracted with DCM and the combined DCM extracts were dried over $Na_2SO_4$. The DCM was evaporated and the remaining clear, colorless oil was subjected to $SiO_2$ chromatography using 3:7 EtOAc:heptane as the eluent. The desired product was recovered as clear, colorless, thick oil. Amount obtained, 741 mg, (82% yield).

To 4.0 ml fuming $HNO_3$ at −45° C. was added a solution of 3-methyl-3H-benzo[c][1,2]oxaborol-1-ol (616 mg, 4.1 mmol) in 1.0 ml nitrobenzene slowly via a syringe while maintaining the reaction temperature between −40 to −45° C. Once the addition was complete the resulting solution was allowed to stir at −45° C. for an additional 45 min before poured into crushed ice (20 g). The ice mixture was allowed to melt and the aqueous solution was extracted with dichloromethane. The combined dichloromethane extracts were dried over $Na_2SO_4$ then evaporated. The crude oil remaining was mixed with one liter 1:1 DCM:heptane. The volume of the solution was reduced on a rotovap by half and the resulting solution was allowed to stand overnight in a −20° C. freezer overnight. The precipitate formed was filtered out, washed with heptanes and vacuum dried to give the titled compound as a white solid. $^1$H NMR (DMSO-$d_6$) δ: 9.49 (br. s., 1H), 8.53 (d, J=2.2 Hz, 1H), 8.30 (dd, J=8.4, 2.3 Hz, 1H), 7.67 (d, J=8.4 Hz, 1H), 5.33 (q, J=6.7 Hz, 1H), 1.43 (d, J=6.7 Hz, 3H). Amount obtained: 612.0 mg (75% yield).

To a solution of 3-methyl-6-nitro-3H-benzo[c][1.2]oxaborol-1-ol (1.33 g, 6.8 mmol) in THF (30 mL) was added HOAc (3.0 mL, 53 mmol). The vessel was vacuum/$N_2$ purged three times and 5% Pd/C (200 mg) was added. The mixture was again vacuum/$N_2$ purged three times then vacuum purged again. $H_2$ was then introduced from a balloon and the reaction was allowed to stir for 2.5 hours. The reaction solution was filtered through a short pad of celite and the filtrate was evaporated to yield the title compound as a dark brown foamy solid $^1$H NMR (DMSO-$d_6$) δ: 8.79 (s, 1H), 6.99 (d, J=8.1 Hz, 1H), 6.82 (d, J=2.0 Hz, 1H), 6.66 (dd, J=8.1, 2.2 Hz, 1H), 5.02 (q, J=6.4 Hz, 1H), 4.95 (br. s, 2H), 1.28 (d, J=6.4 Hz, 3H). Amount obtained: 1.16 g (76%).

To a solution of 6-amino-3-methyl-3H-benzo[c][1,2]oxaborol-1-ol acetate salt (102 mg, 0.46 mmol) in DCM (2 mL) was added $Et_3N$ (128.5 µL, 0.92 mmol). The mixture was cooled to 0° C. and the 2-trifluoromethyl-4-fluorobenzoyl chloride (77.0 µL, 0.51 mmol) was added slowly via a syringe. The resulting solution was allowed to warm to room temperature gradually and stir for 2 hours. The reaction solution was diluted with DCM, washed with 1N HCl, $H_2O$ and then dried over $Na_2SO_4$, filtered and the filtrate was concentrated under reduced pressure and the crude material was subjected to flash chromatography (Isco Companion, 4 g $SiO_2$ cartridge, $SiO_2$ solid load, neat heptanes to neat EtOAc gradient over 45 min, flow rate=18 ml/min). The title compound was recovered as a white solid: LCMS (M/Z): 354 (M+H); $^1$H NMR (DMSO-$d_6$) δ: 10.57 (s, 1H), 9.15 (s, 1H), 8.06 (d, J=1.8 Hz, 1H), 7.75-7.80 (m, 2H), 7.61-7.70 (m, 2H), 7.35 (d, J=8.2 Hz, 1H), 5.17 (q, J=6.5 Hz, 1H), 1.37 (d, J=6.5 Hz, 3H). Amount obtained: 98.3 mg (61%).

2 N-(1-Hydroxy-3-methyl-1,3-dihydro-benzo[c][1,2]oxaborol-6-yl)-2-trifluoromethyl-benzamide

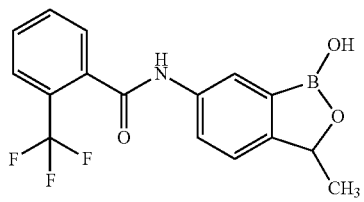 [SMILES: CC1OB(O)c2cc(NC(=O)c3ccccc3C(F)(F)F)ccc21]

The title compound was prepared using a procedure similar to that of 4-fluoro-N-(1-hydroxy-3-methyl-1,3-dihydro-benzo[c][1,2]oxaborol-6-yl-2-trifluoromethyl benzamide with 2-trifluoromethyl-benzoyl chloride replacing 2-trifluoromethyl-4-fluorobenzoyl chloride. Data: LCMS (M/Z): 336 (M+H); $^1$H NMR (DMSO-$d_6$) δ: 10.55 (s, 1H), 8.08 (d, J=1.8 Hz, 1H), 7.83 (d, J=7.6 Hz, 1H), 7.75-7.81 (m, 1H), 7.67-7.73 (m, 2H), 7.64 (dd, J=8.2, 2.0 Hz, 1H), 7.35 (d, J=8.2 Hz, 1H), 5.17 (q, J=6.5 Hz, 1H), 1.37 (d, J=6.5 Hz, 3H).

3 4-Fluoro-N-(1-hydroxy-3-methyl-1,3-dihydro-benzo[c][1,2]oxaborol-6-yl)-benzamide

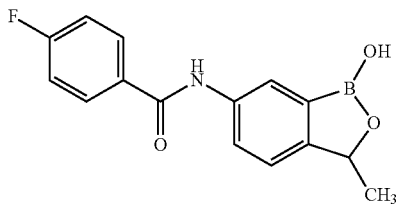

The title compound was prepared using a procedure similar to that of 4-fluoro-N-(1-hydroxy-3-methyl-1,3-dihydro-benzo[c][1,2]oxaborol-6-yl-2-trifluoromethyl benzamide with 4-fluorobenzoyl chloride replacing 2-trifluoromethyl-4-fluorobenzoyl chloride. Data: LCMS (M/Z): 286 (M+H); $^1$H NMR (DMSO-$d_6$) δ: 10.28 (s, 1H), 9.12 (s, 1H), 8.09 (d, J=1.9 Hz, 1H), 7.98-8.06 (m, 3H), 7.73 (dd, J=8.2, 2.0 Hz, 1H), 7.34-7.37 (m, 2H), 5.17 (q, J=6.5 Hz, 1H), 1.38 (d, J=6.5 Hz, 3H).

4 2-Chloro-N-(1-hydroxy-3-methyl-1,3-dihydro-benzo[c][1,2]oxaborol-6-yl)-benzamide

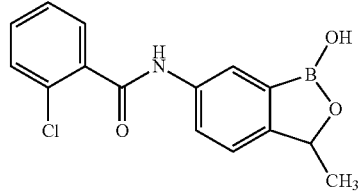 [SMILES: CC1OB(O)c2cc(NC(=O)c3ccccc3Cl)ccc21]

The title compound was prepared using a procedure similar to that of 4-fluoro-N-(1-hydroxy-3-methyl-1,3-dihydro-benzo[c][1,2]oxaborol-6-yl-2-trifluoromethyl benzamide with 2-chlorobenzoyl chloride replacing 2-trifluoromethyl-4-fluorobenzoyl chloride. Data: LCMS (M/Z): 302 (M+H); $^1$H NMR (DMSO-$d_6$) δ: 10.50 (s, 1H), 9.15 (s, 1H), 8.10 (d, J=1.8 Hz, 1H), 7.68 (dd, J=8.2, 2.0 Hz, 1H), 7.53-7.57 (m, 1H), 7.42-7.51 (m, 2H), 7.35 (d, J=8.2 Hz, 1H), 5.17 (q, J=6.5 Hz, 1H), 1.37 (d, J=6.6 Hz, 3H).

5 N-(1-Hydroxy-3-methyl-1,3-dihydro-benzo[c][1,2]oxaborol-6-yl)-4-methoxy-benzamide

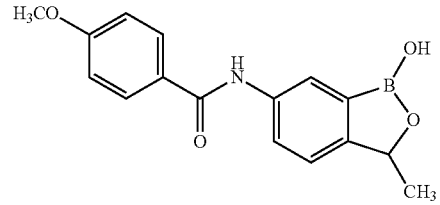

The title compound was prepared using a procedure similar to that of 4-fluoro-N-(1-hydroxy-3-methyl-1,3-dihydro-benzo[c][1,2]oxaborol-6-yl-2-trifluoromethyl benzamide with 4-methoxybenzoyl chloride replacing 2-trifluoromethyl-4-fluorobenzoyl chloride. Data: LCMS (M/Z): 298 (M+H); $^1$H NMR (DMSO-$d_6$) δ: 10.10 (s, 1H), 9.10 (s, 1H), 8.09 (d, J=1.8 Hz, 1H), 7.94-7.97 (m, 2H), 7.73 (dd, J=8.2, 2.0 Hz, 1H), 7.34 (d, J=8.2 Hz, 1H), 7.03-7.06 (m, 2H), 5.17 (q, J=6.5 Hz, 1H), 1.37 (d, J=6.5 Hz, 3H).

6 N-(1-Hydroxy-3-methyl-1,3-dihydro-benzo[c][1,2]oxaborol-6-yl)-3-methoxy-benzamide

The title compound was prepared using a procedure similar to that of 4-fluoro-N-(1-hydroxy-3-methyl-1,3-dihydro-benzo[c][1,2]oxaborol-6-yl-2-trifluoromethyl benzamide with 3-methoxybenzoyl chloride replacing 2-trifluoromethyl-4-fluorobenzoyl chloride. Data: LCMS (M/Z): 298

(M+H); ¹H NMR (DMSO-d₆) δ: 10.21 (s, 1H), 9.10 (s, 1H), 8.04-8.09 (m, 1H), 7.72 (dd, J=8.2, 2.0 Hz, 1H), 7.45-7.53 (m, 2H), 7.38-7.44 (m, 1H), 7.33 (d, J=8.2 Hz, 1H), 7.10-7.14 (m, 1H), 5.16 (q, J=6.5 Hz, 1H), 3.80 (s, 3H), 1.36 (d, J=6.5 Hz, 3H).

7 N-(1-Hydroxy-3-methyl-1,3-dihydro-benzo[c][1,2]oxaborol-6-yl)-4-methyl-benzamide

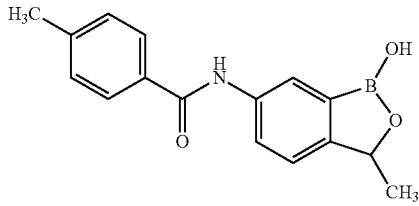 [SMILES: Cc1ccc(C(=O)Nc2ccc3c(c2)B(O)OC3C)cc1]

The title compound was prepared using a procedure similar to that of 4-fluoro-N-(1-hydroxy-3-methyl-1,3-dihydro-benzo[c][1,2]oxaborol-6-yl-2-trifluoromethyl benzamide with 4-methylbenzoyl chloride replacing 2-trifluoromethyl-4-fluorobenzoyl chloride. Data: LCMS (M/Z): 282 (M+H); ¹H NMR (DMSO-d₆) δ: 10.15 (s, 1H), 9.09 (s, 1H), 8.08 (d, J=1.8 Hz, 1H), 7.85 (d, J=8.2 Hz, 2H), 7.72 (dd, J=8.2, 2.0 Hz, 1H), 7.26-7.35 (m, 3H), 5.15 (q, J=6.5 Hz, 1H), 2.35 (s, 3H), 1.36 (d, J=6.5 Hz, 3H).

8 2-Fluoro-N-(1-hydroxy-3-methyl-1,3-dihydro-benzo[c][1,2]oxaborol-6-yl)-benzamide

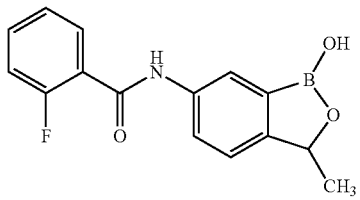 [SMILES: CC1OB(O)c2cc(NC(=O)c3ccccc3F)ccc21]

The title compound was prepared using a procedure similar to that of 4-fluoro-N-(1-hydroxy-3-methyl-1,3-dihydro-benzo[c][1,2]oxaborol-6-yl-2-trifluoromethyl benzamide with 2-fluorobenzoyl chloride replacing 2-trifluoromethyl-4-fluorobenzoyl chloride. Data: LCMS (M/Z): 286 (M+H); ¹H NMR (DMSO-d₆) δ: 10.39 (s, 1H), 9.13 (s, 1H), 8.03-8.10 (m, 1H), 7.68 (dd, J=8.2, 1.8 Hz, 1H), 7.63 (td, J=7.5, 1.6 Hz, 1H), 7.50-7.58 (m, 1H), 7.24-7.37 (m, 3H), 5.15 (q, J=6.5 Hz, 1H), 1.35 (d, J=6.5 Hz, 3H).

9 4-Chloro-N-(1-hydroxy-3-methyl-1,3-dihydro-benzo[c][1,2]oxaborol-6-yl)-benzamide

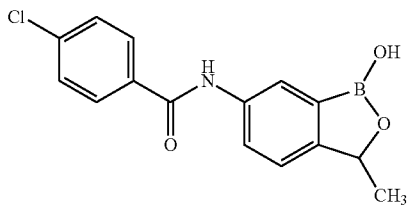 [SMILES: CC1OB(O)c2cc(NC(=O)c3ccc(Cl)cc3)ccc21]

The title compound was prepared using a procedure similar to that of 4-fluoro-N-(1-hydroxy-3-methyl-1,3-dihydro-benzo[c][1,2]oxaborol-6-yl-2-trifluoromethyl benzamide with 4-chlorobenzoyl chloride replacing 2-trifluoromethyl-4-fluorobenzoyl chloride. Data: LCMS (M/Z): 302 (M+H); ¹H NMR (DMSO-d₆) δ: 10.31 (s, 1H), 9.11 (s, 1H), 8.08 (d, J=1.9 Hz, 1H), 7.93-7.99 (m, 2H), 7.71 (dd, J=8.2, 2.0 Hz, 1H), 7.55-7.60 (m, 2H), 7.34 (d, J=8.2 Hz, 1H), 5.16 (q, J=6.5 Hz, 1H), 1.36 (d, J=6.6 Hz, 3H).

10 3-Fluoro-N-(1-hydroxy-3-methyl-1,3-dihydro-benzo[c][1,2]oxaborol-6-yl)-benzamide

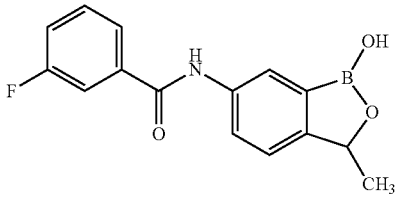 [SMILES: CC1OB(O)c2cc(NC(=O)c3cccc(F)c3)ccc21]

The title compound was prepared using a procedure similar to that of 4-fluoro-N-(1-hydroxy-3-methyl-1,3-dihydro-benzo[c][1,2]oxaborol-6-yl-2-trifluoromethyl benzamide with 3-fluorobenzoyl chloride replacing 2-trifluoromethyl-4-fluorobenzoyl chloride. Data: LCMS (M/Z): 286 (M+H); ¹H NMR (DMSO-d₆) δ: 10.31 (s, 1H), 9.09-9.15 (m, 1H), 8.08 (d, J=1.8 Hz, 1H), 7.77-7.81 (m, 1H), 7.69-7.76 (m, 2H), 7.57-7.59 (m, 1H), 7.56 (d, J=5.8 Hz, 1H), 7.38-7.44 (m, 1H), 7.34 (d, J=8.2 Hz, 1H), 5.16 (q, J=6.6 Hz, 1H), 1.36 (d, J=6.6 Hz, 3H).

11 3-Chloro-N-(1-hydroxy-3-methyl-1,3-dihydro-benzo[c][1,2]oxaborol-6-yl)-benzamide

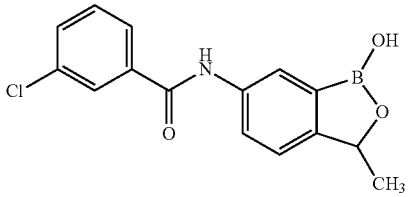 [SMILES: CC1OB(O)c2cc(NC(=O)c3cccc(Cl)c3)ccc21]

The title compound was prepared using a procedure similar to that of 4-fluoro-N-(1-hydroxy-3-methyl-1,3-dihydro-benzo[c][1,2]oxaborol-6-yl-2-trifluoromethyl benzamide with 3-chlorobenzoyl chloride replacing 2-trifluoromethyl-4-fluorobenzoyl chloride. Data: LCMS (M/Z): 302 (M+H); ¹H NMR (DMSO-d₆) δ: 10.34 (s, 1H), 9.12 (s, 1H), 8.08 (d, J=1.9 Hz, 1H), 7.98 (t, J=1.8 Hz, 1H), 7.89 (dt, J=7.8, 1.3 Hz, 1H), 7.71 (dd, J=8.2, 2.0 Hz, 1H), 7.60-7.65 (m, 1H), 7.55 (d, J=7.9 Hz, 1H), 7.34 (d, J=8.2 Hz, 1H), 5.16 (q, J=6.5 Hz, 1H), 1.36 (d, J=6.6 Hz, 3H).

12 2,4-Difluoro-N-(1-hydroxy-3-methyl-1,3-dihydro-benzo[c][1,2]oxaborol-6-yl)-benzamide

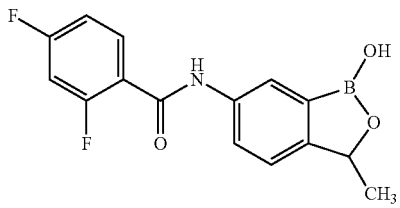 [SMILES: CC1OB(O)c2cc(NC(=O)c3ccc(F)cc3F)ccc21]

The title compound was prepared using a procedure similar to that of 4-fluoro-N-(1-hydroxy-3-methyl-1,3-dihydro-benzo[c][1,2]oxaborol-6-yl-2-trifluoromethyl benzamide with 2,4-difluorobenzoyl chloride replacing 2-trifluoromethyl-4-fluorobenzoyl chloride. Data: LCMS (M/Z): 304 (M+H); $^1$H NMR (DMSO-$d_6$) δ: 10.39 (s, 1H), 9.13 (s, 1H), 8.02-8.07 (m, 1H), 7.72 (dd, J=8.3, 1.6 Hz, 1H), 7.68 (dd, J=7.7, 5.9 Hz, 1H), 7.36-7.42 (m, 1H), 7.33 (d, J=8.2 Hz, 1H), 7.19 (td, J=8.5, 2.5 Hz, 1H), 5.15 (q, J=6.5 Hz, 1H), 1.35 (d, J=6.5 Hz, 3H).

13 2-Chloro-4-fluoro-N-(1-hydroxy-3-methyl-1,3-dihydro-benzo[c][1,2]oxaborol-6-yl)-benzamide

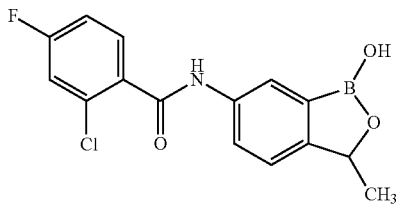

The title compound was prepared using a procedure similar to that of 4-fluoro-N-(1-hydroxy-3-methyl-1,3-dihydro-benzo[c][1,2]oxaborol-6-yl-2-trifluoromethyl benzamide with 4-fluoro-2-chlorobenzoyl chloride replacing 2-trifluoromethyl-4-fluorobenzoyl chloride. Data: LCMS (M/Z): 320 (M+H); $^1$H NMR (DMSO-$d_6$) δ: 10.49 (s, 1H), 9.13 (s, 1H), 8.06 (d, J=1.8 Hz, 1H), 7.63-7.69 (m, 2H), 7.55 (dd, J=9.0, 2.5 Hz, 1H), 7.28-7.37 (m, 2H), 5.15 (q, J=6.5 Hz, 1H), 1.35 (d, J=6.5 Hz, 3H).

14 2-Bromo-N-(1-hydroxy-3-methyl-1,3-dihydro-benzo[c][1,2]oxaborol-6-yl)-benzamide

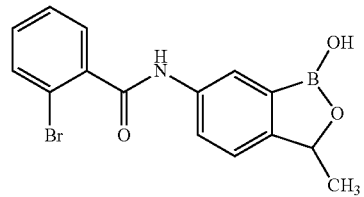

The title compound was prepared using a procedure similar to that of 4-fluoro-N-(1-hydroxy-3-methyl-1,3-dihydro-benzo[c][1,2]oxaborol-6-yl-2-trifluoromethyl benzamide with 2-bromobenzoyl chloride replacing 2-trifluoromethyl-4-fluorobenzoyl chloride. Data: LCMS (M/Z): 347 (M+H); $^1$H NMR (DMSO-$d_6$) δ: 10.46 (s, 1H), 9.13 (s, 1H), 8.08 (d, J=1.8 Hz, 1H), 7.66-7.71 (m, 2H), 7.65 (d, J=2.0 Hz, 1H), 7.51 (d, J=1.8 Hz, 1H), 7.46 (td, J=7.4, 1.0 Hz, 1H), 7.39 (dd, J=7.8, 1.8 Hz, 1H), 7.33 (d, J=8.2 Hz, 1H), 5.15 (q, J=6.5 Hz, 1H), 1.35 (d, J=6.5 Hz, 3H).

15 N-(1-Hydroxy-3-methyl-1,3-dihydro-benzo[c][1,2]oxaborol-6-yl)-2-iodo-benzamide

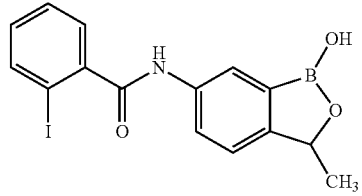 [SMILES: CC1OB(O)c2cc(NC(=O)c3ccccc3I)ccc21]

The title compound was prepared using a procedure similar to that of 4-fluoro-N-(1-hydroxy-3-methyl-1,3-dihydro-benzo[c][1,2]oxaborol-6-yl-2-trifluoromethyl benzamide with 2-iodobenzoyl chloride replacing 2-trifluoromethyl-4-fluorobenzoyl chloride. Data: LCMS (M/Z): 394 (M+H); $^1$H NMR (DMSO-$d_6$) δ: 10.40 (s, 1H), 9.13 (s, 1H), 8.08 (d, J=1.8 Hz, 1H), 7.90 (d, J=8.0 Hz, 1H), 7.66 (dd, J=8.2, 2.0 Hz, 1H), 7.41-7.49 (m, 2H), 7.33 (d, J=8.2 Hz, 1H), 7.19 (ddd, J=7.9, 6.7, 2.4 Hz, 1H), 5.15 (q, J=6.5 Hz, 1H), 1.35 (d, J=6.5 Hz, 3H).

16 2-Bromo-4-fluoro-N-(1-hydroxy-3-methyl-1,3-dihydro-benzo[c][1,2]oxaborol-6-yl)-benzamide

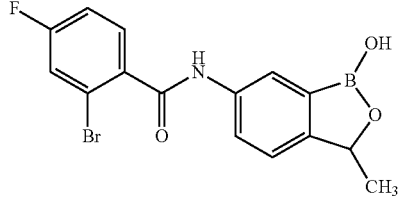 [SMILES: CC1OB(O)c2cc(NC(=O)c3ccc(F)cc3Br)ccc21]

The title compound was prepared using a procedure similar to that of 4-fluoro-N-(1-hydroxy-3-methyl-1,3-dihydro-benzo[c][1,2]oxaborol-6-yl-2-trifluoromethyl benzamide with 2-bromo-4-fluorobenzoyl chloride replacing 2-trifluoromethyl-4-fluorobenzoyl chloride. Data: LCMS (M/Z): 364 (M); $^1$H NMR (DMSO-$d_6$) δ: 10.46 (s, 1H), 8.06 (d, J=1.8 Hz, 1H), 7.58-7.70 (m, 3H), 7.29-7.38 (m, 2H), 5.15 (q, J=6.5 Hz, 1H), 1.35 (d, J=6.5 Hz, 3H).

17 N-(3-Cyclopentyl-1-hydroxy-1,3-dihydro-benzo[c][1,2]oxaborol-6-yl)-2-trifluoromethyl-benzamide

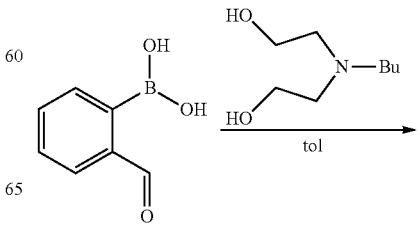

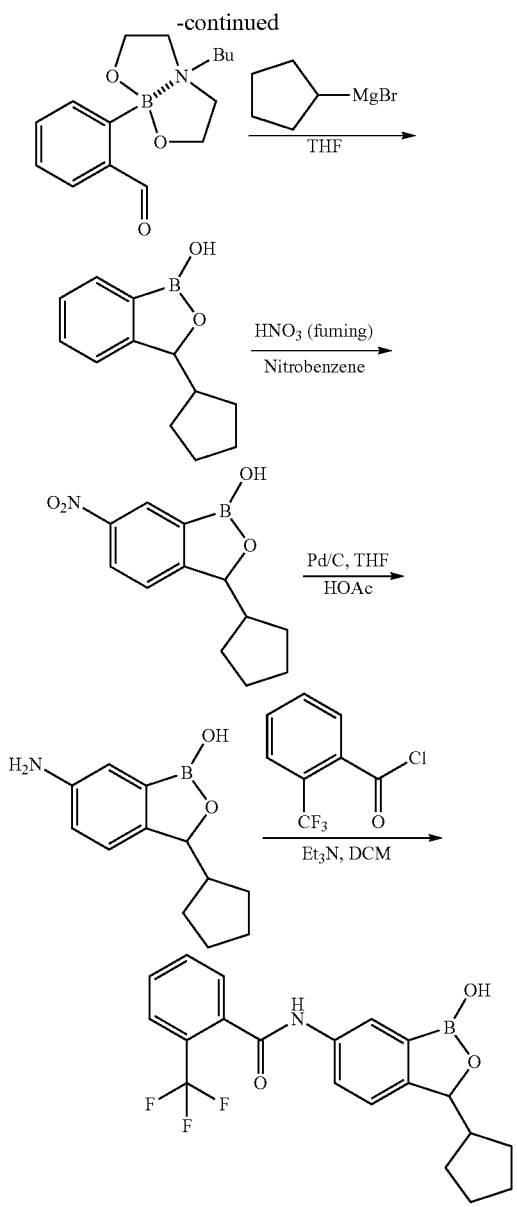

To a suspension of 2-formylphenylboronic acid (4.5 g, 30.0 mmol) in toluene (40 mL) was added N-butyldiethanolamine (5.2 mL, 31.5 mmol, 1.05 equiv.) via a syringe. The mixture was heated at 50° C. for two hours. After cooling to room temperature, the toluene was and the remaining yellow oil was treated with heptanes (50 mL) and the mixture was again evaporated under reduced pressure. The resulting yellow solid was crushed into small pieces and washed with heptanes to give the title compound as a white powder. $^1$H NMR (chloroform-d) δ: 10.92 (s, 1H), 7.87 (dd, J=7.7, 1.1 Hz, 1H), 7.83 (d, J=7.5 Hz, 1H), 7.48 (td, J=7.4, 1.3 Hz, 1H), 7.33-7.40 (m, 1H), 4.03-4.26 (m, 4H), 3.07-3.14 (m, 4H), 2.23-2.36 (m, 2H), 1.41-1.54 (m, 2H), 1.00-1.15 (m, 2H), 0.77 (t, J=7.3 Hz, 3H). Amount obtained, 9.0 g, (100% yield).

To a solution of 2-(2'-formylphenyl)-6-butyl[1,3,6,2]dioxazaborocan (5.0 g, 18.1 mmol) in THF (100 mL) at −45° C. was added cyclopentyl magnesium bromide (9.1 mL, 2.0 M solution in THF, 18.1 mmol) via a syringe. The mixture was allowed to warm to room temperature gradually over 1 h before being quenched with HCl (20 mL, 6N). The acidic mixture was stirred for 1 h and was extracted with EtOAc (3×). Combined organics was washed with H$_2$O, brine, dried over Na$_2$SO$_4$, filtered and the filtrate was concentrated under reduced pressure. The residue was applied to silica chromatography eluting with EtOAc/heptanes (0:100 to 100:0) to give the title compound e as a colorless oil. $^1$H NMR (DMSO-d$_6$) δ: 9.07 (s, 1H), 7.69 (d, J=7.2 Hz, 1H), 7.37-7.47 (m, 2H), 7.28-7.36 (m, 1H), 5.12 (d, J=4.7 Hz, 1H), 2.27 (td, J=8.2, 4.9 Hz, 1H), 1.78-1.90 (m, 1H), 1.56-1.74 (m, 3H), 1.39-1.56 (m, 4H), 1.20-1.34 (m, 1H).

To 20.0 ml fuming HNO$_3$ at −45° C. was added a solution of 3-cyclopentyl-3H-benzo[c][1,2]oxaborol-1-ol (1.4 g, 7.0 mmol) in 3.0 ml nitrobenzene slowly via a syringe while maintaining the reaction temperature between −40 to −45° C. Once the addition was complete the resulting solution was allowed to stir at −45° C. for an additional 45 min before poured into crushed ice (60 g). The ice mixture was allowed to warm to room temperature and the precipitate formed was filtered out, washed with heptanes and vacuum dried to give the titled compound as a white solid. $^1$H NMR (DMSO-d$_6$) δ: 9.53 (s, 1H), 8.55 (d, J=2.2 Hz, 1H), 8.32 (dd, J=8.4, 2.3 Hz, 1H), 7.70 (d, J=8.5 Hz, 1H), 5.29 (d, J=4.6 Hz, 1H), 2.31-2.42 (m, 1H), 1.80-1.92 (m, 1H), 1.57-1.71 (m, 2H), 1.38-1.57 (m, 3H), 1.17-1.30 (m, 1H), 0.93-1.06 (m, 1H).

To a solution of 3-cyclopentyl-6-nitro-3H-benzo[c][1,2]oxaborol-1-ol (970 mg, 3.9 mmol) in THF (20 mL) was added HOAc (2.0 mL, 33 mmol). The vessel was vacuum/N$_2$ purged three times and 5% Pd/C (200 mg) was added. The mixture was again vacuum/N$_2$ purged three times then vacuum purged again. H$_2$ was then introduced from a balloon and the reaction was allowed to stir for 2.5 hours. The reaction solution was filtered through a short pad of celite and the filtrate was evaporated to yield the title compound as a dark brown foamy solid.

To a solution of 6-amino-3-cyclopentyl-3H-benzo[c][1,2]oxaborol-1-ol acetate salt (86.8 mg, 0.4 mmol) in DCM (10 mL) was added Et$_3$N (220 µL, 1.6 mmol). The mixture was cooled to 0° C. and the 2-trifluoromethylbenzoyl chloride (64.6 µL, 0.44 mmol) was added slowly via a syringe. The resulting solution was allowed to warm to room temperature gradually and stir overnight. The reaction solution was diluted with DCM, washed with 1N HCl, H$_2$O and then dried over Na$_2$SO$_4$, filtered and the filtrate was concentrated under reduced pressure and the crude material was subjected to flash chromatography eluting with MeOH/DCM (0:100 to 10:90) to give the title compound was a white solid LCMS (M/Z): 390 (M+H); $^1$H NMR (acetone) δ: 9.59 (br. s., 1H), 8.17 (d, J=1.9 Hz, 1H), 7.78-7.90 (m, 2H), 7.74-7.76 (m, 2H), 7.66-7.72 (m, 2H), 7.39 (d, J=8.2 Hz, 1H), 5.13 (d, J=4.8 Hz, 1H), 2.31 (td, J=8.2, 4.8 Hz, 1H), 1.81-1.93 (m, 1H), 1.60-1.75 (m, 2H), 1.42-1.60 (m, 3H), 1.29-1.41 (m, 1H), 1.08-1.22 (m, 1H).

18 2-Chloro-N-(3-cyclopentyl-1-hydroxy-1,3-dihydro-benzo[c][1,2]oxaborol-6-yl)-benzamide

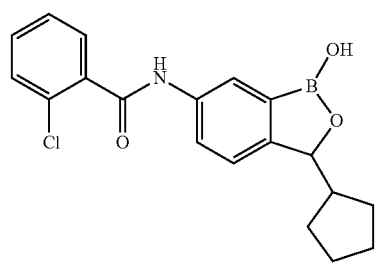 [SMILES: O=C(Nc1ccc2c(c1)B(O)OC2C1CCCC1)c1ccccc1Cl]

The title compound was prepared using a procedure similar to that of N-(3-cyclopentyl-1-hydroxy-1,3-dihydro-benzo[c][1,2]oxaborol-6-yl)-2-trifluoromethyl-benzamide with 2-chlorobenzoyl chloride replacing 2-trifluoromethyl-benzoyl chloride. Data: LCMS (M/Z): 356 (M+H); $^1$H NMR (acetone) δ: 9.51 (br. s., 1H), 8.18 (d, J=1.8 Hz, 1H), 7.79 (dd, J=8.2, 2.0 Hz, 1H), 7.60 (dd, J=7.0, 1.7 Hz, 1H), 7.36-7.52 (m, 5H), 5.13 (d, J=4.8 Hz, 1H), 2.32 (quin, J=8.2 Hz, 1H), 1.82-1.92 (m, 1H), 1.63-1.74 (m, 2H), 1.52-1.59 (m, 2H), 1.30-1.40 (m, 1H), 1.07-1.15 (m, 1H), 0.80-0.89 (m, 1H).

19 N-(3-Cyclopentyl-1-hydroxy-1,3-dihydro-benzo[c][1,2]oxaborol-6-yl)-4-fluoro-2-trifluoromethyl-benzamide

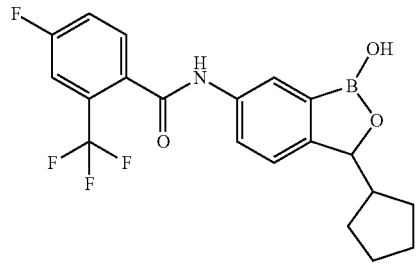 [SMILES: O=C(Nc1ccc2c(c1)B(O)OC2C1CCCC1)c1ccc(F)cc1C(F)(F)F]

The title compound was prepared using a procedure similar to that of N-(3-cyclopentyl-1-hydroxy-1,3-dihydro-benzo[c][1,2]oxaborol-6-yl)-2-trifluoromethyl-benzamide with 2-trifluoromethyl-4-fluorobenzoyl chloride replacing 2-trifluoromethylbenzoyl chloride. Data: LCMS (M/Z): 430 (M+23); $^1$H NMR (acetone) δ: 9.64 (br. s., 1H), 8.14 (d, J=1.9 Hz, 1H), 7.83 (dd, J=8.5, 5.4 Hz, 1H), 7.71 (dd, J=8.2, 2.0 Hz, 1H), 7.50-7.64 (m, 2H), 7.39 (d, J=8.2 Hz, 1H), 5.13 (d, J=4.8 Hz, 1H), 2.25-2.37 (m, J=8.2, 8.2, 8.2, 8.2, 4.8 Hz, 1H), 1.82-1.92 (m, 1H), 1.62-1.74 (m, 2H), 1.44-1.59 (m, 3H), 1.30-1.40 (m, 1H), 1.10-1.19 (m, 1H).

20 N-(3-Cyclopentyl-1-hydroxy-1,3-dihydro-benzo[c][1,2]oxaborol-6-yl)-4-fluoro-benzamide

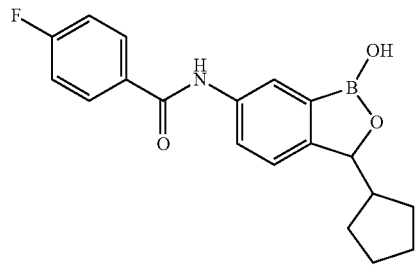 [SMILES: O=C(Nc1ccc2c(c1)B(O)OC2C1CCCC1)c1ccc(F)cc1]

The title compound was prepared using a procedure similar to that of N-(3-cyclopentyl-1-hydroxy-1,3-dihydro-benzo[c][1,2]oxaborol-6-yl)-2-trifluoromethyl-benzamide with 2-fluorobenzoyl chloride replacing 2-trifluoromethyl-benzoyl chloride. Data: LCMS (M/Z): 340 (M+H); $^1$H NMR (acetone) δ: 9.54 (br. s., 1H), 8.17 (d, J=2.0 Hz, 1H), 8.03-8.11 (m, 3H), 7.80 (dd, J=8.3, 2.1 Hz, 1H), 7.37 (d, J=8.2 Hz, 1H), 7.22-7.30 (m, 2H), 5.12 (d, J=4.8 Hz, 1H), 2.26-2.35 (m, 1H), 1.81-1.91 (m, 1H), 1.62-1.73 (m, 2H), 1.49-1.57 (m, 2H), 1.40-1.49 (m, 1H), 1.30-1.39 (m, 1H), 1.09-1.20 (m, 1H).

21 N-(3-Cyclopentyl-1-hydroxy-1,3-dihydro-benzo[c][1,2]oxaborol-6-yl)-acetamide

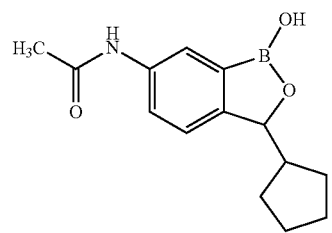 [SMILES: CC(=O)Nc1ccc2c(c1)B(O)OC2C1CCCC1]

The title compound was isolated from the crude reaction mixture obtained in the synthesis of N-(3-cyclopentyl-1-hydroxy-1,3-dihydro-benzo[c][1,2]oxaborol-6-yl)-4-fluoro-benzamide by flash chromatography. It was formed by reaction of residual acetic acid in the 6-aminooxaborole starting material under the influence of excess acid chloride via a mixed anhydride formed in situ. Data: LCMS (M/Z): 260 (M+H); $^1$H NMR (acetone) δ: 9.13 (br. s., 1H), 7.98 (d, J=1.8 Hz, 1H), 7.61 (dd, J=8.3, 2.0 Hz, 1H), 7.29 (d, J=8.2 Hz, 1H), 5.08 (d, J=4.9 Hz, 1H), 2.19-2.28 (m, 1H), 2.05 (s, 3H), 1.78-1.90 (m, 1H), 1.59-1.72 (m, 2H), 1.40-1.58 (m, 4H), 1.25-1.38 (m, 1H), 1.12-1.16 (m, 1H).

22 N-(1-Hydroxy-3-isobutyl-1,3-dihydro-benzo[c][1,2]oxaborol-6-yl)-2-trifluoromethyl-benzamide

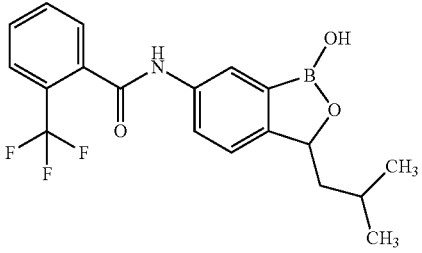 [SMILES: CC(C)CC1OB(O)c2cc(NC(=O)c3ccccc3C(F)(F)F)ccc21]

The title compound was prepared using a procedure similar to that of N-(3-cyclopentyl-1-hydroxy-1,3-dihydro-benzo[c][1,2]oxaborol-6-yl)-2-trifluoromethyl-benzamide with isobutyl magnesium bromide replacing cyclopentyl magnesium bromide. Data: LCMS (M/Z): 378 (M+H); $^1$H NMR (DMSO-$d_6$) δ: 10.53 (s, 1H), 9.13 (s, 1H), 8.06 (d, J=1.9 Hz, 1H), 7.81 (d, J=7.5 Hz, 1H), 7.73-7.79 (m, 1H), 7.65-7.71 (m, 2H), 7.62 (dd, J=8.2, 2.0 Hz, 1H), 7.31 (d, J=8.2 Hz, 1H), 5.10 (dd, J=9.8, 3.0 Hz, 1H), 1.81-1.92 (m, 1H), 1.65 (ddd, J=13.9, 9.0, 3.1 Hz, 1H), 1.27 (ddd, J=14.1, 9.7, 4.6 Hz, 1H), 0.98 (d, J=6.6 Hz, 3H), 0.89 (d, J=6.7 Hz, 3H).

23 4-Fluoro-N-(1-hydroxy-3-isobutyl-1,3-dihydro-benzo[c][1,2]oxaborol-6-yl)-2-trifluoromethyl-benzamide

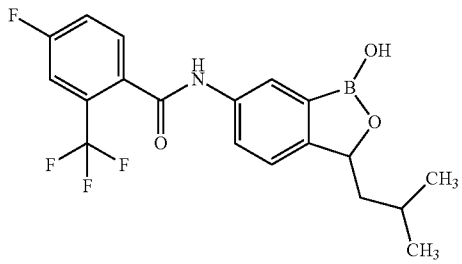 [SMILES: CC(C)CC1OB(O)c2cc(NC(=O)c3ccc(F)cc3C(F)(F)F)ccc21]

The title compound was prepared using a procedure similar to that of N-(3-cyclopentyl-1-hydroxy-1,3-dihydro-benzo[c][1,2]oxaborol-6-yl)-2-trifluoromethyl-benzamide with 2-trifluoromethyl-4-fluorobenzoyl chloride replacing 2-trifluoromethylbenzoyl chloride, and with isobutyl magnesium bromide replacing cyclopentyl magnesium bromide. Data: LCMS (M/Z): 396 (M+H); $^1$H NMR (DMSO-$d_6$) δ: 10.54 (s, 1H), 9.13 (s, 1H), 8.03 (d, J=1.8 Hz, 1H), 7.73-7.81 (m, 2H), 7.58-7.68 (m, 2H), 7.31 (d, J=8.2 Hz, 1H), 5.10 (dd, J=9.8, 3.1 Hz, 1H), 1.60-1.69 (m, 1H), 1.21-1.31 (m, 1H), 0.98 (d, J=6.5 Hz, 3H), 0.89 (d, J=6.7 Hz, 3H), 0.85 (t, J=7.0 Hz, 1H).

24 4-Fluoro-N-(1-hydroxy-3-isobutyl-1,3-dihydro-benzo[c][1,2]oxaborol-6-yl)-benzamide

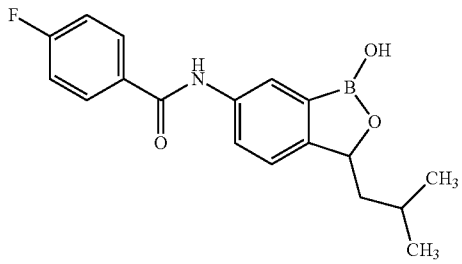 [SMILES: CC(C)CC1OB(O)c2cc(NC(=O)c3ccc(F)cc3)ccc21]

The title compound was prepared using a procedure similar to that of N-(3-cyclopentyl-1-hydroxy-1,3-dihydro-benzo[c][1,2]oxaborol-6-yl)-2-trifluoromethyl-benzamide with 4-fluorobenzoyl chloride replacing 2-trifluoromethyl-benzoyl chloride, and with isobutyl magnesium bromide replacing cyclopentyl magnesium bromide. Data: LCMS (M/Z): 328 (M+H); $^1$H NMR (DMSO-$d_6$) δ: 10.25 (s, 1H), 9.11 (s, 1H), 8.07 (d, J=1.9 Hz, 1H), 7.98-8.04 (m, 2H), 7.71 (dd, J=8.2, 2.0 Hz, 1H), 7.29-7.37 (m, 3H), 5.11 (dd, J=9.8, 3.1 Hz, 1H), 1.81-1.93 (m, 1H), 1.65 (ddd, J=13.9, 9.0, 3.2 Hz, 1H), 1.27 (ddd, J=14.1, 9.7, 4.7 Hz, 1H), 0.98 (d, J=6.5 Hz, 3H), 0.89 (d, J=6.7 Hz, 3H).

25 2-Chloro-N-(1-hydroxy-3-isobutyl-1,3-dihydro-benzo[c][1,2]oxaborol-6-yl)-benzamide

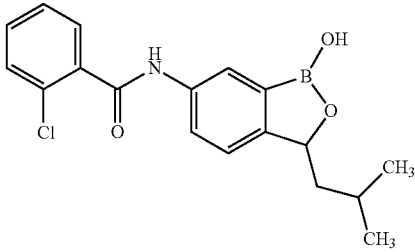 [SMILES: CC(C)CC1OB(O)c2cc(NC(=O)c3ccccc3Cl)ccc21]

The title compound was prepared using a procedure similar to that of N-(3-cyclopentyl-1-hydroxy-1,3-dihydro-benzo[c][1,2]oxaborol-6-yl)-2-trifluoromethyl-benzamide with 2-chlorobenzoyl chloride replacing 2-trifluoromethyl-benzoyl chloride, and with isobutyl magnesium bromide replacing cyclopentyl magnesium bromide. Data: LCMS (M/Z): 344 (M+H); $^1$H NMR (DMSO-$d_6$) δ: 10.47 (s, 1H), 9.13 (s, 1H), 8.07 (d, J=1.8 Hz, 1H), 7.66 (dd, J=8.2, 2.0 Hz, 1H), 7.51-7.55 (m, 1H), 7.38-7.50 (m, 2H), 7.30 (d, J=8.2 Hz, 1H), 5.10 (dd, J=9.8, 3.0 Hz, 1H), 1.79-1.92 (m, 1H), 1.65 (ddd, J=13.8, 9.0, 3.1 Hz, 1H), 1.26 (ddd, J=14.0, 9.7, 4.7 Hz, 1H), 0.98 (d, J=6.5 Hz, 3H), 0.89 (d, J=6.7 Hz, 3H).

26 N-(1-Hydroxy-3,3-dimethyl-1,3-dihydro-benzo[c][1,2]oxaborol-6-yl)-benzamide

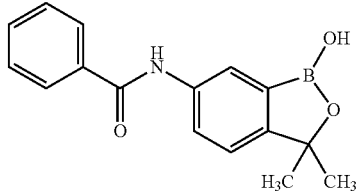 [SMILES: CC1(C)OB(O)c2cc(NC(=O)c3ccccc3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with benzoyl chloride replacing 2-trifluoromethyl-4-fluorobenzoyl chloride. Data: LCMS (M/Z): 282 (M+H); $^1$H NMR (DMSO-$d_6$) δ: 1.45 (s, 6 H) 7.38 (d, J=8.2 Hz, 1 H) 7.50-7.62 (m, 3 H) 7.75 (dd, J=8.2, 2.1 Hz, 1 H) 7.93-8.00 (m, 2 H) 8.08 (d, J=1.7 Hz, 1 H) 9.06 (s, 1 H) 10.27 (s, 1 H).

27 N-(1-Hydroxy-3,3-dimethyl-1,3-dihydro-benzo[c][1,2]oxaborol-6-yl)-2-methylbenzamide

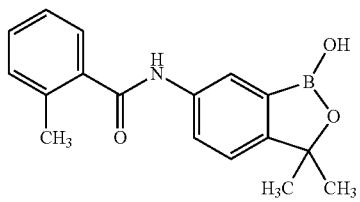 [SMILES: Cc1ccccc1C(=O)Nc1ccc2c(c1)B(O)OC2(C)C]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-toluoyl chloride replacing 2-trifluoromethyl-4-fluorobenzoyl chloride. Data: LCMS (M/Z): 296 (M+H); ¹H NMR (DMSO-d₆) δ: 1.44 (s, 6 H) 2.39 (s, 3 H) 7.31 (d, J=7.5 Hz, 2 H) 7.34-7.42 (m, 2 H) 7.45 (d, J=7.5 Hz, 1 H) 7.69 (d, J=1.8 Hz, 1 H) 8.09 (d, J=1.3 Hz, 1 H) 9.06 (s, 1H) 10.30 (s, 1 H).

28 N-(1-Hydroxy-3,3-dimethyl-1,3-dihydro-benzo[c][1,2]oxaborol-6-yl)-3-methyl-benzamide

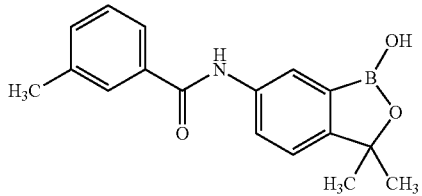

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 3-methyl-benzoyl chloride replacing 2-trifluoromethyl-4-fluorobenzoyl chloride. Data: LCMS (M/Z): 296 (M+H); ¹H NMR (DMSO-d₆) δ: 1.45 (s, 6 H) 2.40 (s, 3 H) 7.40 (t, J=5.8 Hz, 2 H) 7.74 (td, J=7.5, 2.3 Hz, 3 H) 8.07 (d, J=1.7 Hz, 1 H) 10.21 (s, 1 H).

29 N-(1-Hydroxy-3,3-dimethyl-1,3-dihydro-benzo[c][1,2]oxaborol-6-yl)-4-methyl-benzamide

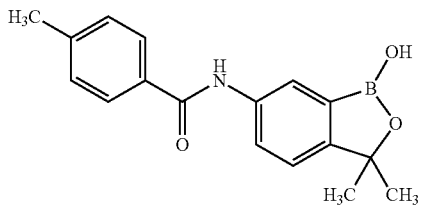

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-methyl-benzoyl chloride replacing 2-trifluoromethyl-4-fluorobenzoyl chloride. Data: LCMS (M/Z): 296 (M+H); ¹H NMR (DMSO-d₆) δ: 1.45 (s, 6 H) 2.39 (s, 3 H) 7.36 (dd, J=15.0, 8.1 Hz, 3 H) 7.74 (dd, J=8.2, 2.0 Hz, 1 H) 7.88 (d, J=8.2 Hz, 2 H) 8.07 (d, J=1.8 Hz, 1 H) 9.05 (s, 1 H) 10.17 (s, 1 H).

30 4-Ethyl-N-(1-hydroxy-3,3-dimethyl-1,3-dihydro-benzo[c][1,2]oxaborol-6-yl)-benzamide

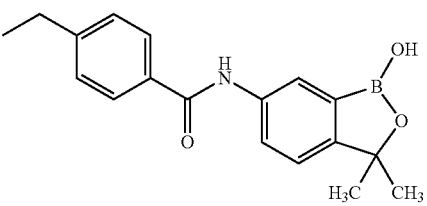 [SMILES: CCc1ccc(C(=O)Nc2ccc3c(c2)B(O)OC3(C)C)cc1]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-ethyl-benzoyl chloride replacing 2-trifluoromethyl-4-fluorobenzoyl chloride. Data: LCMS (M/Z): 310 (M+H); ¹H NMR (DMSO-d₆) δ: 1.17 (t, J=7.6 Hz, 3 H) 1.41 (s, 6 H) 2.64 (d, J=7.6 Hz, 2 H) 7.33 (dd, J=8.2, 4.5 Hz, 3 H) 7.71 (dd, J=8.2, 2.0 Hz, 1 H) 7.87 (d, J=8.2 Hz, 2 H) 8.04 (d, J=1.9 Hz, 1 H) 9.02 (s, 1 H) 10.15 (s, 1 H).

31 N-(1-Hydroxy-3,3-dimethyl-1,3-dihydro-benzo[c][1,2]oxaborol-6-yl)-4-propyl-benzamide

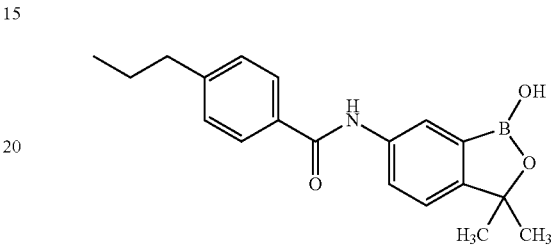

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-propyl-benzoyl chloride replacing 2-trifluoromethyl-4-fluorobenzoyl chloride. Data: LCMS (M/Z): 324 (M+H); ¹H NMR (DMSO-d₆) δ: 0.86 (t, J=7.3 Hz, 3 H) 1.41 (s, 6 H) 1.53-1.64 (m, 2 H) 2.59 (t, J=7.5 Hz, 2 H) 7.30 (d, J=8.2 Hz, 2 H) 7.33 (d, J=8.2 Hz, 1 H) 7.71 (dd, J=8.2, 2.0 Hz, 1 H) 7.85 (d, J=8.2 Hz, 2 H) 8.04 (d, J=1.9 Hz, 1 H) 8.98-9.05 (m, 1 H) 10.15 (s, 1 H).

32 4-Butyl-N-(1-hydroxy-3,3-dimethyl-1,3-dihydro-benzo[c][1,2]oxaborol-6-yl)-benzamide

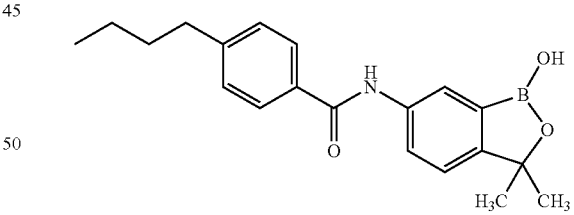

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-butyl-benzoyl chloride replacing 2-trifluoromethyl-4-fluorobenzoyl chloride. Data: LCMS (M/Z): 338 (M+H); ¹H NMR (DMSO-d₆) δ: 0.91 (t, J=7.3 Hz, 3 H) 1.32 (dq, J=14.8, 7.4 Hz, 2 H) 1.45 (s, 6 H) 1.59 (quin, J=7.5 Hz, 2 H) 2.66 (t, J=7.6 Hz, 2 H) 7.36 (dd, J=10.8, 8.3 Hz, 3 H) 7.74 (dd, J=8.2, 2.0 Hz, 1 H) 7.88 (d, J=8.2 Hz, 2 H) 8.07 (d, J=1.8 Hz, 1 H) 9.06 (br. s., 1 H) 10.18 (s, 1 H).

33 4-tert-Butyl-N-(1-hydroxy-3,3-dimethyl-1,3-dihydro-benzo[c][1,2]oxaborol-6-yl)-benzamide

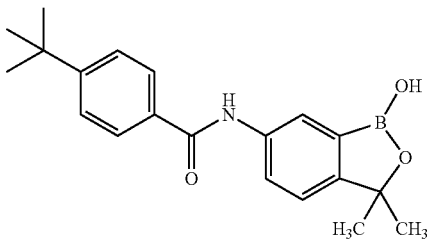 [SMILES: CC(C)(C)c1ccc(C(=O)Nc2ccc3c(c2)B(O)OC3(C)C)cc1]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-tert-butylbenzoyl chloride replacing 2-trifluoromethyl-4-fluorobenzoyl chloride. Data: LCMS (M/Z): 338 (M+H); $^1$H NMR (DMSO-d$_6$) δ: 1.32 (s, 9 H) 1.45 (s, 6 H) 7.37 (d, J=8.2 Hz, 1 H) 7.51-7.57 (m, 2 H) 7.74 (dd, J=8.2, 2.0 Hz, 1 H) 7.87-7.92 (m, 2 H) 8.07 (d, J=1.8 Hz, 1 H) 9.05 (s, 1H) 10.18 (s, 1 H).

34 N-(1-Hydroxy-3,3-dimethyl-1,3-dihydro-benzo[c][1,2]oxaborol-6-yl)-2-trifluoromethyl-benzamide

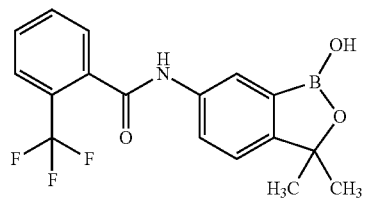 [SMILES: CC1(C)OB(O)c2cc(NC(=O)c3ccccc3C(F)(F)F)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-trifluoromethylbenzoyl chloride replacing 2-trifluoromethyl-4-fluorobenzoyl chloride. Data: LCMS (M/Z): 350 (M+H); $^1$H NMR (DMSO-d$_6$) δ: 10.56 (s, 1H), 9.09 (s, 1H), 8.05 (d, J=1.8 Hz, 1H), 7.85 (d, J=7.8 Hz, 1H), 7.78-7.83 (m, 1H), 7.68-7.74 (m, 2H), 7.65 (dd, J=8.2, 2.0 Hz, 1H), 7.38 (d, J=8.2 Hz, 1H), 1.45 (s, 6H).

35 N-(1-Hydroxy-3,3-dimethyl-1,3-dihydro-benzo[c][1,2]oxaborol-6-yl)-3-trifluoromethyl-benzamide

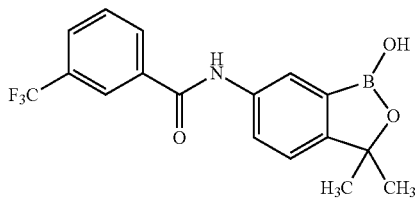 [SMILES: CC1(C)OB(O)c2cc(NC(=O)c3cccc(C(F)(F)F)c3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 3-trifluoromethyl-benzoyl chloride replacing 2-trifluoromethyl-4-fluorobenzoyl chloride. Data: LCMS (M/Z): 350 (M+H); $^1$H NMR (DMSO-d$_6$) δ: 1.46 (s, 6 H) 7.41 (d, J=8.2 Hz, 1 H) 7.72-7.82 (m, 2 H) 7.96 (s, 1 H) 8.07 (d, J=1.9 Hz, 1 H) 8.26-8.32 (m, 2 H) 9.08 (s, 1 H) 10.49 (s, 1 H).

36 N-(1-Hydroxy-3,3-dimethyl-1,3-dihydro-benzo[c][1,2]oxaborol-6-yl)-4-trifluoromethyl-benzamide

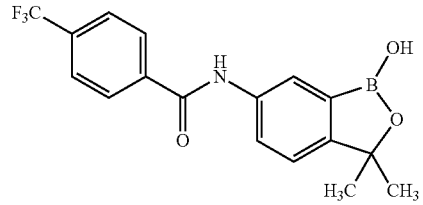 [SMILES: CC1(C)OB(O)c2cc(NC(=O)c3ccc(C(F)(F)F)cc3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-trifluoromethyl-benzoyl chloride replacing 2-trifluoromethyl-4-fluorobenzoyl chloride. Data: LCMS (M/Z): 350 (M+H); $^1$H NMR (DMSO-d$_6$) δ: 1.45 (s, 6 H) 7.41 (d, J=8.2 Hz, 1 H) 7.75 (dd, J=8.2, 2.0 Hz, 1 H) 7.92 (d, J=8.3 Hz, 2 H) 8.09 (d, J=1.8 Hz, 1 H) 8.16 (d, J=8.1 Hz, 2 H) 9.10 (s, 1 H) 10.50 (s, 1 H).

37 2-Fluoro-N-(1-hydroxy-3,3-dimethyl-1,3-dihydro-benzo[c][1,2]oxaborol-6-yl)-benzamide

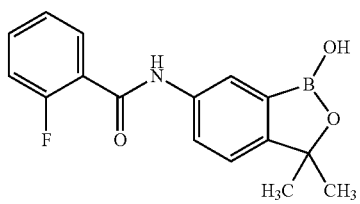

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-fluoro-benzoyl chloride replacing 2-trifluoromethyl-4-fluorobenzoyl chloride. Data: LCMS (M/Z): 300 (M+H); $^1$H NMR (DMSO-d$_6$) δ: 1.41 (s, 6 H) 7.24-7.37 (m, 3 H) 7.50-7.58 (m, 1 H) 7.60-7.69 (m, 2 H) 8.01 (d, J=1.7 Hz, 1 H) 9.04 (s, 1 H) 10.38 (s, 1 H).

38 2-Chloro-N-(1-hydroxy-3,3-dimethyl-1,3-dihydro-benzo[c][1,2]oxaborol-6-yl)-benzamide

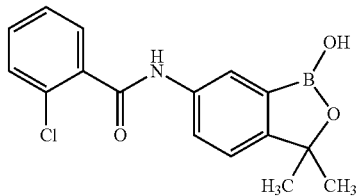 [SMILES: CC1(C)OB(O)c2cc(NC(=O)c3ccccc3F)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-chlorobenzoyl chloride replacing 2-trifluoromethyl-4-fluorobenzoyl chloride. Data: LCMS (M/Z): 316 (M+H); ¹H NMR (DMSO-d₆) δ: 10.51 (s, 1H), 9.09 (s, 1H), 8.07 (d, J=1.8 Hz, 1H), 7.66-7.73 (m, 1H), 7.56-7.58 (m, 1H), 7.44-7.54 (m, 2H), 7.28-7.42 (m, 2H), 1.44 (s, 6H).

39 2-Bromo-N-(1-hydroxy-3,3-dimethyl-1,3-dihydro-benzo[c][1,2]oxaborol-6-yl)-benzamide

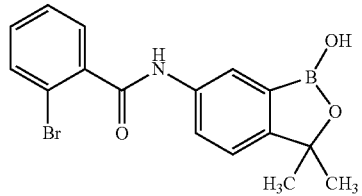 [SMILES: CC1(C)OB(O)c2cc(NC(=O)c3ccccc3Br)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-bromobenzoyl chloride replacing 2-trifluoromethyl-4-fluorobenzoyl chloride. Data: LCMS (M/Z): 360 (M); ¹H NMR (DMSO-d₆) δ: 10.44 (s, 1H), 9.05 (s, 1H), 8.03 (d, J=2.0 Hz, 1H), 7.66 (dd, J=17.4, 7.5 Hz, 1H), 7.66 (dd, J=15.3, 8.7 Hz, 1H), 7.44-7.53 (m, 2H), 7.32-7.41 (m, 2H), 1.40 (s, 6H).

40 N-(1-Hydroxy-3,3-dimethyl-1,3-dihydro-benzo[c][1,2]oxaborol-6-yl)-2-iodo-benzamide

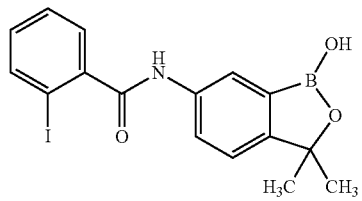 [SMILES: CC1(C)OB(O)c2cc(NC(=O)c3ccccc3I)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-iodo-benzoyl chloride replacing 2-trifluoromethyl-4-fluorobenzoyl chloride. Data: LCMS (M/Z): 407 (M+H); ¹H NMR (DMSO-d₆) δ: 1.44 (s, 6 H) 7.23 (ddd, J=7.9, 7.0, 2.1 Hz, 1 H) 7.38 (d, J=8.2 Hz, 1 H) 7.43-7.58 (m, 2 H) 7.68 (dd, J=8.3, 2.1 Hz, 1 H) 7.93 (d, J=7.8 Hz, 1 H) 8.07 (d, J=1.8 Hz, 1 H) 9.08 (s, 1 H) 10.42 (s, 1 H).

41 3-Fluoro-N-(1-hydroxy-3,3-dimethyl-1,3-dihydro-benzo[c][1,2]oxaborol-6-yl)-benzamide

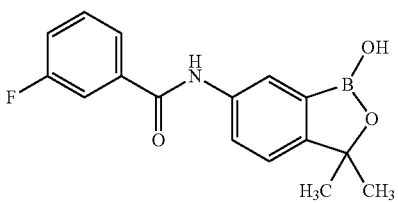 [SMILES: CC1(C)OB(O)c2cc(NC(=O)c3cccc(F)c3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 3-fluoro-benzoyl chloride replacing 2-trifluoromethyl-4-fluorobenzoyl chloride. Data: LCMS (M/Z): 300 (M+H); ¹H NMR (DMSO-d₆) δ: 1.45 (s, 6 H) 7.40 (d, J=8.2 Hz, 1 H) 7.42-7.48 (m, 1 H) 7.59 (d, J=5.9 Hz, 1 H) 7.74 (dd, J=8.2, 2.0 Hz, 1 H) 7.76-7.80 (m, 1 H) 7.83 (d, J=7.9 Hz, 1 H) 8.07 (d, J=1.9 Hz, 1 H) 9.01-9.11 (m, 1 H) 10.33 (s, 1 H).

42 3-Chloro-N-(1-hydroxy-3,3-dimethyl-1,3-dihydro-benzo[c][1,2]oxaborol-6-yl)-benzamide

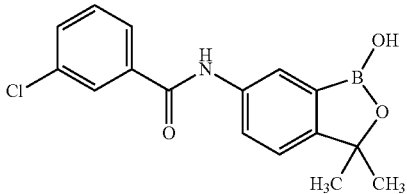 [SMILES: CC1(C)OB(O)c2cc(NC(=O)c3cccc(Cl)c3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 3-chloro-benzoyl chloride replacing 2-trifluoromethyl-4-fluorobenzoyl chloride. Data: LCMS (M/Z): 316 (M+H); ¹H NMR (DMSO-d₆) δ: 1.45 (s, 6 H) 7.40 (d, J=8.2 Hz, 1 H) 7.54-7.60 (m, 1 H) 7.66 (dd, J=2.1, 1.0 Hz, 1 H) 7.73 (dd, J=8.2, 2.0 Hz, 1 H) 7.91-7.95 (m, 1 H) 8.01 (t, J=1.8 Hz, 1 H) 8.07 (d, J=1.9 Hz, 1 H) 9.07 (s, 1 H) 10.37 (s, 1H).

43 3-Bromo-N-(1-hydroxy-3,3-dimethyl-1,3-dihydro-benzo[c][1,2]oxaborol-6-yl)-benzamide

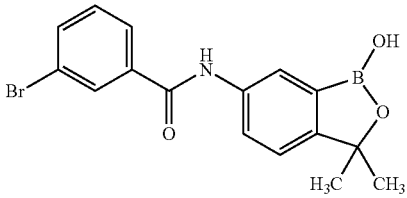 [SMILES: CC1(C)OB(O)c2cc(NC(=O)c3cccc(Br)c3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 3-bromo-benzoyl chloride replacing 2-trifluoromethyl-4-fluorobenzoyl chloride. Data: LCMS (M/Z): 362 (M+H); ¹H NMR (DMSO-d₆) δ: 1.45 (s, 6 H) 7.39 (d, J=8.3 Hz, 1 H) 7.51 (t, J=7.9 Hz, 1 H) 7.73 (dd, J=8.3, 2.0 Hz, 1 H) 7.80 (ddd, J=8.0, 2.0, 1.0 Hz, 1 H) 7.94-7.99 (m, 1 H) 8.07 (d, J=1.9 Hz, 1 H) 8.15 (t, J=1.8 Hz, 1 H) 9.07 (s, 1 H) 10.37 (s, 1 H).

44 4-Fluoro-N-(1-hydroxy-3,3-dimethyl-1,3-dihydro-benzo[c][1,2]oxaborol-6-yl)-benzamide

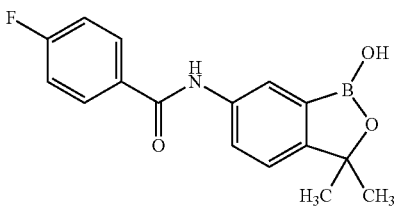 [SMILES: CC1(C)OB(O)c2cc(NC(=O)c3ccc(F)cc3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-fluorobenzoyl chloride replacing 2-trifluoromethyl-4-fluorobenzoyl chloride. Data: LCMS (M/Z): 300 (M+H); $^1$H NMR (DMSO-$d_6$) δ: 10.28 (s, 1H), 9.06 (s, 1H), 8.01-8.08 (m, 3H), 7.84 (dd, J=8.3, 2.0 Hz, 1H), 7.74 (dd, J=8.3, 2.0 Hz, 1H), 7.34-7.45 (m, 3H), 1.45 (s, 6H).

45 4-Chloro-N-(1-hydroxy-3,3-dimethyl-1,3-dihydro-benzo[c][1,2]oxaborol-6-yl)-benzamide

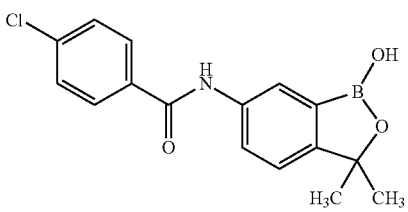 [SMILES: CC1(C)OB(O)c2cc(NC(=O)c3ccc(Cl)cc3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-chlorobenzoyl chloride replacing 2-trifluoromethyl-4-fluorobenzoyl chloride. Data: LCMS (M/Z): 316 (M+H); $^1$H NMR (DMSO-$d_6$) δ: 1.45 (s, 6 H) 7.39 (d, J=8.2 Hz, 1 H) 7.57-7.65 (m, 2 H) 7.73 (dd, J=8.2, 2.0 Hz, 1 H) 7.99 (d, J=8.6 Hz, 2 H) 8.06 (d, J=1.9 Hz, 1 H) 9.07 (s, 1 H) 10.33 (s, 1 H).

46 N-(1-Hydroxy-3,3-dimethyl-1,3-dihydro-benzo[c][1,2]oxaborol-6-yl)-2-methoxy-benzamide

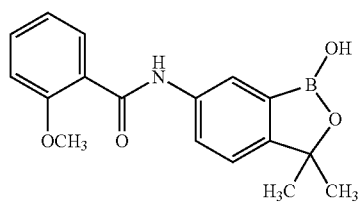

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-methoxy-benzoyl chloride replacing 2-trifluoromethyl-4-fluorobenzoyl chloride. Data: LCMS (M/Z): 312 (M+H); $^1$H NMR (DMSO-$d_6$) δ: 1.45 (s, 6 H) 3.80 (s, 1 H) 3.84 (s, 3 H) 7.13-7.20 (m, 2 H) 7.36-7.57 (m, 7 H) 7.74 (dd, J=8.2, 2.0 Hz, 1 H) 8.06 (d, J=1.8 Hz, 1 H) 9.01-9.09 (m, 1 H) 10.23 (s, 1 H).

47 N-(1-Hydroxy-3,3-dimethyl-1,3-dihydro-benzo[c][1,2]oxaborol-6-yl)-3-methoxy-benzamide

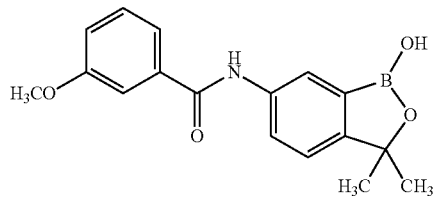

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 3-methoxy-benzoyl chloride replacing 2-trifluoromethyl-4-fluorobenzoyl chloride. Data: LCMS (M/Z): 312 (M+H); $^1$H NMR (DMSO-$d_6$) δ: 1.45 (s, 6 H) 3.80 (s, 1 H) 3.84 (s, 3 H) 7.13-7.20 (m, 2 H) 7.36-7.57 (m, 7 H) 7.74 (dd, J=8.2, 2.0 Hz, 1 H) 8.06 (d, J=1.8 Hz, 1 H) 9.01-9.09 (m, 1 H) 10.23 (s, 1 H).

48 N-(1-Hydroxy-3,3-dimethyl-1,3-dihydro-benzo[c][1,2]oxaborol-6-yl)-4-methoxy-benzamide

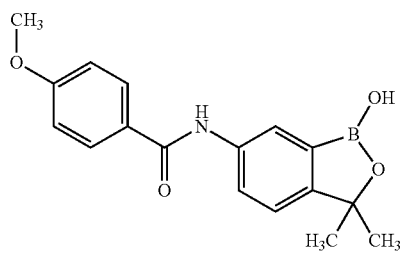 [SMILES: COc1ccc(C(=O)Nc2ccc3c(c2)B(O)OC3(C)C)cc1]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-methoxybenzoyl chloride replacing 2-trifluoromethyl-4-fluorobenzoyl chloride. Data: LCMS (M/Z): 312 (M+H); $^1$H NMR (chloroform-d) δ: 7.74-7.92 (m, 5H), 7.20-7.25 (m, 1H), 6.91-6.97 (m, 2H), 3.84 (s, 3H), 1.52 (s, 6H).

49 2-Ethoxy-N-(1-hydroxy-3,3-dimethyl-1,3-dihydro-benzo[c][1,2]oxaborol-6-yl)-benzamide

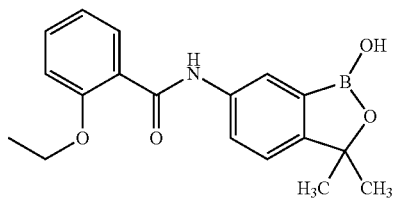 [SMILES: CCOc1ccccc1C(=O)Nc1ccc2c(c1)B(O)OC2(C)C]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-ethoxy-benzoyl chloride replacing 2-trifluoromethyl-4-fluorobenzoyl chloride. Data: LCMS (M/Z): 326 (M+H); $^1$H NMR (DMSO-d$_6$) δ: 1.37 (t, J=6.9 Hz, 3 H) 1.40 (s, 6 H) 4.15 (q, J=6.9 Hz, 2 H) 7.03 (t, J=7.2 Hz, 1 H) 7.13 (d, J=8.3 Hz, 1 H) 7.33 (d, J=8.2 Hz, 1 H) 7.41-7.50 (m, 1 H) 7.68 (ddd, J=7.9, 6.1, 1.9 Hz, 2 H) 8.00 (d, J=1.7 Hz, 1 H) 9.04 (s, 1 H) 10.11 (s, 1 H).

50 N-(1-Hydroxy-3,3-dimethyl-1,3-dihydro-benzo[c][1,2]oxaborol-6-yl)-4-pentyloxy-benzamide

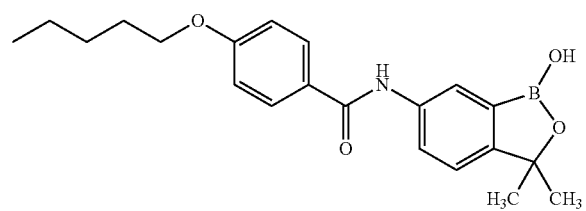 [SMILES: CCCCCOc1ccc(C(=O)Nc2ccc3c(c2)B(O)OC3(C)C)cc1]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-pentyloxy-benzoyl chloride replacing 2-trifluoromethyl-4-fluorobenzoyl chloride. Data: LCMS (M/Z): 368 (M+H); $^1$H NMR (DMSO-d$_6$) δ: 0.83-0.89 (m, 3 H) 1.27-1.38 (m, 4 H) 1.41 (s, 6 H) 1.65-1.74 (m, 2 H) 4.00 (t, J=6.5 Hz, 2 H) 6.98-7.04 (m, 2 H) 7.32 (d, J=8.2 Hz, 1 H) 7.70 (dd, J=8.2, 2.0 Hz, 1 H) 7.92 (d, J=8.9 Hz, 2 H) 8.03 (d, J=1.8 Hz, 1 H) 8.95-9.06 (m, 1 H) 10.06 (s, 1 H).

51 N-(1-Hydroxy-3,3-dimethyl-1,3-dihydro-benzo[c][1,2]oxaborol-6-yl)-2-trifluoromethoxy-benzamide

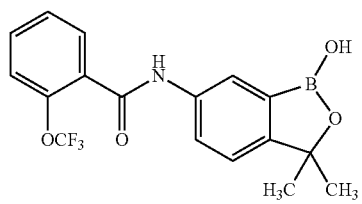 [SMILES: CC1(C)OB(O)c2cc(NC(=O)c3ccccc3OC(F)(F)F)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-trifluoromethoxy-benzoyl chloride replacing 2-trifluoromethyl-4-fluorobenzoyl chloride. Data: LCMS (M/Z): 366 (M+H); $^1$H NMR (DMSO-d$_6$) δ: 1.44 (s, 6 H) 7.39 (s, 1 H) 7.45-7.61 (m, 2 H) 7.65 (s, 3 H) 8.04 (d, J=1.8 Hz, 1 H) 9.08 (s, 1 H) 10.49 (s, 1 H).

52 N-(1-Hydroxy-3,3-dimethyl-1,3-dihydro-benzo[c][1,2]oxaborol-6-yl)-3-trifluoromethoxy-benzamide

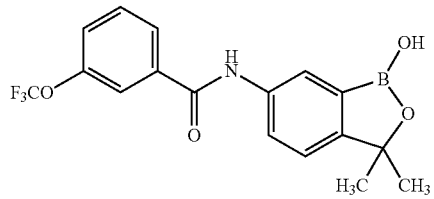 [SMILES: CC1(C)OB(O)c2cc(NC(=O)c3cccc(OC(F)(F)F)c3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 3-trifluoromethoxy-benzoyl chloride replacing 2-trifluoromethyl-4-fluorobenzoyl chloride. Data: LCMS (M/Z): 366 (M+H); $^1$H NMR (DMSO-d$_6$) δ: 1.45 (s, 6 H) 7.41 (d, J=8.2 Hz, 1 H) 7.57-7.65 (m, 1 H) 7.70 (t, J=8.0 Hz, 1 H) 7.74 (dd, J=8.2, 1.9 Hz, 1 H) 7.92 (s, 1 H) 8.02 (d, J=7.8 Hz, 1 H) 8.06 (d, J=1.6 Hz, 1 H) 9.07 (s, 1 H) 10.40 (s, 1 H).

53 N-(1-Hydroxy-3,3-dimethyl-1,3-dihydro-benzo[c][1,2]oxaborol-6-yl)-4-trifluoromethoxy-benzamide

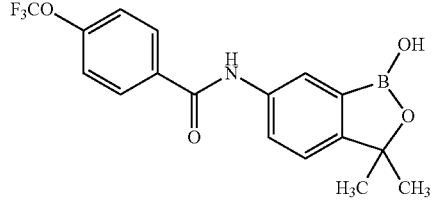

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-trifluoromethoxy-benzoyl chloride replacing 2-trifluoromethyl-4-fluorobenzoyl chloride. Data: LCMS (M/Z): 366 (M+H); $^1$H NMR (DMSO-d$_6$) δ: 1.45 (s, 6 H) 7.39 (d, J=8.2 Hz, 1 H) 7.53 (d, J=8.0 Hz, 2 H) 7.74 (dd, J=8.2, 2.0 Hz, 1 H) 8.06-8.09 (m, 2 H) 8.09-8.11 (m, 1 H) 9.07 (br. s., 1 H) 10.37 (s, 1 H).

54 N-(1-Hydroxy-3,3-dimethyl-1,3-dihydro-benzo[c][1,2]oxaborol-6-yl)-4-trifluoromethylsulfanyl-benzamide

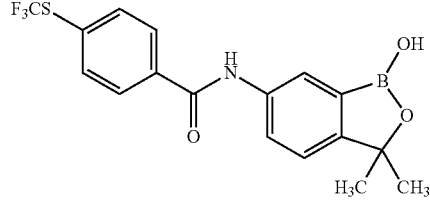

The title compound was prepared using a procedure similar to that of 4-fluoro-N-(1-hydroxy-3,3-dimethyl-1,3- dihydro-benzo[c][1,2]oxaborol-6-yl-2-trifluoromethyl benzamide with 4-trifluoromethylsulfanyl-benzoyl chloride replacing 2-trifluoromethyl-4-fluorobenzoyl chloride. Data: LCMS (M/Z): 382 (M+H); $^1$H NMR (DMSO-d$_6$) δ: 1.45 (s, 6 H) 7.40 (d, J=8.2 Hz, 1 H) 7.74 (dd, J=8.2, 2.0 Hz, 1 H) 7.89 (d, J=8.3 Hz, 2 H) 8.04-8.10 (m, 3 H) 9.04-9.12 (m, 1 H) 10.46 (s, 1 H).

55 N-(1-Hydroxy-3,3-dimethyl-1,3-dihydro-benzo[c][1,2]oxaborol-6-yl)-2-nitro-benzamide

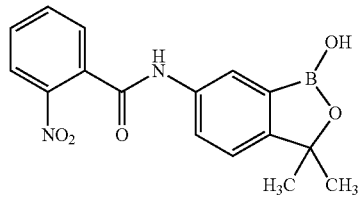 [SMILES: CC1(C)OB(O)c2cc(NC(=O)c3ccccc3[N+](=O)[O-])ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-nitro-benzoyl chloride replacing 2-trifluoromethyl-4-fluorobenzoyl chloride. Data: LCMS (M/Z): 327 (M+H); $^1$H NMR (DMSO-d$_6$) δ: 1.41 (s, 6 H) 7.36 (d, J=8.2 Hz, 1 H) 7.60 (dd, J=8.2, 2.0 Hz, 1 H) 7.73 (d, J=7.5 Hz, 2 H) 7.81-7.87 (m, 1 H) 7.98 (d, J=1.9 Hz, 1 H) 8.11 (d, J=8.2 Hz, 1 H) 9.06 (s, 1 H) 10.63 (s, 1 H).

56 N-(1-Hydroxy-3,3-dimethyl-1,3-dihydro-benzo[c][1,2]oxaborol-6-yl)-4-nitro-benzamide

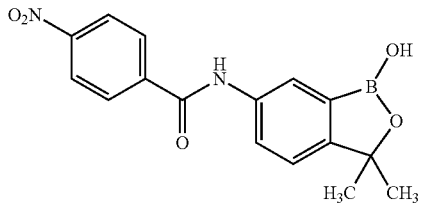

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-nitro-benzoyl chloride replacing 2-trifluoromethyl-4-fluorobenzoyl chloride. Data: LCMS (M/Z): 327 (M+H); $^1$H NMR (DMSO-d$_6$) δ: 1.45 (s, 6 H) 7.41 (d, J=8.2 Hz, 1 H) 7.75 (dd, J=8.2, 2.0 Hz, 1 H) 8.09 (d, J=1.8 Hz, 1 H) 8.19 (d, J=8.9 Hz, 2 H) 8.38 (d, J=8.8 Hz, 2 H) 9.09 (s, 1 H) 10.59 (s, 1 H).

57 4-Cyano-N-(1-hydroxy-3,3-dimethyl-1,3-dihydro-benzo[c][1,2]oxaborol-6-yl)-benzamide

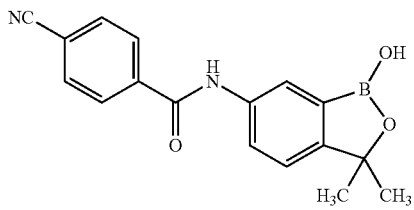 [SMILES: CC1(C)OB(O)c2cc(NC(=O)c3ccc(C#N)cc3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-cyano-benzoyl chloride replacing 2-trifluoromethyl-4-fluorobenzoyl chloride. Data: LCMS (M/Z): 307 (M+H); $^1$H NMR (DMSO-d$_6$) δ: 1.45 (s, 6 H) 7.40 (d, J=8.2 Hz, 1 H) 7.74 (dd, J=8.2, 2.0 Hz, 1 H) 8.00-8.06 (m, 2 H) 8.06-8.14 (m, 3 H) 9.09 (s, 1 H) 10.50 (s, 1 H).

58 N-(1-Hydroxy-3,3-dimethyl-1,3-dihydro-benzo[c][1,2]oxaborol-6-yl)-terephthalamic acid methyl ester

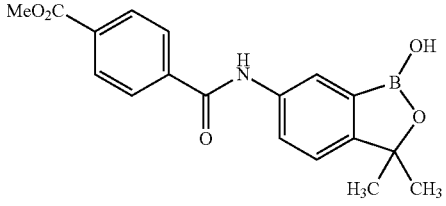 [SMILES: COC(=O)c1ccc(C(=O)Nc2ccc3c(c2)B(O)OC3(C)C)cc1]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-chlorocarbonyl-benzoic acid methyl ester replacing 2-trifluoromethyl-4-fluorobenzoyl chloride. Data: LCMS (M/Z): 340 (M+H); $^1$H NMR (DMSO-d$_6$) δ: 1.41 (s, 6 H) 3.86 (s, 3 H) 7.36 (d, J=8.2 Hz, 1 H) 7.71 (dd, J=8.2, 2.0 Hz, 1 H) 8.03-8.07 (m, 5 H) 9.04 (s, 1 H) 10.42 (s, 1 H).

59 4-Acetylamino-N-(1-hydroxy-3,3-dimethyl-1,3-dihydro-benzo[c][1,2]oxaborol-6-yl)-benzamide

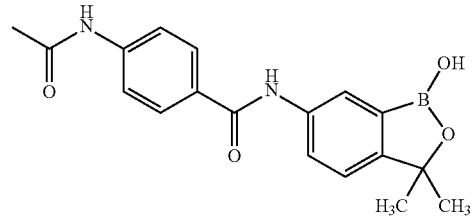 [SMILES: CC(=O)Nc1ccc(C(=O)Nc2ccc3c(c2)B(O)OC3(C)C)cc1]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-acetylamino-benzoyl chloride replacing 2-trifluoromethyl-4-fluorobenzoyl chloride. Data: LCMS (M/Z): 339 (M+H); $^1$H NMR (DMSO-d$_6$) δ: 1.45 (s, 6 H) 2.09 (s, 3 H) 7.37 (d, J=8.4 Hz, 1 H) 7.65-7.77 (m, 3 H) 7.93 (d, J=8.6 Hz, 2 H) 8.05 (d, J=2.0 Hz, 1 H) 9.06 (s, 1 H) 10.13 (s, 1 H) 10.22 (s, 1 H).

60 N-(1-Hydroxy-3,3-dimethyl-1,3-dihydro-benzo[c][1,2]oxaborol-6-yl)-4-thiophen-2-yl-benzamide

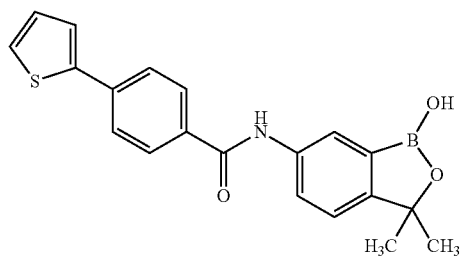 [SMILES: CC1(C)OB(O)c2cc(NC(=O)c3ccc(-c4cccs4)cc3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-thiophen-2-yl-benzoyl chloride replacing 2-trifluoromethyl-4-fluorobenzoyl chloride. Data: LCMS (M/Z): 364 (M+H); $^1$H NMR (DMSO-d$_6$) δ: 1.42 (s, 6 H) 7.16 (dd, J=4.6, 4.1 Hz, 1 H) 7.35 (d, J=8.2 Hz, 1 H) 7.63 (dd, J=13.3, 4.3 Hz, 2 H) 7.73 (dd, J=8.2, 1.9 Hz, 1 H) 7.79 (d, J=8.2 Hz, 2 H) 7.99 (d, J=8.4 Hz, 2 H) 8.05 (d, J=1.6 Hz, 1 H) 9.03 (s, 1 H) 10.25 (s, 1 H).

61 N-(1-Hydroxy-3,3-dimethyl-1,3-dihydro-benzo[c][1,2]oxaborol-6-yl)-4-morpholin-4-yl-benzamide

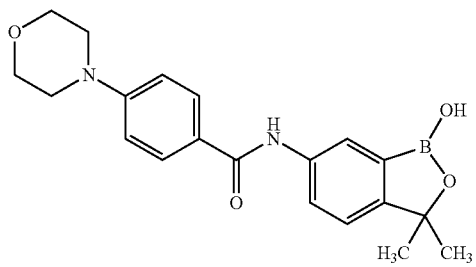 [SMILES: CC1(C)OB(O)c2cc(NC(=O)c3ccc(N4CCOCC4)cc3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-morpholin-4-yl-benzoyl chloride replacing 2-trifluoromethyl-4-fluorobenzoyl chloride. Data: LCMS (M/Z): 367 (M+H); $^1$H NMR (DMSO-d$_6$) δ: 1.44 (s, 6 H) 3.26 (d, J=4.7 Hz, 4 H) 3.71-3.79 (m, 4 H) 7.03 (d, J=9.0 Hz, 2 H) 7.35 (d, J=8.2 Hz, 1 H) 7.73 (dd, J=8.3, 2.1 Hz, 1 H) 7.90 (d, J=8.8 Hz, 2 H) 8.05 (d, J=2.0 Hz, 1 H) 8.46 (s, 1 H) 9.99 (s, 1 H).

62 Biphenyl-4-carboxylic acid (1-hydroxy-3,3-dimethyl-1,3-dihydro-benzo[c][1,2]oxaborol-6-yl)-amide

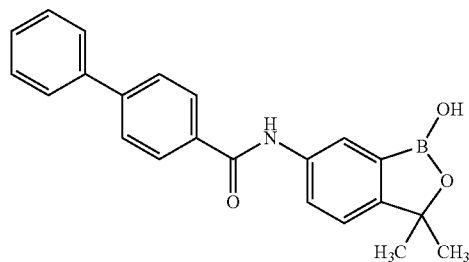 [SMILES: CC1(C)OB(O)c2cc(NC(=O)c3ccc(-c4ccccc4)cc3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with biphenyl-4-carbonyl chloride replacing 2-trifluoromethyl-4-fluorobenzoyl chloride. Data: LCMS (M/Z): 358 (M+H); $^1$H NMR (DMSO-d$_6$) δ: 1.46 (s, 6 H) 7.37-7.45 (m, 2 H) 7.48-7.55 (m, 2 H) 7.74-7.79 (m, 3 H) 7.84 (d, J=8.3 Hz, 2 H) 8.05-8.12 (m, 3 H) 9.03-9.11 (m, 1 H) 10.32 (s, 1 H).

63 2,4-Difluoro-N-(1-hydroxy-3,3-dimethyl-1,3-dihydro-benzo[c][1,2]oxaborol-6-yl)-benzamide

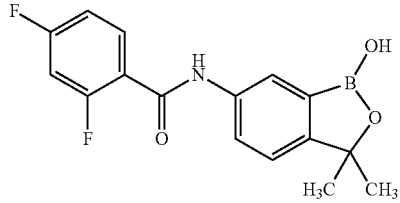

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2,4-difluorobenzoyl chloride replacing 2-trifluoromethyl-4-fluorobenzoyl chloride. Data: LCMS (M/Z): 318 (M+H); $^1$H NMR (DMSO-d$_6$) δ: 10.37 (s, 1H), 9.04 (s, 1H), 7.99 (d, J=1.6 Hz, 1H), 7.72 (td, J=8.4, 6.7 Hz, 1H), 7.65 (dd, J=8.2, 1.9 Hz, 1H), 7.32-7.42 (m, 2H), 7.19 (td, J=8.4, 2.3 Hz, 1H), 1.40 (s, 6H).

64 2,6-Difluoro-N-(1-hydroxy-3,3-dimethyl-1,3-dihydro-benzo[c][1,2]oxaborol-6-yl)-benzamide

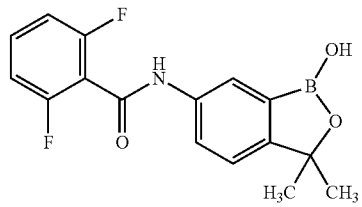

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2,6-difluoro-benzoyl chloride replacing 2-trifluoromethyl-4-fluorobenzoyl chloride. Data: LCMS (M/Z): 318 (M+H); $^1$H NMR (DMSO-d$_6$) δ: 1.44 (s, 6 H) 7.25 (t, J=8.0 Hz, 2 H) 7.40 (d, J=8.2 Hz, 1 H) 7.59 (s, 1 H) 7.66 (dd, J=8.2, 2.0 Hz, 1 H) 8.04 (d, J=1.9 Hz, 1 H) 9.10 (s, 1 H) 10.79 (s, 1 H).

65 2,4-Dichloro-N-(1-hydroxy-3,3-dimethyl-1,3-dihydro-benzo[c][1,2]oxaborol-6-yl)-benzamide

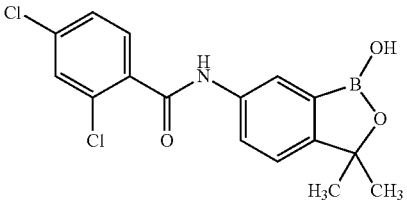 [SMILES: CC1(C)OB(O)c2cc(NC(=O)c3ccc(Cl)cc3Cl)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2,4-dichloro-benzoyl chloride replacing 2-trifluoromethyl-4-fluorobenzoyl chloride. Data: LCMS (M/Z):

350 (M+H); $^1$H NMR (DMSO-d$_6$) δ: 1.44 (s, 6 H) 7.39 (d, J=8.2 Hz, 1 H) 7.54-7.58 (m, 1 H) 7.60-7.70 (m, 2 H) 7.77 (d, J=1.9 Hz, 1 H) 8.04 (d, J=1.7 Hz, 1 H) 9.09 (s, 1 H) 10.54 (s, 1 H).

66 2,3-Dichloro-N-(1-hydroxy-3,3-dimethyl-1,3-dihydro-benzo[c][1,2]oxaborol-6-yl)-benzamide

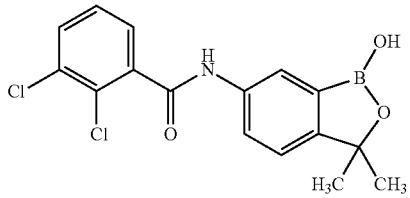 [SMILES: CC1(C)OB(O)c2cc(NC(=O)c3cccc(Cl)c3Cl)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2,3-dichloro-benzoyl chloride replacing 2-trifluoromethyl-4-fluorobenzoyl chloride. Data: LCMS (M/Z): 350 (M+H); $^1$H NMR (DMSO-d$_6$) δ: 1.44 (s, 6 H) 7.39 (d, J=8.2 Hz, 1 H) 7.45-7.52 (m, 1 H) 7.52-7.59 (m, 1 H) 7.67 (dd, J=8.2, 2.0 Hz, 1 H) 7.77 (dd, J=7.9, 1.7 Hz, 1 H) 8.05 (d, J=1.8 Hz, 1 H) 9.09 (s, 1 H) 10.59 (s, 1 H).

67 3,4-Dichloro-N-(1-hydroxy-3,3-dimethyl-1,3-dihydro-benzo[c][1,2]oxaborol-6-yl)-benzamide

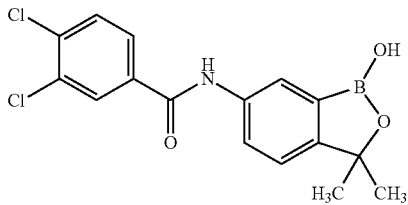 [SMILES: CC1(C)OB(O)c2cc(NC(=O)c3ccc(Cl)c(Cl)c3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 3,4-dichloro-benzoyl chloride replacing 2-trifluoromethyl-4-fluorobenzoyl chloride. Data: LCMS (M/Z): 351 (M+H); $^1$H NMR (DMSO-d$_6$) δ: 1.45 (s, 6 H) 7.40 (d, J=8.2 Hz, 1 H) 7.73 (dd, J=8.2, 1.9 Hz, 1 H) 7.83 (d, J=8.4 Hz, 1 H) 7.95 (dd, J=8.3, 2.0 Hz, 1 H) 8.06 (d, J=1.6 Hz, 1 H) 8.22 (d, J=2.0 Hz, 1 H) 9.08 (s, 1 H) 10.41 (s, 1 H).

68 2,6-Dichloro-N-(1-hydroxy-3,3-dimethyl-1,3-dihydro-benzo[c][1,2]oxaborol-6-yl)-benzamide

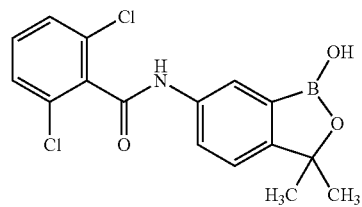 [SMILES: CC1(C)OB(O)c2cc(NC(=O)c3c(Cl)cccc3Cl)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2,6-dichloro-benzoyl chloride replacing 2-trifluoromethyl-4-fluorobenzoyl chloride. Data: LCMS (M/Z): 350 (M+H); $^1$H NMR (DMSO-d$_6$) δ: 1.44 (s, 6 H) 7.40 (d, J=8.2 Hz, 1 H) 7.46-7.55 (m, 1 H) 7.56-7.62 (m, 2 H) 7.64 (dd, J=8.2, 2.0 Hz, 1 H) 8.05 (d, J=1.8 Hz, 1 H) 9.10 (s, 1 H) 10.74 (s, 1 H).

69 2-Chloro-4-fluoro-N-(1-hydroxy-3,3-dimethyl-1,3-dihydro-benzo[c][1,2]oxaborol-6-yl)-benzamide

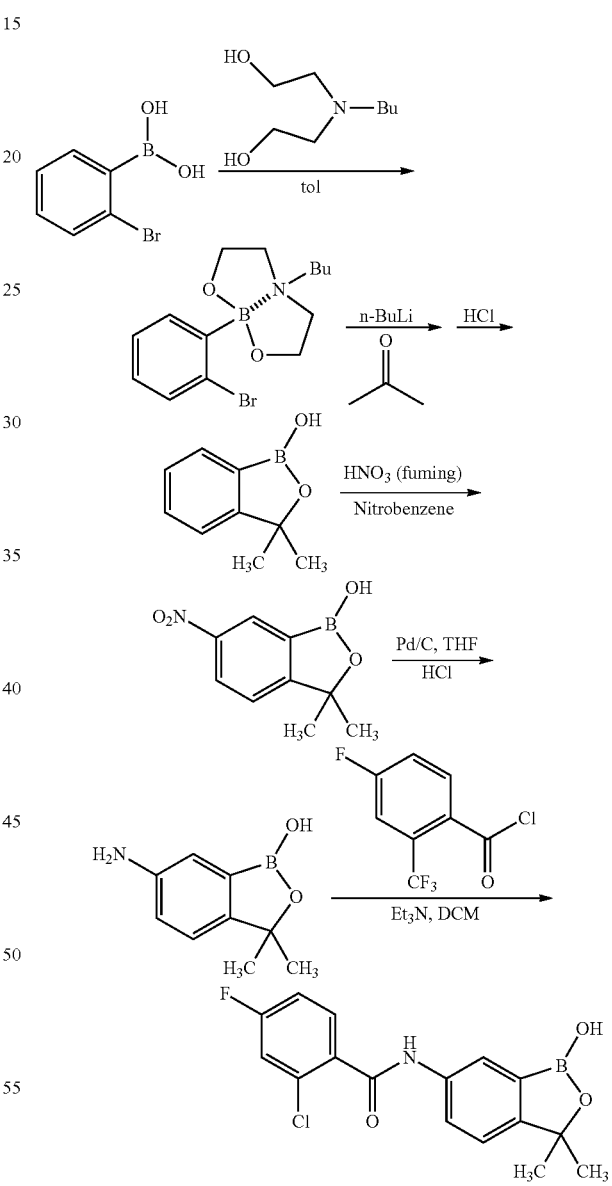

To a suspension of 2-bromophenylboronic acid (75.0 g, 373.4 mmol) in toluene (525 mL) was added N-butyldiethanolamine (64.1 mL, 392.1 mmol, 1.05 equiv.) via a syringe. The mixture was heated at 50° C. for two hours. After cooling to room temperature, the toluene was evaporated under reduced pressure and the remaining clear colorless oil was treated with heptanes (500 mL). The heptanes mixture was then sonicated for 5 min and the resulting suspension was allowed to stand at room temperature overnight. The solid that precipitated was collected by filtration, washed with heptanes, and dried in a vacuum oven overnight to yield the title compound as a white solid. $^1$H NMR (400 MHz, CHLOROFORM-d) ppm 0.86 (t, J=7.4 Hz, 3 H) 1.14-1.25 (m, 2 H) 1.51-1.62 (m, 2 H) 2.61-2.70 (m, 2 H) 3.01-3.11 (m, 2 H) 3.26-3.37 (m, 2 H) 4.09-4.26 (m, 4 H) 7.10 (td, J=7.6, 2.0 Hz, 1 H) 7.24 (td, J=7.3, 1.1 Hz, 1 H) 7.51 (d, J=7.9 Hz, 1 H) 7.81 (dd, J=7.4, 1.9 Hz, 1 H). Amount obtained, 123.7 g (98.6% yield).

3,3-Dimethyl-3H-benzo[c][1,2]oxaborol-1-ol

To a solution of 2-(2'-bromophenyl)-6-butyl[1,3,6,2]dioxazaborocan (93.1 g, 277.1 mmol) in THF (2.3 L) at −78° C. was added n-BuLi (133.0 mL, 2.5M in hexane, 332.5 mmol, 1.2 equiv.) dropwise via a syringe over a period of 10 min while maintaining reaction temperature at −78° C. After the addition the reaction solution was stirred for 20 min at −78° C. before acetone (23.2 mL, 387.9 mmol, 1.4 equiv.) was added dropwise via a syringe over a period of 10 min while maintaining the reaction temperature at −78° C. The resulting mixture was allowed to stir for 20 min at −78° C. then warm to room temperature gradually. Once the reaction vessel reached room temperature, 6N HCl solution (1 L) was added and the mixture was stirred for an additional 30 min. The mixture was extracted with EtOAc (3×). The EtOAc extracts were dried over Na$_2$SO$_4$, filtered and concentrated under reduced pressure. The light yellow oil was then subjected to flash chromatography (Isco Companion, 80 g SiO$_2$ cartridge, solid loaded SiO$_2$, neat heptanes to 20:80 EtOAc gradient at 60 ml/min for 90 min). The title compound was recovered as clear colorless oil. $^1$H NMR (400 MHz, DMSO-d$_6$) δ ppm 1.44 (s, 6 H) 7.31 (d, J=1.1 Hz, 1 H) 7.38-7.47 (m, 2 H) 7.66 (d, J=7.2 Hz, 1 H) 8.99 (s, 1 H). Amount obtained: 16.9 g (37.7% yield).

3,3-Dimethyl-6-nitro-3H-benzo[c][1,2]oxaborol-1-ol

To 106 mL fuming HNO$_3$ at −45° C. was slowly added a solution of 3,3-dimethyl-3H-benzo[c][1,2]oxaborol-1-ol (16.9 g, 104.3 mmol) in 10.5 mL nitrobenzene via a syringe while maintaining the reaction temperature between −40 to −45° C. Once the addition was complete the resulting solution was allowed to stir at −45° C. for an additional 45 min before poured into crushed ice. The ice mixture was allowed to melt and the aqueous solution was extracted with DCM (3×). The combined DCM extracts were dried over Na$_2$SO$_4$ then evaporated. The crude oil remaining was mixed with one liter 1:1 DCM/heptanes. The volume of the solution was reduced under reduced pressure by half and the resulting solution was allowed to stand overnight in a −20° C. freezer. The precipitate formed was filtered out, washed with heptanes and vacuum dried to give the titled compound as a white solid. $^1$H NMR (400 MHz, DMSO-d$_6$) δ ppm 1.46 (s, 6 H) 7.69 (d, J=8.4 Hz, 1 H) 8.28 (dd, J=8.4, 2.3 Hz, 1 H) 8.48 (d, J=2.2 Hz, 1 H) 9.41 (br. s., 1 H). Amount obtained: 11.2 g (51.8% yield).

2-Chloro-4-fluoro-N-(1-hydroxy-3,3-dimethyl-1,3-dihydro-benzo[c][1,2]oxaborol-6-yl)-benzamide A solution of 3,3-dimethyl-6-nitro-3H-benzo[c][1,2]oxaborol-1-ol (500 mg, 2.4 mmol) in THF (60 mL) was pass through H-Cube equipped with a 10% Pd/C Catcart (30×4 mm). The flow rate was set at 1.0 mL/min and TLC indicated complete consumption of starting material after one run. To the obtained light yellow solution was added Et$_3$N (1.1 mL, 7.7 mmol, 3.2 equiv.), followed by drop wise addition of 2-cloro-4-fluoro-benzoyl chloride (0.51 mL, 3.8 mmol, 1.6 equiv.). The mixture was allowed to stir at room temperature over 18 h before poured into a 1:1 mixture of EtOAc/HCl (1 N). The layers were separated and the aqueous phase was extracted with EtOAc (3×). Combined organics was washed with H$_2$O, brine and concentrated under reduced pressure to give a white solid. The solid was dissolved in minimal amount of THF and treated with heptanes. The precipitate was collected by filtration and washed with heptanes to give the title compound as a white solid. LCMS (M/Z): 334 (M+H); $^1$H NMR (DMSO-d$_6$) δ: 10.49 (s, 1H), 9.06 (s, 1H), 8.01 (d, J=1.7 Hz, 1H), 7.60-7.65 (m, 2H), 7.55 (dd, J=9.0, 2.5 Hz, 1H), 7.28-7.37 (m, 2H), 1.40 (s, 6H). Amount obtained: 726 mg, (91.2% yield).

70 3-Chloro-2-fluoro-N-(1-hydroxy-3,3-dimethyl-1,3-dihydro-benzo[c][1,2]oxaborol-6-yl)-benzamide

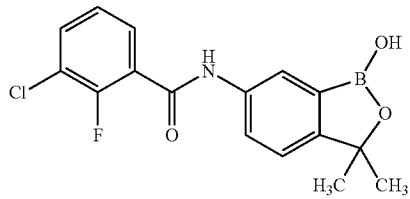 [SMILES: CC1(C)OB(O)c2cc(NC(=O)c3cccc(Cl)c3F)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 3-chloro-2-fluoro-benzoyl chloride replacing 2-trifluoromethyl-4-fluorobenzoyl chloride. Data: LCMS (M/Z): 334 (M+H); $^1$H NMR (DMSO-d$_6$) δ: 1.44 (s, 6 H) 7.38 (t, J=8.4 Hz, 2 H) 7.61-7.66 (m, 1 H) 7.68 (dd, J=8.2, 2.0 Hz, 1 H) 7.73-7.79 (m, 1 H) 8.04 (d, J=1.8 Hz, 1 H) 9.10 (s, 1 H) 10.56 (s, 1 H).

71 4-Chloro-2-fluoro-N-(1-hydroxy-3,3-dimethyl-1,3-dihydro-benzo[c][1,2]oxaborol-6-yl)-benzamide

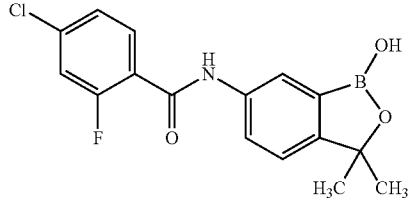 [SMILES: CC1(C)OB(O)c2cc(NC(=O)c3ccc(Cl)cc3F)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-chloro-2-fluoro-benzoyl chloride replacing 2-trifluoromethyl-4-fluorobenzoyl chloride. Data: LCMS (M/Z): 334 (M+H); $^1$H NMR (DMSO-d$_6$) δ: 1.44 (s, 6 H) 7.39 (d, J=8.2 Hz, 1 H) 7.44 (dd, J=8.3, 1.9 Hz, 1 H) 7.62 (dd, J=10.0, 1.9 Hz, 1 H) 7.67-7.70 (m, 1 H) 7.70-7.74 (m, 1 H) 8.03 (d, J=1.5 Hz, 1 H) 9.09 (s, 1 H) 10.46 (s, 1 H).

72 5-Chloro-2-fluoro-N-(1-hydroxy-3,3-dimethyl-1,3-dihydro-benzo[c][1,2]oxaborol-6-yl)-benzamide

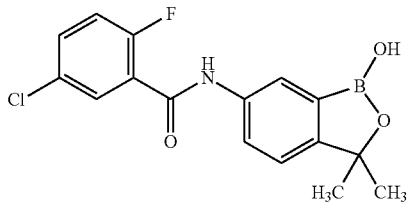 [SMILES: CC1(C)OB(O)c2cc(NC(=O)c3cc(Cl)ccc3F)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 5-chloro-2-fluoro-benzoyl chloride replacing 2-trifluoromethyl-4-fluorobenzoyl chloride. Data: LCMS (M/Z): 334 (M+H); $^1$H NMR (DMSO-$d_6$) δ: 1.44 (s, 6 H) 7.37-7.47 (m, 2 H) 7.68 (dd, J=8.2, 2.0 Hz, 2 H) 7.73 (dd, J=5.9, 2.7 Hz, 1 H) 8.04 (d, J=1.8 Hz, 1 H) 9.09 (s, 1 H) 10.52 (s, 1 H).

73 2-Chloro-6-fluoro-N-(1-hydroxy-3,3-dimethyl-1,3-dihydro-benzo[c][1,2]oxaborol-6-yl)-benzamide

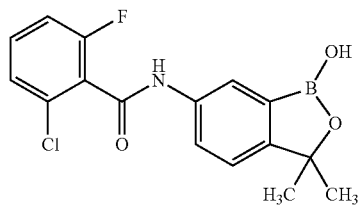

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-chloro-6-fluoro-benzoyl chloride replacing 2-trifluoromethyl-4-fluorobenzoyl chloride. Data: LCMS (M/Z): 334 (M+H); $^1$H NMR (DMSO-$d_6$) δ: 1.44 (s, 6 H) 7.37-7.43 (m, 2 H) 7.45 (d, J=8.0 Hz, 1 H) 7.55 (td, J=8.2, 6.2 Hz, 1 H) 7.65 (dd, J=8.2, 2.0 Hz, 1 H) 8.05 (d, J=2.0 Hz, 1 H) 9.10 (s, 1 H) 10.78 (s, 1 H).

74 2-Bromo-4-fluoro-N-(1-hydroxy-3,3-dimethyl-1,3-dihydro-benzo[c][1,2]oxaborol-6-yl)-benzamide

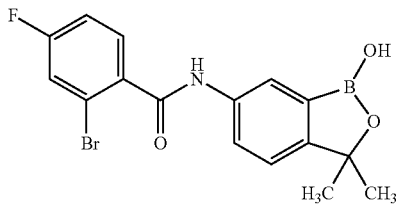 [SMILES: CC1(C)OB(O)c2cc(NC(=O)c3ccc(F)cc3Br)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-bromo-4-fluorobenzoyl chloride replacing 2-trifluoromethyl-4-fluorobenzoyl chloride. Data: LCMS (M/Z): 378 (M); $^1$H NMR (DMSO-$d_6$) δ: 10.45 (s, 1H), 9.05 (s, 1H), 8.01 (d, J=1.8 Hz, 1H), 7.59-7.71 (m, 3H), 7.31-7.39 (m, 2H), 1.40 (s, 6H).

75 2-Bromo-4-chloro-N-(1-hydroxy-3,3-dimethyl-1,3-dihydro-benzo[c][1,2]oxaborol-6-yl)-benzamide

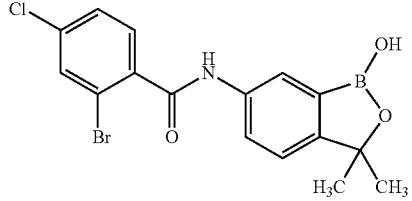 [SMILES: CC1(C)OB(O)c2cc(NC(=O)c3ccc(Cl)cc3Br)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-bromo-4-chloro-benzoyl chloride replacing 2-trifluoromethyl-4-fluorobenzoyl chloride. Data: LCMS (M/Z): 395 (M+H); $^1$H NMR (DMSO-$d_6$) δ: 1.40 (s, 6 H) 7.35 (d, J=8.2 Hz, 1 H) 7.56 (d, J=1.0 Hz, 2 H) 7.63 (dd, J=8.2, 2.0 Hz, 1 H) 7.85 (t, J=1.1 Hz, 1 H) 8.00 (d, J=1.9 Hz, 1 H) 9.05 (s, 1 H) 10.48 (s, 1 H).

76 4-Bromo-2-chloro-N-(1-hydroxy-3,3-dimethyl-1,3-dihydro-benzo[c][1,2]oxaborol-6-yl)-benzamide

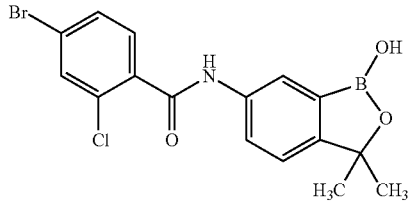

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-bromo-2-chloro-benzoyl chloride replacing 2-trifluoromethyl-4-fluorobenzoyl chloride. Data: LCMS (M/Z): 395 (M+H); $^1$H NMR (DMSO-$d_6$) δ: 1.40 (s, 6 H) 7.35 (d, J=8.2 Hz, 1 H) 7.51 (d, J=8.2 Hz, 1 H) 7.64 (td, J=8.1, 1.9 Hz, 2 H) 7.84 (d, J=1.9 Hz, 1 H) 8.00 (d, J=1.9 Hz, 1 H) 9.00-9.11 (m, 1 H) 10.50 (s, 1 H).

77 2-Chloro-N-(1-hydroxy-3,3-dimethyl-1,3-dihydro-benzo[c][1,2]oxaborol-6-yl)-4-iodo-benzamide

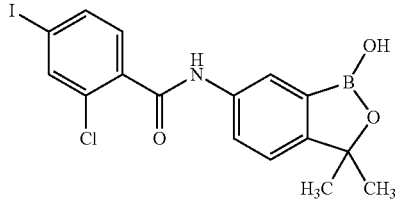 [SMILES: CC1(C)OB(O)c2cc(NC(=O)c3ccc(I)cc3Cl)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-chloro-4-iodo-benzoyl chloride replacing 2-trifluoromethyl-4-fluorobenzoyl chloride. Data: LCMS (M/Z): 442 (M+H); $^1$H NMR (DMSO-d$_6$) δ: 1.44 (s, 6 H) 7.37 (dd, J=8.1, 5.6 Hz, 2 H) 7.66 (dd, J=8.4, 2.0 Hz, 1 H) 7.84 (dd, J=8.0, 1.6 Hz, 1 H) 8.02 (dd, J=1.0 Hz, 2 H) 9.09 (s, 1 H) 10.52 (s, 1 H).

78 N-(1-Hydroxy-3,3-dimethyl-1,3-dihydro-benzo[c][1,2]oxaborol-6-yl)-2,4-dimethyl-benzamide

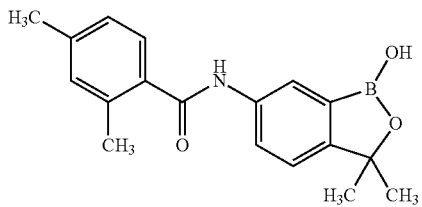 [SMILES: CC1(C)OB(O)c2cc(NC(=O)c3ccc(C(F)(F)F)cc3C(F)(F)F)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2,4-dimethyl-benzoyl chloride replacing 2-trifluoromethyl-4-fluorobenzoyl chloride. Data: LCMS (M/Z): 310 (M+H); $^1$H NMR (DMSO-d$_6$) δ: 1.40 (s, 6 H) 2.28 (s, 3 H) 2.32 (s, 3 H) 7.04-7.10 (m, 2 H) 7.32 (dd, J=7.9, 2.6 Hz, 2 H) 7.65 (dd, J=8.2, 1.8 Hz, 1 H) 8.01-8.05 (m, 1 H) 9.01 (s, 1 H) 10.17 (s, 1 H).

79 N-(1-Hydroxy-3,3-dimethyl-1,3-dihydro-benzo[c][1,2]oxaborol-6-yl)-2,4-bis-trifluoromethyl-benzamide

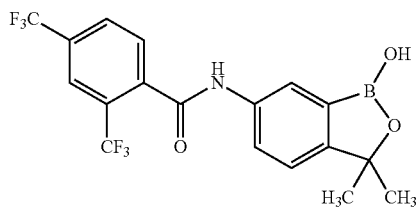

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2,4-bis-trifluoromethyl-benzoyl chloride replacing 2-trifluoromethyl-4-fluorobenzoyl chloride. Data: LCMS (M/Z): 418 (M+H); $^1$H NMR (DMSO-d$_6$) δ: 1.44 (s, 6 H) 7.40 (d, J=8.2 Hz, 1 H) 7.65 (dd, J=8.2, 1.9 Hz, 1 H) 7.97 (d, J=8.0 Hz, 1 H) 8.03 (d, J=1.6 Hz, 1 H) 8.18-8.25 (m, 2 H) 9.10-9.15 (m, 1 H) 10.76 (s, 1 H).

80 N-(1-Hydroxy-3,3-dimethyl-1,3-dihydro-benzo[c][1,2]oxaborol-6-yl)-3,5-bis-trifluoromethyl-benzamide

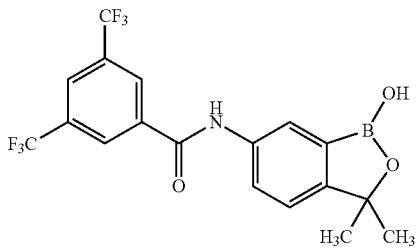 [SMILES: CC1(C)OB(O)c2cc(NC(=O)c3cc(C(F)(F)F)cc(C(F)(F)F)c3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 3,5-bis-trifluoromethyl-benzoyl chloride replacing 2-trifluoromethyl-4-fluorobenzoyl chloride. Data: LCMS (M/Z): 418 (M+H); $^1$H NMR (DMSO-d$_6$) δ: 1.46 (s, 6 H) 7.44 (d, J=8.2 Hz, 1 H) 7.76 (dd, J=8.2, 2.0 Hz, 1 H) 8.07 (d, J=1.9 Hz, 1 H) 8.37 (s, 1 H) 8.62 (s, 2 H) 9.10 (s, 1 H) 10.68 (s, 1 H).

81 N-(1-Hydroxy-3,3-dimethyl-1,3-dihydro-benzo[c][1,2]oxaborol-6-yl)-2,5-bis-trifluoromethyl-benzamide

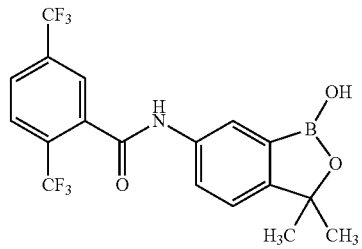

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2,5-bis-trifluoromethyl-benzoyl chloride replacing 2-trifluoromethyl-4-fluorobenzoyl chloride. Data: LCMS (M/Z): 418 (M+H); $^1$H NMR (DMSO-d$_6$) δ: 1.45 (s, 6 H) 7.40 (d, J=8.2 Hz, 1 H) 7.64 (dd, J=8.2, 2.0 Hz, 1 H) 8.03 (d, J=2.0 Hz, 1 H) 8.12 (s, 2 H) 8.16 (s, 1 H) 9.10 (s, 1 H) 10.70 (s, 1 H).

82 4-Fluoro-N-(1-hydroxy-3,3-dimethyl-1,3-dihydro-benzo[c][1,2]oxaborol-6-yl-2-trifluoromethyl benzamide

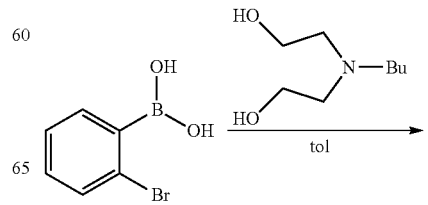

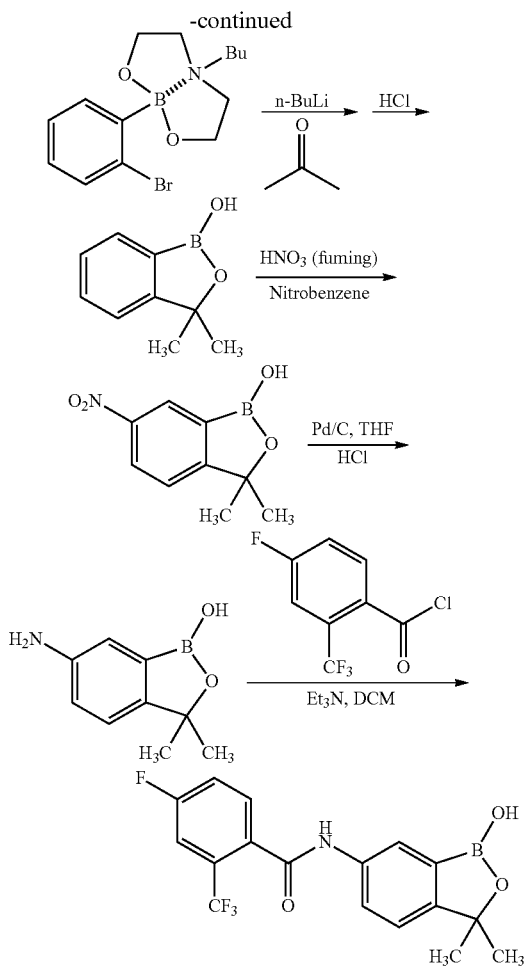

To a suspension of 2-bromophenylboronic acid (10.0 g, 49.7 mmol) in toluene (70 mL) was added N-butyldiethanolamine (8.5 mL, 52.2 mmol, 1.05 equiv.) via a syringe. The mixture was heated at 50° C. for two hours. After cooling to room temperature, the toluene was evaporated under reduced pressure and the remaining clear colorless crude oil was treated with heptanes (~500 mL). The heptanes mixture was then sonicated ~5 min and the resulting suspension was allowed to stand at room temperature overnight. The solid that precipitated was collected by filtration, washed with heptanes, and dried in a vacuum oven overnight to yield a white solid as the titled compound. $^1$H NMR (400 MHz, CHLOROFORM-d) δ ppm 0.86 (t, J=7.4 Hz, 3 H) 1.14-1.25 (m, 2 H) 1.51-1.62 (m, 2 H) 2.61-2.70 (m, 2 H) 3.01-3.11 (m, 2 H) 3.26-3.37 (m, 2 H) 4.09-4.26 (m, 4 H) 7.10 (td, J=7.6, 2.0 Hz, 1 H) 7.24 (td, J=7.3, 1.1 Hz, 1 H) 7.51 (d, J=7.9 Hz, 1 H) 7.81 (dd, J=7.4, 1.9 Hz, 1 H). Amount obtained, 16.0 g, (98% yield).

To a solution of 2-(2'-bromophenyl)-6-butyl[1,3,6,2]dioxazaborocan (3.0 g, 9.2 mmol) in THF (76 mL) at −78° C. was added n-BuLi (4.4 mL, 2.5M in hexane, 11.0 mmol, 1.2 equiv.) dropwise via a syringe over a period of 10 min while maintaining reaction temperature at −78° C. After the addition the reaction solution was stirred 20 min at −78° C. before acetone (946 μL, 12.8 mmol, 1.4 equiv.) was added dropwise via a syringe over a period of 10 min while maintaining the reaction temperature at −78° C. The resulting mixture was allowed to stir for 20 min at −78° C. then warm to room temperature gradually. Once the reaction vessel reached room temperature, 6M HCl solution (30 mL) was added and the mixture was stirred for 30 min. The mixture was extracted with EtOAc (3×). The EtOAc extracts were dried over Na$_2$SO$_4$, filtered and concentrated under reduced pressure. The crude slightly yellow in color residual oil remaining was then subjected to flash chromatography (Isco Companion, 80 g SiO$_2$ cartridge, solid loaded SiO$_2$, neat heptane to 20:80 EtOAc gradient at 60 ml/min for 90 min). The product was recovered as clear colorless oil. $^1$H NMR (400 MHz, DMSO-d$_6$) δ ppm 1.44 (s, 6 H) 7.31 (d, J=1.1 Hz, 1 H) 7.38-7.47 (m, 2 H) 7.66 (d, J=7.2 Hz, 1 H) 8.99 (s, 1 H). Amount obtained: 1.76 g (61%).

To 14.2 ml fuming HNO$_3$ at −45° C. was added a solution of 3,3-dimethyl-3H-benzo[c][1,2]oxaborol-1-ol (2.28 g, 14.1 mmol) in 3.0 ml nitrobenzene slowly via a syringe while maintaining the reaction temperature between −40 to −45° C. Once the addition was complete the resulting solution was allowed to stir at −45° C. for an additional 45 min before poured into crushed ice (600 g). The ice mixture was allowed to melt and the aqueous solution was extracted with dichloromethane. The combined dichloromethane extracts were dried over Na$_2$SO$_4$ then evaporated. The crude oil remaining was mixed with one liter 1:1 DCM:heptane. The volume of the solution was reduced on a rotovap by half and the resulting solution was allowed to stand overnight in a −20° C. freezer overnight. The precipitate formed was filtered out, washed with heptanes and vacuum dried to give the titled compound as a white solid. $^1$H NMR (400 MHz, DMSO-d$_6$) δ ppm 1.46 (s, 6 H) 7.69 (d, J=8.4 Hz, 1 H) 8.28 (dd, J=8.4, 2.3 Hz, 1 H) 8.48 (d, J=2.2 Hz, 1 H) 9.41 (br. s., 1 H). Amount obtained: 2.01 g (68%).

To a solution of 3,3-dimethyl-6-nitro-3H-benzo[c][1.2]oxaborol-1-ol (790 mg, 3.8 mmol) in THF (20 mL) was added HOAc (1.7 mL, 30 mmol). The vessel was vacuum/N$_2$ purged three times and 5% Pd/C (200 mg) was added. The mixture was again vacuum/N$_2$ purged three times then vacuum purged again. H$_2$ was then introduced from a balloon and the reaction was allowed to stir for 2.5 hours. The reaction solution was filtered through a short pad of celite and the filtrate was evaporated to yield the title compound as a dark brown foamy solid. $^1$H NMR (400 MHz, DMSO-d$_6$) δ ppm 1.36 (s, 6 H) 4.94 (s, 2 H) 6.66 (dd, J=8.1, 2.2 Hz, 1 H) 6.79 (d, J=2.0 Hz, 1 H) 7.01 (d, J=8.1 Hz, 1 H) 8.72 (s, 1 H). Amount obtained: 670 mg (89%).

To a solution of 6-amino-3,3-dimethyl-3H-benzo[c][1,2]oxaborol-1-ol acetate salt (100 mg, 0.42 mmol) in DCM (2 mL) was added Et$_3$N (117.3 μL, 0.84 mmol). The mixture was cooled to 0° C. and the 2-trifluoromethyl-4-fluorobenzoyl chloride (70.0 μL, 0.46 mmol) was added slowly via a syringe. The resulting solution was allowed to warm to room temperature gradually and stir for 2 hours. The reaction solution was diluted with DCM, washed with 1N HCl, H$_2$O and then dried over Na$_2$SO$_4$, filtered and the filtrate was concentrated under reduced pressure and the crude material was subjected to flash chromatography (Isco Companion, 4 g SiO$_2$ cartridge, SiO$_2$ solid load, neat heptanes to neat EtOAc gradient over 45 min, flow rate=18 ml/min). The title compound was recovered as a white foam. LCMS (M/Z): 368 (M+H); $^1$H NMR (DMSO-d$_6$) δ: 10.58 (s, 1H), 9.11 (s, 1H), 8.02 (d, J=1.7 Hz, 1H), 7.75-7.83 (m, 2H), 7.60-7.71 (m, 2H), 7.38 (d, J=8.2 Hz, 1H), 1.44 (s, 6H). Amount obtained: 144.6 mg (93% yield).

Alternate Synthesis

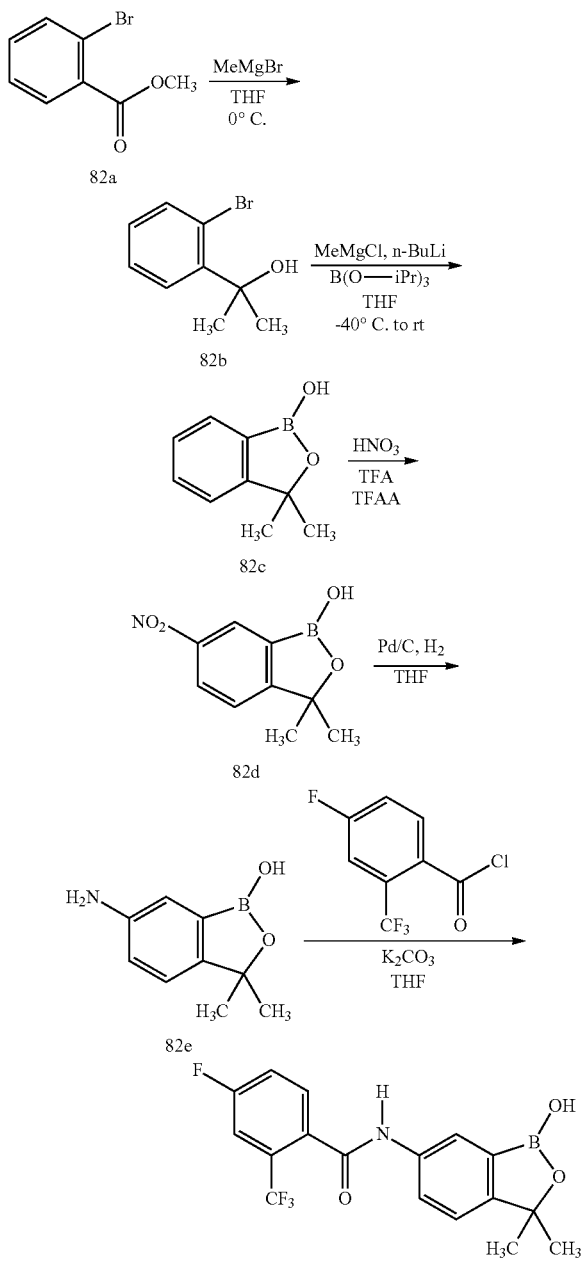

82b

A 500 mL round-bottomed-flask equipped with a magnetic stir bar and ice-H$_2$O bath was charged with 82a (18.4 g, 85.5 mmol) and anhydrous THF (200 mL). MeMgCl (68 mL, 3.0M in 2-methylTHF) was added dropwise through an additional funnel. The mixture was allowed to warm to rt. gradually and stirred overnight. After cooling back to 0° C., the white milky suspension was carefully treated with HCl (3M) until the upper layer turned clear with white precipitate at the bottom of the flask (pH=6). The upper clear solution was decanted into a separatory funnel. The precipitate was rinsed with methyl tert-butyl ether (MTBE) (100 mL) 3 times. Combined MTBE with the clear solution and the mixture was washed with H$_2$O (100 mL) 3 times, brine (100 mL), dried over MgSO$_4$, filtered and concentrated under reduced pressure to give 82b as a light yellow oil (20.2 g, 100%).

82c

A 50 mL round-bottomed-flask equipped with a magnetic stir bar and ice-H$_2$O bath was charged with 82b (860 mg, 4.0 mmol) and anhydrous THF (20 mL). MeMgBr (1.3 mL, 2.0 M in THF) was slowly added via a syringe. The mixture was stirred at 0° C. for 10 minute and the ice bath was replaced with a dry ice-acetone bath at −40° C. BuLi (1.9 mL, 2.5 M in hexanes) was added dropwise via a syringe. The resulting mixture was stirred at −40° C. for another 2 h before B(O-ipr)$_3$ (1.4 mL, 4.8 mmol) was added dropwise. The mixture was allowed to warm up to rt gradually and stirred overnight. After carefully quenched the reaction with H$_2$O (1 mL), HCl (3M, 10 mL) was added and the mixture was stirred at rt for 1 h. The mixture was extracted with EtOAc (20 mL) 3 times. Combined extracts was washed with H$_2$O (20 mL), brine (20 mL), dried over MgSO$_4$, filtered and concentrated under reduced pressure to give a clear oil. The oil solidified overnight to give 82c as a pale yellow waxy solid (544 mg, 82.4%).

82d

A 3 L round-bottomed-flask equipped with a mechanical stirrer, thermocouple and ice bath was charged with 82c (86.2 g of 58 wt %, 309 mmol) and trifluoroacetic acid (259 mL). Trifluoroacetic anhydride (129 mL, 926 mmol) was added in one portion. An exotherm of 18° C. was observed. The solution was again cooled to 0° C. and 90% nitric acid (18.0 mL, 386 mmol) was added via syringe pump over 2 h. After the addition was complete, the solution was aged for 1 h. Water (1.75 L) was added. Note: Initially the quench is quite exothermic. Add the water in 5 mL aliquots until the exotherm subsides. The resulting suspension was stirred for 16 h while warming to rt. The solids were collected on a frit, rinsed with water (2×500 mL), and air dried to constant weight to provide 50.3 g of crude 82d as a free-flowing orange solid. Note: the crude 82d can be carried forward without recrystallization. The solid was charged to a 1 L three-necked round-bottomed-flask equipped with a nitrogen inlet adapter, thermocouple, heating mantle and mechanical stirrer. Isopropylacetate (IPAc, 75 mL) was added and the resulting slurry was warmed to 75° C. and heptanes (250 mL) was added over 15 min while maintaining an internal temp of >65° C. The slurry was allowed to cool to rt over night. The solids were collected on a frit and rinsed with 10% IPAc/heptanes (100 mL) and then heptanes (100 mL). The product was air dried to constant weight to provide a tan solid (31.7 g, 58%).

82e

A 500 mL round-bottomed-flask equipped with a magnetic stir bar, thermocouple and septum was charged with 82d (29.7 g, 192 mmol) and THF (150 mL, anhydrous stabilizer free). The vessel was inerted by cycling vacuum the nitrogen three times and 5% Pd/C (6.0 g, 50% wet, Degussa type NO/W) was added. The vessel was again inerted by cycling vacuum then nitrogen three times. A hydrogen filled balloon was attached via needle and the atmosphere was changed by cycling vacuum the hydrogen three times. The slurry was stirred vigorously for 16 h. The atmosphere was changed again to nitrogen by cycling vacuum then nitrogen three times. The mixture was filtered through a 1" pad of celite and the cake was rinsed with THF (50 mL). Concentration in vacuo provided a light tan powder (26.82 g). In a 500 mL round bottomed-flask, the solids were slurried in IPAc (50 mL) and warmed in an 80° C. water bath. Heptanes (150 mL) were added over 10 min. The resulting slurry was allowed to cool to rt and stir for 16 h. The solids were collected on a frit, rinsed with heptanes (50 mL) and air dried to provide an off-white solid (24.39 g, 96%).

4-Fluoro-N-(1-hydroxy-3,3-dimethyl-1,3-dihydro-benzo[c][1,2]oxaborol-6-yl-2-trifluoromethyl benzamide A 1 L three-necked round-bottomed-flask equipped with a nitrogen inlet adapter, mechanical stirrer and thermocouple was charged with 82e (15.7 g, 88.4 mmol), THF (160 mL, anhydrous, stabilizer free) and K₂CO₃ (14.7 g, 106 mmol). The suspension was stirred at rt and 4-fluoro-2-(trifluoromethyl)benzoyl chloride (22.0 g, 97.3 mmol) was added over 10 min. The resulting suspension was aged for 24 h at rt. Water (80 mL) and isopropyl acetate (160 mL) were added and the phases were partitioned. The organic phase was further extracted with water (80 mL) and then brine (50 mL). The organic phase was dried over MgSO₄ (20 g) and concentrated in vacuo to provide a tan solid (34.26 g). The solid was dissolved with acetone (195 mL) and transferred to a mechanically stirred 1 L round-bottomed-flask. Distilled water (113 mL) was added in one portion and the mixture was stirred for 30 min to produce a seed bed and then additional distilled water (60 mL) was added over 30 min. The suspension was stirred at rt overnight and the solids were collected on a frit. The cake was rinsed with 1:1 acetone/water (100 mL) and air dried to constant weight to provide an off-white solid (30.5 g, 94%).

Alternate Synthesis

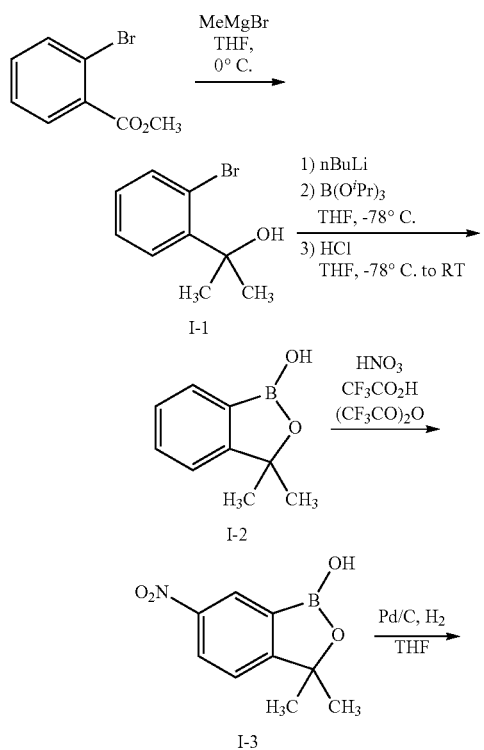

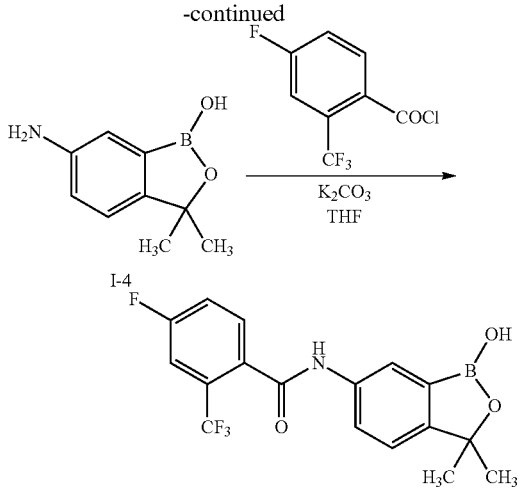

I-1

A 72 L round-bottomed-flask was equipped with a cold bath, mechanical stirrer, nitrogen inlet adaptor, oxygen sensor, thermo well and 2 L dropping funnel. The flask was charged with methyl 2-bromobenzoate (2513 g, 11.7 mol) and the system was flushed with nitrogen to <0.1% O₂. THF (18 L, anhydrous, inhibitor free) was added and the cold bath was charged with ice and acetone. When the internal temp reached −4° C., MeMgBr (11.6 L of a 3M solution in ether, 34.8 mol) was added via dropping funnel over 3 h. The internal temp was maintained below 15° C. throughout. At the end of addition, the cold bath was drained and the reaction was aged overnight at ambient temperature. The bath was again charged with ice and acetone and the suspension cooled to below 15° C. HPLC indicated incomplete conversion (92:8 product, starting ester), so additional MeMgBr (2.3 L of a 3M solution in ether) was added. After 1 h, HPLC showed the conversion to be >99:1. The reaction was quenched by slow addition of 1N HCl (42 L) keeping the internal temp below 15° C. throughout. At the end of the quench, the pH was adjusted to 6 with 1N HCl. The mixture was extracted with MTBE (10 L then 2×5 L). The combined organic phases were dried over MgSO₄, filtered and concentrated via rotary evaporation to provide 2482 g of 2-(2-bromophenyl)-propan-2-ol as a pale yellow oil. ¹H NMR (CHLOROFORM-d) δ: 7.62-7.67 (m, 1H), 7.53-7.58 (m, 1H), 7.24-7.30 (m, 1H), 7.03-7.10 (m, 1H), 1.70-1.75 (m, 6H).

I-2

A 72 L round-bottomed-flask was equipped with a mechanical stirrer, O₂ sensor, thermo well, 2 L dropping funnel, N₂ inlet adaptor, and cold bath. The vessel was inerted to 0.01% O₂ and charged with THF (27 L, anhydrous, inhibitor free). The resulting solution was cooled to −70° C. using dry ice and acetone and n-BuLi (8.2 L of a 2.5M solution in heptane, 20.5 mol) was added over 1 h. 2-(2-Bromophenyl)-propan-2-ol (1994 g, 9.27 mol) was dissolved in THF (9 L) and the solution was added to the BuLi via dropping funnel over 2 h, keeping the internal temp below −70° C. The resulting thin yellow suspension was aged for 30 min then B(OiPr)₃ (2441 g, 13.0 mol) was added rapidly via addition funnel. The cold bath was drained and the mixture was allowed to warm to room temperature while aging over night. HPLC analysis shows an 81:19 ratio of desired product: 2-phenyl-2-propanol. The mixture was cooled to −10° C. and 2N HCl (9.3 L) was added via dropping funnel over 30 min, keeping the reaction mixture below 10° C. After 3 h, the pH was adjusted to 4 with additional HCl. The reaction mixture was extracted with MTBE (2×4 L). The combined organic phases were concentrated to provide 2028 g of a heavy oil. The oil was dissolved in MTBE (14 L) and extracted with 1N NaOH (4.6, then 5, then 4 L). The aqueous phases were combined and acidified with 2N HCl (6.8 L) to a pH of 4-5. The mixture was extracted with MTBE (5 L). The organic phase was dried over MgSO$_4$ (282 g) and concentrated to provide 1450 g (ca 60 wt %) of 3,3-dimethyl-3H-benzo[c][1,2]oxaborol-1-ol as a waxy white solid. LC/MS: m/z 163 (M+H)'; $^1$H NMR (DMSO-d$_6$) δ: 8.96 (br. s., 1H), 7.62 (d, J=7.2 Hz, 1H), 7.33-7.45 (m, 2H), 7.25-7.30 (m, 1H), 1.40 (s, 6H).

I-3

A 22 L round-bottomed-flask equipped with a mechanical stirrer, thermocouple, 2 L dropping funnel and cold bath was charged with 3,3-dimethyl-3H-benzo[c][1,2]oxaborol-1-ol (508 g, 300 g contained, 1.85 mol) and trifluoroacetic acid (1.54 L). The solution was cooled to 5° C. Trifluoroacetic anhydride (722 mL, 5.56 mol, 3.00 eq) was added via dropping funnel over 15 min. After aging at 0-3° C. for 30 min, nitric acid (90% fuming, 108 mL, 2.31 mol, 1.5 eq) was added dropwise over 2 h 50 min keeping the internal temp below 5° C. After aging for 1 h, icewater (10.4 L) was added over 50 min maintaining the reaction temp below 15° C. to provide a slurry. The slurry was aged at 0° C. overnight to provide an orange suspension. The solids were collected on a frit, rinsed with cold water (5 L) and air dried under a stream of air to constant weight (ca 24 h) to provide 364 g of 3,3-dimethyl-6-nitro-3H-benzo[c][1,2]oxaborol-1-ol as a 92.4 wt % pure solid (88%). LC/MS: m/z 208 (M+H)'; $^1$H NMR (DMSO-d$_6$) δ: 8.52 (d, J=2.2 Hz, 1H), 8.32 (dd, J=8.4, 2.2 Hz, 1H), 7.74 (d, J=8.4 Hz, 1H), 1.50 (s, 6H)

I-4

A 2 gallon stirred pressure vessel was charged with 3,3-dimethyl-6-nitro-3H-benzo[c][1,2]oxaborol-1-ol (966 g, 812 g corrected, 3.92 mol), 5% Pd/C (193 g, 50% wet, Degussa type 101 NO/W) and THF (4.83 L, inhibitor free). The vessel was sealed, the atmosphere was changed to H$_2$ (5 psi) and the reaction was fun for 16 h. An exotherm to 30° C. was observed over about 30 min. The vessel was purged with N$_2$, and completion of reaction was determined by HPLC. The reaction was vacuum filtered through a pad of celite (very slow filtration) and the filter cake was rinsed with THF (2 L). The filtrate was concentrated via rotary evaporation to provide 982 g of a dark brown solid. This was transferred to a 22 L round-bottomed-flask and warmed to 80° C. in iPAc (1.83 L) to provide a dark brown slurry. The slurry was cooled to 60° C. and heptanes (5.49 L) were added over 2 h. The slurry was allowed to age with stirring over night while cooling to room temperature. The solids were collected on a frit, rinsed with heptanes (4 L) and air dried to provide a dark brown solid (747 g).

The solids (747 g) were transferred to a 22 L rbf and slurried in iPAc (3 L) at 70° C. The batch was allowed to cool to 40° C. and heptanes (3 L) were added over 5 h. The slurry was aged at room temperature over night and the solids were collected on a frit, rinsed with 1:1 iPAc/heptanes (2 L) then heptanes (1 L) and air dried to provide 554 g of 6-amino-3,3-dimethyl-3H-benzo[c][1,2]oxaborol-1-ol as a brown solid. $^1$H NMR (400 MHz, DMSO-d$_6$) δ ppm 1.36 (s, 6 H) 4.94 (s, 2 H) 6.66 (dd, J=8.1, 2.2 Hz, 1 H) 6.79 (d, J=2.0 Hz, 1 H) 7.01 (d, J=8.1 Hz, 1 H) 8.72 (s, 1 H).

4-Fluoro-N-(1-hydroxy-3,3-dimethyl-1,3-dihydro-benzo[c][1,2]oxaborol-6-yl)-2-trifluoromethyl benzamide A 22 L four-necked round-bottomed-flask equipped with a nitrogen inlet adapter, mechanical stirrer and thermocouple was charged with 6-amino-3,3-dimethyl-3H-benzo[c][1,2] oxaborol-1-ol (554 g, 3.13 mol), THF (5.5 L, anhydrous, stabilizer free) and K$_2$CO$_3$ (865 g, 6.26 mol). The suspension was stirred at room temperature for 30 min and 4-fluoro-2-(trifluoromethyl)benzoyl chloride (780 g, 3.44 mol) was added over 30 min. The resulting suspension was aged for 24 h at room temperature. HPLC showed unreacted 6-amino-3,3-dimethyl-3H-benzo[c][1,2]oxaborol-1-ol so an additional 42 mL of the acid chloride was added. After 30 min, water (2.8 L) and isopropyl acetate (5.5 L) were added and the phases were partitioned. The organic phase was further extracted with water (2.8 L) and then brine (2.8 L). The organic phase was dried over MgSO$_4$ and concentrated in vacuo to provide a tan solid. The solid was dissolved with acetone (3.0 L) and transferred to a mechanically stirred 50 L round-bottomed-flask. Distilled water (2.0 L) was added in one portion and the mixture was stirred for 30 min to produce a seed bed and then additional water (1.0 L) was added over 30 min. The suspension was stirred at room temperature overnight and the solids were collected on a frit. The cake was rinsed with 1:1 acetone/water (1.0 L) and air dried to constant weight to provide 4-fluoro-N-(1-hydroxy-3,3-dimethyl-1,3-dihydro-benzo[c][1,2]oxaborol-6-yl)-2-trifluoromethyl benzamide as a dark tan solid (1.3 kg).

Recrystallization of 4-Fluoro-N-(1-hydroxy-3,3-dimethyl-1,3-dihydro-benzo[c][1,2]oxaborol-6-yl)-2-trifluoromethyl benzamide A 22 L round-bottomed-flask was charged with the dark tan crude 4-fluoro-N-(1-hydroxy-3,3-dimethyl-1,3-dihydro-benzo[c][1,2]oxaborol-6-yl)-2-trifluoromethyl benzamide (1.3 kg), acetone (8 L) and Darco G-60 (55 g, 400 mesh) and water (5.3 L). The resulting suspension was stirred for 15 min, filtered through a pad of celite (ca 500 g) to provide a brown solution. The celite pad was washed with 60% acetone/water (8 L). The combined filtrate and rinse were transferred to a 50 L round-bottomed-flask and water (2 L) was added. The solution was seeded (5 g) to initiate crystallization and additional water (2.2 L) was added slowly via addition funnel. After aging at room temperature overnight, the solids were collected and the filter cake was rinsed with 30% acetone/water (4 L). The solids were air dried for 24 h then dried in a room temperature vacuum oven for 5 days to constant weight to provide 969 g (72% recovery) of 4-fluoro-N-(1-hydroxy-3,3-dimethyl-1,3-dihydro-benzo[c] [1,2]oxaborol-6-yl)-2-trifluoromethyl benzamide as a light tan solid.

LC/MS: m/z 368 (M+H)$^+$; $^1$H NMR (400 MHz, DMSO-d6) δ ppm 1.44 (s, 5 H) 1.49 (s, 2 H) 7.39 (d, J=8.2 Hz, 1 H) 7.61-7.76 (m, 2 H) 7.77-7.84 (m, 2 H) 7.86-7.90 (m, 0 H) 8.03 (d, J=1.7 Hz, 1 H) 9.09 (s, 1 H) 10.58 (s, 1 H).

Formation of Potassium Salt

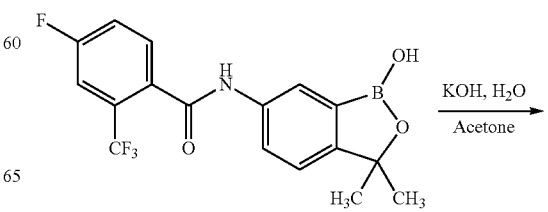

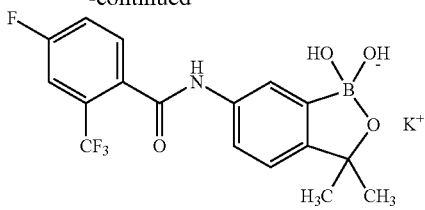

To a 500 mL three-neck flask fitted with a mechanical stirrer was charged KOH (1.51 g, 26.9 mmol, 1.0 eq.). Under a nitrogen atmosphere, anhydrous acetone (140 mL) and H₂O (2.5 mL, 5 eq.) were added via syringe. A solution of 4-fluoro-N-(1-hydroxy-3,3-dimethyl-1,3-dihydro-benzo[c][1,2]oxaborol-6-yl-2-trifluoromethyl benzamide (10.0 g, 27.2 mmol, 1.0 eq.) in anhydrous acetone (60 mL) was added to the flask with vigorous stirring. The resulting clear solution was stirred at room temperature. The potassium salt precipitated from the solution over ca. 4 hours to afford a thick suspension. The precipitate was collected by filtration, washed with acetone (200 mL) and dried in a vacuum oven overnight to afford a white solid (10.6 g, 91.9% yield). ¹H NMR (methanol-d₄) δ: 7.70-7.76 (m, 1H), 7.53-7.60 (m, 2H), 7.47-7.53 (m, 1H), 7.33-7.36 (m, 1H), 7.01-7.06 (m, 1H), 1.46 (s, 6H); M.P. (range) 197-200° C.; Elemental analysis: Theory: C 48.25%, H 3.57%, N 3.31%, K 9.24%; Found: C 48.70%, H 3.41%, N 3.25%, K 9.19%.

83 2-Fluoro-N-(1-hydroxy-3,3-dimethyl-1,3-dihydro-benzo[c][1,2]oxaborol-6-yl)-3-trifluoromethyl-benzamide

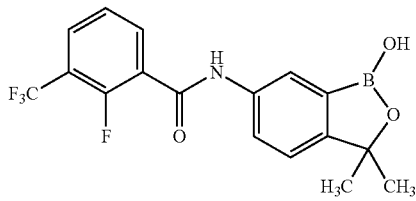 [SMILES: CC1(C)OB(O)c2cc(NC(=O)c3cccc(C(F)(F)F)c3F)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-fluoro-3-trifluoromethyl-benzoyl chloride replacing 2-trifluoromethyl-4-fluorobenzoyl chloride. Data: LCMS (M/Z): 368 (M+H); ¹H NMR (DMSO-d₆) δ: 1.45 (s, 6 H) 7.41 (d, J=8.2 Hz, 1 H) 7.55 (t, J=7.8 Hz, 1 H) 7.68 (dd, J=8.2, 2.0 Hz, 1 H) 7.93-8.03 (m, 2 H) 8.05 (d, J=1.8 Hz, 1 H) 9.10 (s, 1 H) 10.64 (s, 1 H).

84 2-Fluoro-N-(1-hydroxy-3,3-dimethyl-1,3-dihydro-benzo[c][1,2]oxaborol-6-yl)-4-trifluoromethyl-benzamide

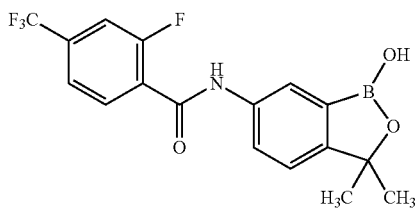

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-fluoro-4-trifluoromethyl-benzoyl chloride replacing 2-trifluoromethyl-4-fluorobenzoyl chloride. Data: LCMS (M/Z): 368 (M+H); ¹H NMR (DMSO-d₆) δ: 1.45 (s, 6 H) 7.41 (d, J=8.3 Hz, 1 H) 7.67-7.76 (m, 2 H) 7.86-7.92 (m, 2 H) 8.04 (d, J=1.9 Hz, 1 H) 9.10 (s, 1 H) 10.62 (s, 1 H).

85 2-Fluoro-N-(1-hydroxy-3,3-dimethyl-1,3-dihydro-benzo[c][1,2]oxaborol-6-yl)-5-trifluoromethyl-benzamide

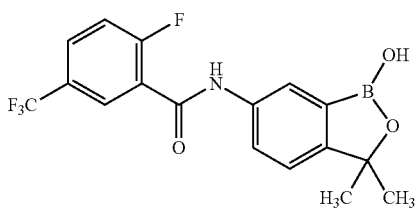 [SMILES: CC1(C)OB(O)c2cc(NC(=O)c3cc(C(F)(F)F)ccc3F)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-fluoro-5-trifluoromethyl-benzoyl chloride replacing 2-trifluoromethyl-4-fluorobenzoyl chloride. Data: LCMS (M/Z): 368 (M+H); ¹H NMR (DMSO-d₆) δ: 1.45 (s, 6 H) 7.41 (d, J=8.2 Hz, 1 H) 7.62 (s, 1 H) 7.69 (dd, J=8.2, 2.0 Hz, 1 H) 7.96-8.02 (m, 1 H) 8.03-8.08 (m, 2 H) 9.10 (s, 1 H) 10.60 (s, 1 H).

86 2-Fluoro-N-(1-hydroxy-3,3-dimethyl-1,3-dihydro-benzo[c][1,2]oxaborol-6-yl)-6-trifluoromethyl-benzamide

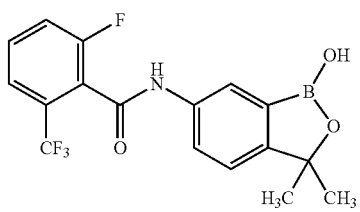

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-fluoro-6-trifluoromethyl-benzoyl chloride replacing 2-trifluoromethyl-4-fluorobenzoyl chloride. Data: LCMS (M/Z): 368 (M+H); ¹H NMR (DMSO-d₆) δ: 1.44 (s, 6 H) 7.40 (d, J=8.2 Hz, 1 H) 7.54-7.65 (m, 1 H) 7.67-7.81 (m, 3 H) 7.97-8.05 (m, 1 H) 9.10 (s, 1 H) 10.80 (s, 1 H).

87 4-Fluoro-N-(1-hydroxy-3,3-dimethyl-1,3-dihydro-benzo[c][1,2]oxaborol-6-yl)-2-methyl-benzamide

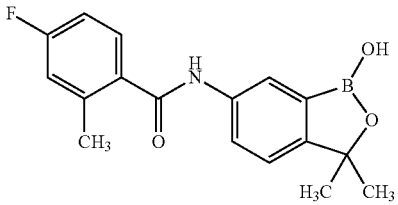 [SMILES: Cc1cc(F)ccc1C(=O)Nc1ccc2c(c1)B(O)OC2(C)C]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-fluoro-2-methyl-benzoyl chloride replacing 2-trifluoromethyl-4-fluorobenzoyl chloride. Data: LCMS (M/Z): 314 (M+H); $^1$H NMR (DMSO-$d_6$) δ: 1.44 (s, 6 H) 2.41 (s, 3 H) 7.10-7.21 (m, 2 H) 7.37 (d, J=8.2 Hz, 1 H) 7.50-7.55 (m, 1 H) 7.68 (d, J=1.7 Hz, 1 H) 8.07 (d, J=1.2 Hz, 1 H) 9.06 (s, 1 H) 10.30 (s, 1 H).

88 5-Fluoro-N-(1-hydroxy-3,3-dimethyl-1,3-dihydro-benzo[c][1,2]oxaborol-6-yl)-2-trifluoromethyl-benzamide

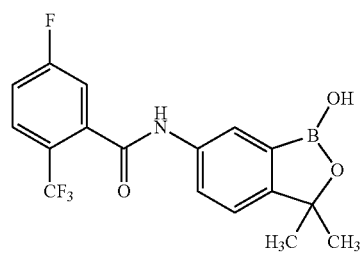 [SMILES: CC1(C)OB(O)c2cc(NC(=O)c3cc(F)ccc3C(F)(F)F)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 5-fluoro-2-trifluoromethyl-benzoyl chloride replacing 2-trifluoromethyl-4-fluorobenzoyl chloride. Data: LCMS (M/Z): 368 (M+H); $^1$H NMR (DMSO-$d_6$) δ: 1.44 (s, 6 H) 7.39 (d, J=8.4 Hz, 1 H) 7.57 (td, J=8.5, 2.5 Hz, 1 H) 7.63 (dd, J=8.2, 2.0 Hz, 1 H) 7.68 (dd, J=8.6, 2.5 Hz, 1 H) 7.94 (dd, J=9.0, 5.1 Hz, 1 H) 8.03 (d, J=2.0 Hz, 1 H) 9.10 (s, 1 H) 10.62 (s, 1 H).

89 2-Chloro-N-(1-hydroxy-3,3-dimethyl-1,3-dihydro-benzo[c][1,2]oxaborol-6-yl)-4-methyl-benzamide

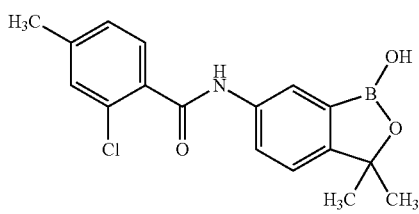

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-chloro-4-methyl-benzoyl chloride replacing 2-trifluoromethyl-4-fluorobenzoyl chloride. Data: LCMS (M/Z): 330 (M+H); $^1$H NMR (DMSO-$d_6$) δ: 1.44 (s, 6 H) 2.36 (s, 3 H) 7.24-7.29 (m, 1 H) 7.34-7.42 (m, 2H) 7.46 (d, J=7.8 Hz, 1 H) 7.65-7.69 (m, 1 H) 8.05 (dd, J=1.8, 0.4 Hz, 1 H) 9.07 (s, 1 H) 10.42 (s, 1 H).

90 2-Chloro-N-(1-hydroxy-3,3-dimethyl-1,3-dihydro-benzo[c][1,2]oxaborol-6-yl)-5-trifluoromethyl-benzamide

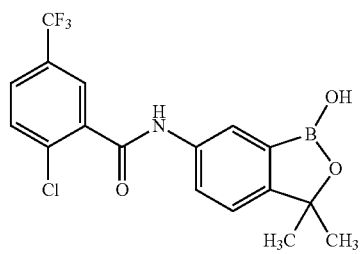 [SMILES: CC1(C)OB(O)c2cc(NC(=O)c3cc(C(F)(F)F)ccc3Cl)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-chloro-5-trifluoromethyl-benzoyl chloride replacing 2-trifluoromethyl-4-fluorobenzoyl chloride. Data: LCMS (M/Z): 384 (M+H); $^1$H NMR (DMSO-$d_6$) δ: 1.49 (s, 6 H) 7.40 (d, J=8.2 Hz, 1 H) 7.77 (d, J=8.2 Hz, 2 H) 7.83 (s, 1 H) 7.99 (s, 1 H) 8.13 (d, J=1.7 Hz, 1 H) 9.73 (br. s., 1 H).

91 4-Bromo-N-(1-hydroxy-3,3-dimethyl-1,3-dihydro-benzo[c][1,2]oxaborol-6-yl)-2-methyl-benzamide

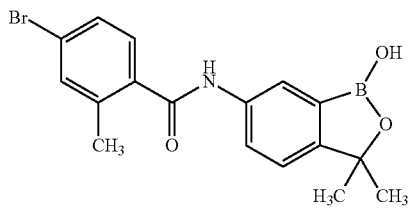

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-bromo-2-methyl-benzoyl chloride replacing 2-trifluoromethyl-4-fluorobenzoyl chloride. Data: LCMS (M/Z): 375 (M+H); $^1$H NMR (DMSO-$d_6$) δ: 1.40 (s, 6 H) 2.35 (s, 3 H) 7.33 (d, J=8.2 Hz, 1 H) 7.38 (d, J=8.2 Hz, 1 H) 7.46 (d, J=1.9 Hz, 1 H) 7.53 (d, J=1.6 Hz, 1 H) 7.64 (d, J=1.9 Hz, 1 H) 8.02 (d, J=1.6 Hz, 1 H) 8.98-9.07 (m, 1 H) 10.31 (s, 1 H).

92 2-Chloro-N-(1-hydroxy-3,3-dimethyl-1,3-dihydro-benzo[c][1,2]oxaborol-6-yl-5-nitro-benzamide

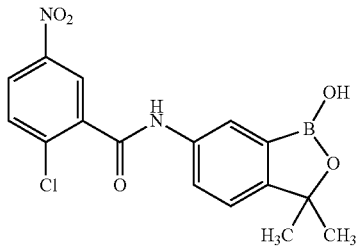 [SMILES: CC1(C)OB(O)c2cc(NC(=O)c3cc([N+](=O)[O-])ccc3Cl)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-chloro-5-nitro-benzoyl chloride replacing 2-trifluoromethyl-4-fluorobenzoyl chloride. Data: LCMS (M/Z): 361 (M+H); $^1$H NMR (DMSO-$d_6$) δ: 1.45 (s, 6 H) 7.41 (d, J=8.2 Hz, 1 H) 7.68 (dd, J=8.3, 2.1 Hz, 1 H) 7.90 (d, J=8.8 Hz, 1 H) 8.05 (d, J=1.8 Hz, 1 H) 8.34 (dd, J=8.9, 2.8 Hz, 1 H) 8.45 (d, J=2.7 Hz, 1 H) 9.11 (s, 1 H) 10.71 (s, 1 H).

93 2-Chloro-N-(1-hydroxy-3,3-dimethyl-1,3-dihydro-benzo[c][1,2]oxaborol-6-yl-4-nitro-benzamide

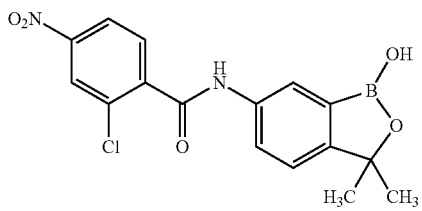 [SMILES: CC1(C)OB(O)c2cc(NC(=O)c3ccc([N+](=O)[O-])cc3Cl)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-chloro-4-nitro-benzoyl chloride replacing 2-trifluoromethyl-4-fluorobenzoyl chloride. Data: LCMS (M/Z): 361 (M+H); $^1$H NMR (DMSO-$d_6$) δ: 1.45 (s, 6 H) 7.41 (d, J=8.2 Hz, 1 H) 7.68 (dd, J=8.2, 2.0 Hz, 1 H) 7.90 (d, J=8.4 Hz, 1 H) 8.05 (d, J=1.9 Hz, 1 H) 8.30 (dd, J=8.4, 2.2 Hz, 1 H) 8.43 (d, J=2.1 Hz, 1 H) 9.11 (s, 1 H) 10.75 (s, 1 H).

94 N-(1-Hydroxy-3,3-dimethyl-1,3-dihydro-benzo[c][1,2]oxaborol-6-O-2,4-dimethoxy-benzamide

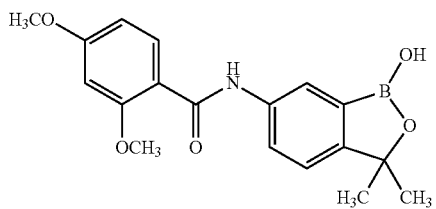 [SMILES: COc1ccc(C(=O)Nc2ccc3c(c2)B(O)OC3(C)C)c(OC)c1]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2,4-dimethoxy-benzoyl chloride replacing 2-trifluoromethyl-4-fluorobenzoyl chloride. Data: LCMS (M/Z): 342 (M+H); $^1$H NMR (DMSO-$d_6$) δ: 1.44 (s, 6 H) 3.84 (s, 3 H) 3.96 (s, 3 H) 6.67 (dd, J=8.6, 2.2 Hz, 1 H) 6.71 (d, J=2.1 Hz, 1 H) 7.36 (d, J=8.2 Hz, 1 H) 7.71 (dd, J=8.2, 1.6 Hz, 1 H) 7.76 (d, J=8.5 Hz, 1 H) 8.01 (d, J=1.3 Hz, 1 H) 9.92 (s, 1 H).

95 N-(1-Hydroxy-3,3-dimethyl-1,3-dihydro-benzo[c][1,2]oxaborol-6-yl)-4-methoxy-3-methyl-benzamide

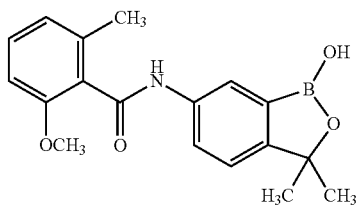 [SMILES: COc1cccc(C)c1C(=O)Nc1ccc2c(c1)B(O)OC2(C)C]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 4-methoxy-3-methyl-benzoyl chloride replacing 2-trifluoromethyl-4-fluorobenzoyl chloride. Data: LCMS (M/Z): 326 (M+H); $^1$H NMR (DMSO-$d_6$) δ: 1.45 (s, 6 H) 2.22 (s, 3 H) 3.87 (s, 3 H) 7.06 (d, J=8.6 Hz, 1 H) 7.37 (d, J=8.2 Hz, 1 H) 7.72 (dd, J=8.2, 2.0 Hz, 1 H) 7.81 (s, 1 H) 7.86 (dd, J=8.4, 2.1 Hz, 1 H) 8.05 (d, J=2.0 Hz, 1 H) 9.04 (s, 1 H) 10.05 (s, 1 H).

96 N-(1-Hydroxy-3,3-dimethyl-1,3-dihydro-benzo[c][1,2]oxaborol-6-yl)-2,6-dimethoxy-benzamide The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2,6-dimethoxy-benzoyl chloride replacing 2-trifluoromethyl-4-fluorobenzoyl chloride. Data: LCMS (M/Z): 342 (M+H); $^1$H NMR (DMSO-$d_6$) δ: 1.43 (s, 6 H) 3.76 (s, 6 H) 6.73 (d, J=8.4 Hz, 2 H) 7.23-7.43 (m, 2 H) 7.65 (dd, J=8.2, 1.8 Hz, 1 H) 8.06 (d, J=1.6 Hz, 1 H) 10.19 (s, 1 H).

97  2-Chloro-N-(1-hydroxy-3,3-dimethyl-1,3-dihydro-benzo[c][1,2]oxaborol-6-yl)-4-vinyl-benzamide

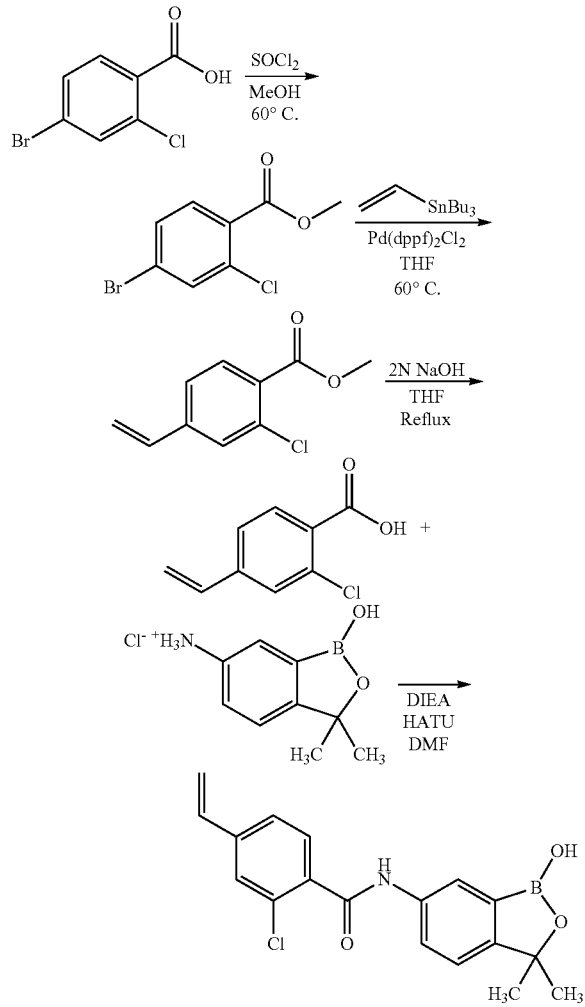

To a solution of 4-bromo-2-chlorobenzoic acid (5 g, 21.2 mmol) in 50 mL of methanol was added thionyl chloride (1.4 mL, 19.8 mmol) drop-wise. The reaction was heated to 60° C. After 3 hours the reaction was allowed to cool back to room temperature and concentrated down to give 4-bromo-2-chlorobenzoic acid methyl ester as an orange liquid. Amount obtained: 4.65 g (95%). LCMS (M/Z): 249 (M+H). $^1$H NMR (Chloroform-d) δ: 3.92 (s, 3 H) 7.45 (dd, J=8.4, 2.0 Hz, 1 H) 7.63 (d, J=2.0 Hz, 1 H) 7.72 (d, J=8.4 Hz, 1 H).

To a solution of 4-bromo-2-chlorobenzoic acid methyl ester (500 mg, 2 mmol) in THF (15 mL) was added tributyl(vinyl)tin (620 µl, 2.1 mmol) and PdCl$_2$(dppf)-$_2$-DCM (165 mg, 0.2 mmol). The solution was heated to 60° C. for 12 hours. The crude reaction mixture was then concentrated down and taken up in 20 mL EtOAc and 100 mL concentrated KF solution. The reaction stirred at room temperature for 3 hours, filtered through a pad of celite and concentrated down. The residual oil was subjected to flash chromatography (Isco Companion, 40 g SiO$_2$ cartridge, solid loaded SiO$_2$, neat heptanes to EtOAc gradient) to give 2-chloro-4-vinylbenzoic acid as a yellow oil. Amount obtained: 235 mg (60%). LCMS (M/Z): 197 (M+H). $^1$H NMR (Chloroform-d) δ: 3.93 (s, 3 H) 5.42 (d, J=10.9 Hz, 1 H) 5.86 (d, J=17.6 Hz, 1 H) 6.66 (dd, J=17.6, 10.7 Hz, 1 H) 7.28-7.35 (m, 1 H) 7.43-7.50 (m, 1 H) 7.82 (d, J=8.0 Hz, 1 H).

To solution of 2-chloro-4-vinyl-benzoic acid methyl ester (50 mg, 0.26 mmol) in THF (2 ml) was added 2M NaOH (1 ml). The solution was heated to 70° C. for 1 hour. The reaction was cooled back to room temperature and brought to a pH of ~3 with 1M HCl. The aqueous solution was extracted with EtOAc (3×). The combined organic extracts were washed with brine, dried over Na$_2$SO$_4$, filtered and concentrated down under reduced pressure to give 2-chloro-4-vinyl benzoic acid as a white solid. Amount obtained: 40.3 mg (86%). LCMS (M/Z): 183 (M+H); $^1$H NMR (Chloroform-d) δ: 5.47 (d, J=10.9 Hz, 1 H) 5.93 (s, 1 H) 6.70 (dd, J=17.6, 10.9 Hz, 1 H) 7.38 (dd, J=8.2, 1.8 Hz, 1 H) 7.52 (s, 1 H) 8.02 (d, J=8.0 Hz, 1 H).

To a solution of 2-chloro-4-vinyl benzoic acid (44 mg, 0.24 mmol) in DMF (2 mL) was added HATU (55 mg, 0.15 mmol) and DIEA (25 mg, 0.21 mmol). After 1 hour 6-amino-3,3-dimethyl-3H-benzo[c][1,2]oxaborol-1-ol hydrochloride salt (30 mg, 0.14 mmol) was added. After 12 hours the reaction was concentrated down under reduced pressure onto celite. The crude material was subjected to flash chromatography (Isco Companion, 4 g SiO$_2$ cartridge, SiO$_2$ solid load, neat DCM to 10% MeOH gradient) to give 2-Chloro-N-(1-hydroxy-3,3-dimethyl-1,3-dihydro-benzo[c][1,2]oxaborol-6-yl)-4-vinyl-benzamide as a white powder. Amount obtained: 20.8 mg (48%). Data: LCMS (M/Z): 342 (M+H); $^1$H NMR (DMSO-d$_6$) δ: 1.36-1.59 (m, 6 H) 5.42 (d, J=11.1 Hz, 1 H) 6.02 (d, J=17.8 Hz, 1 H) 6.79 (dd, J=17.7, 11.0 Hz, 1 H) 7.33-7.46 (m, 1 H) 7.56 (s, 2 H) 7.69 (d, J=1.6 Hz, 2 H) 8.05 (dd, J=1.7, 0.5 Hz, 1 H) 9.00 (br. s, 1 H) 10.35-10.62 (m, 1 H).

98  4-Allyl-2-chloro-N-(1-hydroxy-3,3-dimethyl-1,3-dihydro-benzo[c][1,2]oxaborol-6-yl)-benzamide

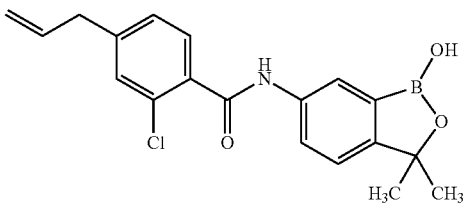 [SMILES: C=CCc1ccc(C(=O)Nc2ccc3c(c2)B(O)OC3(C)C)c(Cl)c1]

The title compound was prepared using a procedure similar to that of 2-chloro-N-(1-hydroxy-3,3-dimethyl-1,3-dihydro-benzo[c][1,2]oxaborol-6-yl)-4-vinyl-benzamide with allyltributyltin replacing tributyl(vinyl)tin. Data: LCMS (M/Z): 356 (M+H); $^1$H NMR (DMSO-d$_6$) δ: 1.44 (s, 6 H) 3.44 (d, J=6.8 Hz, 2 H) 5.04-5.22 (m, 2 H) 5.87-6.06 (m, 1 H) 7.28 (d, J=9.0 Hz, 1 H) 7.35-7.41 (m, 2 H) 7.50 (s, 1 H) 7.68 (dd, J=8.3, 2.0 Hz, 1 H) 8.05 (d, J=1.8 Hz, 1 H) 9.09 (br. s., 1 H) 10.45 (s, 1 H).

99 2-Chloro-N-(1-hydroxy-3,3-dimethyl-1,3-dihydro-benzo[c][1,2]oxaborol-6-yl)-4-(2-methyl-propenyl)-benzamide

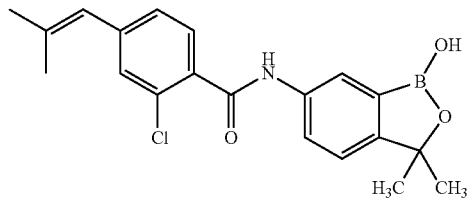 [SMILES: CC(C)=Cc1ccc(C(=O)Nc2ccc3c(c2)B(O)OC3(C)C)c(Cl)c1]

The title compound was prepared using a procedure similar to that of 2-chloro-N-(1-hydroxy-3,3-dimethyl-1,3-dihydro-benzo[c][1,2]oxaborol-6-yl)-4-vinyl-benzamide with 2-methylpropenyl-1-tributylstannane replacing tributyl(vinyl)tin. Data: LCMS (M/Z): 370 (M+H); $^1$H NMR (DMSO-d$_6$) δ: 1.44 (s, 6 H) 1.83-1.95 (m, 6 H) 6.31 (s, 1 H) 7.31 (dt, J=8.0, 0.9 Hz, 1 H) 7.34-7.40 (m, 2 H) 7.53 (d, J=7.8 Hz, 1 H) 7.68 (dd, J=8.3, 2.0 Hz, 1 H) 8.06 (dd, J=1.8, 0.4 Hz, 1 H) 9.09 (s, 1 H) 10.47 (s, 1 H).

100 2-Chloro-N-(1-hydroxy-3,3-dimethyl-1,3-dihydro-benzo[c][1,2]oxaborol-6-yl)-4-isopropenyl-benzamide

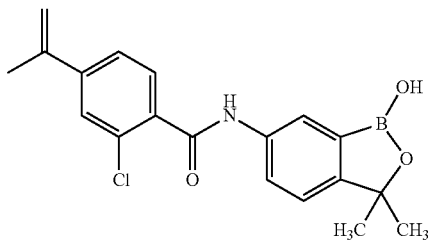 [SMILES: C=C(C)c1ccc(C(=O)Nc2ccc3c(c2)B(O)OC3(C)C)c(Cl)c1]

The title compound was prepared using a procedure similar to that of 2-chloro-N-(1-hydroxy-3,3-dimethyl-1,3-dihydro-benzo[c][1,2]oxaborol-6-yl)-4-vinyl-benzamide with isopropenyl tributylstannane replacing tributyl(vinyl)tin. Data: LCMS (M/Z): 356 (M+H); $^1$H NMR (DMSO-d$_6$) δ: 1.44 (s, 6 H) 2.14 (s, 3 H) 5.24 (s, 1 H) 5.57 (s, 1 H) 7.38 (d, J=8.2 Hz, 1 H) 7.57 (ddd, J=1.5, 1.0, 0.8 Hz, 2 H) 7.62-7.66 (m, 1 H) 7.69 (dd, J=8.2, 2.0 Hz, 1 H) 8.05 (dd, J=1.6, 0.6 Hz, 1 H) 9.09 (br. s., 1 H) 10.49 (s, 1 H).

101 2-Chloro-N-(1-hydroxy-3,3-dimethyl-1,3-dihydro-benzo[c][1,2]oxaborol-6-yl)-4-isopropyl-benzamide

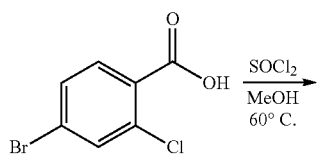

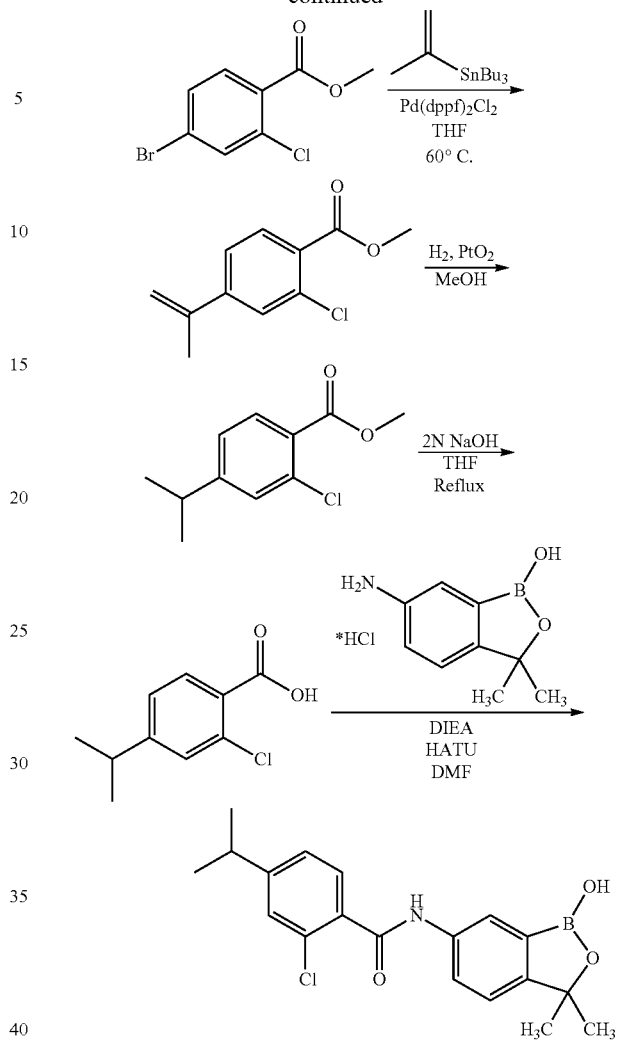

To a solution of 4-bromo-2-chlorobenzioc acid (5 g, 21.2 mmol) in 50 mL of methanol was added thionyl chloride (1.4 mL, 19.8 mmol) drop-wise. The reaction was heated to 60° C. After 3 hours the reaction was allowed to cool back to room temperature and concentrated down to give 4-bromo-2-chlorobenzoic acid methyl ester as an orange liquid. Amount obtained: 4.65 g (95%). LCMS (M/Z): 249 (M+H). $^1$H NMR (Chloroform-d) δ: 3.92 (s, 3 H) 7.45 (dd, J=8.4, 2.0 Hz, 1 H) 7.63 (d, J=2.0 Hz, 1 H) 7.72 (d, J=8.4 Hz, 1 H).

To a solution of 4-bromo-2-chlorobenzoic acid methyl ester (500 mg, 2 mmol) in THF (15 mL) was added isopropenyltributylstannane (700 mg, 2.1 mmol) and PdCl$_2$(dppf)$_2$-DCM (165 mg, 0.2 mmol). The solution was heated to 60° C. for 12 hours. The crude reaction mixture was then concentrated down and taken up in 20 mL EtOAc and 100 mL concentrated KF solution. The reaction stirred at room temperature for 3 hours, filtered through a pad of celite and concentrated down. The residual oil was subjected to flash chromatography (Isco Companion, 40 g SiO$_2$ cartridge, solid loaded SiO$_2$, neat heptanes to EtOAc gradient) to give 2-chloro-4-isopropenyl-benzoic acid methyl ester as a yellow oil. Amount obtained: 230.6 mg (55%). LCMS (M/Z): 211 (M+H).

A solution of 2-chloro-4-isopropenyl-benzoic acid methyl ester (100 mg, 0.48 mmol) in MeOH (8.0 mL) was passed through H-cube equipped with a PtO₂ cartridge. The solution was concentrated down to give 2-chloro-4-isopropyl-benzoic acid methyl ester as a yellow oil. Amount obtained: 68.0 mg (67%). ¹H NMR (Chloroform-d) δ: 1.26 (d, J=6.8 Hz, 6 H) 2.92 (m, J=14.0, 6.9, 6.9 Hz, 1 H) 7.17 (dd, J=8.1, 1.9 Hz, 1 H) 7.31 (d, J=2.0 Hz, 1 H) 7.79 (d, J=8.0 Hz, 1 H).

To solution of 2-chloro-4-isopropyl-benzoic acid methyl ester (68 mg, 0.33 mmol) in THF (3 ml) was added 2M NaOH (3 ml). The solution was heated to 70° C. for 1 hour. The reaction was cooled back to room temperature and brought to a pH of ~3 with 1M HCl. The aqueous solution was extracted with EtOAc (3×). The combined organic extracts were washed with brine, dried over Na₂SO₄, filtered and concentrated down under reduced pressure to give 2-chloro-4-isopropyl-benzoic acid as a yellow solid. Amount obtained: 62.7 mg (96%). ¹H NMR (Chloroform-d) δ: 1.28 (d, J=6.8 Hz, 6 H) 2.95 (m, J=14.0, 6.9, 6.9 Hz, 1 H) 7.22 (dd, J=8.1, 1.7 Hz, 1 H) 7.36 (d, J=1.6 Hz, 1 H) 7.99 (d, J=8.2 Hz, 1 H).

To a solution of 2-chloro-4-isopropyl-benzoic acid (63 mg, 0.33 mmol) in DMF (4 mL) was added HATU (90 mg, 0.23 mmol) and DIEA (43 mg, 0.33 mmol). After 1 hour 6-amino-3,3-dimethyl-3H-benzo[c][1,2]oxaborol-1-ol hydrochloride salt (50 mg, 0.22 mmol) was added. After 12 hours the reaction was concentrated down under reduced pressure onto celite. The crude material was subjected to flash chromatography (Isco Companion, 4 g SiO₂ cartridge, SiO₂ solid load, neat DCM to 10% MeOH gradient) to give 2-Chloro-N-(1-hydroxy-3,3-dimethyl-1,3-dihydro-benzo[c][1,2]oxaborol-6-yl)-4-isopropyl-benzamide as a white powder. Amount obtained: 6.3 mg (8%). Data: LCMS (M/Z): 358 (M+H); ¹H NMR (DMSO-d₆) δ: 1.23 (d, J=6.8 Hz, 6 H) 1.44 (s, 6 H) 2.97 (dt, J=13.8, 6.9 Hz, 1 H) 7.29-7.41 (m, 2H) 7.43 (d, J=1.4 Hz, 1 H) 7.49 (d, J=7.8 Hz, 1 H) 7.68 (dd, J=8.3, 1.9 Hz, 1 H) 8.05 (dd, J=1.7, 0.5 Hz, 1 H) 9.08 (br. s, 1 H) 10.45 (s, 1 H).

102 2-Chloro-N-(1-hydroxy-3,3-dihydro-benzo[c][1,2]oxaborol-6-yl)-4-propyl-benzamide

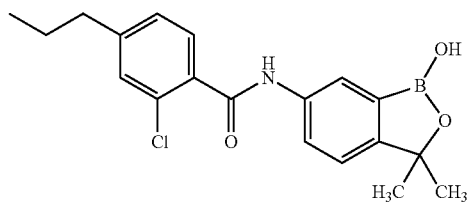 [SMILES: CCCc1ccc(C(=O)Nc2ccc3c(c2)B(O)OC3(C)C)c(Cl)c1]

The title compound was prepared using a procedure similar to that of 2-chloro-N-(1-hydroxy-3,3-dimethyl-1,3-dihydro-benzo[c][1,2]oxaborol-6-yl)-4-isopropyl-benzamide with allyltributylstannane replacing isopropenyltributylstannane. Data: LCMS (M/Z): 358 (M+H); ¹H NMR (DMSO-d₆) δ: 0.91 (t, J=7.3 Hz, 3 H) 1.44 (s, 6 H) 1.61 (sxt, J=7.4 Hz, 2 H) 2.61 (t, J=7.8 Hz, 2 H) 7.28 (d, J=1.0 Hz, 1 H) 7.37 (d, J=8.3 Hz, 1 H) 7.40 (s, 1 H) 7.48 (d, J=7.8 Hz, 1 H) 7.68 (dd, J=8.2, 2.1 Hz, 1 H) 8.06 (d, J=1.0 Hz, 1 H) 9.03 (br. s, 1 H) 10.44 (s, 1 H).

103 2-Chloro-N-(1-hydroxy-3,3-dimethyl-1,3-dihydro-benzo[c][1,2]oxaborol-6-yl-4-isobutyl-benzamide

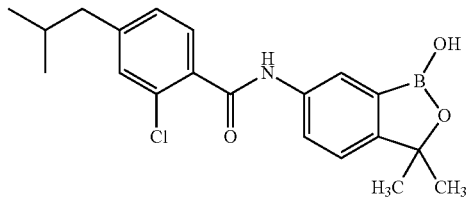 [SMILES: CC(C)Cc1ccc(C(=O)Nc2ccc3c(c2)B(O)OC3(C)C)c(Cl)c1]

The title compound was prepared using a procedure similar to that of 2-chloro-N-(1-hydroxy-3,3-dimethyl-1,3-dihydro-benzo[c][1,2]oxaborol-6-yl)-4-isopropyl-benzamide with 2-methylpropene-1-tributylstannane replacing isopropenyltributylstannane. Data: LCMS (M/Z): 372 (M+H); ¹H NMR (DMSO-d₆) δ: 0.89 (d, J=6.6 Hz, 6 H) 1.44 (s, 6 H) 1.88 (m, J=13.0, 6.7, 6.7 Hz, 1 H) 7.25 (dd, J=7.2, 1.1 Hz, 1 H) 7.37 (s, 2 H) 7.38 (s, 1 H) 7.49 (d, J=7.8 Hz, 2 H) 7.68 (dd, J=8.2, 2.1 Hz, 1 H) 8.06 (d, J=1.0 Hz, 1 H) 9.09 (br. s, 1 H) 10.44 (s, 1 H).

104 2-Chloro-3,6-difluoro-N-(1-hydroxy-3,3-dimethyl-1,3-dihydro-benzo[c][1,2]oxaborol-6-yl)-benzamide

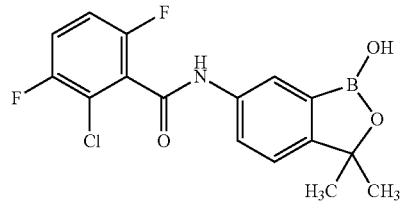 [SMILES: CC1(C)OB(O)c2cc(NC(=O)c3c(F)ccc(F)c3Cl)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-chloro-3,6-difluoro-benzoyl chloride replacing 2-trifluoromethyl-4-fluorobenzoyl chloride. Data: LCMS (M/Z): 352 (M+H); ¹H NMR (DMSO-d₆) δ: 1.44 (s, 6 H) 7.41 (d, J=8.2 Hz, 1 H) 7.48 (td, J=8.7, 3.8 Hz, 1 H) 7.58-7.70 (m, 2 H) 8.04 (d, J=1.8 Hz, 1 H) 9.14 (s, 1 H) 10.87 (s, 1 H).

105 2,4,6-Trichloro-N-(1-hydroxy-3,3-dimethyl-1,3-dihydro-benzo[c][1,2]oxaborol-6-yl)-benzamide

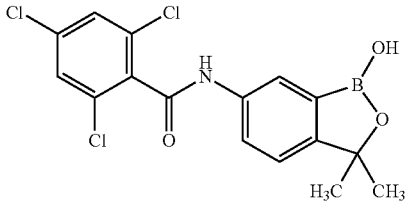 [SMILES: CC1(C)OB(O)c2cc(NC(=O)c3c(Cl)cc(Cl)cc3Cl)ccc21]

The title compound was prepared using a procedure similar to that of 4-fluoro-N-(1-hydroxy-3,3-dimethyl-1,3- dihydro-benzo[c][1,2]oxaborol-6-yl-2-trifluoromethyl benzamide with 2,4,6-trichloro-benzoyl chloride replacing 2-trifluoromethyl-4-fluorobenzoyl chloride. Data: LCMS (M/Z): 385 (M+H); $^1$H NMR (DMSO-$d_6$) δ: 1.44 (s, 6 H) 7.40 (d, J=8.2 Hz, 1 H) 7.63 (dd, J=8.2, 2.0 Hz, 1 H) 7.84 (s, 2 H) 8.02 (d, J=1.0 Hz, 1 H) 9.10 (s, 1 H) 10.76 (s, 1 H).

106 N-(1-Hydroxy-3,3-dimethyl-1,3-dihydro-benzo[c][1,2]oxaborol-6-yl)-3,4,5-trimethoxy-benzamide

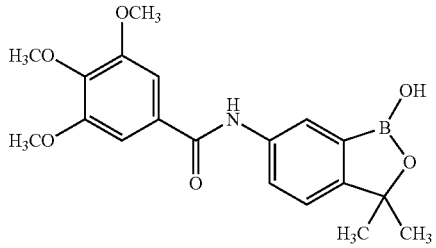 [SMILES: COc1cc(C(=O)Nc2ccc3c(c2)B(O)OC3(C)C)cc(OC)c1OC]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 3,4,5-trimethoxy-benzoyl chloride replacing 2-trifluoromethyl-4-fluorobenzoyl chloride. Data: LCMS (M/Z): 372 (M+H); $^1$H NMR (DMSO-$d_6$) δ: 1.45 (s, 6 H) 3.73 (s, 3 H) 3.87 (s, 6 H) 7.29 (s, 2 H) 7.40 (d, J=8.2 Hz, 1 H) 7.74 (dd, J=8.2, 1.8 Hz, 1 H) 7.99 (d, J=1.5 Hz, 1 H) 10.14 (s, 1 H).

107 2-Chloro-6-fluoro-N-(1-hydroxy-3,3-dimethyl-1,3-dihydro-benzo[c][1,2]oxaborol-6-yl)-3-methyl-benzamide

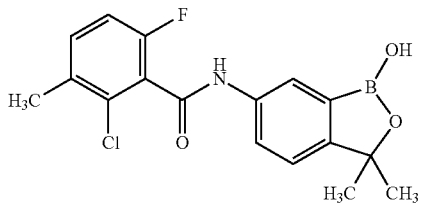 [SMILES: Cc1ccc(F)c(C(=O)Nc2ccc3c(c2)B(O)OC3(C)C)c1Cl]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-chloro-6-fluoro-3-methyl-benzoyl chloride replacing 2-trifluoromethyl-4-fluorobenzoyl chloride. Data: LCMS (M/Z): 348 (M+H); $^1$H NMR (DMSO-$d_6$) δ: 1.44 (s, 6 H) 2.36 (s, 3 H) 7.29 (t, J=8.6 Hz, 1 H) 7.39 (d, J=8.2 Hz, 1 H) 7.51 (dd, J=8.6, 6.2 Hz, 1 H) 7.64 (dd, J=8.2, 2.0 Hz, 1 H) 8.05 (d, J=1.8 Hz, 1 H) 9.10 (s, 1 H) 10.74 (s, 1 H).

108 6-Chloro-2-fluoro-N-(1-hydroxy-3,3-dimethyl-1,3-dihydro-benzo[c][1,2]oxaborol-6-yl)-3-methyl-benzamide

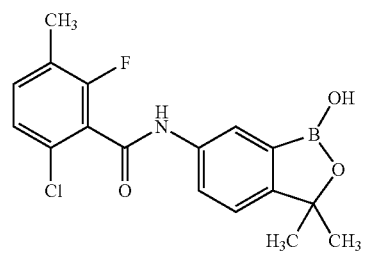 [SMILES: Cc1ccc(Cl)c(C(=O)Nc2ccc3c(c2)B(O)OC3(C)C)c1F]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 6-chloro-2-fluoro-3-methyl-benzoyl chloride replacing 2-trifluoromethyl-4-fluorobenzoyl chloride. Data: LCMS (M/Z): 348 (M+H); $^1$H NMR (DMSO-$d_6$) δ: 1.44 (s, 6 H) 2.26-2.30 (m, 3 H) 7.31-7.36 (m, 1 H) 7.36-7.47 (m, 2 H) 7.64 (dd, J=8.3, 2.0 Hz, 1 H) 8.05 (d, J=2.0 Hz, 1 H) 9.10 (s, 1 H) 10.73 (s, 1 H).

109 3-Chloro-2-fluoro-N-(1-hydroxy-3,3-dimethyl-1,3-dihydro-benzo[c][1,2]oxaborol-6-yl)-6-trifluoromethyl-benzamide

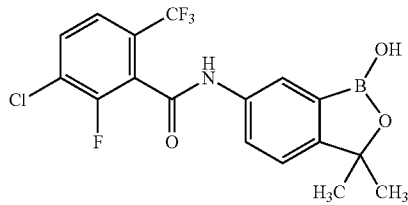 [SMILES: CC1(C)OB(O)c2cc(NC(=O)c3c(C(F)(F)F)ccc(Cl)c3F)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 3-chloro-2-fluoro-6-trifluoromethyl-benzoyl chloride replacing 2-trifluoromethyl-4-fluorobenzoyl chloride. Data: LCMS (M/Z): 402 (M+H); $^1$H NMR (DMSO-$d_6$) δ: 1.45 (s, 6 H) 7.42 (d, J=8.2 Hz, 1 H) 7.59 (dd, J=8.2, 1.9 Hz, 1 H) 7.77 (d, J=8.5 Hz, 1 H) 7.89-8.10 (m, 2 H) 9.12 (br. s., 1 H) 10.88 (s, 1 H).

110 2,3,4,5,6-Pentafluoro-N-(1-hydroxy-3,3-dimethyl-1,3-dihydro-benzo[c][1,2]oxaborol-6-yl)-benzamide

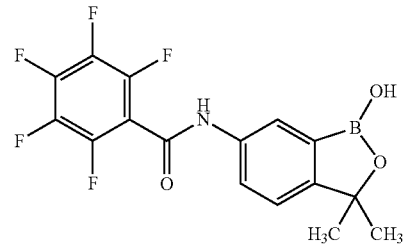 [SMILES: CC1(C)OB(O)c2cc(NC(=O)c3c(F)c(F)c(F)c(F)c3F)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2,3,4,5,6-pentafluoro-benzoyl chloride replacing 2-trifluoromethyl-4-fluorobenzoyl chloride. Data: LCMS (M/Z): 372 (M+H); $^1$H NMR (DMSO-$d_6$) δ: 1.45 (s, 6 H) 7.43 (d, J=8.2 Hz, 1 H) 7.64 (dd, J=8.2, 2.0 Hz, 1 H) 8.02 (d, J=1.9 Hz, 1 H) 9.13 (s, 1 H) 11.00 (s, 1 H).

111 Naphthalene-1-carboxylic acid (1-hydroxy-3,3-dimethyl-1,3-dihydro-benzo[c][1,2]oxaborol-6-yl)-amide

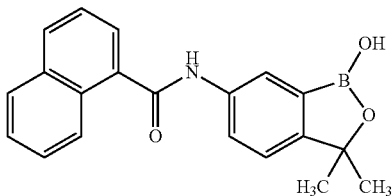 [SMILES: CC1(C)OB(O)c2cc(NC(=O)c3cccc4ccccc34)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with naphthalene-1-carbonyl chloride replacing 2-trifluoromethyl-4-fluorobenzoyl chloride. Data: LCMS (M/Z): 332 (M+H); $^1$H NMR (DMSO-d$_6$) δ: 1.46 (s, 6 H) 7.40 (d, J=8.4 Hz, 1 H) 7.55-7.66 (m, 3 H) 7.72-7.81 (m, 2 H) 7.99-8.05 (m, 1 H) 8.08 (d, J=8.4 Hz, 1 H) 8.12-8.22 (m, 2 H) 9.09 (s, 1 H) 10.58 (s, 1 H).

112 Naphthalene-2-carboxylic acid (1-hydroxy-3,3-dimethyl-1,3-dihydrobenzo[c][1,2]oxaborol-6-yl)-amide

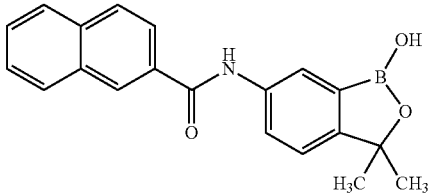 [SMILES: CC1(C)OB(O)c2cc(NC(=O)c3ccc4ccccc4c3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-naphthoyl chloride replacing 2-trifluoromethyl-4-fluorobenzoyl chloride. Data: LCMS (M/Z): 332 (M+H); $^1$H NMR (DMSO-d$_6$) δ: 1.47 (s, 6 H) 7.41 (d, J=8.2 Hz, 1 H) 7.59-7.69 (m, 2 H) 7.80 (dd, J=8.2, 1.9 Hz, 1 H) 7.99-8.16 (m, 5 H) 8.59 (s, 1 H) 9.08 (s, 1 H) 10.45 (s, 1 H).

113 Quinoline-8-carboxylic acid (1-hydroxy-3,3-dimethyl-1,3-dihydro-benzo[c][1,2]oxaborol-6-yl)-amide

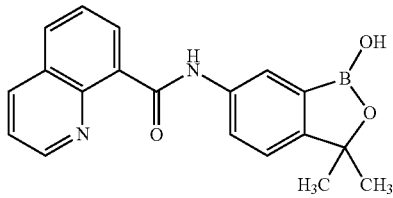 [SMILES: CC1(C)OB(O)c2cc(NC(=O)c3cccc4cccnc34)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with quinoline-8-carbonyl chloride replacing 2-trifluoromethyl-4-fluorobenzoyl chloride. Data: LCMS (M/Z): 333 (M+H); $^1$H NMR (DMSO-d$_6$) δ: 1.47 (s, 6 H) 7.44 (d, J=8.2 Hz, 1 H) 7.76 (s, 1 H) 7.83 (d, J=7.5 Hz, 1 H) 7.90 (dd, J=8.2, 2.0 Hz, 1 H) 8.18 (s, 1 H) 8.27 (d, J=8.2 Hz, 1 H) 8.61-8.67 (m, 2 H) 9.10 (d, J=3.4 Hz, 1 H) 9.16 (dd, J=4.2, 1.9 Hz, 1 H) 13.19 (d, J=2.3 Hz, 1 H).

114 Pyridine-2-carboxylic acid (1-hydroxy-3,3-dimethyl-1,3-dihydro-benzo[c][1,2]oxaborol-6-yl)-amide

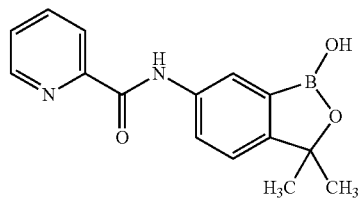 [SMILES: CC1(C)OB(O)c2cc(NC(=O)c3ccccn3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with pyridine-2-carbonyl chloride replacing 2-trifluoromethyl-4-fluorobenzoyl chloride. Data: LCMS (M/Z): 283 (M+H); $^1$H NMR (DMSO-d$_6$) δ: 1.45 (s, 6 H) 7.41 (s, 1 H) 7.65-7.70 (m, 1 H) 7.83 (dd, J=8.2, 2.1 Hz, 1 H) 8.08 (dd, J=7.7, 1.7 Hz, 1 H) 8.15-8.22 (m, 2 H) 8.73-8.77 (m, 1 H) 9.07 (s, 1 H) 10.63 (s, 1 H).

115 N-(1-Hydroxy-3,3-dimethyl-1,3-dihydro-benzo[c][1,2]oxaborol-6-yl)-nicotinamide

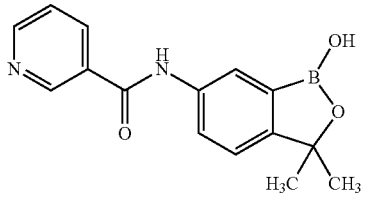 [SMILES: CC1(C)OB(O)c2cc(NC(=O)c3cccnc3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with nicotinoyl chloride replacing 2-trifluoromethyl-4-fluorobenzoyl chloride. Data: LCMS (M/Z): 283 (M+H); $^1$H NMR (DMSO-d$_6$) δ: 1.41 (s, 6 H) 7.37 (d, J=8.2 Hz, 1 H) 7.71 (dd, J=8.2, 1.9 Hz, 1 H) 7.83 (d, J=6.1 Hz, 2 H) 8.04 (s, 1 H) 8.75 (d, J=6.0 Hz, 2 H) 9.06 (s, 1 H) 10.48 (s, 1 H).

116 N-(1-Hydroxy-3,3-dimethyl-1,3-dihydro-benzo[c][1,2]oxaborol-6-yl)-isonicotinamide

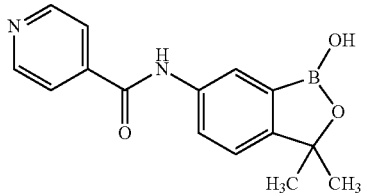 [SMILES: CC1(C)OB(O)c2cc(NC(=O)c3ccncc3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with isonicotinoyl chloride replacing 2-trifluoromethyl-4-fluorobenzoyl chloride. Data: LCMS (M/Z): 283 (M+H); $^1$H NMR (DMSO-d$_6$) δ: 1.45 (s, 6 H) 7.41 (d, J=8.2 Hz, 1 H) 7.75 (dd, J=8.2, 2.0 Hz, 1 H) 7.83-7.90 (m, 2 H) 8.08 (d, J=1.8 Hz, 1 H) 8.74-8.82 (m, 2 H) 9.09 (s, 1 H) 10.52 (s, 1 H).

117 Quinoline-2-carboxylic acid (1-hydroxy-3,3-dimethyl-1,3-dihydro-benzo[c][1,2]oxaborol-6-yl)-amide

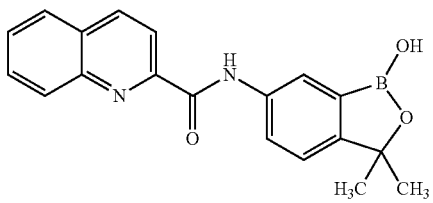

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with quinoline-2-carbonyl chloride replacing 2-trifluoromethyl-4-fluorobenzoyl chloride. Data: LCMS (M/Z): 333 (M+H); $^1$H NMR (DMSO-d$_6$) δ: 1.47 (s, 6 H) 7.44 (d, J=8.2 Hz, 1 H) 7.76 (d, J=1.1 Hz, 1 H) 7.92 (dd, J=8.2, 2.0 Hz, 2 H) 8.13 (d, J=8.2 Hz, 1 H) 8.21-8.30 (m, 3 H) 8.64 (d, J=8.6 Hz, 1 H) 9.10 (s, 1 H) 10.75 (s, 1 H).

118 2-Chloro-N-(1-hydroxy-3,3-dimethyl-1,3-dihydro-[c][1,2]oxaborol-6-yl-6-methyl-nicotinamide

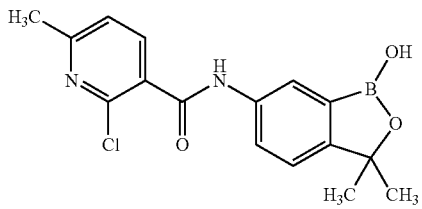 [SMILES: Cc1ccc(C(=O)Nc2ccc3c(c2)B(O)OC3(C)C)c(Cl)n1]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-chloro-6-methyl-nicotinoyl chloride replacing 2-trifluoromethyl-4-fluorobenzoyl chloride. Data: LCMS (M/Z): 331 (M+H); $^1$H NMR (DMSO-d$_6$) δ: 1.44 (s, 6 H) 3.32 (s, 3 H) 7.40 (t, J=7.6 Hz, 2 H) 7.67 (dd, J=8.2, 2.0 Hz, 1 H) 7.94 (d, J=7.7 Hz, 1 H) 8.03 (d, J=1.9 Hz, 1 H) 9.10 (s, 1 H) 10.56 (s, 1 H).

119 Pyrazine-2-carboxylic acid (1-hydroxy-3,3-dimethyl-1,3-dihydro-benzo[c][1,2]oxaborol-6-yl)-amide

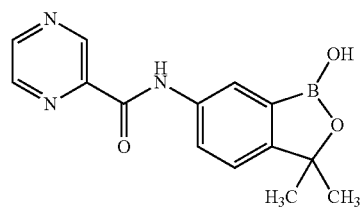 [SMILES: CC1(C)OB(O)c2cc(NC(=O)c3cnccn3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with pyrazine-2-carbonyl chloride replacing 2-trifluoromethyl-4-fluorobenzoyl chloride. Data: LCMS (M/Z): 284 (M+H); $^1$H NMR (DMSO-d$_6$) δ: 1.45 (s, 6 H) 7.41 (d, J=8.2 Hz, 1 H) 7.83 (dd, J=8.3, 2.0 Hz, 1 H) 8.18 (d, J=1.9 Hz, 1 H) 8.82 (dd, J=2.4, 1.5 Hz, 1 H) 8.94 (d, J=2.5 Hz, 1 H) 9.09 (s, 1 H) 9.31 (d, J=1.4 Hz, 1 H) 10.74 (s, 1 H).

120 Furan-3-carboxylic acid (1-hydroxy-3,3-dimethyl-1,3-dihydro-benzo[c][1,2]oxaborol-6-yl)-amide

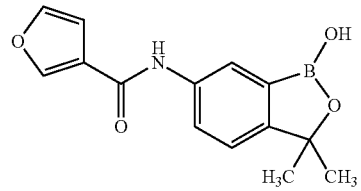 [SMILES: CC1(C)OB(O)c2cc(NC(=O)c3ccoc3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with furan-3-carbonyl chloride replacing 2-trifluoromethyl-4-fluorobenzoyl chloride. Data: LCMS (M/Z): 272 (M+H); $^1$H NMR (DMSO-d$_6$) δ: 1.44 (s, 6 H) 7.01 (d, J=1.1 Hz, 1 H) 7.38 (d, J=8.2 Hz, 1 H) 7.69 (dd, J=8.2, 1.9 Hz, 1 H) 7.79 (t, J=1.7 Hz, 1 H) 7.99 (s, 1 H) 8.37 (d, J=0.5 Hz, 1 H) 9.05 (s, 1 H) 9.93 (s, 1 H).

121 2-Methyl-furan-3-carboxylic acid (1-hydroxy-3,3-dimethyl-1,3-dihydro-benzo[c][1,2]oxaborol-6-yl)-amide

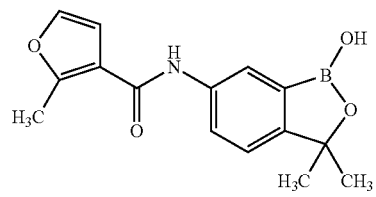 [SMILES: Cc1occc1C(=O)Nc1ccc2c(c1)B(O)OC2(C)C]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2-methyl-furan-3-carbonyl chloride replacing 2-trifluoromethyl-4-fluorobenzoyl chloride. Data: LCMS (M/Z): 286 (M+H); $^1$H NMR (DMSO-d$_6$) δ: 1.44 (s, 6 H) 2.55 (s, 3 H) 7.07 (d, J=2.0 Hz, 1 H) 7.35 (d, J=8.2 Hz, 1 H) 7.59 (d, J=2.0 Hz, 1 H) 7.67 (dd, J=8.2, 2.0 Hz, 1 H) 8.02 (d, J=1.8 Hz, 1 H) 9.03 (s, 1 H) 9.71 (s, 1 H).

122 2,5-Dimethyl-furan-3-carboxylic acid (1-hydroxy-3,3-dimethyl-1,3-dihydro-benzo[c][1,2]oxaborol-6-yl)-amide

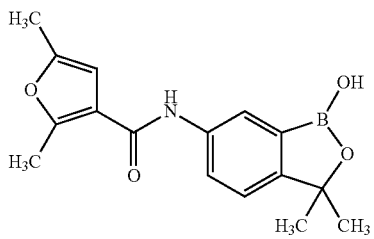 [SMILES: Cc1cc(C(=O)Nc2ccc3c(c2)B(O)OC3(C)C)c(C)o1]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2,5-dimethyl-furan-3-carbonyl chloride replacing 2-trifluoromethyl-4-fluorobenzoyl chloride. Data: LCMS (M/Z): 300 (M+H); $^1$H NMR (DMSO-$d_6$) δ: 1.40 (s, 6 H) 2.22 (s, 3 H) 2.47 (s, 5 H) 6.63 (s, 1 H) 7.31 (d, J=8.2 Hz, 1 H) 7.63 (dd, J=8.2, 1.9 Hz, 1 H) 7.98 (s, 1 H) 8.98 (s, 1 H) 9.56 (s, 1 H).

123 1H-Pyrazole-3-carboxylic acid (1-hydroxy-3,3-dimethyl-1,3-dihydro-benzo[c][1,2]oxaborol-6-yl)-amide

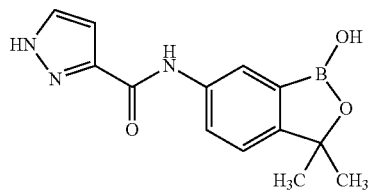 [SMILES: CC1(C)OB(O)c2cc(NC(=O)c3cc[nH]n3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 1H-pyrazole-3-carbonyl chloride replacing 2-trifluoromethyl-4-fluorobenzoyl chloride. Data: LCMS (M/Z): 272 (M+H); $^1$H NMR (DMSO-$d_6$) δ: 1.40 (s, 6 H) 6.66 (dd, J=3.5, 1.7 Hz, 1 H) 7.29 (d, J=3.5 Hz, 1 H) 7.34 (d, J=8.2 Hz, 1 H) 7.67 (dd, J=8.3, 2.0 Hz, 1 H) 7.87-7.92 (m, 1 H) 7.99 (d, J=1.8 Hz, 1 H) 9.02 (s, 1 H) 10.15 (s, 1 H).

124 Thiophene-2-carboxylic acid (1-hydroxy-3,3-dimethyl-1,3-dihydro-benzo[c][1,2]oxaborol-6-yl)-amide

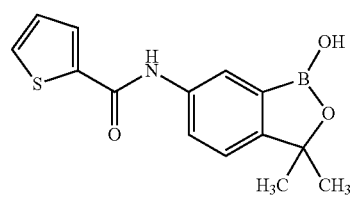 [SMILES: CC1(C)OB(O)c2cc(NC(=O)c3cccs3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with thiophene-2-carbonyl chloride replacing 2-trifluoromethyl-4-fluorobenzoyl chloride. Data: LCMS (M/Z): 288 (M+H); $^1$H NMR (DMSO-$d_6$) δ: 1.45 (s, 6 H) 7.23 (dd, J=5.0, 3.8 Hz, 1 H) 7.39 (d, J=8.2 Hz, 1 H) 7.71 (dd, J=8.2, 2.0 Hz, 1 H) 7.85 (dd, J=5.0, 0.9 Hz, 1 H) 7.98-8.05 (m, 2 H) 9.06 (s, 1 H) 10.25 (s, 1 H).

125 N-(1-Hydroxy-3,3-dimethyl-1,3-dihydro-benzo[c][1,2]oxaborol-6-yl)-2-thiophen-2-yl-acetamide

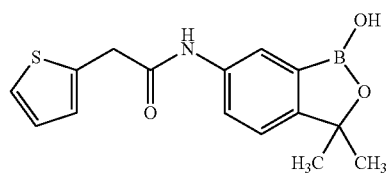 [SMILES: CC1(C)OB(O)c2cc(NC(=O)Cc3cccs3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with thiophen-2-yl-acetyl chloride replacing 2-trifluoromethyl-4-fluorobenzoyl chloride. Data: LCMS (M/Z): 302 (M+H); $^1$H NMR (DMSO-$d_6$) δ: 1.42 (s, 6 H) 3.87 (s, 2 H) 6.95-7.01 (m, 2 H) 7.33 (d, J=8.2 Hz, 1 H) 7.38 (d, J=4.7 Hz, 1 H) 7.58 (dd, J=8.2, 1.9 Hz, 1 H) 7.90 (s, 1 H) 9.04 (s, 1 H) 10.20 (s, 1 H).

126 Cyclopropanecarboxylic acid (1-hydroxy-3,3-dimethyl-1,3-dihydro-benzo[c][1,2]oxaborol-6-yl)-amide

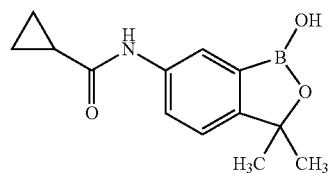

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with cyclopropanecarbonyl chloride replacing 2-trifluoromethyl-4-fluorobenzoyl chloride. Data: LCMS (M/Z): 246 (M+H); $^1$H NMR (DMSO-$d_6$) δ: 0.71-0.78 (m, 4 H) 1.38 (s, 6 H) 1.71-1.79 (m, 1 H) 7.27 (d, J=8.2 Hz, 1 H) 7.56 (dd, J=8.2, 2.0 Hz, 1 H) 7.83 (d, J=1.6 Hz, 1 H) 8.97 (s, 1 H) 10.13 (s, 1 H).

127 Cyclobutanecarboxylic acid (1-hydroxy-3,3-dimethyl-1,3-dihydro-benzo[c][1,2]oxaborol-6-yl)-amide

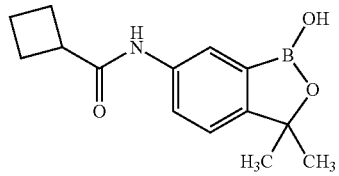 [SMILES: CC1(C)OB(O)c2cc(NC(=O)C3CCC3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with cyclobutanecarbonyl chloride replacing 2-trifluoromethyl-4-fluorobenzoyl chloride. Data: LCMS (M/Z): 260 (M+H); $^1$H NMR (DMSO-d$_6$) δ: 1.38 (s, 6 H) 1.70-1.82 (m, 1 H) 1.85-1.96 (m, 1 H) 2.07 (br. s., 2 H) 2.12-2.24 (m, 2 H) 3.19 (s, 1 H) 7.26 (d, J=8.2 Hz, 1 H) 7.55 (dd, J=8.2, 2.0 Hz, 1 H) 7.86 (d, J=1.7 Hz, 1 H) 8.97 (s, 1 H) 9.67 (s, 1 H).

128 Cyclopentanecarboxylic acid (1-hydroxy-3,3-dimethyl-1,3-dihydro-benzo[c][1,2]oxaborol-6-yl)-amide

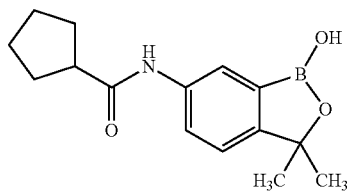 [SMILES: CC1(C)OB(O)c2cc(NC(=O)C3CCCC3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with cyclopentanecarbonyl chloride replacing 2-trifluoromethyl-4-fluorobenzoyl chloride. Data: LCMS (M/Z): 274 (M+H); $^1$H NMR (DMSO-d$_6$) δ: 1.38 (s, 6 H) 1.51 (br. s., 2 H) 1.59-1.73 (m, 4 H) 1.79 (br. s., 2 H) 2.69-2.79 (m, 1 H) 7.26 (d, J=8.2 Hz, 1 H) 7.55 (dd, J=8.2, 2.0 Hz, 1 H) 7.86 (d, J=1.8 Hz, 1 H) 8.96 (s, 1 H) 9.80 (s, 1 H).

129 Cyclohexanecarboxylic acid (1-hydroxy-3,3-dimethyl-1,3-dihydro-benzo[c][1,2]oxaborol-6-yl)-amide

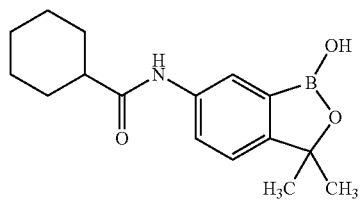 [SMILES: CC1(C)OB(O)c2cc(NC(=O)C3CCCCC3)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with cyclohexanecarbonyl chloride replacing 2-trifluoromethyl-4-fluorobenzoyl chloride. Data: LCMS (M/Z): 288 (M+H); $^1$H NMR (DMSO-d$_6$) δ: 1.09-1.30 (m, 3 H) 1.37 (s, 8 H) 1.57-1.65 (m, 1 H) 1.66-1.80 (m, 4 H) 2.24-2.35 (m, 1 H) 7.26 (d, J=8.2 Hz, 1 H) 7.55 (dd, J=8.2, 2.0 Hz, 1 H) 7.86 (d, J=1.8 Hz, 1 H) 8.96 (s, 1 H) 9.74 (s, 1 H).

130 N-(1-Hydroxy-3,3-dimethyl-1,3-dihydro-benzo[c][1,2]oxaborol-6-yl)-acetamide

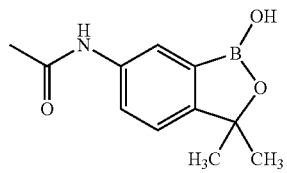 [SMILES: CC(=O)Nc1ccc2c(c1)B(O)OC2(C)C]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with acetyl chloride replacing 2-trifluoromethyl-4-fluorobenzoyl chloride. Data: LCMS (M/Z): 220 (M+H); $^1$H NMR (DMSO-d$_6$) δ: 1.41 (s, 6 H) 2.04 (s, 3 H) 7.31 (d, J=8.2 Hz, 1 H) 7.57 (dd, J=8.2, 1.8 Hz, 1 H) 7.88 (d, J=1.6 Hz, 1 H) 8.47 (s, 1 H) 9.95 (s, 1 H).

131 2,2,3,3,4,4,4-Heptafluoro-N-(1-hydroxy-3,3-dimethyl-1,3-dihydro-benzo[c][1,2]oxaborol-6-yl)-butyramide

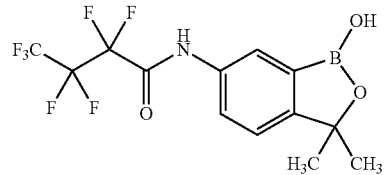 [SMILES: CC1(C)OB(O)c2cc(NC(=O)C(F)(F)C(F)(F)C(F)(F)F)ccc21]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2,2,3,3,4,4,4-heptafluoro-butyryl chloride replacing 2-trifluoromethyl-4-fluorobenzoyl chloride. Data: LCMS (M/Z): 374 (M+H); $^1$H NMR (DMSO-d$_6$) δ: 1.41 (s, 6 H) 7.42 (d, J=8.2 Hz, 1 H) 7.59 (dd, J=8.2, 2.0 Hz, 1 H) 7.92 (d, J=1.9 Hz, 1 H) 11.27 (s, 1 H).

132 N-(1-Hydroxy-3,3-dimethyl-1,3-dihydro-benzo[c][1,2]oxaborol-6-yl)-2,2-dimethyl-butyramide

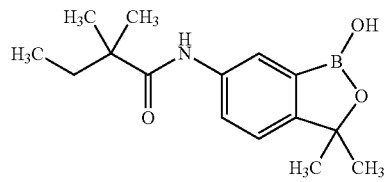 [SMILES: CCC(C)(C)C(=O)Nc1ccc2c(c1)B(O)OC2(C)C]

The title compound was prepared using a procedure similar to that of 4-fluoro-N-(1-hydroxy-3,3-dimethyl-1,3-dihydro-benzo[c][1,2]oxaborol-6-yl-2-trifluoromethyl benzamide with 2,2-dimethyl-butyryl chloride replacing 2-trifluoromethyl-4-fluorobenzoyl chloride. Data: LCMS (M/Z): 276 (M+H); $^1$H NMR (DMSO-d$_6$) δ: 0.76 (t, J=7.4 Hz, 3 H) 1.14 (s, 6 H) 1.38 (s, 6 H) 1.58 (q, J=7.4 Hz, 2 H) 7.27 (d, J=8.2 Hz, 1 H) 7.52 (dd, J=8.2, 2.0 Hz, 1 H) 7.86 (d, J=1.9 Hz, 1 H) 8.93 (s, 1 H) 9.11 (s, 1 H).

133 4-Fluoro-N-(1-hydroxy-3,3-spirocyclopropyl-1,3-dihydro-benzo[c][1,2]oxaborol-6-yl-2-trifluoromethyl benzamide

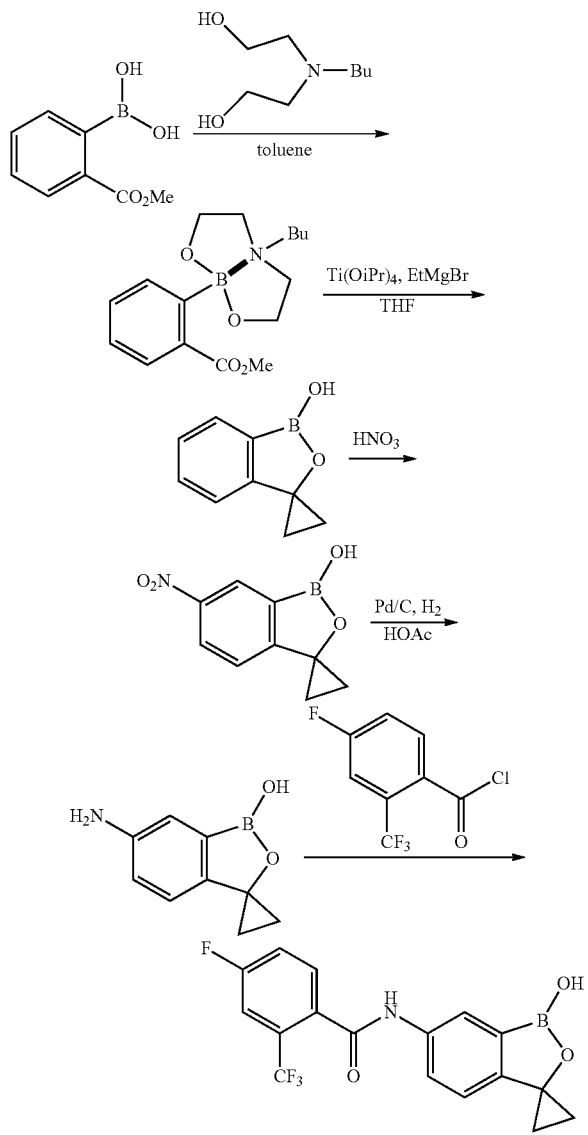

To a suspension of (2-methoxycarbonylphenyl)boronic acid (5.0 g, 27.8 mmol) in toluene (40 mL) was added N-butyldiethanolamine (4.8 mL, 29.2 mmol, 1.05 equiv.) via a syringe. The mixture was heated at 50° C. for two hours. After cooling to room temperature, the toluene was evaporated under reduced pressure and the remaining clear colorless crude oil was treated with heptanes (~500 mL). The heptanes mixture was then sonicated ~5 min and the resulting suspension was allowed to stand at room temperature overnight. The solid that precipitated was collected by filtration, washed with heptanes, and dried in a vacuum oven overnight to yield a white solid as the 2-(2'-methoxycarbonylphenyl)-6-butyl[1,3,6,2]dioxazaborocan. $^1$H NMR (DMSO-d$_6$) δ: 7.55-7.59 (m, 1H), 7.17-7.29 (m, 2H), 7.12-7.14 (m, 1H), 3.85-3.92 (m, 2H), 3.78-3.82 (m, 1H), 3.78 (br. s., 1H), 3.67 (s, 3H), 3.26-3.30 (m, 1H), 3.12 (dt, J=5.2, 2.6 Hz, 2H), 3.03-3.11 (m, 2H), 2.41-2.49 (m, 4H), 1.45-1.55 (m, 2H), 0.98-1.05 (m, 2H), 0.83 (s, 1H), 0.71-0.77 (m, 3H). Amount obtained, 8.3 g, (98.1% yield).

To a solution of 2-(2'-methoxycarbonylphenyl)-6-butyl[1,3,6,2]dioxazaborocan (105 g, 5.0 mmol) in THF (50 mL) was added Ti(OiPr)$_4$ (2.1 mL, 7.0 mmol, 1.4 equiv.); followed by slow addition of EtMgBr (7.0 mL, 2.0 M in Et$_2$O, 14.0 mmol, 2.8 equv.) over a period of 20 min. The reaction mixture was stirred at r.t. for 6 h before being carefully treated with H$_2$O (30 mL). The suspension was filtered and the filtrate was treated with HCl (6N, 30 mL) and stirred over 48 h. The mixture was extracted with EtOAc (3×). The EtOAc extracts were washed with brine, dried over Na$_2$SO$_4$, filtered and concentrated under reduced pressure. The residual oil was subjected to flash chromatography (Isco Companion, 80 g SiO$_2$ cartridge, solid loaded SiO$_2$, neat heptane to EtOAc gradient) to give the 3,3-cyclopropyl-3H-benzo[c][1,2]oxaborol-1-ol as a brown oil. $^1$H NMR (DMSO-d$_6$) δ: 7.67 (d, J=7.3 Hz, 1H), 7.40 (td, J=7.5, 1.1 Hz, 1H), 7.23-7.29 (m, 1H), 7.00 (d, J=7.7 Hz, 1H), 1.36-1.41 (m, 2H), 1.09-1.14 (m, 2H). Amount obtained: 201 mg (25%).

To 2.0 mL fuming HNO$_3$ at −45° C. was added a solution of 3,3-cyclopropyl-3H-benzo[c][1,2]oxaborol-1-ol (201 mg, 1.26 mmol) in 1.0 ml nitrobenzene slowly via a syringe while maintaining the reaction temperature between −40 to −45° C. Once the addition was complete the resulting solution was allowed to stir at −45° C. for an additional 45 min before poured into crushed ice (20 g). The ice mixture was allowed to melt and the aqueous solution was extracted with EtOAc (3×). The combined organic extracts were extracted with NaOH (2N, 3×). Combined aqueous phase was treated with HCl (6N) until pH=3~4. The suspension was extracted with EtOAc (3×) again. The combined organic was washed with brine and concentrated under reduced pressure to give an orange oil. The oil subjected to flash chromatography (Isco Companion, 80 g SiO$_2$ cartridge, solid loaded SiO$_2$, neat heptane to EtOAc gradient) to 3,3-cyclopropyll-6-nitro-3H-benzo[c][1.2]oxaborol-1-ol as a yellow solid. $^1$H NMR (DMSO-d$_6$) δ: 8.53 (d, J=2.1 Hz, 1H), 8.26 (dd, J=8.5, 2.2 Hz, 1H), 7.31 (d, J=8.5 Hz, 1H), 1.50-1.57 (m, 2H), 1.29-1.36 (m, 2H). Amount obtained: 92 mg (30%)

A solution of 3,3-cyclopropyl-6-nitro-3H-benzo[c][1.2]oxaborol-1-ol (87 mg, 0.42 mmol) in THF (6.0 mL) was passed through H-cube equipped with a 10% Pd/C cartridge. The collected light yellow solution was immediately treated with Et$_3$N (190 μL, 1.4 mmol, 3.2 eq.), followed by 4-fluoro-2-trifluoromethyl-benzoyl chloride (100 μL, 0.67 mmol, 1.6 eq.). The resulting mixture was stirred at room temperature overnight. The reaction solution was diluted with EtOAc (20 mL), washed with 1N HCl (10 mL), H$_2$O (10 mL), brine (10 mL) and then dried over Na$_2$SO$_4$, filtered and the filtrate was concentrated under reduced pressure. The oil residue was dissolved in minimum amount of THF and carefully treated with heptanes. The precipitate was collected by filtration and washed with heptanes. The solid was further purified by HPLC to give the title compound as a white solid. LCMS (M/Z): 366 (M+H); $^1$H NMR (DMSO-d$_6$) δ: 10.54 (s, 1H), 9.34 (s, 1H), 8.07 (d, J=1.8 Hz, 1H), 7.74-7.78 (m, 2H), 7.64 (d, J=2.6 Hz, 1H), 7.59 (dd, J=8.3, 2.0 Hz, 1H), 6.99 (d, J=8.2 Hz, 1H), 1.35-1.41 (m, 2H), 1.07-1.13 (m, 2H). Amount obtained: 81 mg (53%).

134 4-Fluoro-N-(1-hydroxy-3,3-spirocyclobutyl-1,3-dihydro-benzo[c][1,2]oxaborol-6-yl-2-trifluoromethyl benzamide

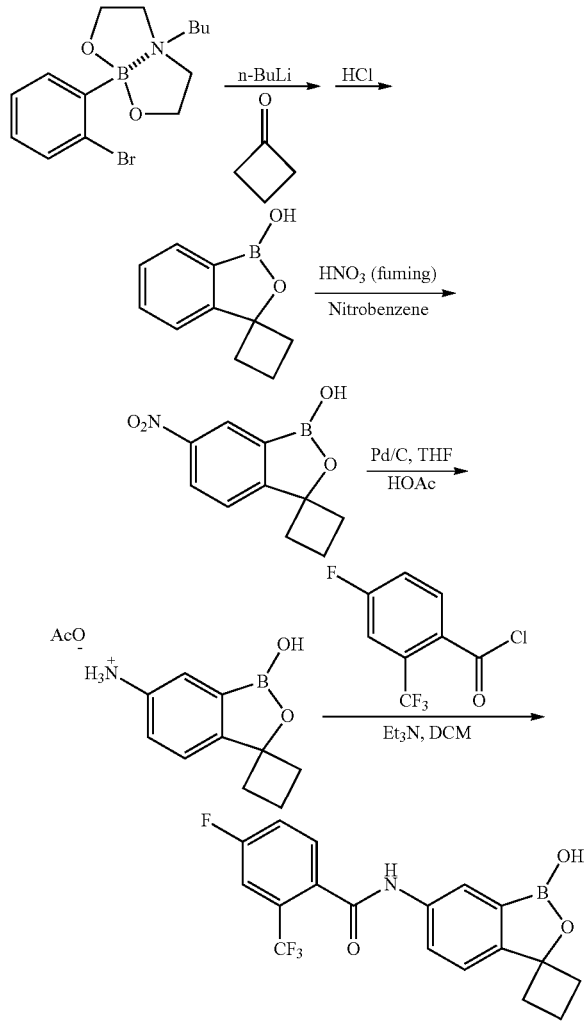

To a solution of 2-(2'-bromophenyl)-6-butyl[1,3,6,2]dioxazaborocan (6.0 g, 18.4 mmol), prepared as described in 4-fluoro-N-(1-hydroxy-3,3-dimethyl-1,3-dihydro-benzo[c][1,2]oxaborol-6-yl-2-trifluoromethyl benzamide, in THF (153 mL) at −78° C. was added n-BuLi (8.8 mL, 2.5M in hexane, 22.0 mmol, 1.2 equiv.) dropwise via a syringe over a period of 20 min while maintaining reaction temperature at −78° C. After the addition the reaction solution was stirred 20 min at −78° C. before cyclobutanone (2.2 mL, 25.7 mmol, 1.4 equiv.) was added dropwise via a syringe over a period of 10 min while maintaining the reaction temperature at −78° C. The resulting mixture was allowed to stir for 20 min at −78° C. then warm to room temperature gradually. Once the reaction vessel reached room temperature, 6N HCl solution (30.6 mL) was added and the mixture was stirred for 30 min. The mixture was extracted with EtOAc (3×). The EtOAc extracts were dried over $Na_2SO_4$, filtered and concentrated under reduced pressure. The crude residual oil remaining was then subjected to flash chromatography (Isco Companion, 80 g $SiO_2$ cartridge, solid loaded $SiO_2$, neat heptane to 20:80 EtOAc gradient at 60 ml/min for 90 min). The product was recovered as clear colorless oil. Amount obtained: 1.42 g (44% yield).

To 7.02 ml fuming $HNO_3$ at −45° C. was added a solution of 3,3-spirocyclobutyl-3H-benzo[c][1,2]oxaborol-1-ol (1.42 g, 8.16 mmol) in 3.0 ml nitrobenzene slowly via a syringe while maintaining the reaction temperature between −40 to −45° C. Once the addition was complete the resulting solution was allowed to stir at −45° C. for an additional 45 min before poured into crushed ice (30 g). The ice mixture was allowed to melt and the aqueous solution was extracted with dichloromethane. The combined dichloromethane extracts were dried over $Na_2SO_4$ then evaporated. The crude oil remaining was mixed with one liter 1:1 DCM:heptane. The volume of the solution was reduced on a rotovap by half and the resulting solution was allowed to stand overnight in a −20° C. freezer overnight. The precipitate formed was filtered out, washed with heptanes and vacuum dried to give the titled compound as a white solid. $^1$H NMR (DMSO-$d_6$) δ: 9.10 (s, 1H), 7.56-7.65 (m, 2H), 7.43-7.51 (m, 1H), 7.25-7.33 (m, 1H), 2.38-2.44 (m, 2H), 2.28-2.35 (m, 2H), 1.97-2.04 (m, 2H). Amount obtained: 1.10 g (62% yield).

To a solution of 3,3-spirocyclobutyl-6-nitro-3H-benzo[c][1,2]oxaborol-ol (673 mg, 3.1 mmol) in THF (20 mL) was added HOAc (1.5 mL, 28 mmol). The vessel was vacuum/$N_2$ purged three times and 5% Pd/C (100 mg) was added. The mixture was again vacuum/$N_2$ purged three times then vacuum purged again. $H_2$ was then introduced from a balloon and the reaction was allowed to stir for 2.5 hours. The reaction solution was filtered through a short pad of celite and the filtrate was evaporated to yield the title compound as a dark brown foamy solid. $^1$H NMR (DMSO-$d_6$) δ: 7.21-7.26 (m, 1H), 6.72-6.75 (m, 1H), 6.69 (dd, J=8.1, 2.2 Hz, 1H), 2.30-2.39 (m, 2H), 2.20-2.29 (m, 2H), 1.89-1.99 (m, 1H), 1.87 (s, 3H). Amount obtained: 703.9 mg (92% yield).

To a solution of 6-amino-3,3-dimethyl-3H-benzo[c][1,2]oxaborol-1-ol acetate salt (101.6 mg, 0.41 mmol) in DCM (4 mL) was added $Et_3N$ (117.3 μL, 0.84 mmol). The mixture was cooled to 0° C. and the 2-trifluoromethyl-4-fluorobenzoyl chloride (70.0 μL, 0.46 mmol) was added slowly via a syringe. The resulting solution was allowed to warm to room temperature gradually and stir for 2 hours. The reaction solution was diluted with DCM, washed with 1N HCl, $H_2O$ and then dried over $Na_2SO_4$, filtered and the filtrate was concentrated under reduced pressure and the crude material was subjected to flash chromatography (Isco Companion, 4 g $SiO_2$ cartridge, $SiO_2$ solid load, neat heptanes to neat EtOAc gradient over 45 min, flow rate=18 ml/min). The title compound was recovered as a white foam. LCMS (M/Z): 380 (M+H); $^1$H NMR (DMSO-$d_6$) δ: 10.49-10.67 (m, 1H), 9.20 (s, 1H), 7.99-8.01 (m, 1H), 7.73-7.80 (m, 2H), 7.60-7.70 (m, 3H), 2.39-2.46 (m, 2H), 2.28-2.37 (m, 2H), 1.93-2.05 (m, 2H). Amount obtained: 80.0 mg (52% yield).

135 2-Chloro-4-fluoro-N-(1-hydroxy-3,3-spirocyclobutyl-1,3-dihydro-benzo[c][1,2]oxaborol-6-yl-benzamide

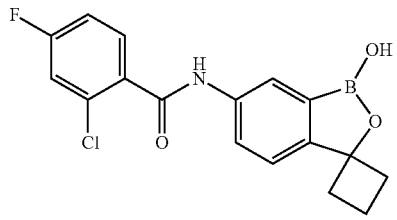 [SMILES: O=C(Nc1ccc2c(c1)B(O)OC21CCC1)c1ccc(F)cc1Cl]

The title compound was prepared using a procedure similar to that of 4-fluoro-N-(1-hydroxy-3,3-spirocyclobutyl-1,3-dihydro-benzo[c][1,2]oxaborol-6-yl-2-trifluoromethyl benzamide with 2-chloro-4-fluorobenzoyl chloride replacing 2-trifluoromethyl-4-fluorobenzoyl chloride. Data: LCMS (M/Z): 346 (M+H); ¹H NMR (DMSO-d₆) δ: 10.50 (s, 1H), 9.19 (s, 1H), 7.99-8.04 (m, 1H), 7.70 (d, J=2.1 Hz, 1H), 7.59-7.67 (m, 2H), 7.55 (dd, J=9.0, 2.5 Hz, 1H), 7.31 (td, J=8.5, 2.6 Hz, 1H), 2.39-2.46 (m, 2H), 2.28-2.37 (m, 2H), 1.93-2.04 (m, 2H).

136 4-Fluoro-N-(1-hydroxy-3,3-spirocyclopentyl-1,3-dihydro-benzo[c][1,2]oxaborol-6-yl-2-trifluoromethyl benzamide

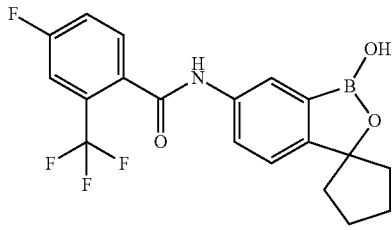 [SMILES: O=C(Nc1ccc2c(c1)B(O)OC21CCCC1)c1ccc(F)cc1C(F)(F)F]

The title compound was prepared using a procedure similar to that of 4-fluoro-N-(1-hydroxy-3,3-spirocyclobutyl-1,3-dihydro-benzo[c][1,2]oxaborol-6-yl-2-trifluoromethyl benzamide with cyclopentanone replacing cyclobutanone. Data: LCMS (M/Z): 394 (M+H); ¹H NMR (acetone) δ: 9.51 (br. s., 1H), 8.14 (d, J=2.0 Hz, 1H), 7.77-7.84 (m, 1H), 7.59-7.63 (m, 1H), 7.56-7.59 (m, 1H), 7.37-7.50 (m, 4H), 1.85-2.09 (m, 8H).

137 2-Chloro-N-(1-hydroxy-3,3-spirocyclopentyl'-1,3-dihydro-benzo[c][1,2]oxaborol-6-yl)-benzamide

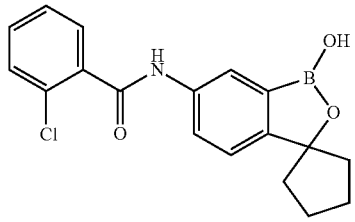 [SMILES: O=C(Nc1ccc2c(c1)B(O)OC21CCCC1)c1ccccc1Cl]

The title compound was prepared using a procedure similar to that of 4-fluoro-N-(1-hydroxy-3,3-spirocyclobutyl-1,3-dihydro-benzo[c][1,2]oxaborol-6-yl-2-trifluoromethyl benzamide with 2-chlorobenzoyl chloride replacing 2-trifluoromethyl-4-fluorobenzoyl chloride with cyclopentanone replacing cyclobutanone. Data: LCMS (M/Z): 342 (M+H); ¹H NMR (acetone) δ: 9.65 (br. s., 1H), 8.10 (d, J=1.7 Hz, 1H), 7.82 (dd, J=8.4, 5.5 Hz, 2H), 7.73 (dd, J=8.3, 2.0 Hz, 1H), 7.51-7.64 (m, 3H), 7.37 (d, J=8.2 Hz, 1H), 1.85-2.03 (m, 8H).

E14 2-Chloro-4-fluoro-N-(1-hydroxy-1,3-dihydro-benzo[c][1,2]oxaborol-6-yl)-benzamide

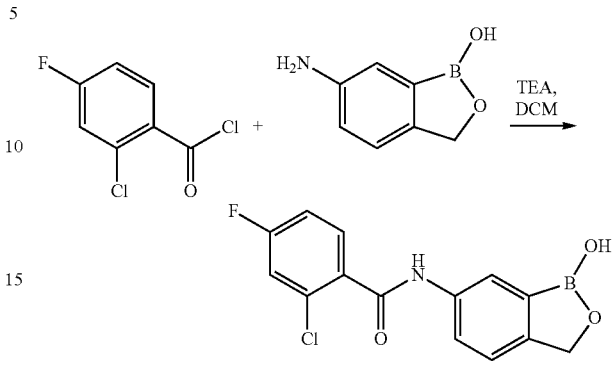

A 250 ml round bottom flask was charged with a mixture of 6-amino-1-hydroxy-2,1-benzoxaborolane hydrochloride (1 g, 5.4 mmol, 1 eq), triethylamine (2.3 ml, 16.2 mmol, 3 eq) and dichloromethane (100 ml). 2-Chloro-4-fluorobenzoyl chloride (1.14 g, 5.9 mmol, 1.1 eq) was added, and the reaction mixture was allowed to stir at room temperature overnight. Aqueous hydrochloric acid (1 M, 50 ml) was added to the mixture and the suspension was vigorously mixed. The resulting white precipitate was then collected by vacuum filtration and dried under vacuum. LCMS (m/e) 306 (M+H). ¹H NMR (400 MHz, DMSO-d₆) δ ppm 4.96 (s, 2H) 7.29-7.45 (m, 2H) 7.59 (dd, J=9.0, 2.3 Hz, 1H) 7.63-7.78 (m, 2H) 8.15 (d, J=1.8 Hz, 1H) 9.25 (s, 1H) 10.53 (s, 1H). Amount Obtained: 1.1 g, 67% yield.

E19 4-Fluoro-N-(1-hydroxy-1,3-dihydro-benzo[c][1,2]oxaborol-6-yl)-2-trifluoromethyl-benzamide

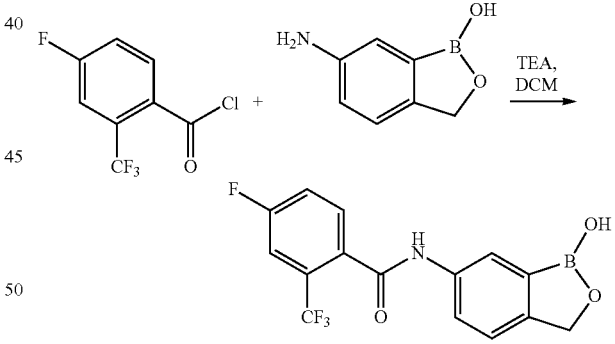

A 500 ml round bottom flask was charged with a mixture of 6-amino-1-hydroxy-2,1-benzoxaborolane hydrochloride (5 g, 26.9 mmol, 1 eq), triethylamine (11.2 ml, 80.7 mmol, 3 eq) and dichloromethane (200 ml). 4-Fluoro-2-(trifluoromethyl)benzoyl chloride (4.3 ml, 28.2 mmol, 1.05 eq) was then added, and the reaction mixture was allowed to stir at room temperature overnight. 1M HCl (100 ml) was added to the mixture and the reaction was stirred for an additional hour. The resulting precipitate was then collected, and the off-white powder was dried under vacuum. LCMS (m/e) 340 (M+H). ¹H NMR (400 MHz, DMSO-d₆) δ ppm 4.96 (s, 2 H) 7.39 (d, J=8.4 Hz, 1 H) 7.61-7.73 (m, 2 H) 7.75-7.87 (m, 2 H) 8.13 (dd, J=1.8, 0.4 Hz, 1 H) 9.25 (s, 1 H) 10.59 (s, 1 H) Amount Obtained: 5.2 g, 57% yield.

Example 2

Trypanosoma brucei brucei High-Throughput Screening Assay Procedure

All experiments were conducted with the bloodstream-form trypanosome *T. brucei brucei* 427 strain obtained from Seattle Biomedical Research Institute (Seattle, Wash.). Parasites were cultured in T-25 vented cap flasks and kept in humidified incubators at 37° C. and 5% $CO_2$. The parasite culture media was complete HMI-9 medium (c.f. Hirumi, Journal of Parasitology 1989, Volume 75, page 985 et seq) containing 10% FBS, 10% Serum Plus medium and penicillin/streptomycin. To ensure log growth phase, trypanosomes were sub-cultured at appropriate dilutions every 2-3 days.

In Vitro Drug Sensitivity Assays

Approximately 50 microliters of log phase cultures were diluted 1:10 in HMI-9 and 10 uL of the diluted culture was removed and counted using a hemocytometer to determine parasite concentration. Parasites were diluted by addition of an appropriate volume of HMI-9 to achieve a final parasite concentration of $2\times10^5$/mL. Compounds to be tested were serially diluted in DMSO and 0.5 uL added to 49.5 uL HMI-9 in triplicate 96-well plates using a Biomek NX liquid handler. Parasites from the diluted stock were added to each well (50 uL) using a Multidrop 384 dispenser to give a final concentration of $1.0\times105$/ml parasites in 0.4% for DMSO. Trypanosomes were incubated with compounds for 72 hrs at 37° C. with 5% $CO_2$. Resazurin (20 uL of 12.5 mg/ml stock) from Sigma-Aldrich was added to each well and plates were incubated for an additional 2-4 hrs. Assay plates were read using an EnVision plate reader at an excitation wavelength of 544 nm and emission of 590 nm. Triplicate data points were averaged to generate sigmoidal dose response curve and determine $IC_{50}$ values using XLfit curve fitting software from IDBS (Guildford, UK).

Biological data for exemplary compounds of the invention is provided in FIG. 1.

Example 3

Method for Estimation of Kinetic Solubility of Compounds of the Invention

The kinetic solubilities of compounds were estimated using a nephelometric (light scattering) method. Briefly, compounds were serially diluted in DMSO, followed by dilution in PBS pH 7.4. After incubation, the amount of light scattered by a compound at each concentration was measured. Clear solutions of soluble compounds do not scatter a light beam passed through the sample well and produce no signal. At concentrations above the solubility limit, the compound precipitates and the precipitant in the well scatters the light, generating a signal. Higher levels of precipitant in a well scatter more light and produce a stronger signal.

A stock solution of compound (25 mM in DMSO) was prepared, and was serially diluted in DMSO in two-fold increments in a row of a 96 well plate to a lowest concentration of 24 μM. A duplicate plate was prepared by transfer of half of the volume of each well to a new plate. Each well containing DMSO solution of the test compound was then diluted further (1:100) with phosphate buffered saline (pH 7.4) to provide aqueous solutions of compound at the following final concentrations: 250, 125, 62.5, 31.3, 15.6, 7.8, 3.9, 2.0, 1.0, 0.5 and 0.2 μM. All liquid handling stages were performed on a Beckman Coulter Biomek NX Laboratory Automation Workstation. Each compound was diluted and tested in duplicate, providing four separate wells at each test concentration.

The test solutions of compound were incubated at room temperature for 90 minutes and then analyzed using a Thermoskan Ascent nephelometric plate reader. The nephelometer protocol included two steps: first, the plate was shaken for 60 seconds at 1200 rpm, then each well of the plate was read in succession with an 800 ms settling delay between measurements. The total measurement time for a single plate was less than 4 minutes.

The four values (in nephelometric units) obtained for each compound at each concentration were averaged and plotted on a log scale versus concentration. The concentration at which the nephelometric signal is >110% of the value obtained for a DMSO/PBS blank is reported as the limit of solubility.

Biological data for exemplary compounds of the invention is provided in FIG. 1.

Example 4

L929 Cells and Cultivation

For evaluation of compound effects on mammalian cells, L929 mouse fibroblast cells were used. Cells were maintained as adherent cultures in T-25 vented cap flasks in a humidified incubator at 37° C. in the presence of 5% $CO_2$. Culture media was D-MEM supplemented with 10% fetal bovine serum and 1% penicillin/streptomycin. L929 cells were maintained below confluent levels by sub-culturing at 1:10 dilution twice weekly using 0.05% trypsin for detachment.

Cytotoxicity Evaluation

Sub-confluent L929 cells were trypsinized, resuspended in fresh media and 10 uL was counted using hemocytometer to determine cell concentration. Cells were diluted to $1\times10^4$/mL in DMEM, dispensed (100 uL) into 96-well plates using a Multidrop 384 dispenser and allowed to attach overnight. Spent media was replaced with 99.5 uL fresh D-MEM and compounds to be tested were serially diluted in DMSO and 0.5 uL added using a Biomek NX liquid handler. Plates were incubated with compounds for 72 hrs at 37° C. with 5% $CO_2$. Resazurin (20 uL of 12.5 mg/ml stock) from Sigma-Aldrich was added to each well and plates were incubated for an additional 3-4 hrs. Assay plates were read using an EnVision plate reader at an excitation wavelength of 544 nm and emission of 590 nm. Single data points were used to generate sigmoidal dose response curves and determine $IC_{50}$ values using XLfit curve fitting software from IDBS (Guildford, UK).

Biological data for exemplary compounds of the invention is provided in FIG. 1.

Example 5

Acute Murine Model A

Female Swiss Webster mice were inoculated with 250,000 parasites of the LAB 110 Eatro strain of *T. b. brucei*. 24 hrs post-infection, treatment was initiated BID for 4 days with 20 mg/kg/dose (40 mg/kg/day) intraperitoneally (IP) or orally (PO), 5 mg/kg BID or 10 mg/kg BID orally (PO). N=3 mice/group. Mice were monitored for 30 days for survival. Pentamidine at 2 mg/kg IP was used as the positive control. After 10 days, 0% of the untreated mice were parasite free. After 10 days, 0% of mice treated with 6-(4-chlorophenylsulfinyl)benzo[c][1,2]oxaborol-1(3H)-ol were parasite free. After 30 days, 100% of mice treated with 10 mg/kg BID of N-(1-hydroxy-1,3-dihydrobenzo[c][1,2]oxaborol-6-yl)-2-(trifluoromethyl)benzamide were parasite free. These results indicate that N-(1-hydroxy-1,3-dihydrobenzo[c][1,2]oxaborol-6-yl)-2-(trifluoromethyl)benzamide can prevent the development of diseases associated with T. b. brucei. These results indicate that N-(1-hydroxy-1,3-dihydrobenzo[c][1,2] oxaborol-6-yl)-2-(trifluoromethyl)benzamide has potential for development to treat early-stage HAT.

TABLE

In vivo data for selected Examples in Acute Murine Model A.

| Example # | Dose (mg/kg) | Mean Survival Days |
|---|---|---|
| Vehicle Control | | 7 |
| 3 | 10 | 18 |
| 4 | 10 | >30 |
| 5 | 10 | >30 |
| 9 | 20 | 8 |
| 82 | 10 | >30 |
| 38 | 10 | 9 |
| 69 | 10 | >30 |
| 135 | 10 | 8 |

Note:
All compounds were dosed for 4 days, BID, orally.

Example 6

Chronic CNS Model

Mice were infected with 10,000 parasites of the TREU 667 strain of T. b. brucei. Twenty one days post-infection mice were treated with a dose of between 6 and 100 mg/kg of the compound, either BID or QD for 7 days intraperitoneally (IP) or orally (PO). Positive control mice were treated with Diminazene (10 mg/kg, IP) on Day 4 post-infection. Negative control mice were treated with Diminazene (10 mg/kg, PO) on Day 21. Since Diminazene is not able to penetrate the CNS, mice treated at Day 21 are not able to cure the infection. Starting 1 week after the end of treatment, mice are monitored for parasitemia and sacrificed if parasites are detected in the blood. Mice that survive 6 months are considered "cured."

For example, treatment with 75 mg/kg of 4-fluoro-N-(1-hydroxy-3,3-dimethyl-1,3-dihydro-benzo[c][1,2]oxaborol-6-yl-2-trifluoromethyl)benzamide BID for 7 days, starting at Day 21 post-infection, resulted in absence of blood parasites through Day 84 in 100% of the mice. In contrast, all animals treated on Day 21 with the non-CNS penetrant drug Diminazene relapsed to exhibit blood parasitemia by Day 49. These results indicate that 4-fluoro-N-(1-hydroxy-3,3-dimethyl-1,3-dihydro-benzo[c][1,2]oxaborol-6-yl-2-trifluoromethyl benzamide has potential for development to treat late-stage HAT.

Example 7

Pharmacokinetic Studies in Mice:

Male CD-1 mice weighing approximately 25 g received the test article (E19 or 82 or E14 or 69) by either intravenous (IV), oral gavage (OG) or intra-peritoneal (IP) routes. Animals in IV group (6-10 animals, 1-2 per time point) received a single bolus injection of approximately 2 mg/kg of the test article. Animals receiving extra-vascular doses were administered the test article as either single OG doses (6-10 animals, 1-2 per time point) of approximately 8 mg/kg, or as 4 repeat doses (over 2 days) of approximately 25 mg/kg or 50 mg/kg by the IP route (6-10 animals, 1-2 per time point).

All doses were administered as clear colorless solutions in either: 50% (v/v) PEG400:20% (v/v) ethanol:30% (v/v) carboxymethylcellulose (0.5% w/v in sterile water for injection, WFI), or as in situ sodium salts in 5% (m/v) dextrose: 2% (v/v) ethanol in DWI. All dose solutions were delivered at 4 mL/kg. Animals were fasted for at least 4 hours before dosing, and for 2 hours after dosing.

Blood samples and brain tissue were sampled from 1 or 2 animals/timepoint/group immediately before dosing and approximately 0.17, 0.5, 1, 2, 3, 4, 6, 8, 12, 18 and 24 hr after dosing for full pharmacokinetic and tissue analysis, or at 0.5, 2 and 4 hours post dosing to assess early-phase CNS disposition.

Bioanalysis for test article in whole blood, plasma or brain tissue was performed by HPLC with tandem mass spectrometry (LC-MSMS). Whole blood and plasma samples were treated with 3 volumes of either acetonitrile or methanol to precipitate plasma proteins. Treated samples were centrifuged and supernatants removed for analysis. Brain tissues were weighed and homogenized mechanically in the presence of 1 volume of phosphate-buffered saline (PBS). The resulting tissue suspensions were then diluted with a further volume of PBS, and then treated in the same manner as whole blood or plasma.

Extracted samples were assayed for test article by means of LC-MSMS employing reversed-phase chromatography coupled to a triple quadrupole mass spectrometer employing electrospray ionization in the positive ion mode. The analytical column was a Phenomenex Luna 3μ C8 50×2 mm, with an online sample purification step performed on a Phenomenex Synergi 4μ Polar RP 50×2 mm column.

Test articles were eluted using a binary mobile phase gradient comprising 5 mM Ammonium Acetate: 0.1% formic acid in either MeOH or $H_2O$.

Non-compartmental analysis of plasma test article concentration versus time was performed in Microsoft Excel to generate pharmacokinetic parameters including: area under the curve (AUC), clearance (as Cl or Cl/F), volume of distribution (Vdss), half-life (t½), and bioavailability (F).

Pharmacokinetic Studies in Rats:

Male Sprague Dawley rats weighing approximately 200 g received test article (E19 or 82) as a single oral gavage (OG) dose of approximately 25 mg/kg (approximately 10 animals per group).

All doses were administered as clear colorless solutions as in situ sodium salts in 5% (m/v) dextrose:2% (v/v) ethanol in DWI. All dose solutions were delivered at 2 mL/kg. Animals were fasted for at least 4 hours before dosing, and for 2 hours after dosing.

Blood and CSF samples and brain tissue were sampled from 1 animal/timepoint/group immediately before dosing and approximately 0.5, 1, 2, 3, 4, 6, 8, 12, 18 and 24 hr after dosing for full pharmacokinetic (plasma and CSF) and tissue (Brain) analysis.

Results:

All compounds demonstrate good plasma PK, but 82 is distinguished from E19, and 69 is distinguished from E14, based on higher concentrations, and extended exposure in CNS compartments.

Plasma PK:

Both E19 and 82 display good exposure (AUC and Cmax), promising bioavailability, prolonged half-life, and low clearance when administered to rodents. 82 is superior to E19 in that it achieves 2-4 fold improved plasma exposure (based on AUC) following matched oral doses to either rats or mice.

CNS Disposition:

PK data obtained demonstrate the efficacy of both E19 and 82 shown in the murine chronic HAT model. However, in both mouse and rat, total brain concentrations of E19 decrease rapidly to levels below the MIC within a few hours after dosing. Elimination from the brain and cerebrospinal fluid (CSF) is more rapid than clearance from plasma, suggesting transporter or disposition mediated loss from central nervous system (CNS) compartments. In contrast, 82 achieved higher concentrations in the brain and CSF, and maintains concentrations above the MIC for extended time periods. The data indicates that 82 is less susceptible to the mechanism(s) driving elimination from CNS.

After a nominal single oral dose of 25 mg/kg to rats 82 maintains levels in brain and CSF above the in vitro MIC for approximately 12 hours, and would be expected to sustain this level for >24 hrs on repeat daily administration. In contrast, E19 concentrations in brain and CSF exceed the MIC for only 4 hours.

Exposure of 82 in mouse and rat brain tissue is approximately 6-12 fold improved over E19, and approximately 4 fold improved in rat CSF.

Dose Proportionality:

E19 and 82 afford generally dose-proportional increases in brain exposure following oral delivery to mice. Plasma exposure also increases with dose, although it becomes greater than proportional at doses above 20 mg/kg.

In rats, exposure of E19 in plasma, brain and CSF compartments increase in a generally proportional manner with dose. Data on the dose proportionality for 82 in rats are currently unavailable.

Results for E19 and 82 in mice are presented in Tables 1a and 1b.

TABLE 1a

Summary plasma and brain pharmacokinetic parameters after oral administration to male CD-1 mice. Data normalized to 25 mg/kg following a nominal 25 mg/kg dose.

|  | Plasma | | Brain | |
| --- | --- | --- | --- | --- |
|  | E19 | 82 | E19 | 82 |
| Cmax (ug/ml) | 10.0 | 9.4 | 6.1 | 7.7 |
| Exposure/trapezoid $AUC_{0-18}$ (hr * µg/ml) | 70.6 | 107.8 | 13.1 | 64.9 |
| Exposure/trapezoid $AUC_{0-inf}$ (hr * µg/ml) | 108.7 | 127.9 | 13.2 | 65.5 |
| t½ (hr) | 17.1 | 6.9 | 2.3 | NA |
| F (% of IV) | 26% | 45% | NA | NA |
| Oral Clearance Cl/F (L/kg/hr) | 0.230 | 0.196 | NA | NA |

TABLE 1b

Fold improvement in key plasma and brain PK parameters for 82 when compared to E19 following oral administration to mice.

|  | Fold improvement 82 vs. E19 in the rat | |
| --- | --- | --- |
|  | Plasma | Brain |
| Cmax (ug/ml) | 1.2 | 1.6 |
| Exposure/trapezoid $AUC_{0-18}$ (hr * µg/ml) | 1.9 | 6.2 |
| Exposure/trapezoid $AUC_{0-inf}$ (hr * µg/ml) | 1.5 | 6.2 |
| t½ (hr) | 0.4 | NA |
| Oral Clearance Cl/F (L/kg/hr) | 1.2 | NA |

Results for E19 and 82 in rats are presented in Tables 2a and 2b.

TABLE 2a

Summary plasma, brain and CSF pharmacokinetic parameters after oral administration to male Sprague Dawley rats. Data normalized to 25 mg/kg following a nominal 25 mg/kg dose.

|  | Plasma | | Brain | | CSF | |
| --- | --- | --- | --- | --- | --- | --- |
|  | E19 | 82 | E19 | 82 | E19 | 82 |
| Cmax (ug/ml) | 12.3 | 17.0 | 2.5 | 7.9 | 1.2 | 1.0 |
| Exposure/trapezoid $AUC_{0-18}$ (hr * µg/ml) | 98.3 | 272 | 12.7 | 120 | 3.8 | 13.6 |
| Exposure/trapezoid $AUC_{0-inf}$ (hr * µg/ml) | 101.6 | 433 | 12.7 | 152 | 3.9 | 16.8 |
| t½ (hr) | 8.1 | 15.5 | 2.6 | 9.5 | 3.1 | 8.7 |
| F (% of IV) | 123.0% | No IV data | NA | NA | NA | NA |
| Oral Clearance Cl/F (L/kg/hr) | 0.261 | 0.092 | NA | NA | NA | NA |

TABLE 2b

Fold improvement in key plasma and CNS PK parameters for 82 when compared to E19 following oral administration to rats.

|  | Fold improvement 82 vs. E19 in the rat | | |
| --- | --- | --- | --- |
|  | Plasma | Brain | CSF |
| Cmax (ug/ml) | 1.4 | 3.2 | 0.8 |
| Exposure/trapezoid $AUC_{0-18}$ (hr * µg/ml) | 2.8 | 9.5 | 3.5 |
| Exposure/trapezoid $AUC_{0-inf}$ (hr * µg/ml) | 4.3 | 12.0 | 4.3 |
| t½ (hr) | 1.9 | 3.7 | 2.8 |
| Oral Clearance Cl/F (L/kg/hr) | 2.8 | NA | NA |

Results for E14 and 69 in mice are presented in Tables 3a and 3b.

TABLE 3a

Summary plasma and brain pharmacokinetic parameters after oral administration to male CD-1 mice. Data normalized to 25 mg/kg.

|  | Plasma | | Brain | |
| --- | --- | --- | --- | --- |
|  | E14 | 69 | E14 | 69 |
| $C_{max}$ (ug/mL) | 3.59 | 7.67 | 2.44 | 3.25 |
| Exposure/trapezoid $AUC_{0-last}$ (hr * ug/mL) | 14.4 | 56.9 | 3.12 | 20.8 |
| Exposure/trapezoid $AUC_{0-inf}$ (hr * ug/mL) | 15.2 | 58.0 | 3.15 | 21.3 |
| t½ (hr) | 2.97 | 3.7 | 1.60 | 1.4 |
| Oral Clearance Cl/F (L/kg/hr) | 1.73 | 0.439 | 8.02 | 1.20 |

TABLE 3b

Fold improvement in key plasma and brain PK parameters for 69 when compared to E14 following oral administration to mice.

|  | Fold improvement 69 vs E14 in the mouse | |
| --- | --- | --- |
|  | Plasma | Brain |
| $C_{max}$ (ug/mL) | 2.1 | 1.3 |
| Exposure/trapezoid $AUC_{0\text{-}last}$ (hr * ug/mL) | 4.0 | 6.7 |
| Exposure/trapezoid $AUC_{0\text{-}inf}$ (hr * ug/mL) | 3.8 | 6.8 |
| t½ (hr) | 1.2 | 0.9 |
| Oral Clearance Cl/F (L/kg/hr) | 3.9 | 6.7 |

Example 8

*Leishmania donovani* Strain and Cultivation

All experiments were conducted with the axenic amastigote-form of the following parasite: *Leishmania donovani* strain 1S-CL2D from Sudan, World Health Organization (WHO) designation: (MHOM/SD/62/1 S-CL2D). Parasites were cultured in T-25 vented cap flasks and kept in humidified incubators at 37° C. and 5% CO2. The axenic parasite culture media was RPMI-1640/MES/pH 5.5 formulated and prepared as described by Debrabant et. al. (*International Journal for Parasitology* 2004, Volume 34, page 205-217). To ensure log growth phase, axenic amastigotes were subcultured at appropriate dilutions every 2-3 days.

In Vitro Drug Sensitivity Assays

Cultures of axenic amastigotes growing in the log phase were passed through a 22 gauge blunt needle to break up the clumps, diluted 1:10 in RPMI-1640/MES medium and counted using hemocytometer to determine parasite concentration. Amastigotes were diluted to $2 \times 10^5$/mL in RPMI-1640/MES medium to generate a 2-fold working concentration for assay. Compounds to be tested were serially diluted in DMSO and 0.5 μL added to 50 μL HMI-9 in triplicate 96-well plates using a Biomek NX liquid handler. Parasites from the diluted stock were added to each well (50 μL) using a Multidrop 384 dispenser to give a final concentration of $1.0 \times 10^5$/ml parasites in 0.5% for DMSO. Amastigotes were incubated with compounds for 72 hrs at 37° C. with 5% $CO_2$. Resazurin (10 μL of 12.5 mg/ml stock) from Sigma-Aldrich was added to each well and plates were incubated for an additional 2-3 hrs. Assay plates were read using an EnVision plate reader at an excitation wavelength of 544 nm and emission of 590 nm. Triplicate data points were averaged to generate sigmoidal dose response curve and determine $IC_{50}$ values using XLfit curve fitting software from IDBS (Guildford, UK).

Biological data for exemplary compounds of the invention is provided in FIG. 1.

Example 9

Activity Against *Trypanosoma brucei rhodesiense*

This stock was isolated in 1982 from a human patient in Tanzania and after several mouse passages cloned and adapted to axenic culture conditions (Baltz et al (1985) *EMBO Journal* 4:1273-1277; Thuita et al (2008) *Acta Tropica* 108:6-10.) Minimum Essential Medium (50 μl) supplemented with 25 mM HEPES, 1 g/l additional glucose, 1% MEM non-essential amino acids (100×), 0.2 mM 2-mercaptoethanol, 1 mM Na-pyruvate and 15% heat inactivated horse serum can be added to each well of a 96-well microtiter plate. Serial drug dilutions of seven 3-fold dilution steps covering a range from 90 to 0.123 μg/m¹ can be prepared. Then $10^4$ bloodstream forms of *T. b. rhodesiense* STIB 900 in 50 μl can be added to each well and the plate can be incubated at 37° C. under a 5% $CO_2$ atmosphere for 72 h. 10 μl Alamar Blue (resazurin, 12.5 mg in 100 ml double-distilled water) can be then added to each well and incubation continued for a further 2-4 h (Raz et al. (1997) *Acta Trop* 68:139-47). Then the plates can be read with a Spectramax Gemini XS microplate fluorometer (Molecular Devices Cooperation, Sunnyvale, Calif., USA) using an excitation wave length of 536 nm and an emission wave length of 588 nm. Data can be analyzed using the microplate reader software Softmax Pro (Molecular Devices Cooperation, Sunnyvale, Calif., USA).

Example 10

Activity Against *T. cruzi*

Rat skeletal myoblasts (L-6 cells) can be seeded in 96-well microtitre plates at 2000 cells/well in 100 μL RPMI 1640 medium with 10% FBS and 2 mM 1-glutamine. After 24 h the medium can be removed and replaced by 100 μl per well containing 5000 trypomastigote forms of *T. cruzi* Tulahuen strain C2C4 containing the β-galactosidase (Lac Z) gene (Buckner et al. (1996) Efficient technique for screening drugs for activity against *Trypanosoma cruzi* using parasites expressing beta-galactosidase, p. 2592-2597, vol. 40). After 48 h the medium can be removed from the wells and replaced by 100 μl fresh medium with or without a serial drug dilution of seven 3-fold dilution steps covering a range from 90 to 0.123 μg/ml. After 96 h of incubation the plates can be inspected under an inverted microscope to assure growth of the controls and sterility. Then the substrate CPRG/Nonidet (50 μl) can be added to all wells. A color reaction can be within 2-6 h and can be read photometrically at 540 nm. Data can be transferred into the graphic programme Softmax Pro (Molecular Devices), to calculated $IC_{50}$ values.

Example 10

Liver S9 Metabolism Assay Conditions

Test System: Liver S9 fractions from male CD1 mice were purchased from XenoTech LLC (Lenexa, Kans.) and stored at −70° C. until use. The activity profile of the major metabolic enzymes, as provided by the vendor for each lot, was stored with the raw data.

Preparation of Test Compound Solutions: A stock solution of each compound was prepared in DMSO at a concentration of 10 mg/mL. Stock solutions were further diluted in DMSO to a concentration of 100 μM for use in the assay. The final assay concentration of test compound in each incubation mixture was 1 μM and the final concentration of DMSO was 1%.

Incubation Conditions: Incubations of test compound with CD1 mouse liver S9 fractions were carried out in duplicate at a final concentration of 1 μM. The incubation mixtures included 100 mM potassium phosphate buffer (pH 7.4) with the following cofactors: 1.14 mM β-NADPH, 1.43 mM glucose-6-phosphate, 1.43 mM uridine 5'-diphosphoglucuronic acid (UDPGA), 9.42 mM potassium chloride, and 2.28 mM magnesium chloride (final assay concentration). The reactions were initiated by the addition of the cofactors to the incubation mixtures. The total incubation contained an S9 protein concentration of 2.5 mg/mL. Incubations were performed at 37° C. in an oxygen and humidity enriched atmosphere with shaking (200 rpm), for time periods of 0, 15, 30, and 60 minutes. At the end of each time period, an aliquot was taken and transferred to a clean 96-well plate containing three volumes of ice cold methanol. Samples were centrifuged at 4200×g for 20 minutes at 15° C. and the supernatants were transferred to new plates. Samples were analyzed by means of reversed-phase LC-MS/MS using the conditions summarized below. Peak areas were measured to calculate the percent of parent compound remaining and the half life.

Liquid Chromatography Settings

Column: Phenomenex Luna C8(2), 3μ, 100 A, 50×2 mm, P/N 00B-4248-B0 with C8 guard cartridge, P/N AJO-4289

Column temp: 60° C.

Mobile Phase:
Aqueous (A): 10 mM ammonium acetate in $H_2O$
Organic (B): 10 mM ammonium acetate in methanol
Flow: 600 μL/minute Gradient Conditions:

| Time (Min) | % A | % B |
|---|---|---|
| 0.00 | 80 | 20 |
| 0.25 | 80 | 20 |
| 3.50 | 10 | 90 |
| 4.00 | 10 | 90 |
| 4.10 | 80 | 20 |
| 4.60 | 80 | 20 |

Total Run Time: 4.60 minutes

Autosampler Settings:
Sample Temp: ambient
Injection Volume: 10 μL (20 μL injected on a 10 μL sample loop)
Wash 1: ACN/$H_2O$ (80:20, v/v)
Wash 2: MeOH Typical Mass Spectrometer Settings:

| Mass spectrometer: | Applied Biosystems API 4000 QTRAP |
|---|---|
| Mode: | Multiple Reaction Monitoring |
| Interface: | Turbo IonSpray |
| Polarity: | Negative |
| IonSpray Voltage | −4200 V |
| Resolution: | Unit/Low |
| Temperature: | 450° C. |
| CUR: | 10 |
| CAD: | High |
| GS1: | 60 |
| GS2: | 40 |

Typical conditions are given. Actual settings used may differ to provide optimal conditions for individual compounds.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having a structure according to the following formula:

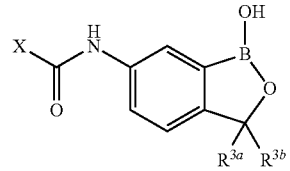

wherein
X is selected from the group consisting of substituted phenyl, substituted or unsubstituted heteroaryl and unsubstituted cycloalkyl; and
$R^{3a}$ and $R^{3b}$, along with the atom to which they are attached, are joined to form cyclopropyl or cyclobutyl or cyclopentyl;
or a salt thereof.

2. The compound of claim 1, or a salt thereof, having a structure according to the following formula:

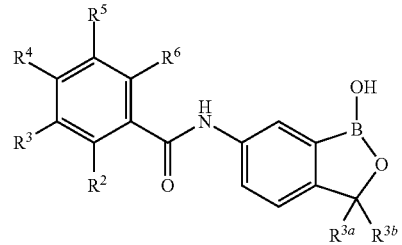

wherein $R^2$, $R^3$, $R^4$, $R^5$ and $R^6$ are the same or different and are each selected from the group consisting of H, halogen, cyano, nitro, unsubstituted $C_1$ or $C_2$ or $C_3$ or $C_4$ or $C_5$ or $C_6$ alkyl, unsubstituted $C_1$ or $C_2$ or $C_3$ or $C_4$ or $C_5$ or $C_6$ alkoxy, halosubstituted $C_1$ or $C_2$ or $C_3$ or $C_4$ or $C_5$ or $C_6$ alkyl, halosubstituted $C_1$ or $C_2$ or $C_3$ or $C_4$ or $C_5$ or $C_6$ alkoxy, unsubstituted $C_1$ or $C_2$ or $C_3$ or $C_4$ or $C_5$ or $C_6$ alkylthio, unsubstituted phenyl, $NR^8R^9$, —$SO_2(R^7)$ and —$SO_2N(R^7)(R^8)$
wherein
$R^7$ is H or unsubstituted $C_1$ or $C_2$ or $C_3$ or $C_4$ or $C_5$ or $C_6$ alkyl;
$R^8$ is H or unsubstituted $C_1$ or $C_2$ or $C_3$ or $C_4$ or $C_5$ or $C_6$ alkyl; and
$R^9$ is selected from the group consisting of H, unsubstituted $C_1$ or $C_2$ or $C_3$ or $C_4$ or $C_5$ or $C_6$ alkyl and —$C(O)R^{10}$
wherein
$R^{10}$ is unsubstituted $C_1$ or $C_2$ or $C_3$ or $C_4$ or $C_5$ or $C_6$ alkyl
with the proviso that $R^2$, $R^3$, $R^4$, $R^5$ and $R^6$ cannot all be H.

3. The compound of claim 2, or a salt thereof, having a structure according to the following formula:

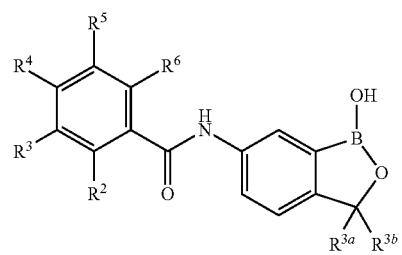

wherein $R^2$, $R^3$, $R^4$, $R^5$ and $R^6$ are the same or different and are each selected from the group consisting of H, F, Cl, CN, $NO_2$, —$CH_3$, —$CH_2CH_3$, $CH(CH_3)_2$, $C(CH_3)_3$, $CF_3$, —$OCH_3$, —$OCH_2CH_3$, —$OCF_3$, —$N(CH_3)_2$, —$NH(C(O)CH_3)$, —$SCH_3$, —$S(O)_2CH_3$, and —$S(O)_2N(CH_3)_2$
with the proviso that $R^2$, $R^3$, $R^4$, $R^5$ and $R^6$ cannot all be H.

4. The compound of claim 2, or a salt thereof, having a structure according to the following formula:

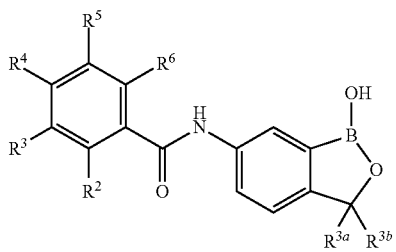

wherein one member selected from the group consisting of $R^2$, $R^3$, $R^4$, $R^5$ and $R^6$ is halogen or cyano or nitro or unsubstituted $C_1$ or $C_2$ or $C_3$ or $C_4$ or $C_5$ or $C_6$ alkyl or unsubstituted $C_1$ or $C_2$ or $C_3$ or $C_4$ or $C_5$ or $C_6$ alkoxy or halosubstituted $C_1$ or $C_2$ or $C_3$ or $C_4$ or $C_5$ or $C_6$ alkyl or halosubstituted $C_1$ or $C_2$ or $C_3$ or $C_4$ or $C_5$ or $C_6$ alkoxy or unsubstituted $C_1$ or $C_2$ or $C_3$ or $C_4$ or $C_5$ or $C_6$ alkylthio or unsubstituted phenyl or $NR^8R^9$ or —$SO_2(R^7)$ or —$SO_2N(R^7)(R^8)$
wherein
$R^7$ is H or unsubstituted $C_1$ or $C_2$ or $C_3$ or $C_4$ or $C_5$ or $C_6$ alkyl;
$R^8$ is H or unsubstituted $C_1$ or $C_2$ or $C_3$ or $C_4$ or $C_5$ or $C_6$ alkyl; and
$R^9$ is a member selected from H, unsubstituted $C_1$ or $C_2$ or $C_3$ or $C_4$ or $C_5$ or $C_6$ alkyl and —$C(O)R^{10}$
wherein
$R^{10}$ is unsubstituted $C_1$ or $C_2$ or $C_3$ or $C_4$ or $C_5$ or $C_6$ alkyl
and the remaining members of $R^2$, $R^3$, $R^4$, $R^5$ and $R^6$ are H.

5. The compound of claim 2, or a salt thereof, having a structure according to the following formula:

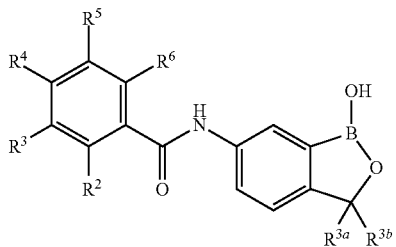

wherein one member selected from $R^2$, $R^3$, $R^4$, $R^5$ and $R^6$ is F, Cl, CN, $NO_2$, —$CH_3$, —$CH_2CH_3$, $CH(CH_3)_2$, $C(CH_3)_3$, $CF_3$, —$OCH_3$, —$OCH_2CH_3$, —$OCF_3$, —$N(CH_3)_2$, —$NH(C(O)CH_3)$, —$SCH_3$, —$S(O)_2CH_3$, or —$S(O)_2N(CH_3)_2$
and the remaining members of $R^2$, $R^3$, $R^4$, $R^5$ and $R^6$ are H.

6. The compound of claim 2, or a salt thereof, wherein
one member selected from $R^2$, $R^3$, $R^4$, $R^5$ and $R^6$ is halogen or unsubstituted $C_1$ or $C_2$ or $C_3$ or $C_4$ or $C_5$ or $C_6$ alkyl or halosubstituted $C_1$ or $C_2$ or $C_3$ or $C_4$ or $C_5$ or $C_6$ alkyl, and
the remaining members of $R^2$, $R^3$, $R^4$, $R^5$ and $R^6$ are H.

7. The compound of claim 6, or a salt thereof, wherein
one member selected from $R^2$, $R^3$, $R^4$, $R^5$ and $R^6$ is a member selected from F, Cl, Br, I, $CH_3$, $CF_3$ and $OCH_3$; and
the remaining members of $R^2$, $R^3$, $R^4$, $R^5$ and $R^6$ are H.

8. The compound of claim 7, or a salt thereof, wherein
one member selected from $R^2$, $R^3$, $R^4$, $R^5$ and $R^6$ is F or Cl or $CH_3$ or $CF_3$; and
the remaining members of $R^2$, $R^3$, $R^4$, $R^5$ and $R^6$ are H.

9. The compound of claim 2, or a salt thereof, wherein
two members selected from $R^2$, $R^3$, $R^4$, $R^5$ and $R^6$ are the same or different and are each selected from halogen; and
the remaining members of $R^2$, $R^3$, $R^4$, $R^5$ and $R^6$ are H.

10. The compound of claim 2, or a salt thereof, wherein
one member selected from $R^2$, $R^3$, $R^4$, $R^5$ and $R^6$ is halogen;
one member selected from $R^2$, $R^3$, $R^4$, $R^5$ and $R^6$ is halogen or unsubstituted $C_1$ or $C_2$ or $C_3$ or $C_4$ or $C_5$ or $C_6$ alkyl or halosubstituted $C_1$ or $C_2$ or $C_3$ or $C_4$ or $C_5$ or $C_6$ alkyl; and
the remaining members of $R^2$, $R^3$, $R^4$, $R^5$ and $R^6$ are H.

11. The compound of claim 10, or a salt thereof, wherein
one member selected from $R^2$, $R^3$, $R^4$, $R^5$ and $R^6$ is halogen;
one member selected from $R^2$, $R^3$, $R^4$, $R^5$ and $R^6$ is F or Cl or Br or I or $CH_3$ or $CF_3$ or $OCH_3$; and
the remaining members of $R^2$, $R^3$, $R^4$, $R^5$ and $R^6$ are H.

12. The compound of claim 2, or a salt thereof, wherein
one member selected from $R^2$, $R^3$, $R^4$, $R^5$ and $R^6$ is F;
one member selected from $R^2$, $R^3$, $R^4$, $R^5$ and $R^6$ is halogen or unsubstituted $C_1$ or $C_2$ or $C_3$ or $C_4$ or $C_5$ or $C_6$ alkyl or halosubstituted $C_1$ or $C_2$ or $C_3$ or $C_4$ or $C_5$ or $C_6$ alkyl; and
the remaining members of $R^2$, $R^3$, $R^4$, $R^5$ and $R^6$ are H.

13. The compound of claim 12, or a salt thereof, wherein
one member selected from $R^2$, $R^3$, $R^4$, $R^5$ and $R^6$ is F; and
one member selected from $R^2$, $R^3$, $R^4$, $R^5$ and $R^6$ is Cl or $CH_3$ or $CF_3$; and
the remaining members of $R^2$, $R^3$, $R^4$, $R^5$ and $R^6$ are H.

14. The compound of claim 2, or a salt thereof, having a structure according to the following formula:

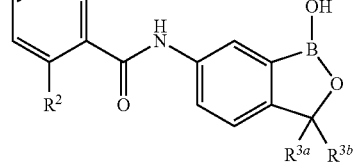

wherein
R² is a member selected from halogen, cyano, nitro, unsubstituted $C_1$ or $C_2$ or $C_3$ or $C_4$ or $C_5$ or $C_6$ alkyl, unsubstituted $C_1$ or $C_2$ or $C_3$ or $C_4$ or $C_5$ or $C_6$ alkoxy, halosubstituted $C_1$ or $C_2$ or $C_3$ or $C_4$ or $C_5$ or $C_6$ alkyl, halosubstituted $C_1$ or $C_2$ or $C_3$ or $C_4$ or $C_5$ or $C_6$ alkoxy, unsubstituted $C_1$ or $C_2$ or $C_3$ or $C_4$ or $C_5$ or $C_6$ alkylthio, unsubstituted phenyl, $NR^8R^9$, $—SO_2(R^7)$ and $—SO_2N(R^7)(R^8)$ wherein
R⁷ is H or unsubstituted $C_1$ or $C_2$ or $C_3$ or $C_4$ or $C_5$ or $C_6$ alkyl;
R⁸ is H or unsubstituted $C_1$ or $C_2$ or $C_3$ or $C_4$ or $C_5$ or $C_6$ alkyl; and
R⁹ is a member selected from H, unsubstituted $C_1$ or $C_2$ or $C_3$ or $C_4$ or $C_5$ or $C_6$ alkyl and $—C(O)R^{10}$ wherein
R¹⁰ is unsubstituted $C_1$ or $C_2$ or $C_3$ or $C_4$ or $C_5$ or $C_6$ alkyl.

15. The compound of claim 14, or a salt thereof, having a structure according to the following formula:

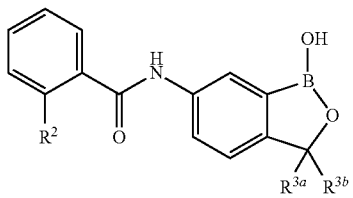

wherein
R² is a member selected from halogen, unsubstituted $C_1$ or $C_2$ or $C_3$ or $C_4$ or $C_5$ or $C_6$ alkyl and halosubstituted $C_1$ or $C_2$ or $C_3$ or $C_4$ or $C_5$ or $C_6$ alkyl.

16. The compound of claim 15, or a salt thereof, wherein R² is a member selected from F, Cl, CH₃ and CF₃.

17. The compound of claim 2, or a salt thereof, having a structure according to the following formula:

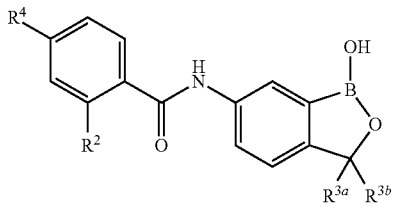

wherein
R⁴ is halogen; and
R² is a member selected from halogen, cyano, nitro, unsubstituted $C_1$ or $C_2$ or $C_3$ or $C_4$ or $C_5$ or $C_6$ alkyl, unsubstituted $C_1$ or $C_2$ or $C_3$ or $C_4$ or $C_5$ or $C_6$ alkoxy, halosubstituted $C_1$ or $C_2$ or $C_3$ or $C_4$ or $C_5$ or $C_6$ alkyl, halosubstituted $C_1$ or $C_2$ or $C_3$ or $C_4$ or $C_5$ or $C_6$ alkoxy, unsubstituted $C_1$ or $C_2$ or $C_3$ or $C_4$ or $C_5$ or $C_6$ alkylthio, unsubstituted phenyl, $NR^8R^9$, $—SO_2(R^7)$ and $—SO_2N(R^7)(R^8)$ wherein
R⁷ is H or unsubstituted $C_1$ or $C_2$ or $C_3$ or $C_4$ or $C_5$ or $C_6$ alkyl;
R⁸ is H or unsubstituted $C_1$ or $C_2$ or $C_3$ or $C_4$ or $C_5$ or $C_6$ alkyl; and
R⁹ is a member selected from H, unsubstituted $C_1$ or $C_2$ or $C_3$ or $C_4$ or $C_5$ or $C_6$ alkyl and $—C(O)R^{10}$ wherein
R¹⁰ is unsubstituted $C_1$ or $C_2$ or $C_3$ or $C_4$ or $C_5$ or $C_6$ alkyl.

18. The compound of claim 2, or a salt thereof, having a structure according to the following formula:

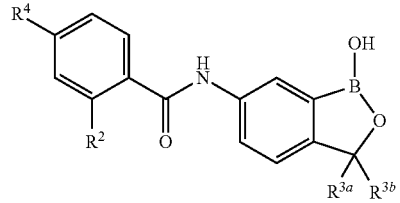

wherein
R⁴ is halogen; and
R² is a member selected from F, Cl, CN, NO₂, —CH₃, —CH₂CH₃, CH(CH₃)₂, C(CH₃)₃, CF₃, —OCH₃, —OCH₂CH₃, —OCF₃, —N(CH₃)₂, —NH(C(O)CH₃), —SCH₃, —S(O)₂CH₃ and —S(O)₂N(CH₃)₂.

19. The compound of claim 2, or a salt thereof, having a structure according to the following formula:

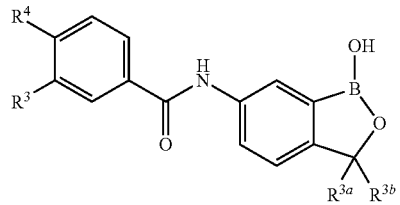

wherein
R⁴ is halogen; and
R³ is a member selected from H, halogen, cyano, nitro, unsubstituted $C_1$ or $C_2$ or $C_3$ or $C_4$ or $C_5$ or $C_6$ alkyl, unsubstituted $C_1$ or $C_2$ or $C_3$ or $C_4$ or $C_5$ or $C_6$ alkoxy, halosubstituted $C_1$ or $C_2$ or $C_3$ or $C_4$ or $C_5$ or $C_6$ alkyl, halosubstituted $C_1$ or $C_2$ or $C_3$ or $C_4$ or $C_5$ or $C_6$ alkoxy, unsubstituted $C_1$ or $C_2$ or $C_3$ or $C_4$ or $C_5$ or $C_6$ alkylthio, unsubstituted phenyl, $NR^8R^9$, $—SO_2(R^7)$ and $—SO_2N(R^7)(R^8)$ wherein
R⁷ is H or unsubstituted $C_1$ or $C_2$ or $C_3$ or $C_4$ or $C_5$ or $C_6$ alkyl;
R⁸ is H or unsubstituted $C_1$ or $C_2$ or $C_3$ or $C_4$ or $C_5$ or $C_6$ alkyl; and
R⁹ is a member selected from H, unsubstituted $C_1$ or $C_2$ or $C_3$ or $C_4$ or $C_5$ or $C_6$ alkyl and $—C(O)R^{10}$ wherein
R¹⁰ is unsubstituted $C_1$ or $C_2$ or $C_3$ or $C_4$ or $C_5$ or $C_6$ alkyl.

20. The compound of claim 2, or a salt thereof, having a structure according to the following formula:

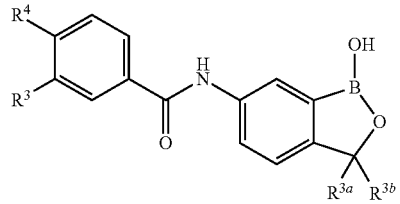

wherein
   $R^4$ is halogen; and
   $R^3$ is a member selected from F, Cl, CN, $NO_2$, —$CH_3$, —$CH_2CH_3$, $CH(CH_3)_2$, $C(CH_3)_3$, $CF_3$, —$OCH_3$, —$OCH_2CH_3$, —$OCF_3$, —$N(CH_3)_2$, —$NH(C(O)CH_3)$, —$SCH_3$, —$S(O)_2CH_3$ and —$S(O)_2N(CH_3)_2$.

21. The compound of claim 2, or a salt thereof, having a structure according to the following formula:

wherein
   $R^2$ is a member selected from H, halogen, cyano, nitro, unsubstituted $C_1$ or $C_2$ or $C_3$ or $C_4$ or $C_5$ or $C_6$ alkyl, unsubstituted $C_1$ or $C_2$ or $C_3$ or $C_4$ or $C_5$ or $C_6$ alkoxy, halosubstituted $C_1$ or $C_2$ or $C_3$ or $C_4$ or $C_5$ or $C_6$ alkyl, halosubstituted $C_1$ or $C_2$ or $C_3$ or $C_4$ or $C_5$ or $C_6$ alkoxy, unsubstituted $C_1$ or $C_2$ or $C_3$ or $C_4$ or $C_5$ or $C_6$ alkylthio, unsubstituted phenyl, $NR^8R^9$, —$SO_2(R^7)$ and —$SO_2N(R^7)(R^8)$
wherein
   $R^7$ is H or unsubstituted $C_1$ or $C_2$ or $C_3$ or $C_4$ or $C_5$ or $C_6$ alkyl;
   $R^8$ is H or unsubstituted $C_1$ or $C_2$ or $C_3$ or $C_4$ or $C_5$ or $C_6$ alkyl; and
   $R^9$ is a member selected from H, unsubstituted $C_1$ or $C_2$ or $C_3$ or $C_4$ or $C_5$ or $C_6$ alkyl and —$C(O)R^{10}$
wherein
   $R^{10}$ is unsubstituted $C_1$ or $C_2$ or $C_3$ or $C_4$ or $C_5$ or $C_6$ alkyl.

22. The compound of claim 2, or a salt thereof, having a structure according to the following formula:

wherein
   $R^2$ is a member selected from F, Cl, CN, $NO_2$, —$CH_3$, —$CH_2CH_3$, $CH(CH_3)_2$, $C(CH_3)_3$, $CF_3$, —$OCH_3$, —$OCH_2CH_3$, —$OCF_3$, —$N(CH_3)_2$, —$NH(C(O)CH_3)$, —$SCH_3$, —$S(O)_2CH_3$ and —$S(O)_2N(CH_3)_2$.

23. The compound of claim 2, or a salt thereof, having a structure according to the following formula:

wherein
   $R^4$ is halogen; and
   $R^2$ is a member selected from Cl, $CH_3$ and $CF_3$.

24. The compound of claim 2, or a salt thereof, having a structure according to the following formula:

wherein
   $R^4$ is halogen; and
   $R^2$ is a member selected from halogen, unsubstituted $C_1$ or $C_2$ or $C_3$ or $C_4$ or $C_5$ or $C_6$ alkyl and halosubstituted $C_1$ or $C_2$ or $C_3$ or $C_4$ or $C_5$ or $C_6$ alkyl.

25. The compound of claim 2, or a salt thereof, having a structure according to the following formula:

wherein
   $R^4$ is halogen and $R^2$ is halogen.

26. A combination comprising the compound of claim 1, or a pharmaceutically acceptable salt thereof, together with at least one other therapeutically active agent.

27. A pharmaceutical formulation comprising:
   a) the compound of claim 1, or a pharmaceutically acceptable salt thereof; and
   b) a pharmaceutically acceptable excipient.

28. The pharmaceutical formulation of claim 27, wherein the pharmaceutical formulation is a unit dosage form.

29. 4-Fluoro-N-(1-hydroxy-3,3-dimethyl-1,3-dihydro-benzo[c][1,2]oxaborol-6-yl)-2-trifluoromethyl benzamide, or a salt thereof.

30. A combination comprising the compound of claim 29, or a pharmaceutically acceptable salt thereof, together with at least one other therapeutically active agent.

31. A pharmaceutical formulation comprising:
a) the compound of claim 29, or a pharmaceutically acceptable salt thereof; and
b) a pharmaceutically acceptable excipient.

32. A compound, which is N-(1-hydroxy-3-isobutyl-1,3-dihydro-benzo[c][1,2]oxaborol-6-yl)-2-trifluoromethyl-benzamide, 4-fluoro-N-(1-hydroxy-3-isobutyl-1,3-dihydro-benzo[c][1,2]oxaborol-6-yl)-2-trifluoromethyl-benzamide, 4-fluoro-N-(1-hydroxy-3-isobutyl-1,3-dihydro-benzo[c][1,2]oxaborol-6-yl)-benzamide, or 2-chloro-N-(1-hydroxy-3-isobutyl-1,3-dihydro-benzo[c][1,2]oxaborol-6-yl)-benzamide; or a salt thereof.

33. A combination comprising the compound of claim 32, or a pharmaceutically acceptable salt thereof, together with at least one other therapeutically active agent.

34. A pharmaceutical formulation comprising:
a) the compound of claim 32, or a pharmaceutically acceptable salt thereof; and
b) a pharmaceutically acceptable excipient.

35. A compound, which is N-(3-cyclopentyl-1-hydroxy-1,3-dihydro-benzo[c][1,2]oxaborol-6-yl)-2-trifluoromethyl-benzamide, 2-chloro-N-(3-cyclopentyl-1-hydroxy-1,3-dihydro-benzo[c][1,2]oxaborol-6-yl)-benzamide, N-(3-cyclopentyl-1-hydroxy-1,3-dihydro-benzo[c][1,2]oxaborol-6-yl)-4-fluoro-2-trifluoromethyl-benzamide, N-(3-cyclopentyl-1-hydroxy-1,3-dihydro-benzo[c][1,2]oxaborol-6-yl)-4-fluoro-benzamide, or N-(3-cyclopentyl-1-hydroxy-1,3-dihydro-benzo[c][1,2]oxaborol-6-yl)-acetamide; or a salt thereof.

36. A combination comprising the compound of claim 35, or a pharmaceutically acceptable salt thereof, together with at least one other therapeutically active agent.

37. A pharmaceutical formulation comprising:
a) the compound of claim 35, or a pharmaceutically acceptable salt thereof; and
b) a pharmaceutically acceptable excipient.

38. A compound, which is N-(1-hydroxy-3,3-dimethyl-1,3-dihydro-benzo[c][1,2]oxaborol-6-yl)-4-thiophen-2-yl-benzamide, N-(1-hydroxy-3,3-dimethyl-1,3-dihydro-benzo[c][1,2]oxaborol-6-yl)-4-morpholin-4-yl-benzamide, or biphenyl-4-carboxylic acid (1-hydroxy-3,3-dimethyl-1,3-dihydro-benzo[c][1,2]oxaborol-6-yl)-amide; or a salt thereof.

39. A combination comprising the compound of claim 38, or a pharmaceutically acceptable salt thereof, together with at least one other therapeutically active agent.

40. A pharmaceutical formulation comprising:
a) the compound of claim 38, or a pharmaceutically acceptable salt thereof; and
b) a pharmaceutically acceptable excipient.

41. The compound of claim 1, which is 4-fluoro-N-(1-hydroxy-3,3-spirocyclopropyl-1,3-dihydro-benzo[c][1,2]oxaborol-6-yl)-2-trifluoromethyl benzamide, 4-fluoro-N-(1-hydroxy-3,3-spirocyclobutyl-1,3-dihydro-benzo[c][1,2]oxaborol-6-yl)-2-trifluoromethyl benzamide, 2-chloro-4-fluoro-N-(1-hydroxy-3,3-spirocyclobutyl-1,3-dihydro-benzo[c][1,2]oxaborol-6-yl)-benzamide, 4-fluoro-N-(1-hydroxy-3,3-spirocyclopentyl-1,3-dihydro-benzo[c][1,2]oxaborol-6-yl)-2-trifluoromethyl benzamide, or 2-chloro-N-(1-hydroxy-3,3-spirocyclopentyl-1,3-dihydro-benzo[c][1,2]oxaborol-6-yl)-benzamide; or a salt thereof.

* * * * *